United States Patent
Lotta et al.

(10) Patent No.: US 11,939,635 B2
(45) Date of Patent: Mar. 26, 2024

(54) TREATMENT OF OBESITY IN SUBJECTS HAVING VARIANT NUCLEIC ACID MOLECULES ENCODING CALCITONIN RECEPTOR (CALCR)

(71) Applicant: Regeneron Pharmaceuticals, Inc., Tarrytown, NY (US)

(72) Inventors: Luca Andrea Lotta, Tarrytown, NY (US); Parsa Akbari, Tarrytown, NY (US); Manuel Allen Revez Ferreira, Tarrytown, NY (US); Aris Baras, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 36 days.

(21) Appl. No.: 17/401,679

(22) Filed: Aug. 13, 2021

(65) Prior Publication Data

US 2022/0049308 A1    Feb. 17, 2022

Related U.S. Application Data

(60) Provisional application No. 63/108,308, filed on Oct. 31, 2020, provisional application No. 63/066,182, filed on Aug. 15, 2020.

(51) Int. Cl.
*C12Q 1/68* (2018.01)
*C12P 19/34* (2006.01)
*C12Q 1/6883* (2018.01)

(52) U.S. Cl.
CPC ...... *C12Q 1/6883* (2013.01); *C12Q 2600/118* (2013.01); *C12Q 2600/156* (2013.01)

(58) Field of Classification Search
CPC ............ C12Q 1/6883; C12Q 2600/106; C12Q 2600/156
See application file for complete search history.

(56) References Cited

U.S. PATENT DOCUMENTS

| | | | |
|---|---|---|---|
| 7,510,876 B2 | 3/2009 | D'Amour et al. | |
| 7,541,185 B2 | 6/2009 | D'Amour et al. | |
| 7,625,753 B2 | 12/2009 | Kelly et al. | |
| 7,704,738 B2 | 4/2010 | D'Amour et al. | |
| 7,985,585 B2 | 7/2011 | D'Amour et al. | |
| 8,216,836 B2 | 7/2012 | D'Amour et al. | |
| 8,268,621 B2 | 9/2012 | Turovets et al. | |
| 8,586,357 B2 | 11/2013 | D'Amour et al. | |
| 8,623,645 B2 | 1/2014 | D'Amour et al. | |
| 8,633,024 B2 | 1/2014 | D'Amour et al. | |
| 8,647,873 B2 | 2/2014 | D'Amour et al. | |
| 8,658,151 B2 | 2/2014 | Kelly et al. | |
| 8,728,805 B2 | 5/2014 | Abramson et al. | |
| 8,986,995 B2 | 3/2015 | Turovets et al. | |
| 9,222,069 B2 | 12/2015 | D'Amour et al. | |
| 9,365,830 B2 | 6/2016 | Schulz et al. | |
| 9,605,243 B2 | 3/2017 | D'Amour et al. | |
| 9,732,318 B2 | 8/2017 | D'Amour et al. | |
| 10,071,130 B2 | 9/2018 | Conzen | |
| 10,179,902 B2 | 1/2019 | D'Amour et al. | |
| 10,421,942 B2 | 9/2019 | D'Amour et al. | |
| 10,465,162 B2 | 11/2019 | D'Amour et al. | |
| 10,494,604 B2 | 12/2019 | Hans-Moore et al. | |
| 10,550,367 B2 | 2/2020 | D'Amour et al. | |
| 10,709,763 B2 | 7/2020 | Seen et al. | |
| 10,988,737 B2 | 4/2021 | Baumert et al. | |
| 10,988,755 B2 | 4/2021 | Skog et al. | |
| 11,078,247 B2 | 8/2021 | Fotin-Mleczek et al. | |
| 2003/0198970 A1 | 10/2003 | Roberts | |
| 2005/0266554 A1 | 12/2005 | D'Amour et al. | |
| 2007/0026393 A1 | 2/2007 | Berlin et al. | |
| 2007/0259368 A1 | 11/2007 | An et al. | |
| 2008/0026396 A1 | 1/2008 | Olek et al. | |
| 2010/0119492 A1 | 5/2010 | Hans et al. | |
| 2010/0151568 A1 | 6/2010 | D'Amour et al. | |
| 2010/0196426 A1 | 8/2010 | Skog et al. | |
| 2011/0003704 A1 | 1/2011 | Skog et al. | |
| 2011/0053157 A1 | 3/2011 | Skog et al. | |
| 2011/0195426 A1 | 8/2011 | Russo et al. | |
| 2012/0142001 A1 | 6/2012 | Skog et al. | |
| 2012/0276624 A1 | 11/2012 | D'Amour et al. | |
| 2013/0131194 A1 | 5/2013 | Skog et al. | |
| 2013/0295574 A1 | 11/2013 | Skog et al. | |
| 2013/0309769 A1 | 11/2013 | Benvenisty et al. | |
| 2014/0134727 A1 | 5/2014 | D'Amour et al. | |
| 2014/0193902 A1 | 7/2014 | D'Amour et al. | |
| 2014/0193905 A1 | 7/2014 | Kelly et al. | |

(Continued)

FOREIGN PATENT DOCUMENTS

| | | |
|---|---|---|
| WO | 1999064627 | 12/1999 |
| WO | 2004042054 | 5/2004 |

(Continued)

OTHER PUBLICATIONS

Jagriti Pal, et al. "Loss-of-Function Mutations in Calcitonin Receptor ( CALCR) Identify Highly Aggressive Glioblastoma with Poor Outcome" Clin Cancer Res, . Mar. 15, 2018;24(6):1448-1458. (Year: 2018).*

French, Simon, and Barry Robson. "What is a conservative substitution?." Journal of molecular Evolution 19 (1983): 171-175. (Year : 1983).*

Akbari et al., "Sequencing of 640,000 exomes identifies GPR75 variants associated with protection from obesity", Science, 2021, 373(6550), pp. eabf8683.

Hjuler et al., "The dual amylin- and calcitonin-receptor agonist KBP-042 increases insulin sensitivity and induces weight loss in rats with obesity: KBP-042, a Weight Loss Drug and Insulin Sensitizer", Obesity, 2016, 24(8), pp. 1712-1722.

Srivastava et al., "Future Pharmacotherapy for Obesity: New Anti-obesity Drugs on the Horizon", Current Obesity Reports, 2018, 7(2), pp. 147-161.

(Continued)

*Primary Examiner* — Stephen T Kapushoc
(74) *Attorney, Agent, or Firm* — Armstrong Teasdale LLP

(57) ABSTRACT

The present disclosure provides methods of treating subjects having obesity and/or increased body mass index (BMI), and methods of identifying subjects having an increased risk of developing obesity and/or BMI.

20 Claims, 8 Drawing Sheets

Specification includes a Sequence Listing.

(56) References Cited

U.S. PATENT DOCUMENTS

| | | |
|---|---|---|
| 2014/0194319 A1 | 7/2014 | Skog et al. |
| 2014/0194613 A1 | 7/2014 | Skog et al. |
| 2014/0322177 A1 | 10/2014 | Abramson et al. |
| 2015/0050728 A1 | 2/2015 | Benvenisty et al. |
| 2016/0017326 A1 | 1/2016 | Kang et al. |
| 2016/0151425 A1 | 6/2016 | Abramson et al. |
| 2016/0281058 A1 | 9/2016 | Schulz et al. |
| 2016/0297883 A1 | 10/2016 | Gallo et al. |
| 2016/0340645 A1 | 11/2016 | D'Amour et al. |
| 2016/0348095 A1 | 12/2016 | Russo et al. |
| 2016/0362678 A1 | 12/2016 | Skog et al. |
| 2017/0029769 A1 | 2/2017 | D'Amour et al. |
| 2017/0088898 A1 | 3/2017 | Skog et al. |
| 2017/0114389 A1 | 4/2017 | Russo et al. |
| 2017/0216365 A1 | 8/2017 | D'Amour et al. |
| 2017/0314075 A1 | 11/2017 | Skog et al. |
| 2018/0051335 A9 | 2/2018 | Skog et al. |
| 2019/0015423 A1 | 1/2019 | Jacobs et al. |
| 2019/0134004 A1 | 5/2019 | Conzen et al. |
| 2019/0233527 A1 | 8/2019 | Kahvejian et al. |
| 2019/0376028 A1 | 12/2019 | D'Amour et al. |
| 2020/0010880 A1 | 1/2020 | Ku et al. |
| 2020/0017824 A1 | 1/2020 | D'Amour et al. |
| 2020/0113950 A1 | 4/2020 | Cohen et al. |
| 2020/0248137 A1 | 8/2020 | D'Amour et al. |
| 2020/0308287 A1 | 10/2020 | Li et al. |
| 2020/0360478 A1 | 11/2020 | Seen et al. |
| 2021/0002296 A1 | 1/2021 | Mainolfi et al. |
| 2021/0202037 A1 | 7/2021 | Stein et al. |
| 2021/0207124 A1 | 7/2021 | Skog et al. |

FOREIGN PATENT DOCUMENTS

| | | |
|---|---|---|
| WO | 2004097422 | 11/2004 |
| WO | 2005116073 | 12/2005 |
| WO | 2006016999 | 2/2006 |
| WO | 2006017134 | 2/2006 |
| WO | 2006071911 | 7/2006 |
| WO | 2009105154 | 8/2009 |
| WO | 2010040571 | 4/2010 |
| WO | 2014185416 | 11/2014 |
| WO | 2016148925 | 9/2016 |
| WO | 2018029586 | 2/2018 |
| WO | 2018039359 | 3/2018 |
| WO | 2019126398 | 6/2019 |

OTHER PUBLICATIONS

Yengo et al., "Meta-analysis of genome-wide association studies for height and body mass index in 700000 individuals of European ancestry", Human Molecular Genetics, 2018, 27(20), pp. 3641-3649.

* cited by examiner

TREATMENT OF OBESITY IN SUBJECTS HAVING VARIANT NUCLEIC ACID MOLECULES ENCODING CALCITONIN RECEPTOR (CALCR)

REFERENCE TO SEQUENCE LISTING

This application includes a Sequence Listing submitted electronically as a text file named 381203402SEQ, created on May 11, 2023 with a size of 310,124 kilobytes. The Sequence Listing is incorporated herein by reference.

FIELD

The present disclosure provides methods of treating a subject having a CALCR variant nucleic acid molecule encoding a CALCR predicted loss-of-function polypeptide with a therapeutic agent that treats or inhibits obesity, and methods of identifying subjects having an increased risk of developing obesity.

BACKGROUND

Obesity and its cardio-metabolic complications, in particular type 2 diabetes and coronary artery disease, account for significant morbidity and mortality globally. There is a substantial unmet medical need for safe and effective weight loss approaches and treatments for obesity.

Lifestyle interventions on diet and physical activity are the first option for the management of obesity and overweight, but efficacy can be limited, and weight regain is common. Bariatric surgery can be highly effective for weight loss in severely obese or high-risk patients, but its use is limited by its invasive nature, cost, risk of perioperative adverse events including perioperative death. While a few therapeutic agents have demonstrated efficacy in weight-reduction, pharmacotherapy for the treatment of obesity is limited by the modest weight loss induced by most therapeutic agents, side effect profile of some agents, contraindications, low compliance, and barriers to treatment including underprescription.

Calcitonin Receptor (CALCR) is a G protein-coupled receptor that is highly expressed in the hypothalamus and other regions of the brain. The peptide hormones calcitonin and amylin are known ligands of CALCR.

SUMMARY

The present disclosure provides methods of treating a subject with a therapeutic agent that treats or inhibits obesity and/or reduces BMI, wherein the subject has obesity and/or increased BMI, the methods comprising the steps of: determining whether the subject has a CALCR variant nucleic acid molecule encoding a CALCR predicted loss-of-function polypeptide by: obtaining or having obtained a biological sample from the subject; and performing or having performed a sequence analysis on the biological sample to determine if the subject has a genotype comprising the CALCR variant nucleic acid molecule; and administering or continuing to administer to the subject the therapeutic agent that treats or inhibits obesity and/or increased BMI in a standard dosage amount to a subject that is CALCR reference; or administering or continuing to administer to the subject the therapeutic agent that treats or inhibits obesity and/or increased BMI in an amount that is the same as or greater than a standard dosage amount to a subject that is heterozygous or homozygous for the CALCR variant nucleic acid molecule; wherein the presence of a genotype having the CALCR variant nucleic acid molecule encoding a CALCR predicted loss-of-function polypeptide indicates the subject has an increased risk of developing obesity and/or increased BMI.

The present disclosure also provides methods of identifying a subject having an increased risk of developing obesity and/or increased BMI, the methods comprising: determining or having determined the presence or absence of a CALCR variant nucleic acid molecule encoding a CALCR predicted loss-of-function polypeptide in a biological sample obtained from the subject; wherein: when the subject is CALCR reference, the subject does not have an increased risk of developing obesity and/or increased BMI; and when the subject is heterozygous or homozygous for a CALCR variant nucleic acid molecule, then the subject has an increased risk of developing obesity and/or increased BMI.

The present disclosure also provides therapeutic agents that treat or inhibit obesity and/or increased BMI for use in the treatment of obesity and/or increased BMI in a subject having: a CALCR variant genomic nucleic acid molecule encoding a CALCR predicted loss-of-function polypeptide; a CALCR variant mRNA molecule encoding a CALCR predicted loss-of-function polypeptide; or a CALCR variant cDNA molecule encoding a CALCR predicted loss-of-function polypeptide.

DESCRIPTION

Figure 1:
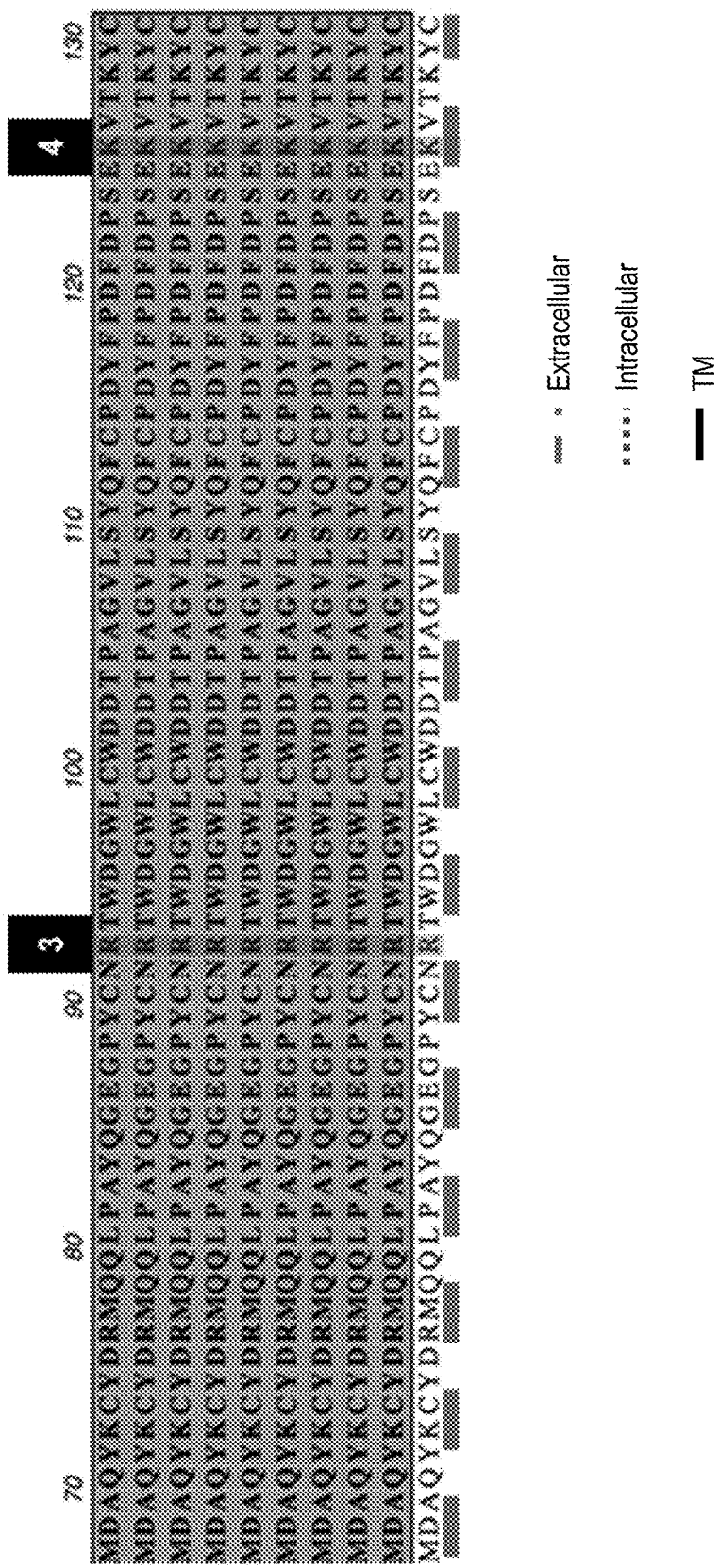
FIG. 1 shows positions of CALCR variants associated with BMI ($p<0.05$) relative to structural domains of the CALCR protein; pink vertical lines indicate variants associated with higher BMI; blue vertical lines indicate variants associated with lower BMI; variants indicated in the black boxes are: 1) S18P, 2) V62I, 3) R92C, 4) K125fs, 5) I178V, 6) S209N, 7) R355Q, 8) F390V, 9) V392I, 10) A422V, 11) R432C, 12) S456F, 13) R461fs, 14) L481P, and 15) N487fs; the amino acid sequences shown are several isoforms of proteins resulting from human CALCR splice variants including, top to bottom, *H. sapiens* NCBI NP_001158209.2 (SEQ ID NO: 31), *H. sapiens* NCBI NP_001158210.1 (Equ. P30988-2) (SEQ ID NO: 32), *H. sapiens* NCBI NP001733.1 (Equ. P30988-2) (SEQ ID NO: 33), *H. sapiens* Uniprot P30988-1 (SEQ ID NO: 34), *H. sapiens* Uniprot P30988-2 (SEQ ID NO: 35), *H. sapiens* Uniprot P30988-3 (SEQ ID NO: 36), *H. sapiens* Uniprot P30988-4 (SEQ ID NO: 37), *H. sapiens* Uniprot P30988-5 (SEQ ID NO: 38), and *H. sapiens* Uniprot P30988-6 (SEQ ID NO: 39); the black underlined portions represent transmembrane domains, the green underlined portions represent the extracellular domain, and the red underlined portions represent the intracellular domain.
Figure 1:
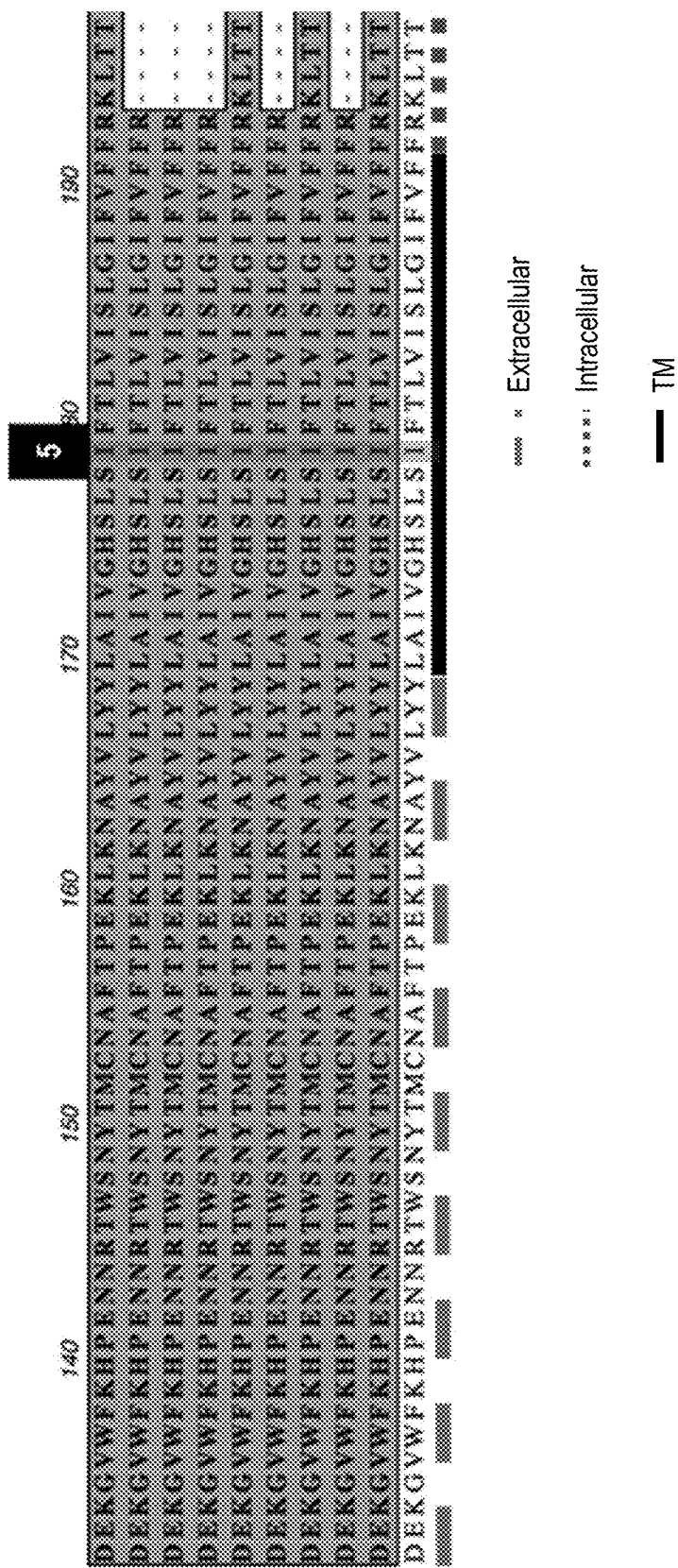
Figure 1:
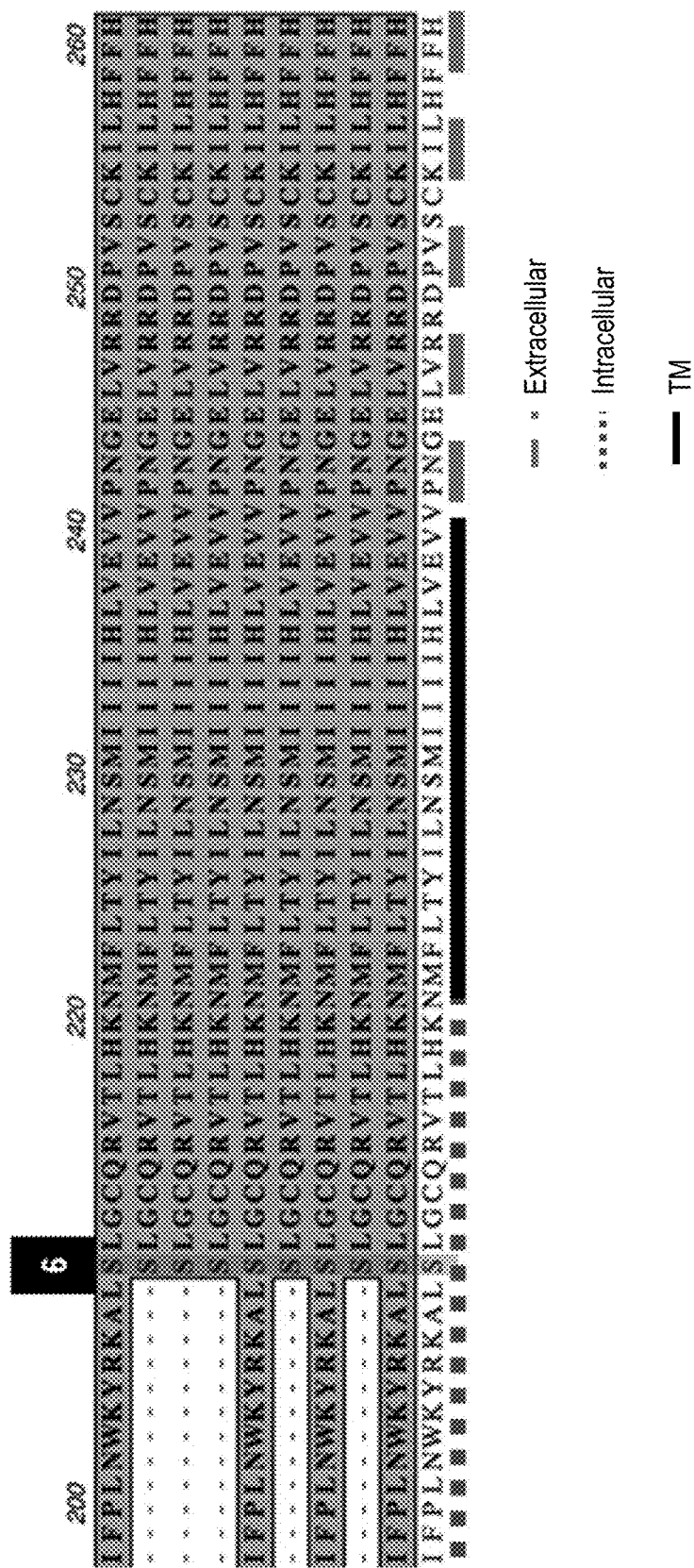
Figure 1:
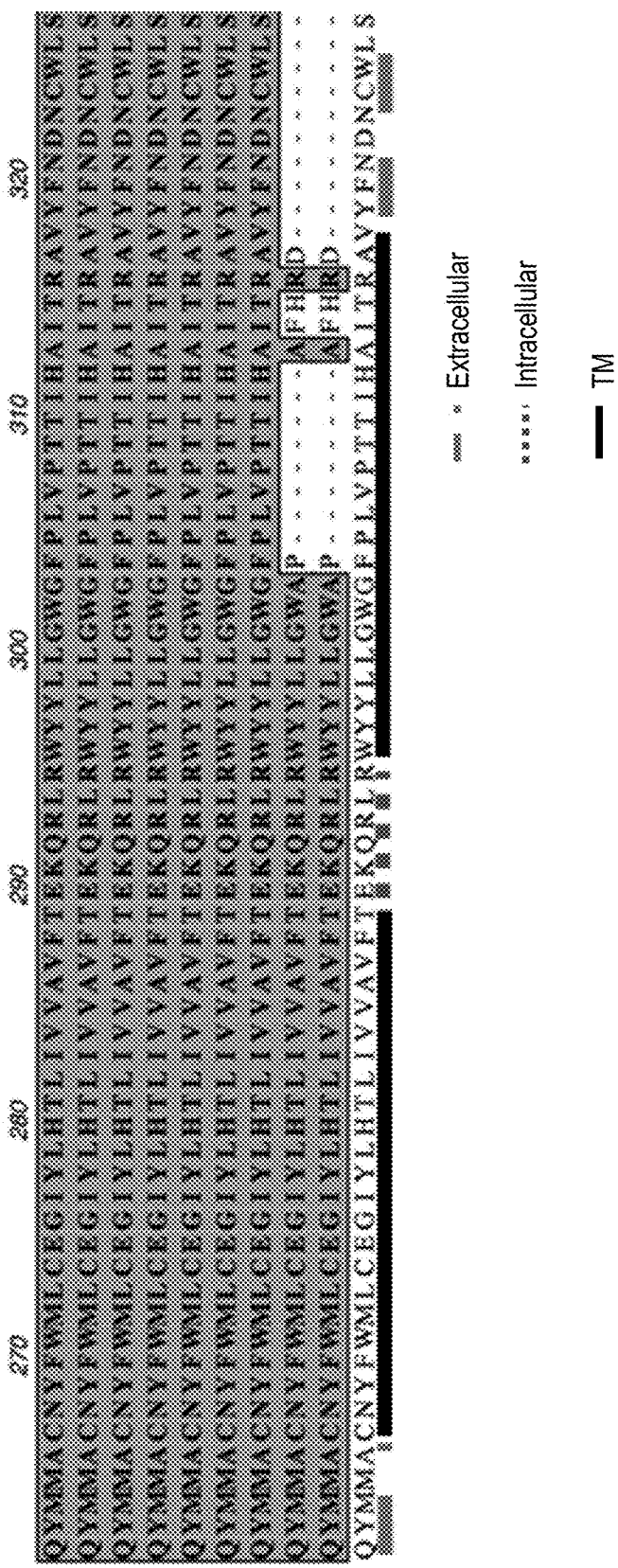
Figure 1:
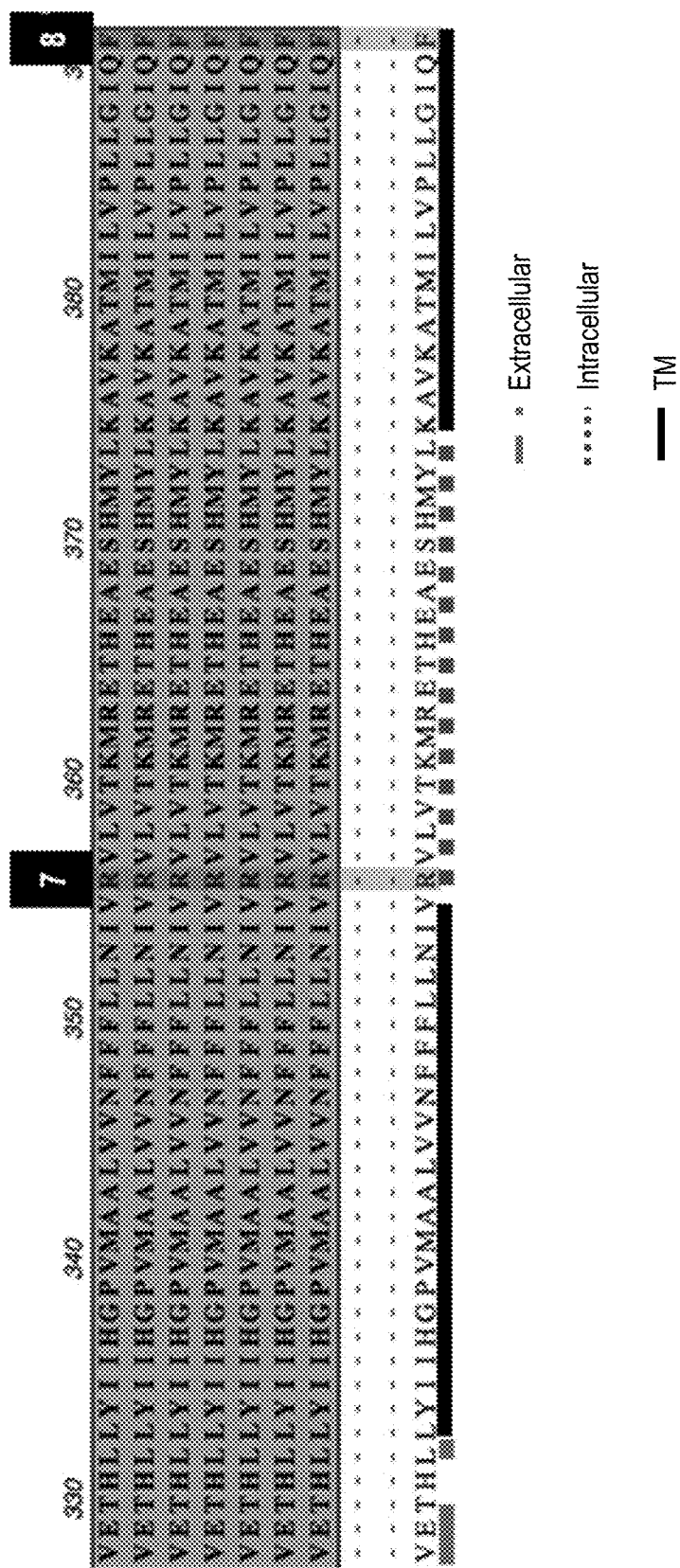
Figure 1:
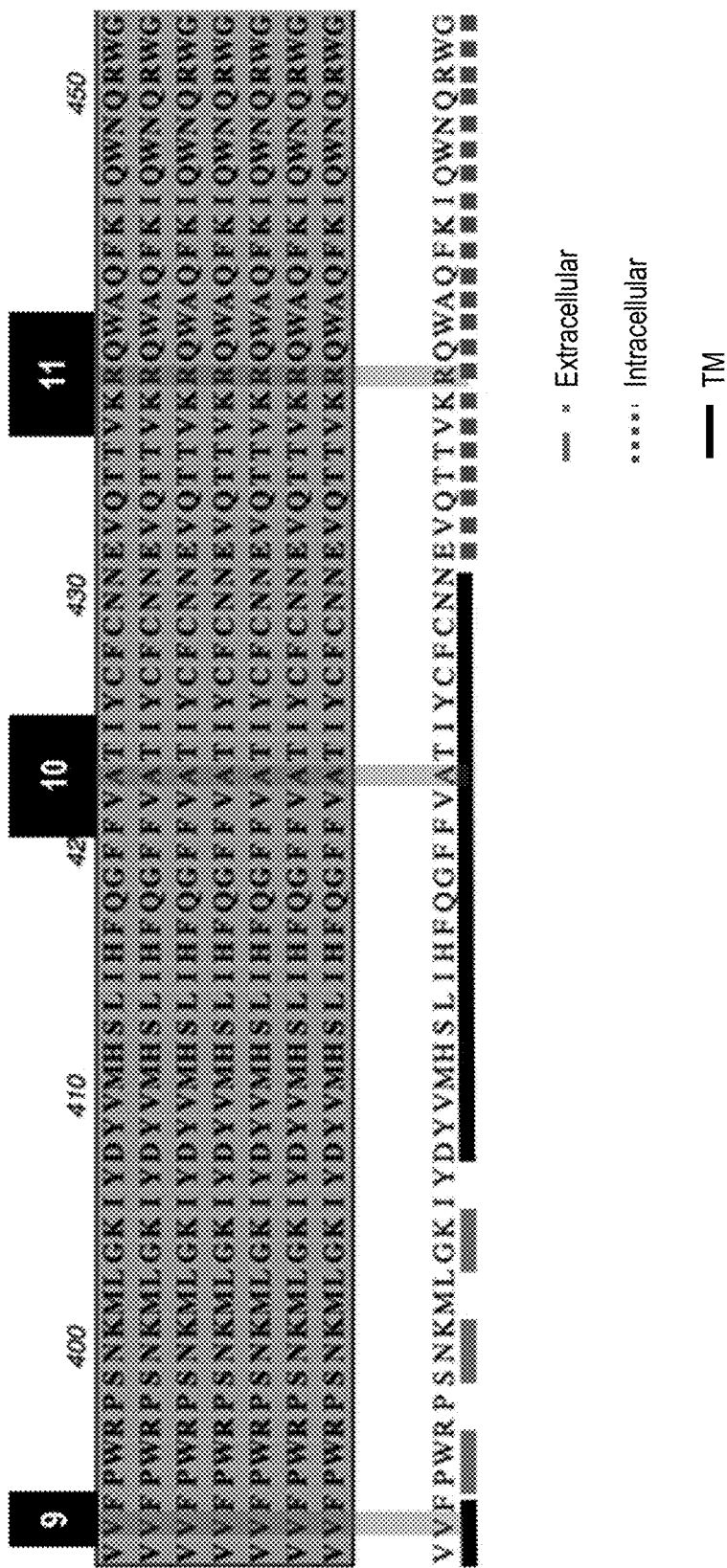
Figure 1:
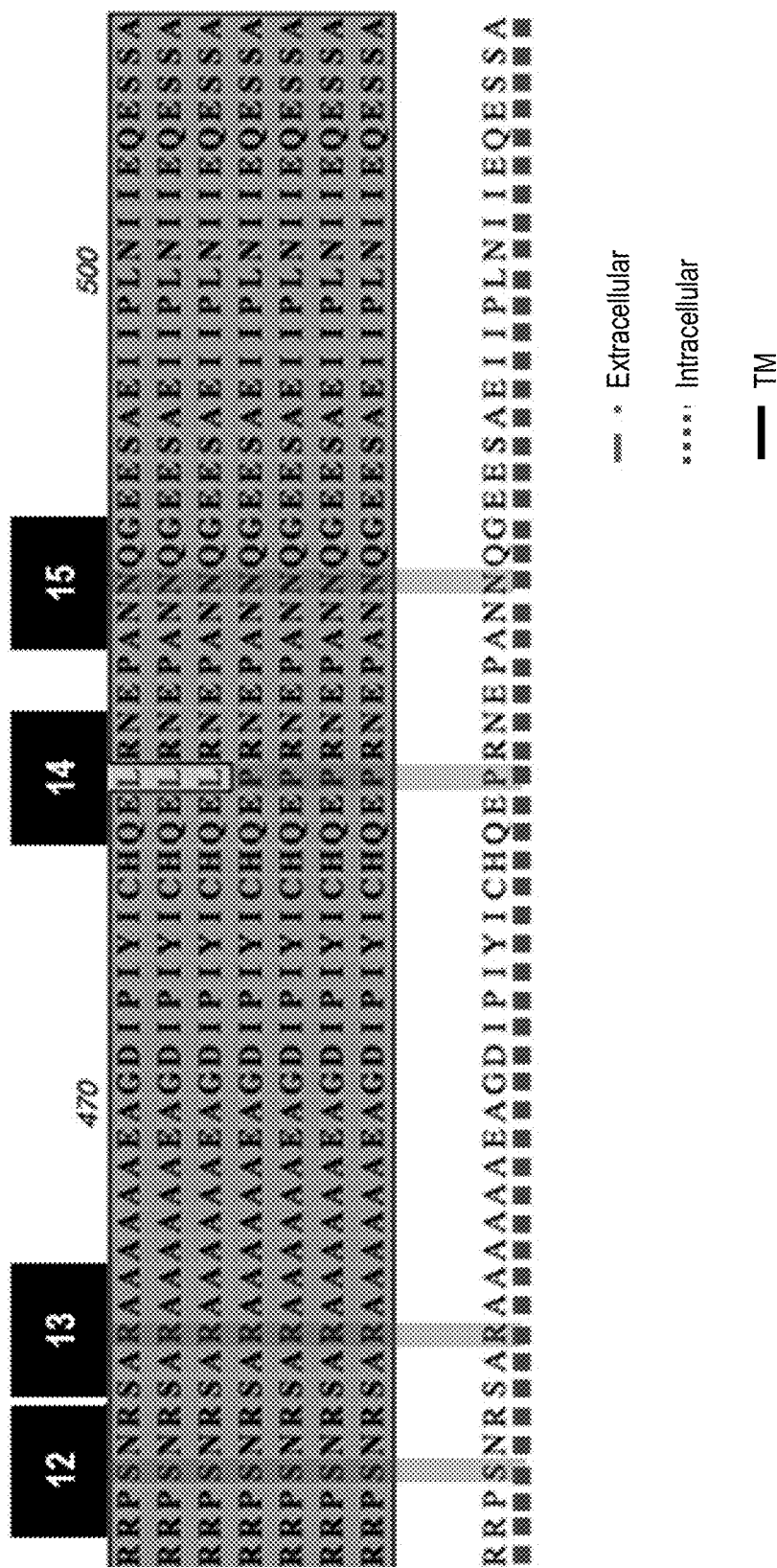

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

It has been observed in accordance with the present disclosure that a gene burden of CALCR variant nucleic acid molecules (whether these variations are homozygous or heterozygous in a particular subject) encoding CALCR loss-of-function polypeptides is associated with an increased risk of developing obesity and/or elevated BMI. It is believed that loss-of-function variants in the CALCR gene or protein have not been associated with obesity or elevated BMI in genome-wide or exome-wide association studies. Therefore, subjects that are homozygous or heterozygous for a CALCR variant nucleic acid molecule encoding a CALCR predicted loss-of-function polypeptide that associate with obesity and/or elevated BMI may be treated such that obesity and/or elevated BMI is inhibited, the symptoms thereof are reduced, and/or development of symptoms is repressed. It is also believed that such subjects having obesity and/or elevated BMI may be treated with therapeutic agents that treat or inhibit obesity and/or increased BMI.

For purposes of the present disclosure, any particular subject, such as a human, can be categorized as having one of three CALCR genotypes: i) CALCR reference; ii) heterozygous for a CALCR variant nucleic acid molecule encoding a CALCR predicted loss-of-function polypeptide; or iii) homozygous for a CALCR variant nucleic acid molecule encoding a CALCR predicted loss-of-function polypeptide. A subject is CALCR reference when the subject does not have a copy of a CALCR variant nucleic acid molecule encoding a CALCR predicted loss-of-function polypeptide. A subject is heterozygous for a CALCR variant nucleic acid molecule encoding a CALCR predicted loss-of-function polypeptide when the subject has a single copy of a CALCR variant nucleic acid molecule encoding a CALCR predicted loss-of-function polypeptide. A CALCR variant nucleic acid molecule is any nucleic acid molecule (such as, a genomic nucleic acid molecule, an mRNA molecule, or a cDNA molecule) encoding a CALCR polypeptide having a partial loss-of-function, a complete loss-of-function, a predicted partial loss-of-function, or a predicted complete loss-of-function. A subject who has a CALCR polypeptide having a partial loss-of-function (or predicted partial loss-of-function) is hypomorphic for CALCR. A subject is homozygous for a CALCR variant nucleic acid molecule encoding a CALCR predicted loss-of-function polypeptide when the subject has two copies (same or different) of a CALCR variant nucleic acid molecule encoding a CALCR predicted loss-of-function polypeptide.

For subjects that are genotyped or determined to be heterozygous or homozygous for a CALCR variant nucleic acid molecule encoding a CALCR predicted loss-of-function polypeptide, such subjects have an increased risk of developing obesity, such as increased BMI, type 1 obesity, type 2 obesity, or type 3 obesity, or have an increased risk of developing increased BMI. For subjects that are genotyped or determined to be heterozygous or homozygous for a CALCR variant nucleic acid molecule encoding a CALCR predicted loss-of-function polypeptide, such subjects can be treated with an agent effective to treat obesity, such as increased BMI, type 1 obesity, type 2 obesity, or type 3 obesity, and/or with an agent effective to treat increased BMI.

In any of the embodiments described herein, the CALCR variant nucleic acid molecule can be any nucleic acid molecule (such as, for example, genomic nucleic acid molecule, mRNA molecule, or cDNA molecule) encoding a CALCR polypeptide having a partial loss-of-function, a complete loss-of-function, a predicted partial loss-of-function, or a predicted complete loss-of-function. In some embodiments, the CALCR variant nucleic acid molecule is associated with a reduced in vitro response to calcitonin, amylin, GCRP, adrenomedullin, or other ligand of CALCR compared with reference CALCR. In some embodiments, the CALCR variant nucleic acid molecule is a CALCR nucleic acid molecule that results or is predicted to result in a premature truncation of a CALCR polypeptide compared to the human reference genome sequence. In some embodiments, the CALCR variant nucleic acid molecule is a variant that is predicted to be damaging by in vitro prediction algorithms such as Polyphen, SIFT, or similar algorithms. In some embodiments, the CALCR variant nucleic acid molecule is a variant that causes or is predicted to cause a nonsynonymous amino-acid substitution in a CALCR polypeptide and whose allele frequency is less than 1/1,000 alleles in the population from which the subject is selected. In some embodiments, the CALCR variant nucleic acid molecule is any rare missense variant (allele frequency <0.1%; or 1 in 1,000 alleles), or any splice-site, stop-gain, start-loss, stop-loss, frameshift, or in-frame indel, or other frameshift CALCR variant. In some embodiments, the subject has one or two of the following CALCR variant nucleic acid molecules: 7:93426412:C:A, 7:93426422:GT:G, 7:93426434:AT:A, 7:93426501:CG:C, 7:93426512:G:GT, 7:93426517:A:AG, 7:93426559:G:A, 7:93426561:G:GC, 7:93426564:C:T, 7:93434252:C:T, 7:93434288:AG:A, 7:93434289:G:GA, 7:93436171:C:A, 7:93436171:C:T, 7:93436171:CTGCAAATATACGG:C, 7:93438056:TCAC: T, 7:93438059:C:G, 7:93438209:C:T, 7:93443603:C:A, 7:93443607:AGCCCAAGAGATAATACC:A, 7:93443648: AAC:A, 7:93443743:AATCTT:A, 7:93443758:C:T, 7:93460832:G:A, 7:93460949:T:C, 7:93462060:T:TA, 7:93462112:T:C, 7:93468789:G:T, 7:93472373:A:G, 7:93472384:C:CT, 7:93472420:C:T, 7:93472428:G:A, 7:93472446:T:TA, 7:93472483:CT:C, 7:93477556:A:C, 7:93477557:C:A, 7:93477628:CCAGCA:C, 7:93477660: AAT:A, 7:93479387:G:A, 7:93479426:G:A, 7:93479450:T: TG, 7:93486979:CATTTTTG:C, 7:93487001:CTT:C, 7:93487008:C:T, 7:93495902:G:T, 7:93495903:C:T, 7:93495930:A:G, 7:93495976:T:A, or 7:93495976:T:C.

In some embodiments, the subject has one or two of the following CALCR variant nucleic acid molecules: 7:93426422:GT:G, 7:93426441:A:G, 7:93426501:CG:C, 7:93426516:G:A, 7:93426571:G:A, 7:93434281:G:A, 7:93436029:C:T, 7:93436035:A:C, 7:93436139:C:T, 7:93460945:C:T, 7:93468758:T:C, 7:93472483:CT:C, 7:93477654:G:A, 7:93479432:C:T, or 7:93486987:A:G. All variants are associated with increased BMI except 7:93426441:A:G and 7:93479432:C:T, which are associated with decreased BMI.

In some embodiments, the subject has one or two of the following variant CALCR polypeptides: S18P, V62I, R92C, K125fs, I178V, S209N, R355Q, F390V, V392I, A422V, R432C, S456F, R461fs, L481P, or N487fs. All variants are associated with increased BMI except V62I and L481P, which are associated with decreased BMI. Numerous human CALCR splice variants lead to several isoforms of proteins, which can be designated by, for example: *H. sapiens* NCBI NP_001158209.2, *H. sapiens* NCBI NP_001158210.1 (Equ. P30988-2), *H. sapiens* NCBI NP_001733.1 (Equ. P30988-2), *H. sapiens* Uniprot P30988-1, *H. sapiens* Uniprot P30988-2, *H. sapiens* Uniprot P30988-3, *H. sapiens* Uniprot P30988-4, *H. sapiens* Uniprot P30988-5, and *H. sapiens* Uniprot P30988-6.

In some embodiments, the subject has one or two of the following CALCR variant nucleic acid molecules: 7:93426364:A:G, 7:93426378:A:G, 7:93426384:T:G, 7:93426385:T:A, 7:93426398:C:G, 7:93426408:T:C, 7:93426412:C:A, 7:93426412:C:T, 7:93426412:C:G, 7:93426414:C:T, 7:93426422:GT:G, 7:93426434:AT:A, 7:93426451:G:A, 7:93426456:A:G, 7:93426469:T:A, 7:93426475:C:A, 7:93426481:C:A, 7:93426490:C:T, 7:93426496:C:A, 7:93426501:CG:C, 7:93426501:C:T, 7:93426502:G:A, 7:93426505:C:G, 7:93426511:G:T, 7:93426511:G:C, 7:93426511:G:A, 7:93426512:G:GT, 7:93426517:A:AG, 7:93426526:T:TC, 7:93426528:C:T, 7:93426530:C:G, 7:93426531:C:G, 7:93426534:C:T, 7:93426534:C:G, 7:93426535:G:C, 7:93426538:G:T, 7:93426543:C:T, 7:93426545:C:G, 7:93426546:T:C, 7:93426561:G:GC, 7:93426563:C:G, 7:93426564:C:T, 7:93426565:A:G, 7:93426571:G:A, 7:93426572:C:A, 7:93426577:C:T, 7:93426585:T:C, 7:93426589:C:T, 7:93434252:C:T, 7:93434261:T:G, 7:93434262:G:C, 7:93434267:A:G, 7:93434269:C:G, 7:93434272:T:A, 7:93434281:G:A, 7:93434285:C:T, 7:93434287:A:G, 7:93434288:AG:A, 7:93434289:GA:G, 7:93435951:C:T, 7:93435971:T:C, 7:93435971:T:A, 7:93435978:C:T, 7:93435980:T:C, 7:93435983:T:A, 7:93435987:A:G, 7:93435988:T:C, 7:93436007:T:C, 7:93436011:A:G, 7:93436023:G:C, 7:93436029:C:T, 7:93436035:A:C, 7:93436059:G:A, 7:93436062:T:C, 7:93436065:T:C, 7:93436091:A:G, 7:93436091:A:C, 7:93436103:G:A, 7:93436103:G:T, 7:93436139:C:G, 7:93436139:C:T, 7:93436140:G:A, 7:93436142:A:T, 7:93436151:A:G, 7:93436166:T:C, 7:93436169:A:G, 7:93436171:C:A, 7:93438056:TCAC:T, 7:93438059:C:G, 7:93438070:G:A, 7:93438070:G:T, 7:93438072:C:A, 7:93438073:A:G, 7:93438074:T:C, 7:93438077:C:G, 7:93438080:G:T, 7:93438080:G:A, 7:93438103:T:C, 7:93438106:G:A, 7:93438115:C:T, 7:93438116:T:C, 7:93438125:A:G, 7:93438127:C:T, 7:93438209:C:T, 7:93438226:C:T, 7:93438229:C:T, 7:93438238:T:G, 7:93438243:T:A, 7:93438247:T:A, 7:93438247:T:C, 7:93438252:G:A, 7:93438256:G:T, 7:93438264:G:A, 7:93438266:G:C, 7:93438270:C:A, 7:93443603:C:A, 7:93443605:C:G, 7:93443607:AGCCCAAGAGATAATACC:A, 7:93443611: CAA:C, 7:93443618:T:C, 7:93443621:T:C, 7:93443623:C: T, 7:93443624:C:A, 7:93443625:A:G, 7:93443628:G:A, 7:93443634:G:A, 7:93443637:G:C, 7:93443642:T:C, 7:93443648:AAC:A, 7:93443652:C:T, 7:93443658:C:T, 7:93443678:T:C, 7:93443681:A:T, 7:93443682:T:G, 7:93443694:G:A, 7:93443696:A:G, 7:93443703:A:G, 7:93443705:T:C, 7:93443708:T:G, 7:93443711:C:G, 7:93443718:T:C, 7:93443719:C:G, 7:93443727:G:C, 7:93443727:G:T, 7:93443729:T:A, 7:93443733:A:G, 7:93443739:G:C, 7:93443739:G:T, 7:93443743:AATCTT: A, 7:93443746:C:G, 7:93443746:C:A, 7:93443758:C:T, 7:93460819:AC:A, 7:93460822:G:A, 7:93460822:G:T, 7:93460826:C:A, 7:93460831:C:A, 7:93460832:G:A, 7:93460835:C:G, 7:93460835:C:T, 7:93460838:G:A, 7:93460842:TC:T, 7:93460845:A:C, 7:93460855:A:C, 7:93460856:C:T, 7:93460856:C:A, 7:93460867:T:C, 7:93460888:T:C, 7:93460891:A:G, 7:93460900:G:T, 7:93460909:A:G, 7:93460919:G:A, 7:93460924:GT:G, 7:93460924:G:T, 7:93460924:G:C, 7:93460931:T:C, 7:93460936:C:T, 7:93460943:G:A, 7:93460945:C:T, 7:93460949:T:A, 7:93460949:T:C, 7:93462060:T:TA, 7:93462062:C:T, 7:93462066:G:A, 7:93462066:G:T, 7:93462067:C:A, 7:93462086:C:G, 7:93462087:A:G, 7:93462090:G:T, 7:93462090:G:A, 7:93462091:GA:G, 7:93462091:G:A, 7:93462097:T:A, 7:93462102:G:T, 7:93462103:T:C, 7:93462104:C:G, 7:93462112:T:C, 7:93468714:C:A, 7:93468717:G:C, 7:93468722:A:C, 7:93468731:TC:T, 7:93468753:G:T, 7:93468758:T:C, 7:93468759:TG:T, 7:93468762:C:T, 7:93468764:A:G, 7:93468769:T:C, 7:93468770:G:GACCCACA, 7:93468772:C:G, 7:93468775:A:G, 7:93468781:G:C, 7:93468787:T:G, 7:93468789:G:T, 7:93468799:T:C, 7:93472374:C:T, 7:93472377:T:C, 7:93472379:A:G, 7:93472381:T:A, 7:93472383:T:C, 7:93472384:C:CT, 7:93472392:T:G, 7:93472400:T:C, 7:93472401:T:G, 7:93472402:G:T, 7:93472412:T:C, 7:93472418:G:T, 7:93472418:GA:G, 7:93472418:G:C, 7:93472424:G:T, 7:93472427:C:T, 7:93472428:G:A, 7:93472432:G:C, 7:93472437:C:T, 7:93472446:T:TA, 7:93472456:AC:A, 7:93472470:A:G, 7:93472473:A:G, 7:93472479:TA:T, 7:93472482:C:T, 7:93472483:CT:C, 7:93472486:T:G, 7:93472488:C:T, 7:93472489:T:C, 7:93477556:A:C, 7:93477557:C:G, 7:93477567:CA:C, 7:93477575:G:A, 7:93477584:T:C, 7:93477587:G:T, 7:93477595:C:A, 7:93477602:G:A, 7:93477602:G:T, 7:93477611:C:A, 7:93477612:C:G, 7:93477617:G:A, 7:93477617:G:T, 7:93477617:G:C, 7:93477620:G:A, 7:93477622:G:C, 7:93477622:G:T, 7:93477623:T:C, 7:93477628:CCAGCA: C, 7:93477633:A:C, 7:93477633:A:G, 7:93477638:C:G, 7:93477639:A:G, 7:93477644:T:C, 7:93477650:G:A, 7:93477650:G:T, 7:93477653:C:T, 7:93477654:G:A, 7:93477656:T:C, 7:93477660:A:G, 7:93477661:A:T, 7:93477668:C:A, 7:93479372:G:A, 7:93479381:G:A, 7:93479383:A:T, 7:93479386:C:T, 7:93479386:C:G, 7:93479387:G:A, 7:93479393:A:T, 7:93479410:T:C, 7:93479413:A:G, 7:93479422:T:C, 7:93479425:C:T, 7:93479426:G:A, 7:93479450:T:TG, 7:93479453:G:T, 7:93479470:G:T, 7:93486934:TAG:T, 7:93486957:A:T, 7:93486979:CATTTTTG:C, 7:93486986:G:A, 7:93486986: G:T, 7:93486995:A:G, 7:93487005:G:T, 7:93487007:C:T, 7:93487008:C:T, 7:93495902:G:A, 7:93495902:G:T, 7:93495903:C:T, 7:93495929:C:T, 7:93495930:A:G, 7:93495976:T:A, 7:93495976:T:C, 7:93426360:G:T, 7:93426391:G:T, 7:93426393:A:T, 7:93426399:T:C, 7:93426433:C:G, 7:93426459:T:A, 7:93426465:G:C, 7:93426483:G:A, 7:93426492:G:T, 7:93426493:C:T, 7:93426519:G:T, 7:93426535:G:T, 7:93426559:G:A, 7:93426570:C:T, 7:93426582:G:T, 7:93435953:T:A, 7:93436006:G:T, 7:93436032:C:G, 7:93436068:T:A, 7:93436113:T:A, 7:93436127:G:A, 7:93438085:T:C, 7:93438095:A:C, 7:93438101:A:T, 7:93438109:T:A, 7:93438112:A:G, 7:93438124:C:T, 7:93438255:G:A, 7:93438259:C:T, 7:93443622:A:G, 7:93443624:C:G, 7:93443657:A:G, 7:93443682:T:A, 7:93443720:A:G, 7:93443734:A:T, 7:93443753:C:G, 7:93460846:T:C, 7:93460906:A:G, 7:93460918:T:C, 7:93460929:C:A, 7:93460930:C:T, 7:93460933:T:C, 7:93460939:C:T, 7:93462086:CA:C, 7:93468759:T:C, 7:93468769:T:G, 7:93468781:G:A, 7:93468787:T:C, 7:93472373:A:G, 7:93472397:G:C, 7:93472415:T:C, 7:93472420:C:T, 7:93472458:C:A, 7:93472472:T:C, 7:93472482:C:A, 7:93477557:C:A, 7:93477566:T:A, 7:93477590:C:T, 7:93477623:T:G, 7:93477626:T:G, 7:93477632:C:A, 7:93477637:C:G, 7:93477644:T:A, 7:93477654:G:C, 7:93477662:T:C, 7:93479371:G:A, 7:93479404:T:C, 7:93479426:G:C, 7:93479456:C:T, 7:93486944:A:G, 7:93487001:CTT:C, 7:93487005:G:A, 7:93495910:T:A, 7:93426376:C:T, 7:93426588:A:C, 7:93434289:G:GA, 7:93435991:C:A, 7:93436005:T:C, 7:93436053:G:A, 7:93436079:G:A, 7:93436110:G:A, 7:93436171: CTGCAAATATACGG:C, 7:93436171:C:T, 7:93438089:T: C, 7:93438092:T:C, 7:93443643:C:T, 7:93443666:A:C, 7:93443750:C:T, 7:93460835:C:A, 7:93460897:T:C, 7:93468782:C:T, 7:93472424:G:A, 7:93472463:T:C, 7:93477599:T:C, 7:93477653:C:A, or 7:93477660:AAT:A.

In any of the embodiments described herein, the CALCR variant nucleic acid molecules have variations at the indicated positions of chromosome 7 using the nucleotide sequence of the CALCR reference genomic nucleic acid molecule (SEQ ID NO:1; ENST00000426151.6 encompassing chr7:93,424,539-93,574,730 in the GRCh38/hg38 human genome assembly; ENSG00000004948.15) as a reference sequence. An additional sequence (ENST00000360249.8 encompassing chr7:93,426,310-93,487,013 in GRCh38/hg38 human genome assembly; ENSG00000004948.15) can also be used as the CALCR reference sequence.

In any of the embodiments described herein, the CALCR variant nucleic acid molecules encoding variations in the protein sequence can include nucleotides at the indicated positions of chromosome 7 using the nucleotide sequence of the CALCR reference genomic nucleic acid molecule (SEQ ID NO:1; ENST00000426151.6 encompassing chr7:93,424,539-93,574,730 in the GRCh38/hg38 human genome assembly; ENSG00000004948.15) as a reference sequence.

Any one or more (i.e., any combination) of the CALCR variants recited herein can be used within any of the methods described herein to determine whether a subject has an increased risk of developing obesity and/or increased BMI. The combinations of particular variants can form a mask used for statistical analysis of the particular correlation of CALCR and increased obesity/BMI risk.

In any of the embodiments described herein, the CALCR predicted loss-of-function polypeptide can be any CALCR polypeptide having a partial loss-of-function, a complete loss-of-function, a predicted partial loss-of-function, or a predicted complete loss-of-function.

In any of the embodiments described herein, the obesity is type 1 obesity, type 2 obesity, or type 3 obesity. In any of the embodiments described herein, the obesity is type 1 obesity. In any of the embodiments described herein, the obesity is type 2 obesity. In any of the embodiments described herein, the obesity is type 3 obesity. In any of the embodiments described herein, the subject has increased BMI.

Symptoms of obesity include, but are not limited to, excess body fat accumulation (particularly around the waist), breathlessness, increased sweating, snoring, inability to cope with sudden physical activity, feeling very tired every day, back and joint pains, skin problems (from moisture accumulating in the folds of skin).

The present disclosure provides methods of treating a subject with a therapeutic agent that treats or inhibits obesity and/or reduces BMI. In these methods, the subject has obesity and/or increased BMI. The methods comprise the steps of determining whether the subject has a CALCR variant nucleic acid molecule encoding a CALCR predicted loss-of-function polypeptide. In these methods, such determination step comprises obtaining or having obtained a biological sample from the subject. In these methods, such determination step also comprises performing or having performed a sequence analysis on the biological sample to determine if the subject has a genotype comprising the CALCR variant nucleic acid molecule. When the subject is CALCR reference, then the methods further comprise administering or continuing to administer to the subject the therapeutic agent that treats or inhibits obesity and/or increased BMI in a standard dosage amount. When the subject is heterozygous or homozygous for the CALCR variant nucleic acid molecule encoding a CALCR predicted loss-of-function polypeptide, then the methods further comprise administering or continuing to administer to the subject the therapeutic agent that treats or inhibits obesity and/or increased BMI in an amount that is the same as or greater than a standard dosage amount. The presence of a genotype having the CALCR variant nucleic acid molecule indicates the subject has an increased risk of developing obesity and/or increased BMI.

In some embodiments, the subject has obesity. In some embodiments, the subject has increased BMI. In some embodiments, the subject is CALCR reference. In some embodiments, the subject is heterozygous for a CALCR variant nucleic acid molecule encoding a CALCR predicted loss-of-function polypeptide. In some embodiments, the subject is homozygous for a CALCR variant nucleic acid molecule encoding a CALCR predicted loss-of-function polypeptide.

In some embodiments, the methods of treatment further comprise detecting the presence or absence of a CALCR variant nucleic acid molecule encoding a CALCR predicted loss-of-function polypeptide in a biological sample from the subject. As used throughout the present disclosure, a "CALCR variant nucleic acid molecule" is any nucleic acid molecule (such as, for example, genomic nucleic acid molecule, mRNA molecule, or cDNA molecule) encoding a CALCR polypeptide having a partial loss-of-function, a complete loss-of-function, a predicted partial loss-of-function, or a predicted complete loss-of-function. In some embodiments, the CALCR variant nucleic acid molecule is associated with a reduced in vitro response to calcitonin, amylin, GCRP, adrenomedullin, or other ligand of CALCR compared with reference CALCR. In some embodiments, the CALCR variant nucleic acid molecule results or is predicted to result in a premature truncation of a CALCR polypeptide compared to the human reference genome sequence. In some embodiments, the CALCR variant nucleic acid molecule is a variant that is predicted to be damaging by in vitro prediction algorithms such as Polyphen, SIFT, or similar algorithms. In some embodiments, the CALCR variant nucleic acid molecule is a variant that causes or is predicted to cause a nonsynonymous amino-acid substitution in CALCR and whose allele frequency is less than 1/1,000 alleles in the population from which the subject is selected. In some embodiments, the CALCR variant nucleic acid molecule is any rare missense variant (allele frequency <0.1%; or 1 in 1,000 alleles), or any splice-site, stop-gain, start-loss, stop-loss, frameshift, or in-frame indel, or other frameshift CALCR variant.

Detecting the presence or absence of a CALCR variant nucleic acid molecule encoding a CALCR predicted loss-of-function polypeptide in a biological sample from a subject and/or determining whether a subject has a CALCR variant nucleic acid molecule encoding a CALCR predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The present disclosure also provides methods of treating a subject with a therapeutic agent that treats or inhibits obesity and/or increased BMI, wherein the subject has obesity and/or increased BMI. In some embodiments, the methods comprise determining whether the subject has a predicted loss-of-function CALCR polypeptide by obtaining or having obtained a biological sample from the subject, and performing or having performed an assay on the biological sample to determine if the subject has a CALCR predicted loss-of-function polypeptide. When the subject does not have a CALCR predicted loss-of-function polypeptide, the therapeutic agent that treats or inhibits obesity and/or increased BMI is administered or continued to be administered to the subject in a standard dosage amount. When the subject has a CALCR predicted loss-of-function polypeptide, the therapeutic agent that treats or inhibits obesity and/or increased BMI is administered or continued to be administered to the subject in an amount that is the same as or greater than a standard dosage amount. The presence of a CALCR predicted loss-of-function polypeptide indicates the subject has an increased risk of developing obesity and/or increased BMI. In some embodiments, the subject has a CALCR predicted loss-of-function polypeptide. In some embodiments, the subject does not have a CALCR predicted loss-of-function polypeptide.

Detecting the presence or absence of a CALCR predicted loss-of-function polypeptide in a biological sample from a subject and/or determining whether a subject has a CALCR predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit obesity and/or increased BMI also include, but are not limited to, sibutramine, orlistat, phentermine, topiramate, lorcaserin, bupropion, Contrave® (naltrexone), Saxenda® (liraglutide), phentermine, diethylpropion, bupropion, metformin, Symlin® (pramlintide), topiramate, zonisamide, Ozempic® (semaglutide), Tirzepatide® (LY3298176), miacalcin, amylin, Myalept® (metreleptin), Qsymia® (phentermine-topiramate), Byetta® (exenatide), Trulicity® (dulaglutide), AM833, davalintide, KBP-088, GCRP, adrenomedullin, leptin, PYY, cholecystokinin, PYY1875, LA-GDF15, PF-06882961, PF-07081532, cotadutide (MED10382), efinopegdutide (HM12525A), pegbelfermin, BIO89-100, efruxifermin, YH-25724, BFKB-8488A, NGM-313, NGM-282, lanifibranor, aldafermin, resmetirom, seladelpar, Ocaliva® (obeticholic acid), AMG 171, NN9215, JNJ-9090, NGM395, NGM120, AV-380, efpeglenatide, AKR-001, Aldafermin (NGM282), RG7992 (BFKB-8488A), BIO89-100, LLF-580, NGM-313, NN-9500, TSLB-1344, YH-25724, LY2405319, PF-05231023, Fc-FGF21(RGE), BMS-986036, TBRIA® (calcitonin), or oxyntomodulin, or any combination thereof. In some embodiments, the therapeutic agent that treats or inhibits obesity and/or increased BMI is sibutramine, orlistat, phentermine, topiramate, lorcaserin, bupropion, naltrexone, liraglutide, phentermine, diethylpropion, bupropion, metformin, pramlintide, topiramate, zonisamide, semaglutide, LY3298176, miacalcin, amylin, metreleptin, phentermine-topiramate, exenatide, dulaglutide, AM833, davalintide, KBP-088, GCRP, adrenomedullin, leptin, PYY, cholecystokinin, PYY1875, LA-GDF15, PF-06882961, PF-07081532, cotadutide (MED10382), efinopegdutide (HM12525A), pegbelfermin, BIO89-100, efruxifermin, YH-25724, BFKB-8488A, NGM-313, NGM-282, lanifibranor, aldafermin, resmetirom, seladelpar, obeticholic acid, AMG 171, NN9215, JNJ-9090, NGM395, NGM120, AV-380, efpeglenatide, AKR-001, Aldafermin (NGM282), RG7992 (BFKB-8488A), BIO89-100, LLF-580, NGM-313, NN-9500, TSLB-1344, YH-25724, LY2405319, PF-05231023, Fc-FGF21(RGE), BMS-986036, calcitonin, or oxyntomodulin, or any combination thereof.

In some embodiments, the therapeutic agent that treats or inhibits obesity and/or reduces BMI is a melanocortin 4 receptor (MC4R) agonist. In some embodiments, the MC4R agonist comprises a protein, a peptide, a nucleic acid molecule, or a small molecule. In some embodiments, the protein is a peptide analog of MC4R. In some embodiments, the peptide is setmelanotide. In some embodiments, the therapeutic agent that treats or inhibits obesity and/or reduces BMI is a combination of setmelanotide and one or more of sibutramine, orlistat, phentermine, lorcaserin, naltrexone, liraglutide, diethylpropion, bupropion, metformin, pramlintide, topiramate, and zonisamide. In some embodiments, the MC4R agonist is a peptide comprising the amino acid sequence His-Phe-Arg-Trp. In some embodiments, the small molecule is 1,2,3R,4-tetrahydroisoquinoline-3-carboxylic acid. In some embodiments, the MC4R agonist is ALB-127158(a).

In some embodiments, the therapeutic agent that treats or inhibits obesity and/or reduces BMI is a CALCR agonist. In some embodiments, the CALCR agonist is calcitonin, amylin, GCRP, adrenomedullin, Symlin® (pramlintide), miacalcin, AM833, davalintide, KBP-088, leptin, PYY, or cholecystokinin, or any combination thereof. In some embodiments, the CALCR agonist is calcitonin, amylin, GCRP, adrenomedullin, pramlintide, miacalcin, AM833, davalintide, KBP-088, leptin, PYY, or cholecystokinin, or any combination thereof. In some embodiments, the CALCR agonist is calcitonin or amylin. In some embodiments, the CALCR agonist is GCRP or adrenomedullin. In some embodiments, the CALCR agonist is a synthetic or non-synthetic CALCR agonist.

In some embodiments, the therapeutic agents that treat or inhibit obesity and/or increased BMI can be administered to subjects with obesity but without a CALCR variant nucleic acid molecule or CALCR predicted loss-of-function polypeptide. In such embodiments, a goal would be to exploit the CALCR-mediated anti-obesity properties in subjects with intact CALCR signaling. In some embodiments, the therapeutic agents that treat or inhibit obesity and/or increased BMI can be administered to subjects with obesity and having the CALCR variant nucleic acid molecule or CALCR predicted loss-of-function polypeptide. In such embodiments, a goal would be to enhance CALCR-mediated anti-obesity properties in subjects with a relative deficiency in CALCR signaling due to their genotype.

In some embodiments, the dose of the therapeutic agents that treat or inhibit obesity and/or increased BMI can be increased by about 10%, by about 20%, by about 30%, by about 40%, by about 50%, by about 60%, by about 70%, by about 80%, or by about 90% for patients or human subjects that are heterozygous or homozygous for a CALCR variant nucleic acid molecule encoding a CALCR predicted loss-of-function polypeptide (i.e., a greater amount than the standard dosage amount) compared to subjects that are CALCR reference (who may receive a standard dosage amount). In some embodiments, the dose of the therapeutic agents that treat or inhibit obesity and/or increased BMI can be increased by about 10%, by about 20%, by about 30%, by about 40%, or by about 50%. In addition, the dose of therapeutic agents that treat or inhibit obesity and/or increased BMI in subjects that are heterozygous or homozygous for a CALCR variant nucleic acid molecule encoding a CALCR predicted loss-of-function polypeptide can be administered more frequently compared to subjects that are CALCR reference.

In some embodiments, the dose of the therapeutic agents that treat or inhibit obesity and/or increased BMI can be increased by about 10%, by about 20%, by about 30%, by about 40%, by about 50%, by about 60%, by about 70%, by about 80%, or by about 90% for subjects that are homozygous for a CALCR variant nucleic acid molecule encoding a CALCR predicted loss-of-function polypeptide compared to subjects that are heterozygous for a CALCR variant nucleic acid molecule encoding a CALCR predicted loss-of-function polypeptide. In some embodiments, the dose of the therapeutic agents that treat or inhibit obesity and/or increased BMI can be increased by about 10%, by about 20%, by about 30%, by about 40%, or by about 50%. In addition, the dose of therapeutic agents that treat or inhibit obesity and/or increased BMI in subjects that are homozygous for a CALCR variant nucleic acid molecule encoding a CALCR predicted loss-of-function polypeptide can be administered more frequently compared to subjects that are heterozygous for a CALCR variant nucleic acid molecule encoding a CALCR predicted loss-of-function polypeptide.

Administration of the therapeutic agents that treat or inhibit obesity and/or increased BMI can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a patient can receive therapy for a prolonged period of time such as, for example, 6 months, 1 year, or more.

Administration of the therapeutic agents that treat or inhibit obesity and/or increased BMI can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in obesity and/or increased BMI, a decrease/reduction in the severity of obesity and/or increased BMI (such as, for example, a reduction or inhibition of development of obesity and/or increased BMI), a decrease/reduction in symptoms and obesity-related effects, delaying the onset of symptoms and obesity-related effects, reducing the severity of symptoms of obesity-related effects, reducing the number of symptoms and obesity-related effects, reducing the latency of symptoms and obesity-related effects, an amelioration of symptoms and obesity-related effects, reducing secondary symptoms, reducing secondary infections, preventing relapse to obesity and/or increased BMI, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of obesity development/progression (such as, for example, a complete or partial avoidance/inhibition or a delay), and an increased survival time of the affected host animal, following administration of a therapeutic protocol. Treatment of obesity and/or increased BMI encompasses the treatment of patients already diagnosed as having any form of obesity and/or increased BMI at any clinical stage or manifestation, the delay of the onset or evolution or aggravation or deterioration of the symptoms or signs of obesity and/or increased BMI, and/or preventing and/or reducing the severity of obesity and/or increased BMI.

The present disclosure also provides methods of identifying a subject having an increased risk of developing obesity and/or increased BMI. These methods comprise determining or having determined the presence or absence of a CALCR variant nucleic acid molecule encoding a CALCR predicted loss-of-function polypeptide in a biological sample obtained from the subject. When the subject is CALCR reference, the subject does not have an increased risk of developing obesity and/or increased BMI. When the subject is heterozygous or homozygous for a CALCR variant nucleic acid molecule encoding a CALCR predicted loss-of-function polypeptide, the subject has an increased risk of developing obesity and/or increased BMI.

In some embodiments, the subject has obesity. In some embodiments, the subject has increased BMI. In some embodiments, the subject is CALCR reference. In some embodiments, the subject is heterozygous for a CALCR variant nucleic acid molecule encoding a CALCR predicted loss-of-function polypeptide. In some embodiments, the subject is homozygous for a CALCR variant nucleic acid molecule encoding a CALCR predicted loss-of-function polypeptide.

Determining whether a subject has a CALCR variant nucleic acid molecule encoding a CALCR predicted loss-of-function polypeptide in a biological sample from a subject and/or determining whether a subject comprises a CALCR variant nucleic acid molecule encoding a CALCR predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing obesity and/or increased BMI, the subject is further treated with a therapeutic agent that treats or inhibits obesity and/or increased BMI, as described herein. In some embodiments, when the subject is heterozygous or homozygous for CALCR variant nucleic acid molecule encoding a CALCR predicted loss-of-function polypeptide, the subject is administered the therapeutic agent that treats or inhibits obesity and/or increased BMI in a dosage amount that is the same as or greater than a standard dosage amount. In some embodiments, when the subject is homozygous for a CALCR variant nucleic acid molecule encoding a CALCR predicted loss-of-function polypeptide, the subject is administered the therapeutic agent that treats or inhibits obesity and/or increased BMI in a dosage amount that is the same as or greater than the dosage amount administered to a subject that is heterozygous for a CALCR variant nucleic acid molecule encoding a CALCR predicted loss-of-function polypeptide. In some embodiments, the subject is CALCR reference. In some embodiments, the subject is heterozygous for a CALCR variant nucleic acid molecule encoding a CALCR predicted loss-of-function polypeptide. In some embodiments, the subject is homozygous for a CALCR variant nucleic acid molecule encoding a CALCR predicted loss-of-function polypeptide.

In some embodiments, the methods can further comprise determining the subject's gene burden of having CALCR variant nucleic acid molecule (genomic, mRNA, or cDNA) encoding a CALCR predicted loss-of-function polypeptide associated with an increased risk of developing obesity and/or increased BMI, and/or CALCR predicted loss-of-function polypeptides associated with an increased risk of developing obesity and/or increased BMI. The gene burden is the aggregate of all variants or rare variants in the CALCR gene, which can be carried out in an association analysis with obesity and/or increased BMI. In some embodiments, the subject is homozygous for one or more CALCR variant nucleic acid molecules encoding a CALCR predicted loss-of-function polypeptide associated with an increased risk of developing obesity and/or increased BMI. In some embodiments, the subject is heterozygous for one or more CALCR variant nucleic acid molecules encoding a CALCR predicted loss-of-function polypeptide associated with an increased risk of developing obesity and/or increased BMI. The result of the association analysis suggests that rare loss-of-function and missense variants of CALCR are associated with increased risk of obesity and increased BMI.

In some embodiments, the subject's gene burden of having any one or more CALCR variant nucleic acid molecules encoding a CALCR predicted loss-of-function polypeptide represents a weighted sum of a plurality of any of the CALCR variant nucleic acid molecules encoding a CALCR predicted loss-of-function polypeptide. In some embodiments, the gene burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the CALCR gene where the gene burden is the number of alleles multiplied by the association estimate with developing obesity and/or increased BMI or related outcome for each allele (e.g., a weighted burden score). This can include any genetic variants, regardless of their genomic annotation, in proximity to the CALCR gene (up to 10 Mb around the gene) that show a non-zero association with obesity- and/or increased BMI-related traits in a genetic association analysis. In some embodiments, when the subject has a gene burden above a desired threshold score, the subject has an increased risk of developing obesity and/or increased BMI. In some embodiments, when the subject has a gene burden below a desired threshold score, the subject has a decreased risk of developing obesity and/or increased BMI.

In some embodiments, the gene burden may be divided into quintiles, e.g., top quintile, intermediate quintile, and bottom quintile, wherein the top quintile of gene burden corresponds to the highest risk group and the bottom quintile of gene burden corresponds to the lowest risk group. In some embodiments, a subject having a greater gene burden comprises the highest weighted gene burdens, including, but not limited to the top 10%, top 20%, top 30%, top 40%, or top 50% of gene burdens from a subject population. In some embodiments, the genetic variants comprise the genetic variants having association with obesity and/or increased BMI in the top 10%, top 20%, top 30%, top 40%, or top 50% of p-value range for the association. In some embodiments, each of the identified genetic variants comprise the genetic variants having association with obesity and/or increased BMI with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with obesity and/or increased BMI with p-value of less than $5 \times 10^{-8}$. In some embodiments, the identified genetic variants comprise genetic variants having association with obesity and/or increased BMI in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having gene burdens in the top decile, quintile, or tertile in a reference population. The threshold of the gene burden is determined on the basis of the nature of the intended practical application and the risk difference that would be considered meaningful for that practical application.

In some embodiments, when a subject is identified as having an increased risk of developing obesity and/or increased BMI, or as having a decreased risk of developing obesity and/or increased BMI, the subject can be treated as described herein.

The present disclosure also provides methods of diagnosing obesity and/or increased BMI in a subject. The methods comprise determining or having determined whether the subject has any one or more of the CALCR variant nucleic acid molecules encoding a CALCR predicted loss-of-function polypeptide described herein. When the subject has a CALCR variant nucleic acid molecule encoding a CALCR predicted loss-of-function polypeptide, and has one or more symptoms of obesity and/or increased BMI, the subject is diagnosed as having obesity and/or increased BMI. In some embodiments, the subject is homozygous for a CALCR variant nucleic acid molecule encoding a CALCR predicted loss-of-function polypeptide. In some embodiments, the subject is heterozygous for a CALCR variant nucleic acid molecule encoding a CALCR predicted loss-of-function polypeptide. In some embodiments, when a subject is identified as having obesity and/or increased BMI (such as having one or more symptoms of obesity and/or increased BMI and being heterozygous or homozygous for a CALCR variant nucleic acid molecule encoding a CALCR predicted loss-of-function polypeptide), the subject is further treated with a therapeutic agent that treats or inhibits obesity and/or increased BMI, such as any of those described herein.

The present disclosure also provides methods of detecting the presence or absence of a CALCR variant genomic nucleic acid molecule encoding a CALCR predicted loss-of-function polypeptide in a biological sample from a subject, and/or a CALCR variant mRNA molecule encoding a CALCR predicted loss-of-function polypeptide in a biological sample from a subject, and/or a CALCR variant cDNA molecule encoding a CALCR predicted loss-of-function polypeptide produced from an mRNA molecule in a biological sample from a subject. It is understood that gene sequences within a population and mRNA molecules encoded by such genes can vary due to polymorphisms such as single-nucleotide polymorphisms.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any CALCR variant nucleic acid molecule encoding a CALCR predicted loss-of-function polypeptide, preliminary processing designed to isolate or enrich the sample for the genomic DNA can be employed. A variety of techniques may be used for this purpose. When detecting the level of any CALCR variant mRNA molecule, different techniques can be used enrich the biological sample with mRNA. Various methods to detect the presence or level of an mRNA or the presence of a particular variant genomic DNA locus can be used.

In some embodiments, detecting a CALCR variant nucleic acid molecule in a subject comprises assaying or performing a sequence analysis on a biological sample obtained from the subject to determine whether a CALCR genomic nucleic acid molecule in the biological sample, and/or a CALCR mRNA molecule in the biological sample, and/or a CALCR cDNA molecule produced from an mRNA molecule in the biological sample, comprises one or more variations that cause a loss-of-function (partial or complete) or are predicted to cause a loss-of-function (partial or complete), such as any of the CALCR variant nucleic acid molecules described herein.

In some embodiments, the methods of detecting the presence or absence of a CALCR variant nucleic acid molecule (such as, for example, a genomic nucleic acid molecule, an mRNA molecule, and/or a cDNA molecule produced from an mRNA molecule) encoding a CALCR predicted loss-of-function polypeptide in a subject, comprise performing an assay on a biological sample obtained from the subject. The assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a CALCR genomic nucleic acid molecule or mRNA molecule, and if mRNA, optionally reverse transcribing the mRNA into cDNA. Such assays can comprise, for example determining the identity of these positions of the particular CALCR nucleic acid molecule. In some embodiments, the method is an in vitro method.

In some embodiments, the determining step, detecting step, or sequence analysis comprises sequencing at least a portion of the nucleotide sequence of the CALCR genomic nucleic acid molecule, the CALCR mRNA molecule, or the CALCR cDNA molecule in the biological sample, wherein the sequenced portion comprises one or more variations that cause a loss-of-function (partial or complete) or are predicted to cause a loss-of-function (partial or complete), such as any of the CALCR variant nucleic acid molecules described herein.

In some embodiments, the determining step, detecting step, or sequence analysis comprises sequencing at least a portion of the nucleotide sequence of the CALCR genomic nucleic acid molecule in the biological sample, the nucleotide sequence of the CALCR mRNA molecule in the biological sample, or the nucleotide sequence of the CALCR cDNA molecule produced from the CALCR mRNA in the biological sample. In some embodiments, the determining step, detecting step, or genotyping assay comprises sequencing at least a portion of the nucleotide sequence of the CALCR genomic nucleic acid molecule in the biological sample. In some embodiments, the determining step, detecting step, or sequence analysis comprises sequencing at least a portion of the nucleotide sequence of the CALCR mRNA molecule in the biological sample. In some embodiments, the determining step, detecting step, or sequence analysis comprises sequencing at least a portion of the nucleotide sequence of the CALCR cDNA molecule produced from the CALCR mRNA molecule in the biological sample.

In some embodiments, the assay or sequence analysis comprises sequencing the entire nucleic acid molecule. In some embodiments, only a CALCR genomic nucleic acid molecule is analyzed. In some embodiments, only a CALCR mRNA is analyzed. In some embodiments, only a CALCR cDNA obtained from CALCR mRNA is analyzed.

In some embodiments, the determining step, detecting step, or sequence analysis comprises: a) amplifying at least a portion of the nucleic acid molecule that encodes the CALCR polypeptide; b) labeling the amplified nucleic acid molecule with a detectable label; c) contacting the labeled nucleic acid molecule with a support comprising an alteration-specific probe; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule; and detecting the detectable label. Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay or sequence analysis comprises contacting the biological sample with a primer or probe, such as an alteration-specific primer or alteration-specific probe, that specifically hybridizes to a CALCR variant genomic nucleic acid molecule, a CALCR variant mRNA molecule, or a CALCR variant cDNA molecule and not the corresponding CALCR reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a CALCR variant genomic nucleic acid molecule, a CALCR variant mRNA molecule, or a CALCR variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneously with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a CALCR predicted loss-of-function polypeptide comprising performing an assay on a sample obtained from a subject to determine whether a CALCR polypeptide in the subject contains one or more variations that causes the polypeptide to have a loss-of-function (partial or complete) or predicted loss-of-function (partial or complete), such as any of the CALCR predicted loss-of-function polypeptides described herein. The CALCR predicted loss-of-function polypeptides can be any of the truncated variant CALCR polypeptides described herein.

In some embodiments, the detecting step comprises sequencing at least a portion of the polypeptide. In some embodiments, the detecting step comprises an immunoassay for detecting the presence of a polypeptide.

In some embodiments, when the subject does not have a CALCR predicted loss-of-function polypeptide, the subject does not have an increased risk of developing obesity, such as type 1 obesity, type 2 obesity, or type 3 obesity, or developing increased BMI. In some embodiments, when the subject has a CALCR predicted loss-of-function polypeptide, then the subject has an increased risk of developing obesity, such as type 1 obesity, type 2 obesity, or type 3 obesity, or developing increased BMI.

In the context of the present disclosure "specifically hybridizes" means that the probe or primer (such as, for example, the alteration-specific probe or alteration-specific primer) does not hybridize to a nucleic acid sequence encoding a CALCR reference genomic nucleic acid molecule, a CALCR reference mRNA molecule, and/or a CALCR reference cDNA molecule.

An "alteration-specific probe" specifically hybridizes to a CALCR variant genomic nucleic acid molecule, a CALCR variant mRNA molecule, or a CALCR variant cDNA molecule, and not the corresponding CALCR reference sequence under stringent conditions.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of a CALCR reference genomic nucleic acid molecule is set forth in SEQ ID NO:1 (ENST00000426151.6 encompassing chr7:93,424,539-93,574,730 in the GRCh38/hg38 human genome assembly; ENSG00000004948.15).

The nucleotide sequence of a CALCR reference mRNA molecule is set forth in SEQ ID NO:2. The nucleotide sequence of another CALCR reference mRNA molecule is set forth in SEQ ID NO:3. The nucleotide sequence of another CALCR reference mRNA molecule is set forth in SEQ ID NO:4. The nucleotide sequence of another CALCR reference mRNA molecule is set forth in SEQ ID NO:5. The nucleotide sequence of another CALCR reference mRNA molecule is set forth in SEQ ID NO:6. The nucleotide sequence of another CALCR reference mRNA molecule is set forth in SEQ ID NO:7. The nucleotide sequence of another CALCR reference mRNA molecule is set forth in SEQ ID NO:8. The nucleotide sequence of another CALCR reference mRNA molecule is set forth in SEQ ID NO:9. The nucleotide sequence of another CALCR reference mRNA molecule is set forth in SEQ ID NO:10. The nucleotide sequence of another CALCR reference mRNA molecule is set forth in SEQ ID NO:11. The nucleotide sequence of another CALCR reference mRNA molecule is set forth in SEQ ID NO:12. The nucleotide sequence of another CALCR reference mRNA molecule is set forth in SEQ ID NO:13.

The nucleotide sequence of a CALCR reference cDNA molecule is set forth in SEQ ID NO:14. The nucleotide sequence of another CALCR reference cDNA molecule is set forth in SEQ ID NO:15. The nucleotide sequence of another CALCR reference cDNA molecule is set forth in SEQ ID NO:16. The nucleotide sequence of another CALCR reference cDNA molecule is set forth in SEQ ID NO:17. The nucleotide sequence of another CALCR reference cDNA molecule is set forth in SEQ ID NO:18. The nucleotide sequence of another CALCR reference cDNA molecule is set forth in SEQ ID NO:19. The nucleotide sequence of another CALCR reference cDNA molecule is set forth in SEQ ID NO:20. The nucleotide sequence of another CALCR reference cDNA molecule is set forth in SEQ ID NO:21. The nucleotide sequence of another CALCR reference cDNA molecule is set forth in SEQ ID NO:22. The nucleotide sequence of another CALCR reference cDNA molecule is set forth in SEQ ID NO:23. The nucleotide sequence of another CALCR reference cDNA molecule is set forth in SEQ ID NO:24. The nucleotide sequence of another CALCR reference cDNA molecule is set forth in SEQ ID NO:25.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

The amino acid sequence of a CALCR reference polypeptide is set forth in SEQ ID NO:26. The amino acid sequence of another CALCR reference polypeptide is set forth in SEQ ID NO:27. The amino acid sequence of another CALCR reference polypeptide is set forth in SEQ ID NO:28. The amino acid sequence of another CALCR reference polypeptide is set forth in SEQ ID NO:29. The amino acid sequence of another CALCR reference polypeptide is set forth in SEQ ID NO:30.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit obesity and/or increased BMI for use in the treatment of obesity and/or increased BMI in a subject having: i) a CALCR variant genomic nucleic acid molecule encoding a CALCR predicted loss-of-function polypeptide; ii) a CALCR variant mRNA molecule encoding a CALCR predicted loss-of-function polypeptide; or iii) a CALCR variant cDNA molecule encoding a CALCR predicted loss-of-function polypeptide.

In some embodiments, the subject has any of the CALCR variant genomic nucleic acid molecules encoding a CALCR predicted loss-of-function polypeptide, CALCR variant mRNA molecules encoding a CALCR predicted loss-of-function polypeptide, and/or CALCR variant cDNA molecules encoding a CALCR predicted loss-of-function polypeptide described herein. In some embodiments, the subject has any of the CALCR variant genomic nucleic acid molecules described herein. In some embodiments, the subject has any of the CALCR variant mRNA molecules described herein. In some embodiments, the subject has any of the CALCR variant cDNA molecules described herein. The therapeutic agents that treat or inhibit obesity and/or increased BMI can be any of the therapeutic agents that treat or inhibit obesity and/or increased BMI described herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: CALCR pLOF Variants are Associated with Elevated BMI and Increased Risk of Obesity The burden of rare nonsynonymous variants in CALCR and several individual variants in the gene are associated with BMI in humans. A genome-wide association (GWAS) analysis resulted in the association of pLOF missense variants in CALCR with increased BMI and increased obesity risk (see, Table 1 and Table 2), constituting the first human genetic evidence linking LOF in CALCR with obesity. Table 1 summarizes the association between CALCR pLOF variants (or pLOF variants plus missense variants with different functional annotation) and increased BMI. Gene burden tests including pLOF, pLOF plus predicted deleterious missense variants (M3.01, M4.01) or pLOF plus all missense variants were associated with higher BMI (M2.01; see Table 1). Table 2 summarizes the association between CALCR pLOF variants (or pLOF variants plus missense variants with different functional annotation) and higher odds of obesity. Gene burden tests including pLOF, pLOF plus predicted deleterious missense variants (M3.01, M4.01) or pLOF plus all missense variants were associated with higher odds of obesity (M2.01; see Table 2). Table 3 lists CALCR pLOF and missense variants included in the analysis. Of over 100 nonsynonymous variants with individual associations results from the meta-analysis, 15 were associated with BMI at $p<0.05$, including two variants associated with lower BMI (FIG. 1). Eight of these 15 variants were in the last extracellular, transmembrane and intracellular domains suggesting a possible role for beta-arrestin related pathways in the BMI associations (FIG. 1). In addition, an exom-wide association with BMI was observed (genetic exposure=pLOF plus missense; Beta 95% CI per allele in SD units=0.10 (0.07, 0.13); p-value=$1.4\times10^{-10}$; AAF=0.0049; Beta 95% CI per allele in $kg/m^2$ units=0.6 (0.4, 0.7); and Beta 95% CI per allele in kg of body weight=1.6 (1.1, 2.1).

TABLE 1

| Exposure | AAF | Per allele beta (95% CI) in SDs | P | Allele counts | Phenotypic means, kg/m² of BMI |
|---|---|---|---|---|---|
| pLOF | 0.001 | 0.14 (0.07, 0.20) | 4.8E−5 | 406,744: 405,915\|829\|0 | 31.1\|32.7 |
| pLOF or missense (M2.01) | 0.006 | 0.07 (0.05, 0.10) | 5.6E−8 | 406,744: 401,754\|4,989\|1 | 31.1\|32.1 |
| pLOF or missense (M3.01) | 0.001 | 0.14 (0.07, 0.20) | 4.8E−5 | 406,744: 405,915\|829\|0 | 31.1\|32.7 |
| pLOF or missense (M4.01) | 0.005 | 0.10 (0.07, 0.13) | 3.0E−10 | 406,744: 402,772\|3,972\|0 | 31.1\|32.0 |

Abbreviations;
AAF, alternative allele frequency;
CI, confidence interval;
SD, standard deviations;
BMI, body mass index;
pLOF, predicted loss of function.

TABLE 2

| Exposure | AAF | Per allele Odds ratio (95% CI) | P | Allele counts-obese cases | Allele counts-non-obese controls |
|---|---|---|---|---|---|
| pLOF | 0.001 | 1.26 (1.04, 1.53) | 0.017 | 132,399: 132,083\|316\|0 | 120,813: 120,580\|233\|0 |
| pLOF or missense (M2.01) | 0.006 | 1.14 (1.05, 1.24) | 0.0011 | 132,399: 130,703\|1,696\|0 | 120,813: 119,398\|1,415\|0 |
| pLOF or missense (M3.01) | 0.001 | 1.26 (1.04, 1.53) | 0.017 | 132,399: 132,083\|316\|0 | 120,813: 120,580\|233\|0 |
| pLOF or missense (M4.01) | 0.005 | 1.21 (1.11, 1.33) | 2.4E−05 | 132,399: 130,984\|1,415\|0 | 120,813: 119,714\|1,099\|0 |

Abbreviations;
AAF, alternative allele frequency;
CI, confidence interval;
pLOF, predicted loss of function.

TABLE 3

| VARIANT | AAF | M1 | M2 | M3 | M4 | Annotation | IS_LOF |
|---|---|---|---|---|---|---|---|
| 7:93426360:G:T | 0.0000065 | false | true | false | true | missense | false |
| 7:93426376:C:T | 0.0000085 | false | true | false | true | missense | false |
| 7:93426378:A:G | 0.000007 | false | true | false | true | missense | false |
| 7:93426384:T:G | 0.0000315 | false | true | false | true | missense | false |
| 7:93426391:G:T | 0.0000065 | false | true | false | true | missense | false |
| 7:93426393:A:T | 0.000013 | false | true | false | true | missense | false |
| 7:93426398:C:G | 0.000049 | false | true | false | true | missense | false |
| 7:93426399:T:C | 0.0000065 | false | true | false | true | missense | false |
| 7:93426404:A:C | 0.0000389 | false | true | false | false | missense | false |
| 7:93426405:C:T | 0.0000175 | false | true | false | true | missense | false |
| 7:93426412:C:A | 0.0000141 | true | true | true | true | stop_gained | true |
| 7:93426412:C:G | 0.0000035 | false | true | false | true | missense | false |
| 7:93426414:C:T | 0.0000035 | false | true | false | true | missense | false |
| 7:93426419:G:C | 0.0000035 | false | true | false | false | missense | false |
| 7:93426419:G:T | 0.000007 | false | true | false | false | missense | false |
| 7:93426422:GT:G | 0.000515 | true | true | true | true | frameshift | true |
| 7:93426433:C:G | 0.0000065 | false | true | false | true | missense | false |
| 7:93426434:AT:A | 0.000042 | true | true | true | true | frameshift | true |
| 7:93426438:C:T | 0.0000035 | false | true | false | false | missense | false |
| 7:93426451:G:A | 0.0000105 | false | true | false | true | missense | false |
| 7:93426459:T:A | 0.0000065 | false | true | false | true | missense | false |
| 7:93426465:G:C | 0.0000065 | false | true | false | true | missense | false |
| 7:93426472:C:T | 0.000007 | false | true | false | false | missense | false |
| 7:93426475:C:T | 0.0000085 | false | true | false | false | missense | false |
| 7:93426477:G:C | 0.0000065 | false | true | false | false | missense | false |
| 7:93426483:G:A | 0.0000065 | false | true | false | true | missense | false |
| 7:93426490:C:T | 0.000007 | false | true | false | true | missense | false |
| 7:93426492:G:T | 0.0000065 | false | true | false | true | missense | false |
| 7:93426496:C:A | 0.0000035 | false | true | false | true | missense | false |
| 7:93426498:G:A | 0.0000035 | false | true | false | false | missense | false |
| 7:93426499:C:T | 0.0000035 | false | true | false | true | missense | false |
| 7:93426501:C:G | 0.0000085 | false | true | false | false | missense | false |
| 7:93426501:CG:C | 0.000014 | true | true | true | true | frameshift | true |
| 7:93426501:C:T | 0.000007 | false | true | false | true | missense | false |
| 7:93426502:G:A | 0.000007 | false | true | false | true | missense | false |
| 7:93426502:G:T | 0.0000085 | false | true | false | false | missense | false |
| 7:93426505:C:G | 0.0000035 | false | true | false | true | missense | false |
| 7:93426511:G:A | 0.0000035 | false | true | false | true | missense | false |
| 7:93426511:G:C | 0.000056 | false | true | false | true | missense | false |
| 7:93426512:G:GT | 0.0000035 | true | true | true | true | frameshift | true |
| 7:93426513:T:C | 0.0000065 | false | true | false | false | missense | false |
| 7:93426514:T:G | 0.0000105 | false | true | false | false | missense | false |
| 7:93426516:G:A | 0.0000324 | false | true | false | false | missense | false |
| 7:93426517:A:AG | 0.000013 | true | true | true | true | frameshift | true |
| 7:93426519:G:T | 0.0000065 | false | true | false | true | missense | false |
| 7:93426520:G:A | 0.0000105 | false | true | false | false | missense | false |
| 7:93426520:G:C | 0.0000085 | false | true | false | false | missense | false |
| 7:93426528:C:T | 0.0000035 | false | true | false | true | missense | false |
| 7:93426529:C:T | 0.0000065 | false | true | false | false | missense | false |
| 7:93426531:C:G | 0.0000035 | false | true | false | true | missense | false |
| 7:93426534:C:T | 0.000028 | false | true | false | true | missense | false |
| 7:93426541:T:C | 0.0000259 | false | true | false | false | missense | false |
| 7:93426545:C:G | 0.0000035 | false | true | false | true | missense | false |
| 7:93426546:T:C | 0.0000035 | false | true | false | true | missense | false |
| 7:93426559:G:A | 0.0000065 | true | true | true | true | stop_gained | true |
| 7:93426561:G:GC | 0.000007 | true | true | true | true | frameshift | true |
| 7:93426562:C:T | 0.000007 | false | true | false | false | missense | false |
| 7:93426563:C:G | 0.0000946 | false | true | false | true | missense | false |
| 7:93426564:C:T | 0.000014 | true | true | true | true | stop_gained | true |

TABLE 3-continued

| VARIANT | AAF | M1 | M2 | M3 | M4 | Annotation | IS_LOF |
|---|---|---|---|---|---|---|---|
| 7:93426565:A:G | 0.0000035 | false | true | false | true | missense | false |
| 7:93426570:C:T | 0.0000259 | false | true | false | true | missense | false |
| 7:93426571:G:A | 0.0000175 | false | true | false | true | missense | false |
| 7:93426572:C:G | 0.0000035 | false | true | false | true | missense | false |
| 7:93426585:T:C | 0.0000035 | false | true | false | true | missense | false |
| 7:93426588:A:C | 0.0000085 | false | true | false | true | missense | false |
| 7:93434252:C:T | 0.0000065 | true | true | true | true | splice_donor | true |
| 7:93434269:C:G | 0.0000035 | false | true | false | true | missense | false |
| 7:93434281:G:A | 0.0000385 | false | true | false | true | missense | false |
| 7:93434285:C:T | 0.0000105 | false | true | false | true | missense | false |
| 7:93434288:AG:A | 0.0000085 | true | true | true | true | frameshift | true |
| 7:93434289:G:GA | 0.0000085 | true | true | true | true | frameshift | true |
| 7:93435953:T:A | 0.0000065 | false | true | false | true | missense | false |
| 7:93435978:C:T | 0.000042 | false | true | false | true | missense | false |
| 7:93435980:T:C | 0.000014 | false | true | false | true | missense | false |
| 7:93435987:A:G | 0.0000065 | false | true | false | true | missense | false |
| 7:93435988:T:C | 0.000013 | false | true | false | true | missense | false |
| 7:93435991:C:A | 0.0000085 | false | true | false | true | missense | false |
| 7:93436000:C:G | 0.000007 | false | true | false | false | missense | false |
| 7:93436005:T:C | 0.0000085 | false | true | false | true | missense | false |
| 7:93436006:G:T | 0.0000065 | false | true | false | true | missense | false |
| 7:93436007:T:C | 0.0000631 | false | true | false | true | missense | false |
| 7:93436023:G:C | 0.0000035 | false | true | false | true | missense | false |
| 7:93436029:C:T | 0.0000105 | false | true | false | true | missense | false |
| 7:93436032:C:G | 0.000013 | false | true | false | true | missense | false |
| 7:93436035:A:C | 0.000028 | false | true | false | true | missense | false |
| 7:93436053:G:A | 0.0000085 | false | true | false | true | missense | false |
| 7:93436059:G:A | 0.000014 | false | true | false | true | missense | false |
| 7:93436065:T:C | 0.000007 | false | true | false | true | missense | false |
| 7:93436068:T:A | 0.0000194 | false | true | false | true | missense | false |
| 7:93436073:T:C | 0.0000065 | false | true | false | false | missense | false |
| 7:93436079:G:A | 0.0000085 | false | true | false | true | missense | false |
| 7:93436095:G:A | 0.0000245 | false | true | false | false | missense | false |
| 7:93436095:G:T | 0.000014 | false | true | false | false | missense | false |
| 7:93436103:G:A | 0.0000806 | false | true | false | true | missense | false |
| 7:93436103:G:T | 0.0000035 | false | true | false | true | missense | false |
| 7:93436110:G:A | 0.0000085 | false | true | false | true | missense | false |
| 7:93436113:T:A | 0.0000065 | false | true | false | true | missense | false |
| 7:93436116:C:T | 0.000007 | false | true | false | false | missense | false |
| 7:93436122:T:G | 0.0000065 | false | true | false | false | missense | false |
| 7:93436127:G:A | 0.0000065 | false | true | false | true | missense | false |
| 7:93436139:C:G | 0.0000105 | false | true | false | true | missense | false |
| 7:93436139:C:T | 0.0002908 | false | true | false | true | missense | false |
| 7:93436140:G:A | 0.000021 | false | true | false | true | missense | false |
| 7:93436151:A:G | 0.0000035 | false | true | false | true | missense | false |
| 7:93436166:T:C | 0.0000035 | false | true | false | true | missense | false |
| 7:93436169:A:G | 0.0000035 | false | true | false | true | missense | false |
| 7:93436171:C:A | 0.0000105 | true | true | true | true | splice_acceptor | true |
| 7:93436171:C:T | 0.0000085 | true | true | true | true | splice_acceptor | true |
| 7:93436171:CTGCAAATATACGG:C | 0.0000169 | true | true | true | true | splice_acceptor | true |
| 7:93438056:TCAC:T | 0.0000259 | true | true | true | true | splice_donor | true |
| 7:93438059:C:G | 0.0000035 | true | true | true | true | splice_donor | true |
| 7:93438070:G:A | 0.000021 | false | true | false | true | missense | false |
| 7:93438070:G:T | 0.000028 | false | true | false | true | missense | false |
| 7:93438072:C:A | 0.0000065 | false | true | false | true | missense | false |
| 7:93438073:A:G | 0.0000035 | false | true | false | true | missense | false |
| 7:93438077:C:G | 0.0000035 | false | true | false | true | missense | false |
| 7:93438085:T:C | 0.0000065 | false | true | false | true | missense | false |
| 7:93438089:T:C | 0.0000085 | false | true | false | true | missense | false |
| 7:93438092:T:C | 0.0000254 | false | true | false | true | missense | false |
| 7:93438095:A:C | 0.0000065 | false | true | false | true | missense | false |
| 7:93438101:A:T | 0.0000065 | false | true | false | true | missense | false |
| 7:93438103:T:C | 0.0000035 | false | true | false | true | missense | false |
| 7:93438106:G:A | 0.0000035 | false | true | false | true | missense | false |
| 7:93438109:T:A | 0.0000065 | false | true | false | true | missense | false |
| 7:93438112:A:G | 0.0000065 | false | true | false | true | missense | false |
| 7:93438115:C:T | 0.000007 | false | true | false | true | missense | false |
| 7:93438125:A:G | 0.0000035 | false | true | false | true | missense | false |
| 7:93438209:C:T | 0.000007 | true | true | true | true | splice_donor | true |
| 7:93438226:C:T | 0.000035 | false | true | false | true | missense | false |
| 7:93438229:C:T | 0.0000035 | false | true | false | true | missense | false |
| 7:93438235:T:C | 0.0000085 | false | true | false | false | missense | false |
| 7:93438243:T:A | 0.0000035 | false | true | false | true | missense | false |
| 7:93438247:T:A | 0.000007 | false | true | false | true | missense | false |
| 7:93438255:G:A | 0.0000389 | false | true | false | true | missense | false |
| 7:93438259:C:T | 0.0000453 | false | true | false | true | missense | false |
| 7:93438264:G:A | 0.0000035 | false | true | false | true | missense | false |

TABLE 3-continued

| VARIANT | AAF | M1 | M2 | M3 | M4 | Annotation | IS_LOF |
|---|---|---|---|---|---|---|---|
| 7:93438270:C:A | 0.0000315 | false | true | false | true | missense | false |
| 7:93443603:C:A | 0.000014 | true | true | true | true | splice_donor | true |
| 7:93443605:C:G | 0.0000035 | false | true | false | true | missense | false |
| 7:93443607:AGCCAAGAGATAATACC:A | 0.0000105 | true | true | true | true | frameshift | true |
| 7:93443621:T:C | 0.000007 | false | true | false | true | missense | false |
| 7:93443622:A:G | 0.000013 | false | true | false | true | missense | false |
| 7:93443624:C:A | 0.0000736 | false | true | false | true | missense | false |
| 7:93443624:C:G | 0.0000065 | false | true | false | true | missense | false |
| 7:93443627:C:T | 0.0000981 | false | true | false | false | missense | false |
| 7:93443628:G:A | 0.0000525 | false | true | false | true | missense | false |
| 7:93443633:C:T | 0.000007 | false | true | false | false | missense | false |
| 7:93443634:G:A | 0.0000876 | false | true | false | true | missense | false |
| 7:93443634:G:T | 0.000007 | false | true | false | false | missense | false |
| 7:93443648:AAC:A | 0.0000035 | true | true | true | true | frameshift | true |
| 7:93443657:A:G | 0.0000065 | false | true | false | true | missense | false |
| 7:93443658:C:T | 0.0000385 | false | true | false | true | missense | false |
| 7:93443666:A:C | 0.0000085 | false | true | false | true | missense | false |
| 7:93443681:A:T | 0.0000035 | false | true | false | true | missense | false |
| 7:93443682:T:A | 0.000013 | false | true | false | true | missense | false |
| 7:93443682:T:G | 0.0000105 | false | true | false | true | missense | false |
| 7:93443696:A:G | 0.000007 | false | true | false | true | missense | false |
| 7:93443703:A:G | 0.0000035 | false | true | false | true | missense | false |
| 7:93443705:T:C | 0.0000035 | false | true | false | true | missense | false |
| 7:93443711:C:G | 0.0000035 | false | true | false | true | missense | false |
| 7:93443714:G:C | 0.0000035 | false | true | false | false | missense | false |
| 7:93443718:T:C | 0.0000035 | false | true | false | true | missense | false |
| 7:93443719:C:G | 0.0000035 | false | true | false | true | missense | false |
| 7:93443720:A:G | 0.000013 | false | true | false | true | missense | false |
| 7:93443727:G:C | 0.0000035 | false | true | false | true | missense | false |
| 7:93443727:G:T | 0.000014 | false | true | false | true | missense | false |
| 7:93443729:T:A | 0.0000035 | false | true | false | true | missense | false |
| 7:93443733:A:G | 0.0000035 | false | true | false | true | missense | false |
| 7:93443734:A:T | 0.0000065 | false | true | false | true | missense | false |
| 7:93443739:G:C | 0.0000035 | false | true | false | true | missense | false |
| 7:93443743:AATCTT:A | 0.0000035 | true | true | true | true | frameshift | true |
| 7:93443746:C:G | 0.000007 | false | true | false | true | missense | false |
| 7:93443750:C:T | 0.0000085 | false | true | false | true | missense | false |
| 7:93443758:C:T | 0.0000259 | true | true | true | true | splice_acceptor | true |
| 7:93460822:G:A | 0.0000105 | false | true | false | true | missense | false |
| 7:93460822:G:T | 0.0002592 | false | true | false | true | missense | false |
| 7:93460826:C:A | 0.0000085 | false | true | false | true | missense | false |
| 7:93460828:C:T | 0.0000712 | false | true | false | false | missense | false |
| 7:93460831:C:T | 0.0000065 | false | true | false | false | missense | false |
| 7:93460832:G:A | 0.0000105 | true | true | true | true | stop_gained | true |
| 7:93460835:C:A | 0.0000085 | false | true | false | true | missense | false |
| 7:93460835:C:T | 0.000007 | false | true | false | true | missense | false |
| 7:93460838:G:A | 0.000013 | false | true | false | true | missense | false |
| 7:93460844:C:T | 0.0000085 | false | true | false | false | missense | false |
| 7:93460845:A:C | 0.0000035 | false | true | false | true | missense | false |
| 7:93460846:T:C | 0.0000065 | false | true | false | true | missense | false |
| 7:93460856:C:T | 0.0000035 | false | true | false | true | missense | false |
| 7:93460867:T:C | 0.0000035 | false | true | false | true | missense | false |
| 7:93460881:C:T | 0.0000065 | false | true | false | false | missense | false |
| 7:93460882:A:G | 0.0000035 | false | true | false | false | missense | false |
| 7:93460897:T:C | 0.0000169 | false | true | false | true | missense | false |
| 7:93460906:A:G | 0.0000065 | false | true | false | true | missense | false |
| 7:93460918:T:C | 0.0000065 | false | true | false | true | missense | false |
| 7:93460924:G:T | 0.0000035 | false | true | false | true | missense | false |
| 7:93460929:C:A | 0.0000065 | false | true | false | true | missense | false |
| 7:93460930:C:T | 0.0000065 | false | true | false | true | missense | false |
| 7:93460931:T:C | 0.0000105 | false | true | false | true | missense | false |
| 7:93460939:C:T | 0.0000065 | false | true | false | true | missense | false |
| 7:93460945:C:T | 0.0002627 | false | true | false | true | missense | false |
| 7:93460949:T:C | 0.0000105 | true | true | true | true | splice_acceptor | true |
| 7:93462060:T:TA | 0.0000876 | true | true | true | true | splice_donor | true |
| 7:93462067:C:A | 0.0000035 | false | true | false | true | missense | false |
| 7:93462090:G:A | 0.000007 | false | true | false | true | missense | false |
| 7:93462091:G:A | 0.0000035 | false | true | false | true | missense | false |
| 7:93462104:C:G | 0.000007 | false | true | false | true | missense | false |
| 7:93462112:T:C | 0.0000035 | true | true | true | true | splice_acceptor | true |
| 7:93468717:G:C | 0.0000035 | false | true | false | true | missense | false |
| 7:93468722:A:C | 0.000007 | false | true | false | true | missense | false |
| 7:93468725:C:T | 0.0000065 | false | true | false | false | missense | false |
| 7:93468750:G:A | 0.0000065 | false | true | false | false | missense | false |
| 7:93468750:G:C | 0.0000035 | false | true | false | false | missense | false |
| 7:93468758:T:C | 0.0009528 | false | true | false | true | missense | false |
| 7:93468759:T:C | 0.0000065 | false | true | false | true | missense | false |

TABLE 3-continued

| VARIANT | AAF | M1 | M2 | M3 | M4 | Annotation | IS_LOF |
| --- | --- | --- | --- | --- | --- | --- | --- |
| 7:93468769:T:G | 0.0000324 | false | true | false | true | missense | false |
| 7:93468781:G:A | 0.0000065 | false | true | false | true | missense | false |
| 7:93468781:G:T | 0.0000035 | false | true | false | true | missense | false |
| 7:93468782:C:T | 0.0000085 | false | true | false | true | missense | false |
| 7:93468787:T:G | 0.0000035 | false | true | false | true | missense | false |
| 7:93468789:G:T | 0.0000035 | true | true | true | true | stop_gained | true |
| 7:93468797:C:T | 0.000007 | false | true | false | false | missense | false |
| 7:93468799:T:C | 0.0001366 | false | true | false | true | missense | false |
| 7:93472373:A:G | 0.0000065 | true | true | true | true | splice_donor | true |
| 7:93472379:A:G | 0.0000035 | false | true | false | true | missense | false |
| 7:93472383:T:C | 0.000007 | false | true | false | true | missense | false |
| 7:93472384:C:CT | 0.0000841 | true | true | true | true | frameshift | true |
| 7:93472392:T:G | 0.0000035 | false | true | false | true | missense | false |
| 7:93472397:G:C | 0.0000453 | false | true | false | true | missense | false |
| 7:93472398:C:A | 0.0000065 | false | true | false | false | missense | false |
| 7:93472412:T:C | 0.000007 | false | true | false | true | missense | false |
| 7:93472415:T:C | 0.000013 | false | true | false | true | missense | false |
| 7:93472418:G:C | 0.0000035 | false | true | false | true | missense | false |
| 7:93472418:G:T | 0.0002802 | false | true | false | true | missense | false |
| 7:93472420:C:T | 0.0000065 | true | true | true | true | stop_gained | true |
| 7:93472424:G:A | 0.0000085 | false | true | false | true | missense | false |
| 7:93472427:C:T | 0.000056 | false | true | false | true | missense | false |
| 7:93472428:G:A | 0.0000035 | true | true | true | true | stop_gained | true |
| 7:93472446:T:TA | 0.0000175 | true | true | true | true | frameshift | true |
| 7:93472454:A:G | 0.0000175 | false | true | false | false | missense | false |
| 7:93472458:C:A | 0.000013 | false | true | false | true | missense | false |
| 7:93472465:A:T | 0.000007 | false | true | false | false | missense | false |
| 7:93472472:T:C | 0.0000065 | false | true | false | true | missense | false |
| 7:93472473:A:G | 0.000013 | false | true | false | true | missense | false |
| 7:93472479:T:C | 0.0000035 | false | true | false | false | missense | false |
| 7:93472482:C:A | 0.0000065 | false | true | false | true | missense | false |
| 7:93472483:CT:C | 0.0000105 | true | true | true | true | frameshift | true |
| 7:93477556:A:C | 0.0000035 | true | true | true | true | splice_donor | true |
| 7:93477557:C:A | 0.000013 | true | true | true | true | splice_donor | true |
| 7:93477566:T:A | 0.0000259 | false | true | false | true | missense | false |
| 7:93477575:G:A | 0.0000035 | false | true | false | true | missense | false |
| 7:93477584:T:C | 0.0000105 | false | true | false | true | missense | false |
| 7:93477590:C:T | 0.0000065 | false | true | false | true | missense | false |
| 7:93477599:T:C | 0.0000254 | false | true | false | true | missense | false |
| 7:93477599:T:G | 0.0000035 | false | true | false | false | missense | false |
| 7:93477602:G:A | 0.0000035 | false | true | false | true | missense | false |
| 7:93477611:C:A | 0.0000035 | false | true | false | true | missense | false |
| 7:93477612:C:G | 0.0000035 | false | true | false | true | missense | false |
| 7:93477617:G:A | 0.0000596 | false | true | false | true | missense | false |
| 7:93477617:G:C | 0.0000035 | false | true | false | true | missense | false |
| 7:93477617:G:T | 0.0000035 | false | true | false | true | missense | false |
| 7:93477620:G:A | 0.0000035 | false | true | false | true | missense | false |
| 7:93477622:G:C | 0.0000035 | false | true | false | true | missense | false |
| 7:93477622:G:T | 0.0000105 | false | true | false | true | missense | false |
| 7:93477623:T:C | 0.0000035 | false | true | false | true | missense | false |
| 7:93477626:T:G | 0.0000065 | false | true | false | true | missense | false |
| 7:93477628:CCAGCA:C | 0.000007 | true | true | true | true | frameshift | true |
| 7:93477632:C:A | 0.0000065 | false | true | false | true | missense | false |
| 7:93477637:C:G | 0.0000065 | false | true | false | true | missense | false |
| 7:93477638:C:G | 0.0000035 | false | true | false | true | missense | false |
| 7:93477639:A:G | 0.000007 | false | true | false | true | missense | false |
| 7:93477644:T:A | 0.0000194 | false | true | false | true | missense | false |
| 7:93477650:G:T | 0.0000035 | false | true | false | true | missense | false |
| 7:93477653:C:A | 0.0000085 | false | true | false | true | missense | false |
| 7:93477653:C:T | 0.000014 | false | true | false | true | missense | false |
| 7:93477654:G:A | 0.0000525 | false | true | false | true | missense | false |
| 7:93477654:G:C | 0.0000065 | false | true | false | true | missense | false |
| 7:93477654:G:T | 0.000007 | false | true | false | true | missense | false |
| 7:93477656:T:C | 0.000007 | false | true | false | true | missense | false |
| 7:93477660:AAT:A | 0.0000085 | true | true | true | true | frameshift | true |
| 7:93477662:T:C | 0.0000065 | false | true | false | true | missense | false |
| 7:93477668:C:A | 0.0000035 | false | true | false | true | missense | false |
| 7:93479360:C:T | 0.0000339 | false | true | false | false | missense | false |
| 7:93479369:C:T | 0.000021 | false | true | false | false | missense | false |
| 7:93479371:G:A | 0.0000324 | false | true | false | true | missense | false |
| 7:93479372:G:A | 0.000007 | false | true | false | true | missense | false |
| 7:93479386:C:T | 0.000007 | false | true | false | true | missense | false |
| 7:93479387:G:A | 0.000014 | true | true | true | true | stop_gained | true |
| 7:93479404:T:C | 0.0000065 | false | true | false | true | missense | false |
| 7:93479410:T:C | 0.0000525 | false | true | false | true | missense | false |
| 7:93479425:C:T | 0.000028 | false | true | false | true | missense | false |
| 7:93479426:G:A | 0.000035 | true | true | true | true | stop_gained | true |
| 7:93479426:G:C | 0.0000065 | false | true | false | true | missense | false |

TABLE 3-continued

| VARIANT | AAF | M1 | M2 | M3 | M4 | Annotation | IS_LOF |
|---|---|---|---|---|---|---|---|
| 7:93479428:C:T | 0.000007 | false | true | false | false | missense | false |
| 7:93479432:C:T | 0.0009739 | false | true | false | false | missense | false |
| 7:93479435:C:T | 0.000007 | false | true | false | false | missense | false |
| 7:93479449:T:G | 0.0000035 | false | true | false | false | missense | false |
| 7:93479450:T:TG | 0.0000035 | true | true | true | true | frameshift | true |
| 7:93479453:G:T | 0.0000385 | false | true | false | true | missense | false |
| 7:93479456:C:T | 0.0000259 | false | true | false | true | missense | false |
| 7:93479470:G:T | 0.0000035 | false | true | false | true | missense | false |
| 7:93479472:T:A | 0.0000175 | false | true | false | false | missense | false |
| 7:93479489:G:C | 0.0000385 | false | true | false | false | missense | false |
| 7:93479501:T:C | 0.0000035 | false | true | false | false | missense | false |
| 7:93479501:T:G | 0.0000085 | false | true | false | false | missense | false |
| 7:93486931:A:T | 0.0000035 | false | true | false | false | missense | false |
| 7:93486932:T:G | 0.0000035 | false | true | false | false | missense | false |
| 7:93486939:G:C | 0.0000035 | false | true | false | false | missense | false |
| 7:93486943:A:C | 0.0000907 | false | true | false | false | missense | false |
| 7:93486944:A:G | 0.0000065 | false | true | false | true | missense | false |
| 7:93486945:A:T | 0.0000035 | false | true | false | false | missense | false |
| 7:93486951:C:T | 0.0000085 | false | true | false | false | missense | false |
| 7:93486956:C:T | 0.0000085 | false | true | false | false | missense | false |
| 7:93486957:A:T | 0.0000065 | false | true | false | true | missense | false |
| 7:93486959:C:T | 0.0000175 | false | true | false | false | missense | false |
| 7:93486962:C:A | 0.0000065 | false | true | false | false | missense | false |
| 7:93486962:C:T | 0.0000035 | false | true | false | false | missense | false |
| 7:93486965:G:A | 0.0000035 | false | true | false | false | missense | false |
| 7:93486979:CATTTTTG:C | 0.0000175 | true | true | true | true | frameshift | true |
| 7:93486996:G:T | 0.0000065 | false | true | false | false | missense | false |
| 7:93487001:CTT:C | 0.0000065 | true | true | true | true | frameshift | true |
| 7:93487005:G:T | 0.0000065 | false | true | false | true | missense | false |
| 7:93487008:C:T | 0.000007 | true | true | true | true | splice_acceptor | true |
| 7:93495902:G:T | 0.0000035 | true | true | true | true | splice_donor | true |
| 7:93495903:C:T | 0.000014 | true | true | true | true | splice_donor | true |
| 7:93495930:A:G | 0.0000035 | true | true | true | true | start_lost | true |
| 7:93495976:T:A | 0.0000105 | true | true | true | true | splice_acceptor | true |
| 7:93495976:T:C | 0.000021 | true | true | true | true | splice_acceptor | true |

Example 2: Expanded CWAS of CALCR Association with Elevated BMI and Increased Risk of Obesity

Participating Cohorts

Discovery genetic association studies were performed in the United Kingdom (UK) Biobank (UKB) cohort, in the MyCode Community Health Initiative cohort from the Geisinger Health System (GHS), and in the Mexico City Prospective Study (MCPS). The UKB is a population-based cohort study of people aged between 40 and 69 years recruited through 22 testing centers in the UK between 2006-2010. A total of 428,719 European ancestry participants with available whole-exome sequencing and clinical phenotype data were included (Table 4). The GHS MyCode study is a health system-based cohort of patients from Central and Eastern Pennsylvania (USA) recruited in 2007-2019. A total of 121,061 European ancestry participants with available whole-exome sequencing and clinical phenotype data were included (Table 4). The MCPS is a cohort study of people aged >35 years recruited from two contiguous urban districts in Mexico City in 2000-2004. A total of 95,846 individuals of Admixed American ancestry with available whole-exome sequencing and clinical phenotype data were included (Table 4).

TABLE 4

Baseline characteristics of individuals included in the exome-wide association study

| Variable | UKB study (N = 428,719) | GHS study (N = 121,061) | MCPS study (N = 95,846) |
|---|---|---|---|
| Age, mean (SD) in years | 57 (8) | 53 (17) | 52 (13) |
| Women, N (%) | 232,553 (54) | 73,769 (61) | 65,330 (68) |
| Body mass index, mean (SD) in kg/m$^2$ | 27.4 (4.8) | 31.1 (7.3) | 29.1 (5.1) |
| Body weight, mean (SD) in kg | 78 (16) | 88 (23) | 70 (14) |
| Blood pressure, mean (SD) in mmHg | | | |
| Systolic | 138 (19) | 124 (11) | 127 (17) |
| Diastolic | 82 (11) | 74 (7) | 83 (10) |
| Low-density lipoprotein cholesterol, mean (SD) in mg/dL | 138 (34) | 107 (29) | Not measured |
| Triglycerides, median (IQR) in mg/dL | 132 (93, 191) | 124 (90, 172) | Not measured |

Abbreviations:
UKB, UK Biobank;
GHS, Geisinger Health System;
MCPS, Mexico City Prospective Study;
SD, standard deviation;
N, number of participants;
IQR, interquartile range.

Phenotype Definitions

Body mass index (BMI) was calculated as weight in kilograms divided by the square of height in meters on the basis of anthropometric measurements taken at one of the study visits. BMI categories were defined on the basis of the World Health Organization classification. BMI values were transformed by the inverse standard normal function, applied within each ancestry group and separately in men and women. Overall and regional body lean and fat masses, percentages and body-surface normalized indices were measured by bioelectrical impedance in the UKB cohort.

Genotype Data

High coverage whole exome sequencing was performed as previously described. NimbleGen probes (VCRome) or a modified version of the xGen design available from Integrated DNA Technologies (IDT) were used for target sequence capture. Sequencing was performed using 75 bp paired-end reads on Illumina v4 HiSeq 2500 or NovaSeq instruments. Sequencing had a coverage depth (ie, number of sequence-reads covering each nucleotide in the target areas of the genome) sufficient to provide greater than 20× coverage over 85% of targeted bases in 96% of VCRome samples and 20× coverage over 90% of targeted bases in 99% of IDT samples. Sequence read alignment and variant calling was based on the GRCh38 Human Genome reference sequence. Ensembl v85 gene definitions were used to determine the functional impact of single nucleotide variants and insertion-deletions. Predicted LOF genetic variants included: a) insertions or deletions resulting in a frameshift; b) insertions, deletions or single nucleotide variants resulting in the introduction of a premature stop codon or in the loss of the transcription start site or stop site; and c) variants in donor or acceptor splice sites. Missense variants were classified for likely functional impact according to the number of in silico prediction algorithms that predicted deleteriousness using SIFT, Polyphen2_HDIV and Polyphen2_HVAR, LRT and MutationTaster. For each gene, the alternative allele frequency (AAF) and functional annotation of each variant determined inclusion into these 7 gene burden exposures: 1) pLOF variants with AAF <1%; 2) pLOF or missense variants predicted deleterious by 5/5 algorithms with AAF <1%; 3) pLOF or missense variants predicted deleterious by 5/5 algorithms with AAF <0.1%; 4) pLOF or missense variants predicted deleterious by at least 1/5 algorithms with AAF <1%; 5) pLOF or missense variants predicted deleterious by at least 1/5 algorithms with AAF <0.1%; 6) pLOF or any missense with AAF <1%; and 7) pLOF or any missense variants with AAF <0.1%.

Generation of a Genome Wide-Polygenic Score for BMI

SNP array genotyping was performed in the UKB as previously described. A polygenic score capturing predisposition to higher BMI due to over 2.5 million common variants was generated using the LDpred software from the results of a previous large genome-wide association study in an independent dataset.

Statistical Analysis

The association with BMI of genetic variants or their gene burden were estimated by fitting mixed-effects regression models using BOLT-LMM v2.3.442 or REGENIE v1.0.43 These approaches account for relatedness and population structure by estimating a polygenic score using genotypes from across the genome. Then, the association of genetic variants or their burden is estimated conditional upon that polygenic score as a covariate. Analyses were further adjusted for age, $age^2$, sex, an age-by-sex interaction term, experimental batch-related covariates, and genetic principal components. To ensure that burden associations were statistically independent of BMI-associated common genetic variants, the gene burden association analyses was further adjusted for common variants identified by fine-mapping genome-wide associations of common alleles with BMI as described in the below. Results across cohorts were pooled using inverse-variance weighted meta-analysis.

The following analyses were performed by the following steps:

1. BMI-associated common variants were identified by performing a genome-wide association study including over 12 million common-to-low-frequency genetic variants imputed using the Haplotype Reference Consortium panel. In the GHS study, imputation was performed separately in samples genotyped with the Illumina Human Omni Express Exome array (OMNI set) and the Global Screening array (GSA set). Dosage data from imputed variants were then merged across the two GHS sets, to obtain a combined dataset for association analysis. Genome-wide association analyses were performed in the GHS, UKB and MCPS cohorts separately by fitting mixed-effects linear regression models using BOLT-LMM or REGENIE. Results from the UKB and GHS analyses were then combined by inverse variance-weighted meta-analysis to obtain a genome-wide meta-analysis in the European subset of the discovery cohorts.

2. To identify conditionally-independent genetic association signals driven by common variants, fine-mapping at genomic regions harboring genetic variants associated with BMI was performed at the genome-wide significance threshold of $p<5\times10'$ using the FINEMAP software. Linkage disequilibrium was estimated using genetic data from the exact set of individuals included in the genome-wide association analyses. Fine-mapping was performed separately in the meta-analysis of the European ancestry GHS and UKB cohorts and in the Admixed American ancestry analysis in the MCPS cohort.

3. For each locus that was fine-mapped, the 95% credible variant set was identified that had the highest posterior probability of being causal and retained the lead common variant(s) (minor allele frequency $\geq 1\%$) for that set. In total, 1,769 independent associations with common variants in the European ancestry subset and 134 associations in the smaller Admixed American subset were identified.

4. In each cohort, exome-wide association analyses for gene burden associations was performed using as covariates the genotypes of BMI-associated common variants identified by fine-mapping within the relevant ancestry group for that cohort. The results of the exome-wide analyses within each cohort were then meta-analyzed to obtain estimates for gene burden associations that are independent of BMI-associated common variants (Table 5; CALCR; genomic coordinates 7:93426355; pLOF plus missesnse (1/5); AAF <0.1%).

Results

In an exome-wide analysis of 645,626 individuals, CALCR was one of sixteen genes for which the burden of rare nonsynonymous genetic variants was associated with BMI at the exome-wide level of statistical significance ($p<3.6\times10^{-07}$, a Bonferroni correction for 20,000 genes and seven variant selection models; Table 5). The CALCR association was consistent across the constituent datasets of the meta-analysis (Table 6).

Five of the sixteen genes encode G-protein coupled receptors (GPCRs; the largest class of drug targets in the human genome) expressed in the brain and central nervous system, including CALCR. This study provides the first human genetic evidence linking rare coding variation in CALCR to BMI and obesity-related phenotypes.

TABLE 5

| Beta (95% CI) per allele in SD units of BMI | P | AAF, fraction of 1 | Genotype Counts RR\|RA\|AA genotypes | Beta (95% CI) per allele in kg/m² units of BMI | Beta (95% CI) per allele in kgs of body weight | Beta (95% CI) per allele in lbs of body weight |
|---|---|---|---|---|---|---|
| 0.08 (0.06, 0.11) | $1.9 \times 10^{-12}$ | 0.0048 | 639,416\|6,208\|2 | 0.5 (0.3, 0.6) | 1.3 (1.0, 1.7) | 2.9 (2.1, 3.7) |

Table 5 reports genes for which the gene burden of rare nonsynonymous variants was associated with body mass index at the exome-wide level of statistical significance ($p<3.6 \times 10-7$). Analyses were performed in 645,626 participants from the UKB, GHS and MCPS studies. Genomic coordinates reflect chromosome and physical position in base pairs according to Genome Reference Consortium Human Build 38. Abbreviations: CI, confidence interval; SD, standard deviation; BMI, body mass index; AAF, alternative allele frequency; RR, reference-reference genotype; RA, reference-alternative heterozygous genotype; AA, alternative-alternative homozygous genotype; pLOF, predicted loss of function; Missense (1/5), missense variant predicted to be deleterious by at least 1 out of 5 in silico prediction algorithms; Missense (5/5), missense variant predicted to be deleterious by 5 out of 5 in silico prediction algorithms.

TABLE 6

CALCR association results in UKB, GHS and MCPS cohorts with body mass index in the exome-wide analysis

| Genetic exposure, variant type; allele frequency cut-off in % | Study | Beta (95% CI) per allele in SD units of BMI | p | AAF, fraction of 1 | Genotype counts, RR\|RA\|AA genotypes |
|---|---|---|---|---|---|
| pLOF plus deleterious missense (1/5); AAF < 0.1% | UKB | 0.07 (0.04, 0.09) | 6.7E-06 | 0.0049 | 424,507\|4,212\|0 |
| pLOF plus deleterious missense (1/5); AAF < 0.1% | MCPS | 0.09 (0.02, 0.16) | 7.0E-03 | 0.0044 | 94,999\|845\|2 |
| pLOF plus deleterious missense (1/5); AAF < 0.1% | GHS | 0.17 (0.11, 0.22) | 6.9E-10 | 0.0048 | 119,910\|1,151\|0 |

Abbreviations:
BMI, body mass index;
SD, standard deviations;
pLOF, predicted loss of function;
AAF, alternative allele frequency;
RR, reference-reference genotype;
RA, reference-alternative heterozygous genotype;
AA, alternative-alternative homozygous genotype;
UKB, UK Biobank;
GHS, Geisinger Health System MyCode study;
MCPS, Mexico City Prospective Study A novel association of the burden of rare (AAF <0.1%) CALCR pLOF mutations was identified and predicted-deleterious missense variants in the calcitonin receptor gene with 0.08 SDs (~0.5 kg/m²) higher BMI and 20% higher odds of obesity (OR, 1.20; 95% CI, 1.12, 1.20; p=$8.9 \times 10^{-07}$; Table 5 and Table 7). In addition, the burden of CALCR pLOF genetic variants alone (such as, excluding missense variants) was associated with higher BMI (Table 8), indicating that loss-of-function in CALCR is associated with higher BMI and obesity risk in humans

TABLE 7

CALCR Association with risk of obesity in a meta-analysis of UKB, GHS and MCPS for the 16 genes associated with body mass index in the exome-wide analysis and for the two loss-of-function missense variants in GIPR

| Genetic exposure, variant type; allele frequency cut-off in % | Per-allele OR (95% CI) for obesity | p | AAF, fraction of 1 | Genotype counts (cases), RR\|RA\|AA genotypes | Genotype counts (controls), RR\|RA\|AA genotypes |
|---|---|---|---|---|---|
| pLOF plus deleterious missense (1/5); AAF < 0.1% | 1.20 (1.12, 1.29) | 8.9E-07 | 0.00484 | 198,592\|2,065\|1 | 184,749\|1,680\|0 |

Abbreviations:
OR, odds ratio;
CI, confidence intervals;
pLOF, predicted loss of function;
AAF, alternative allele frequency.
Results are from a meta-analysis of the UKB, GHS and MCPS studies.

TABLE 8

CALCR association with BMI in ancillary analyses of this study

| Genetic exposure, variant type; frequency cutoff in % | Description | Beta (95% CI) per allele in SD units of BMI | p |
|---|---|---|---|
| pLOF; AAF < 1% | Main analysis | 0.10 (0.05, 0.15) | 2.3E-04 |

Abbreviations:
CI, confidence intervals;
SD, standard deviations;
BMI, body mass index;
pLOF, predicted loss of function;
AAF, alternative allele frequency.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject with a therapeutic agent that treats or inhibits obesity and/or reduces body mass index (BMI), wherein the subject has obesity and/or increased BMI, the method comprising the steps of:
   determining whether the subject has a Calcitonin Receptor (CALCR) variant nucleic acid molecule encoding a CALCR predicted loss-of-function polypeptide by:
   obtaining or having obtained a biological sample from the subject; and
   performing or having performed a sequence analysis on the biological sample to determine if the subject has a genotype comprising the CALCR variant nucleic acid molecule; and
   administering or continuing to administer to the subject the therapeutic agent that treats or inhibits obesity and/or increased BMI in a standard dosage amount to a subject that is CALCR reference and does not have a copy of a CALCR variant nucleic acid molecule encoding a CALCR predicted loss-of-function polypeptide; or
   administering or continuing to administer to the subject the therapeutic agent that treats or inhibits obesity and/or increased BMI in an amount that is the same as or greater than a standard dosage amount to a subject that is heterozygous or homozygous for the CALCR variant nucleic acid molecule; and
   wherein the CALCR predicted loss-of-function polypeptide comprises S18P, R92C, K125fs, I178V, S209N, R355Q, F390V, V392I, A422V, R432C, S456F, R461fs, or N487fs.

2. The method according to claim 1, wherein the CALCR variant nucleic acid molecule is a genomic nucleic acid molecule, an mRNA molecule, or a cDNA molecule produced from an mRNA molecule.

3. The method according to claim 2, wherein the sequence analysis comprises sequencing at least a portion of the nucleotide sequence of the CALCR genomic nucleic acid molecule in the biological sample, the CALCR mRNA molecule in the biological sample, or the CALCR cDNA molecule produced from an mRNA molecule in the biological sample.

4. The method according to claim 1, wherein the sequence analysis comprises:
   a) amplifying at least a portion of the nucleic acid molecule that encodes the CALCR polypeptide;
   b) labeling the amplified nucleic acid molecule with a detectable label;
   c) contacting the labeled nucleic acid molecule with a support comprising a probe which specifically hybridizes to the CALCR variant nucleic acid molecule encoding a CALCR predicted loss-of-function polypeptide; and
   d) detecting the detectable label.

5. The method according to claim 1, wherein the sequence analysis comprises:
   contacting the nucleic acid molecule in the biological sample with a probe which specifically hybridizes to the CALCR variant nucleic acid molecule encoding a CALCR predicted loss-of-function polypeptide, wherein the probe comprises a detectable label; and
   detecting the detectable label.

6. The method according to claim 1, wherein the therapeutic agent that treats or inhibits obesity and/or reduces BMI is chosen from sibutramine, orlistat, phentermine, lorcaserin, naltrexone, liraglutide, diethylpropion, bupropion, metformin, pramlintide, topiramate, and zonisamide, or any combination thereof.

7. The method according to claim 1, wherein the therapeutic agent that treats or inhibits obesity and/or reduces BMI is a melanocortin 4 receptor (MC4R) agonist.

8. The method according to claim 7, wherein the MC4R agonist is selected from the group consisting of a peptide analog of MC4R, a peptide comprising the amino acid sequence His-Phe-Arg-Trp, setmelanotide, 1,2,3R,4-tetra-hydroisoquinoline-3-carboxylic acid, and ALB-127158(a).

9. The method according to claim 1, wherein the therapeutic agent that treats or inhibits obesity and/or reduces BMI is a CALCR agonist.

10. The method according to claim 9, wherein the CALCR agonist is calcitoni or amylin.

11. A method of identifying and treating a subject having an increased risk of developing obesity and/or increased body mass index (BMI), the method comprising:
   identifying a subject having an increased risk of developing obesity and/or increased body mass index (BMI) by determining or having determined the presence of a Calcitonin Receptor (CALCR) variant nucleic acid molecule encoding a CALCR predicted loss-of-function polypeptide in a biological sample obtained from the subject;
   wherein the CALCR predicted loss-of-function polypeptide comprises S18P, R92C, K125fs, I178V, S209N, R355O, F390V, V392I, A422V, R432C, S456F, R461fs, or N487fs; and
   administering a therapeutic agent that treats or inhibits obesity and/or increased BMI to a subject that is heterozygous or homozygous for the CALCR variant nucleic acid molecule.

12. The method according to claim 11, wherein the CALCR variant nucleic acid molecule is a genomic nucleic acid molecule, an mRNA molecule, or a cDNA molecule produced from an mRNA molecule.

13. The method according to claim 12, wherein the determining step comprises sequencing at least a portion of the nucleotide sequence of the CALCR genomic nucleic acid molecule in the biological sample, the CALCR mRNA molecule in the biological sample, or the CALCR cDNA molecule produced from an mRNA molecule in the biological sample.

14. The method according to claim 11, wherein the determining step comprises:
   a) amplifying at least a portion of the nucleic acid molecule that encodes the CALCR polypeptide;
   b) labeling the amplified nucleic acid molecule with a detectable label;
   c) contacting the labeled nucleic acid molecule with a support comprising a probe which specifically hybridizes to the CALCR variant nucleic acid molecule encoding a CALCR predicted loss-of-function polypeptide; and
   d) detecting the detectable label.

15. The method according to claim 11, wherein the determining step comprises:
   contacting the nucleic acid molecule in the biological sample with a probe which specifically hybridizes to the CALCR variant nucleic acid molecule encoding a CALCR predicted loss-of-function polypeptide, wherein the probe comprises a detectable label; and detecting the detectable label.

16. The method according to claim 11, wherein the therapeutic agent that treats or inhibits obesity and/or reduces BMI is chosen from sibutramine, orlistat, phentermine, lorcaserin, naltrexone, liraglutide, diethylpropion, bupropion, metformin, pramlintide, topiramate, and zonisamide, or any combination thereof.

17. The method according to claim 11, wherein the therapeutic agent that treats or inhibits obesity and/or reduces BMI is a melanocortin 4 receptor (MC4R) agonist.

18. The method according to claim 17, wherein the MC4R agonist is selected from the group consisting of a peptide analog of MC4R, a peptide comprising the amino acid sequence His-Phe-Arg-Trp, setmelanotide, 1,2,3R,4-tetra-hydroisoquinoline-3-carboxylic acid, and ALB-127158(a).

19. The method according to claim 11, wherein the therapeutic agent that treats or inhibits obesity and/or reduces BMI is a CALCR agonist.

20. The method according to claim 19, wherein the CALCR agonist is calcitonin or amylin.

* * * * *

SEQUENCE LISTING

<160> NUMBER OF SEQ ID NOS: 39

<210> SEQ ID NO 1
<211> LENGTH: 150192
<212> TYPE: DNA
<213> ORGANISM: homo sapien

<400> SEQUENCE: 1

| | | | | | |
|---|---|---|---|---|---|
| agcttcacag | ctgggagagc | gcaggaaggc | gccgggaagg | tgagcctcct | ggactctggg | 60 |
| gaggtagaaa | gcaagccagg | ggaaagaaca | gttgtctttt | agctgataat | acaacctaga | 120 |
| cttgggtctg | aaccacctaa | gacagattta | aagtgtcaga | aaaccaggag | aggggcggag | 180 |
| agggaggact | gagactaacg | cagtttgctc | tcgcatcaaa | ctaggaaagc | cagcccacca | 240 |
| gcgtctgggt | gggctgcgcc | gcgcggctgg | cggaccttcc | cgggttggag | aagtgcgcac | 300 |
| gtccgcacct | caccctgcgg | ctgacatctc | ctgcccagga | gatgggcgct | gaagcttgag | 360 |
| cgcctgagtc | cctggagcca | cacctgcgaa | cacccttttgc | ttctattgag | ctgtgcccag | 420 |
| ccgcccagtg | acagaattcc | aggtaaggag | cgtttggaaa | tgagcgggac | ttaacgattt | 480 |
| ggggtgtcca | agggatgttt | aacagtgcag | gtgctatagg | caccttgctt | tttgattata | 540 |
| gaaatgtggt | ttgattgcgg | tgcttgtggt | tctcatgtag | ggtcagctag | gtcttagatg | 600 |
| cttttacttta | cccttgtcaa | agaaaaaaga | aaaataggtg | tcctgggaag | agccaacaac | 660 |
| ttatggtttc | gtattgaaga | atcgtttgat | ttcttgtgac | ttttactatg | ttgttcatat | 720 |
| caattttccc | tcaaaagttt | tattctccaa | cttattgggt | aggaaaatta | cggaggttaa | 780 |
| agttgtgaat | tttcccaaag | ggtgtttatt | aactgacaaa | catataatat | cagcatctat | 840 |
| aagatgtgtc | atggttgttc | tggatattgg | aaatgagcac | agtagtgaat | ggagttgctt | 900 |
| gttaagtcat | gttttacaga | gaatagtttt | ccaacaatca | tttatgcata | gcagccattc | 960 |
| ttcacaccta | ttaggaaaaa | tatgttgtgt | gcatagtttc | caaagagta | ctcttttttca | 1020 |
| tgatgctctt | cccaagcctg | ggtgaaagac | atcaagaaaa | gctgtaacaa | attaattcct | 1080 |
| tttctcaaaa | cattcattttt | ccttgaggtc | caagtcaaaa | atcaacaata | caattgagat | 1140 |
| tagtaaacta | tcatacagac | tttatttggc | aaatctacct | aagaaaagtt | tcatatgaaa | 1200 |
| gctttaacct | aatactatgt | gacatatgca | agaagagaac | gcagggtttc | acttgccgat | 1260 |
| cttaaggaga | ccctgactat | ttccaggctg | tggttaaccg | gaatcaagtt | atctatgtaa | 1320 |
| ggctatttgt | tgaaattatt | cggtgattga | aggtgaaatg | ttcaaaataa | gtcaaagttt | 1380 |
| tacaatgtag | ttcttaaagc | taatctttaa | attacagagc | gtccgagttt | aagtctgtct | 1440 |
| taaatgatca | tagaaagcaa | atattttatg | tatttgggcc | agttgactta | ccattaagga | 1500 |
| caaagtagga | atgcttttag | tattatggaa | tttataaagt | gtaatttcta | ataggatatt | 1560 |
| gctagcctat | gagttcagta | gtaaaataac | tcagctttaa | aaagttgaga | ttgctggtta | 1620 |
| tacaccagta | ttatgagaga | aactaagatg | attagatttg | taaaaccttt | acagtttaag | 1680 |
| ttggtattct | cagtggatac | tcatttctac | tcaatatttt | aacataactc | aaaacatcca | 1740 |
| tcagccagga | tttgttctgg | ttcaatgcct | ctaacctgta | gttatttta | tgaactatag | 1800 |
| cccaagaata | atatctggtc | atattataaa | atgttctaag | tttattcatt | ggctacatca | 1860 |
| acacaataag | taaacaagaa | atcttcatta | taaccagttt | ataagaacac | atagataatc | 1920 |
| ttggagttgt | tttgtttcat | gattctcaaa | gttaaaaaga | aatagctgat | ataaatacgt | 1980 |
| cttctgtttc | tcattttgaa | actggaggta | atgattgatg | gtggatggag | agcatttgct | 2040 |
| ctaatcagtt | gaagaaaggg | agctaactat | tagtttagtt | gtgccatggc | aattctgttc | 2100 |

```
ttgatgaacc tctcagactc tgtcaatgtt aacatgaatg gaaatattat ctactgttgg   2160 ttttattag agtcctagtg aaatggaaat aggagaccgg taatggtttc aatgataatc    2220
taaatcagta ttctcaactc gggctgcaaa ttagggttaa taggagaact ttcaaaaaat   2280
acggatgctc agccttaccc caattcaatc aaatcagaat atctgtggaa agggtctgca   2340
atttgatgta tttctttagg tgattgtaat atgcaaccag gattgagagc cactgaccaa   2400
gagggtttcc accagacttg gtagaactca ttgatgtggg aggcttttga taaaaataaa   2460
tgttgtttgt tatatcgctg gtcaaatagt ttttctttta aaaaaagaa acatatatgt    2520 ataaacatac atatatatgt ataacttgat cttacaatta aagaaaaat attttaatat    2580 ttgatgttag atatttagac cgtaacagct tctcggaaaa acatttttta tccagaaaac   2640
aagctattga gtttgaaatt gatctgccca tccagaaaat gttttagtaa atgaactcca   2700
gctttaagag atgttgaaaa taatacttga tgaaacatac aatttcatct ccttttgctt   2760
aagacctgta tactgtgtaa agtacaaata cgtacccttt tgaaagagga gaagaggaa    2820 aatagcatca ttcccCttgg cacactaact accatatacc cggtgccaat gataatctag   2880
tacttttaca aaaaatatgt tttaagctaa gagtagcctt gtgagttaca agctattatc   2940
attattttat gtatgaggaa attgaggacc cattagatta atgaactcgc tcaaagccac   3000
gaaccaagta aattaaaaat atatttgaac ccaggtcttt ttaagttcaa tgatggatta   3060
cattatatat ttatttacat atttgtattt tttacaactt aacagcagca tttatttaga   3120
gataatataa gttaagagta caaattctgg cacagctctg cttgagtttg acttctgatt   3180
ccataacttt ctatctgtgt gatttgggca cataatgtaa cttctcggtg ccttaatttt   3240
ctttgtagaa taagaattaa atgagttaat atttgtaaag catttgggta ggtgtctggt   3300
acatggtaag ttctatgtgt tatatttttt taaatgtcat tcattcaaaa aaatttttat   3360
tgttatatgc caagcattgc actaagcctg aagatacata gacaaataag tcatatccct   3420
atcctcaagg atgtcgtgtc tagtagagaa tgacaagaac ataagtaatc atcccaatca   3480
ggtatagatc ttttacttaa ttaaaagcat cattcttga caactgtgtg cttttccatg    3540
tgaatgtgat cttccagagc ttcatataat gagtgttata aaaccaagtg ataagatttt   3600
gtgttttcat aatgatacta acttgttttc aattctagta tcaaaacaca gaaaatcata   3660
ttaacatatg tttctggctt cccttataca tttagaaaac cagcaatata gagaggtttg   3720
agatctttaa aattttatat taaaagtgaa tcatgaagat agaacattgg agaataatca   3780
gtagaaaaaa tgttatcagt atctgttcct caatacttct aacagtaatt ttcttgaatt   3840
ggcttttcaa aaacagtttt gtctgattag aatgtagttt tggttttgtt tttaagaaaa   3900
aaaatgtttc agggaagaaa gagtggatca caggatacag aaaaatgtcc ctaatacaag   3960
ttggcaaggc aacatatacc tcattgaagc tggcagcact tcctagtcta tgcctgcagc   4020
tctgcacagc tgcctggtac ctccagggta ccagtggata cctgaggtat aagattctgt   4080
ctttgttaaa aattaaagtc cctgtttatt ttttaaaaat agcatataaa ttggtattct   4140
ttgtaccaga ataacacaga taatctaaac tcaaggagtt atttctcaaa gaagtaaagt   4200
acctggttca gtgaaatatt taactattcc atttcactaa aatttatgtt taactatttc   4260
agtaaaattt atgtctttcc tctctcttat caagtctcag actacctcca gttttttccca   4320 tggatgctac attttcttc ctctaagtat cgctgccaca cctctagttt aagttttat     4380 tatcattaat aaaatattta ttctcctaat attcagtcac attaagtttc tatgtgctaa   4440
```

```
cttcagtgtt atagaacatg gttagacttg ttttctaatc tttaatttct cccctctgt    4500 tcataattat tcagtaatgg tccaaggact gcaagactta gaaccctct tcagcctggt    4560 atttaagatg tttcatggta taatcctagt ttagctttcc tatccaagtc aggtagaaaa    4620
cctcaacagc tccttaattt tagttctgaa gctgtagtta caccagaaaa attgactcct    4680
gatttggagt ccattcttca ctttaaccc tgtgcccttg catgtcaacc tcagtctata    4740
ttcttctgcc tcaaaattga agtgtgtgtg tgtgtgtgtg tgtgtgtgtg tgtgtccctt    4800
tacatcaatg gttccattgt agagctgctt ttctttggtt ttcatgtctc gctgcaaccc    4860
tagtctcact ccctgccctt tatttgtccg gtggttcaga attcaacatt tcaaatctta    4920
ccttccttca tccttaaaat gtattaatca ttctcccata acacatctaa caaatttcca    4980
tcctatagct ttgctcatat tttaaaactg aataaatatg tactaagtgc ctattatgtc    5040
ctagtcaggg gatattgtga cagattacag atcctgattt catggggaat ggaaaagaca    5100
gacaaaccaa caaacattat acagccctgt ggtatgtatt ccaatagaga atgccatga    5160 gggtgcctag ccggacaacc agcccggaca tcagggaaat tttctaggga ggttacccta    5220
aagggcatat gattcagcat tgaaatgaca gaacagaatg agctagataa agaggggaag    5280
aaatgaagtg ttacaggcag gacaccagat tgtggcttga aacaacatgg tgacttgggg    5340
aaaccacagg tatttttgtt gccccagcag ggttaaagga cacagattat acacaaagaa    5400
gcttgcatgc ctaccatact aaagggtttg cattttatca ggaagatagt ggggggtcct    5460
tgaaggagtt aatataggtt actgaaataa tcagatttgc cattttggta gatctctctg    5520
gtggaaaata agaggcatat tagattgaaa aaaaggatgg atacagatta actggacaca    5580
cgcagcccta ctgcagtgac agagggaaga atcaattagg gcctccttgt tggagacaga    5640
aaagaaaaaa aaacgaaatt atttttaagg tagattttgt aggatttggt gaacgataga    5700
aattagaggt gagatgaaag agaaaaattg tatgatgaat tccaggcctc tttcatggat    5760
aataagagag atgtgatgtc attccaccaag tcgggacaag gagtattttg gacaggcaag    5820
ataaatagtt gaatttggag gaaaaaaaaa taatgtcttt ggctcatcca tgtgatgatg    5880
ttaagtagaa gtgcatatag aaattagtgc ctcaagagag aatttggtac tagaaatata    5940
aatttaagag acatagtgaa tctatttcag ctgacagcat aggaataaag catattatct    6000
ctggagaagt aaaacaggg aataagaaa gaaacatag aggaaaaaat taaggtaga    6060 aaattaaaag aaaagtaaaa catcttagaa tcctggaaag caccaatatt taagggaaa    6120 tggaaaacaa tcctgcaaaa aaaagacaga gatgaaagac tacaggagag agacagagag    6180
agagagagag agagagagag agagagagag agagagagag aaagtaattt tatggaaacc    6240
agggaggaga aagcgagcac tcatgcggga tgttaccagt agatcaagtg ggataaggat    6300
tgagagctcg caattgcatt taattgagag caattttagt cgtgagttgg gtgtgggttg    6360
agaaataaat gtgaaatgag gaatggaga cactgattgt acacaataat ttcaatcagt    6420
ttgagacgcc tgccttactt tattttccct ttttgaaagg tgcagtctcc taaagcttaa    6480
cttacatgct gcttccttct ttttagcctt tcctggacag cgtttaatcc ccccaacaaa    6540
gatgtcatat cacatcatga ttgatatccc ttgttttaga gtttccagag gtcccatgca    6600
tgtgagctgt gtgcgtttgc atgtgtatga atatataggt atatattaaa tacccatgta    6660
gtatgtaaag tattttctc tgttgccatg cattccattga aataatttc ttaatctctt    6720 tattatgata gtgtatgggg agaaaaatga gtttataagc ccctgccctc aataataatg    6780
atctggaaat tctaggattt ctgcatatac caaatatttt ccagactgtt tgtgtactta    6840
```

```
aaagttgcat agagcaggat gagttcatgt cctttgcagg gacatggatg aagctggaaa    6900
ccatcattct cagcaaacta tcacaaggac agtggcatgt tctcactcat aggtgggaat    6960
tgaacaatga gaacacttgg acacagggca gggaacatca cacactgggg cctgttgggg    7020 ggcaggggc tggggaggg atagcatcag aagaaatacc taatgtaaat gacgagttga     7080
tgagtgcagc aaaccaacat ggcacatgta tacctatgta acaaacctgc acgttgtgca    7140
cgtgtaccct agaacttaaa gtataattaa aaaaaaaact ttttataaaa aaatttgca     7200 tagataaatt tttcaggcca aatatagcaa tttttgaatc acaaattata acattttata    7260
cttgttttat ggtggtttaa tctccctttt gtattatttt cttatttctc tatcagatta   7320
caaaagacag ggtcatcatt atttctttgt cccagcacat ccaggagacc ctctcttctc   7380
ttagagaaat tagttaagac ttccctaaat gtgtccataa ataaagtgtt tttatttct    7440 cctgcacact gaggcttaaa gttttcttgt tttaagttat caactagctg tttccccaga   7500
gctttcagct attcatctgt agtacttcct ccaaaccaat aattcattca tattcttaac   7560
atccattctt ctattttggg tttgagttgg ttttctttag tgagcattta aaacatagca   7620
cacatattca gaacatagca ttcagtttaa tcatgcagaa ctgttcccca acagccctct   7680
gccctcttaa tcacaaagtc atacctctat ttctcctctg cttcttgcac taggctggag   7740
ctacttaggt ggtatttata cctcttatag gcaagaaaaa caaaactaaa ctaaacattt   7800
ttccttctca ttttcctaat gtggatccaa gccctgaaag caattaatcc taaattgttt   7860
gaatagctga ttttccgcaa gttaatatta atacctccta gatttcccag gtataactaa   7920
aaatagaaaa caaaaacaaa aacaaaaaac agctactatt cattgagccc ttactgtgtg   7980
caggatacaa tgatactcag tgacttcctg agacaatcat atggtatatt atcaagccca   8040
ttctacaggt aaggaaatag ggcagaaaac ttacagggac ccagcaaggt tcatacatct   8100
ctgagtggca gagctggaac tcaaacctaa gttcgcctaa aaccaaaaga ctatgctctc   8160
tctgctgctg tactcaaatg gaattttgaa ggcgacttag acgtttctttt attttaatat   8220 aattggtata ttaattgtct tagatgatca gagcctgtaa gtaacagaat taggagcctc   8280
tctcaatgga tatttcagcc gatctcttat aggctttaaa ctcagctctc caactcaatc   8340
aggccaccgg aactgtgact ataccctaaa ccaaattcca gccttttggt ataacctgga   8400
atagttcagg atcacacttc atattaagtt tacattccag atagctaagt atacaaacat   8460
aacattactg cacagaaaaa aaagtgaaaa tgtgatatag ttcttctagg atttcatagg   8520
tttttattgt ctgtcccaaa tctgtctatt aagtaggcag acatcaagta aatttaattg   8580
caaatggatt ttagtttggt gtcagctctt aataaatatg aaaattatat ttattgtatt   8640
ataggaaaaa aatctctttta ataataataa ttttaaaga aaagctttgc tttttgagat    8700
ttcctctcta gtgaggtgtt cataaagtca atgcaggcaa caagggaaaa agaaaggaaa   8760
attgtactgc tgccaaattt aaattttaaa ttgacttgac tcatccatta attaacccaa   8820
cttccagcat aattatttgt ttctaacctt aagtctgaca gatagaattc tttcaagtat   8880
gaggatgtat catagaaaac attggtgttt atggacattg gaatgaatt tctttcgccc     8940 aagattcaca gaagttcatg gcacagggta cataataatg caaattgctt tagcaccttc   9000
ttcactgggc cttctacagg actgaaaggt cagggtatta gaccactttt tcattactaa   9060
catcacatag actgcaaagg tggcactaag gcaaaatccc agcaaagtgg tgaatgatcc   9120
ttgctcgagg gccaatttag aaaaaaataa aaatttactg ggtggcttct tttcctattc   9180
```

-continued

```
aaaatgaaaa caattgtatt gcatcccatg aggaaaatat atattcttca aattagatgt    9240
gttattttag tgaatacaag gtcaatgaga aacttagcat ttcttctcag ctactaaaat    9300
attaatatct gggcatattt gaagagtagc aatgtggagt ccacaaatat caaaactgga    9360
agttatggtc tgcattttaa tttgttaaag aggcatctct agcatttgaa gtaatgctat    9420
atatcttctt gataactaat attttaccct tagtattatt caggagccca gtgcattcat    9480
taaagaggag accatagcag agatgacata ttttccaacc aggaggtaat agttctgcca    9540
tgaaaactcc agccttctga ctccacatct agtgctctcc ctaaaggaac tgcaaagttg    9600
cagggagcca ttagcaaatg cagaaaaata tgtgcattaa tgtacttata gatgacctca    9660
aagacagtta aacacatgaa taagagtggc tctgcattac attgtataag aggcagaact    9720
tgtctctcat gtcccctccc cttctgctag tttgtcccgc acctaccatt catatagtat    9780
tctcatttat tctagaagcc agccttccta aggaaaagcc tcactgtttg agtctttcca    9840
caatatctct ctaaactccc tttgtcccta cttcaaaatt aattacttttt attttgccct    9900 attcctacaa cgcctgcttt ctgcaaagta tgacagtgaa gtaaacacgg ctaccttca    9960 ggaaaaaaaa aaaattggc tgggtgtggt ggcccactcc tgtaatccca gtattttggg    10020
aggctgaggc aggtggatca cctgaggtca ggaattcaag gccagcctgg ccaacatagc    10080
gaaaccccgt ctctactaaa aatacaaaaa attagctgag ggtagtggtg tgcgcctgta    10140
atcccagcta cttgggaggc tgaggcagga gaatcgcttg aacccgggag gcagaggttg    10200
cagtgagccg agatagtgcc attgcactcc atcctgggca acaagagcaa aactccattt    10260
tttttttttt aaaagtgtag tatcaatgtt aatgatgtgt tctttgatca aatgtgtttg    10320
agtctttatt cccaaccttg aagaagcttt atactaaact taagcatgtt aaaagcttaa    10380
tatccactgc ctctaaggta gccagaccag tgtcatctat cacttggacc actccaacaa    10440
ccttccatct gacctgccca ccagcactct gtccccccccc acacattcac cacttggttc    10500
ccaaagtgct ctctttctgg tagattctcg gaaattaaat gatagtgttg gcactgattg    10560
gaatataatc taaacagaga caagtgtgaa actttgatca aacccagatt cccagaaatg    10620
tgtaatttct acttctctaaa aaaaaagtag gttgtgaaaa cttcaagaa aactgggata    10680 tgaaatagac attgaaatat ttcaataata acaataatgg taataatagc taacacatag    10740
tacttactat gagccagtaa ttttctatgc cttttatcga ttttaaggta tttaaatttc    10800
gcagccaccc tctaaggtag gtactatttc acactcttac tcataaggaa actgaagaac    10860
agagaggtaa gtatcctact gaagaacaca cagctaatat gatggattcg gaaatgaacc    10920
aaggaggtct agctccagta tgtaagtaaa tcagaaaagg gaagtgtgct cgttataaat    10980
gcatgacagc caaagctctg tcgttaggat ataaaatgtc tttcagtttt gcattttgtg    11040
tgcctttgag cagcagatcc atgggtagaa agtaaagaga attaaatagc gattttttctt    11100 atttattcta aatattaacc tctacagctg tcatgggatg tactcaggct tatagtattc    11160
cactctgcat tgtgatttac acaaagggaa aattgtgctt tgccaggttg acatctcatt    11220
cataaaaatt agagtcaaat gcaaaaacct aatctgcttt actcttttaa aggtgtgatt    11280
tctactaaca aaatgcaaaa tacaactctt agcaaaacat ggctctaaat agaatttcaa    11340
aaccatacat tgattactta catgaaaatt agtcagaaac ccatggtatg tatggtttta    11400
atgatgtgga gagaaaaaga gtggtctaaa aatggcaagt aaaaaataca ttgaatttta    11460
attaggctaa aaatagtcaa gtttcctatt cactcacttg gaaatgataa actttccaag    11520
atctattttg gagcatggca actctttttcc atgtgttcta aatggtctca tttccctata    11580
```

```
tgatgactac cttggcactc tgtgtacttg tgcaacggga gggatttgtt ctgatactga   11640
aaggaaactt tgtgtgtact tccatgttca ggctacacag cctttgcaa gtgactttta    11700 tttactattt ctgatatttt taaatttatt taccatattt gaggttattt tcttttctaa   11760 tgtaattta gctcttttat ttaccgtttt taaattttc atacgttcta tatttgaaca     11820
tgctttagtc caaagctttt tcccttcat tgctccagct cattttaaaa ataataaaag    11880
aaagaatatt gatctcaaac cttaactgct tacattagat tatccaattt ccccatgaat   11940
tagaaaattg ttaggatatt cttattgaa gagccaagat tatagtaatg caggctgatt    12000
ttatctattt gttttactcc atcactgtcc agaatcttcc agctggccag attttgcccc   12060
acattaaata aagaaaggg ttgggttcca gatataatca caatgatgac tagtgggcaa    12120
caggtgtggg agataaatgc accatgggtg attccttgag ttgtccagga cacctgaaaa   12180
tataagctta tgcaggaaag aaagcaagta tgtctggtct taccatcata ctcatcttac   12240
tcatatccaa gctggaggtg ttttattaat tataatgtct tcattgtttt tgttgttgt    12300 tgttgttgtt gttgttgttc cttttataa tacttgttaa gtagagctcc tgaatagata    12360
ttgctcagtc tttaagtgaa aatcacgcat atgttttgct tttaacacta ttatcaggct   12420
tgttgataca tgccaagcta tgtacaaaca tgcattacct catttaggct ccacagcaac   12480
tctgaaaact aggtactta tctctccaat ttacagatac gaagactgaa atcaaagaa     12540 gctaaataaa ttaataatca taagaaataa gaataaaaat aattactatt attactaata   12600
atagtgttaa gttaaattta aaactaacat ttattgaagg cttaatataa agattcttgg   12660
atgaatcatt ccatttaatt ctcataataa tcatattatt atgagactta catgatttat   12720 tgttatacc attttaactc caggaaatga tgaggcttag agacatagag atcgtataac     12780
cagaagcaga ggcaggattt aaacctaaaa tacctaacta cagagctcac ggtctgaatc   12840
accgtcctgt actcctactg aaggcagagc acacattttt acccagggcc tgtttgctga   12900
acagcctgtg attttcagg gtctcacaca gcttttaatc taaaacagtg tttctcaaat    12960
ctggtctaat gatccatgct gatccacgac agggtttcag ggtttcactg tctggcagca   13020
aaataaaaag atagaagata attttaagag ttttttcttac cattaagtat gttcaattta   13080
aagaatcaca ctttgttctg ggattatatc ctttcccttc tggatcaaaa atatccctcc   13140
tttttatcta atgatggtga tagttgatga tagtatttt taaactctt ttaattaaca     13200 attataaatt tcttaaccct atgtccctg cctcacactg gaaaggaat tgtattatt       13260 tatctggaaa attttaaaat ctgggctctt ttgaaaaagc aaaaatgcta ttagggaatg   13320
aagggtggta cccaaagcaa cttctgtaag agtgtccaag attaagcctt atgctaggca   13380
gtagcatttt atggttttta aagaattttc aaggatgcag gctacacttg aaaaaaaatg   13440
atgttattag tgtgtgaata tatttttata gaatagcact gttcagatac aaaacactta   13500
aactttgact gagtcatgtg catgcaacct actaagtgct tacacattca gcatctcatt   13560
tgatctgcac ccaacactcc gtgacacagt gctactgtaa cagaaaggaa atacaacagg   13620
atatacttct tatttgtatt attcagcctc tcttagcctc agtttccttt taggaaggaa   13680
ttgtttctat cttaaaggat tatttcgtgg attgtaaata atgtaggaaa aaatttggtc   13740
atggcacaag gcatatagca gtcaataact gctatctatt gttgtaatga ttatgatcct   13800
cattttacaa ttgagaaaac tacaactcag attaaagcat gagttaaagt agttcatcgg   13860
gttaagtgat gaagttggag cttgagacaa attctatctg catccccaa gcttcttttg   13920
```

```
gttatccctc acccacaatt ctatatgcat cccaaacttt atcttcacta tcccacacca    13980
caattttagt aatggttaga agctgagaaa tgccactgat ttaaatgtgc ctccaccatt    14040
ctgtagatat gtgtctttgt ccacatggtc acagcaaata aacttttcag tagaaaaatc    14100
aaataaaatt taaaatgatt cattgtacat atcaagccaa taaagttgt attagaacaa     14160 atagtataaa ttaaaattgt aaagattttc agatgatctg aaaagtagga tcctacagtg    14220
cataaaggag gccgtggctg aaggtcacca gtttaagggg aaggtaaaat ttgaaggtat    14280
ctgtaaaaga tacctcattg tataataggt gcataccagc agatatattt ttcaaaatta    14340
tagataccaa tagtcagtgt gcttatttat gttatttg ttttggttt aaattaccta      14400 gagagtgacg tcatctctct agggtagagc attgttttaa ttgtcaatgg aatattagaa    14460
aaagtgggtg tgtcactgat tccttagtaa aaagctttat tttcatcata attctaaaga    14520
ataaagagtt tctgtctttt taaagagaaa gcagaagtat gacatagttc agtcctcaaa    14580
gggagaaaat gaggaaggaa aaacagtttc ttttccttc tttcagaggg ctttgttttt     14640
ctcttactgt aacatactca ttagggtccc atctcttgtt ttgagctcat cagagagttg    14700
gattttaaat agctgtttct aatatattca gagacaagta aatactgaat atacactgtg    14760
ttgtgagaat gagtatcaca aacttaaaag atttaacagt tattaagttt catatcttcc    14820
tgtgatttag ggtggaaatt tgcagcagag agattattac atgttatgta agccaccaga    14880
cagaaaggac aacaaagtcc caatctccaa agggaagttg agttataaga gacaggaata    14940
ccagtgagaa gtatgagaga gtgggtggga gataatgttt agaatctctt ttgctgcccg    15000
caatttatga aaatggcttg aaaatattta tggtcaaaga ccgaaatatt tcttcaaaga    15060
agattagctt tgctccatta aaagtaatga gtagaaatat taaaaaaaaa aaaagtttta    15120
agtacctgag tatcttgcca gcaactgacc accactgcta aaagtgagga gagacacagc    15180
tttcatcatt gggactgcag tttatttcag gtaatggaaa tattttggat gaaataatag    15240
attgactaat gacacaaata aatcattctg ctaagcccaca aaagggcaaa ggtcttggta   15300
cataacccag gagggtgtga aagtcacttt ttaataggca agctgcaaaa aaccagattg    15360
gcctggttct gctgaacagc aatcatggaa actgatgtgt tgtgtcttag ggactgaggg    15420 gaggggtgg aaaagttttg gctcctcagt atctaattaa gcaggactgt gctttggaca    15480
gcctggtttg tgtgtgtgaa tctgggtaag aaagaggtgt ggtagaagct tgcctaatgt    15540
gcctactaat ttttaaagtt acaatttgct gccagtctta ccatattttc tcaaataatt    15600
tttcaaactt cccttttatc ctcatgacat ggaagttgat gacagggaca agaattttt     15660 ttgttgttgt tatttgacag attttaaac ctcccatgtc atcccaacac actgctctcc     15720
ttgctgcact caagtggtga ttttctcact ttaatcagca attgaatcac ccaaagggct    15780
tgtcaaaaca gattgctggc cccactccca gagtttctga ttcagtctaa ggtgaggccc    15840
aaggatttgc atttctagta agttctcagg tcattttgtt gctgttggtc aagctatcaa    15900
gctcgcattc cttccccggg atctcatttg acatactctc ttccccatcg tttccacagt    15960
tcaagaggtt ttgagtgaag catttcagat tctttgcttc atcactaccc atgtttctaa    16020 tattttctt tcttccagta atttctttcc aatattccaa atttatatga gaagaactg      16080 tgtaaataag aaaaaaaagg ttttttatt ccagttaaat gatgataaat ataataagag     16140 tctttatttta aaagactatc aagaacagca agacatgtga aacctacctt tttcctctca   16200
atatctctac tgattctttg agaaatacag agaaacaatg aatctctatt tacttcaaat    16260
ggcattcttc taactcacta aaggtgaaag ttccaggaaa tatttttct ttctaaaaca     16320
```

```
aatagcagag taaataatgt cattttaagt agtataaata aataaacatt atcaaaccat   16380
ggtatacaaa gaaataaaga ttctaccaat ataactactt tgaaagctac tgctactgga   16440
agaataattt tataaagcac aagaattgtt ttatttcttt ctaaaaattg gatacaaggc   16500
agtaggtaga aggatattta tatttttgtt ttatattgtt ttctgtattc atgattaatt   16560
tcatcagtaa gaattttaa gaaacagtaa aaaaaaaaa aaggtgttaa aaaagactac     16620
aagatttaag tttgtttatt caactcacct atattgagtg cctagtctga gctaagtatt   16680
attttaggca attataataa agacaaggcg acatttccct gaaagcctct aaatcacaaa   16740
ctaggtaata aacaaataaa caaatataac taaaagatta aaaagagtta gggtcttgct   16800
ttttcaaggg tcaaaacata ccatgaagct gaaatagcta aagtactaca gtactgacac   16860
agaaaaggat aaatagatta aggaaacaaa atggagtcta ggaacatatt ggaatttagt   16920
atatgataac attggcattt taaatcagtg gcaaaatgac agaaaattca aagcagatat   16980
ctaccttcta tcatactcag aaacaaatat tgatacacta ggagaaacac aagatgatac   17040
atttgttata atctaggtgt tataatcata aacataacac aaaacccaaa agccaaaaga   17100
taaagagaga atgagacttg actatatcta aatataaaat ttctatatgg tgataaattc    17160
tgaaaataat aatatgtcaa ctaacagcat ggaaaaagta ttcacaatca actaacagca   17220
tggaaaaagt attcacgatg tatagaacaa ataatattca ttgaacacat attctgtacc   17280
aagcaccata ctaaaaattt acaatcacca tgttattttt aagacttaaa aactatcatt   17340
tttttcttgt atatgttaat tagcttgatt tagccattcc acaatgtata catatatcaa   17400
aacataaagt tgcataccat aaatatatat ataatattaa tttgtcaatt tttaaatttt   17460
ttaaagaaat aaaaactatc agatgtgtac tcttattatc ttcattttat acataagcag   17520
tctgagattg gagacatttg gtaaagtgcc agtcatctag caagaaagag gcaaaactgg   17580
gattcaaatt cagatgtctc tgactccaaa gttattaaac actgaggtaa aaagagtttc   17640
tataaattca aaataaaaag gacaaaatgt aggaagtcat gggagatgaa ccaaatggcc   17700
aaggtagtta tgataagaca tttagcctca ctaataatca aagagaagca gaaaatttag   17760
tattacttgt gaaaattaca aatcccatat gctttggctc agcatttcta catatttct    17820 accctacaga aatgcgagtc tttctgtaca tatctttagg tgcatctaga atattctttg   17880
caatatcatt tgtagtattt caaagacgga tattgcctaa atgccaatca ataggaaat    17940 actcaaatgt attatgccat acacctattt caaaagaatg aggcagatct atatgtactg   18000
acatgaaaat atggtcatca tatattaagt aaaaagaaag tttcaggaaa aaatatatat   18060
atatagataa aaaagatcct gttgtgtaaa attatacatt ctacacatgc ctatgtgcac   18120
agaaaaatgt ctagaatggt aaacctgaaa ttattaactg tttctacttc tgagaagtta   18180
tgttggagaa gtagaatggg tatgagggaa aacttttaca cataaaataa attacaaaac   18240
aaaagttatc tccagtttag atttcataat ttaaatatg tattttgtta aaggcaatca    18300 gaaaaaata taatggaaaa tattttagag caaatttaa tgaaaaagtg aaagacattt     18360
aaagacattt gaactcaaac agtgtagacc agttgttctt gaagaggatc tcagaaatcc   18420
aggaaaatac ttctcactta tatctgactg aagaatatca gtgcccttta gggtcaggct   18480
ttgctttcat gccaatatca ggccactgat aataaggtct atccaaattc catttctgtt   18540
ttcatcctcc atcccactc tactgttta aagcaaacag ttaccctgga gaaaaaatt     18600 caagtatccc caagtatctt gatgacttaa ggataacctc aatggattca gaaataattc    18660
```

```
catggccatg ttcatttagg aactctttgc aggatgcagt atttggttaa gggaagccct   18720
acagtgtgaa atatctgtcc caagcaattg ctatttgagt cacctctgta ttacagaaga   18780
gttttactct tttcattatt gttctaaaag atctcaatgg acatgactgt tttcattaaa   18840
ataaaaatag ggcagaaaaa cttgttcatt cataaatgcg ataaatatct gtccactgat   18900
cagcccaagt ctagtttcct tcctatcaag ttcttgttta ttaagacctg ttttttaaaaa   18960 tatgatttca gattatatgt tagctttatg cttctacccg ttttaataaa catatgataa   19020
actcagtgct gtgcttaatc tatgccactt tgatataatt actggactgt accaataaac   19080
tatttgccaa gtttggaatt caatgttttcc catttgataa atggttgaaa tggtaaatcc   19140
tttcaaaaca actggaaggt agacatcatt caaaatgctt agggttttttg ttgttgttgt   19200 tgttgtttcc ttctccataa atgactttttt gcagtttaaa ccactatcaa atttatttgg   19260
actgctaacc ctagtccttt cctgtctatt ccagatgacc ccaggagtat gcaggcttgt   19320
tatttcttcc ccatagctag tttgagagta atgagtcagc ctttttctag cacatccata   19380
gtgcctcagg accctgcatt aactgtatcc acactgttttt caagcacaga aatgatgggg   19440
cattgctgga gcatgatcag ataaaagtcc ccttccaact atcaaaccct gacctccttt   19500
tattcatccg aggagttctc cagtgctctg cagagtactg acacatgagt agtatgcctg   19560
tttgacatcc cctctcatct ggctgggacc tgcttacaca gaagttccca gcagccctca   19620
agcccaaggg agatggaacc tagcaattcc ctgtaaccag catcgcctgt cccctcagtg   19680
gggtcagtac ccagactctg gagtcagaga ttctaagatc aagtcttggt cttgctagtt   19740
actgccaata tggcctacaa aaacaatttt aattttctca tgcttcagtt ttctcacata   19800
atcaataggg atgatcctag ctctcagatt tactgtgtca ataaagactg aatgattaag   19860
gttctcagca catgactagt gcagaataag tgctcaaata gtgatattgt gtactttcta   19920
aaatgacatg tacgtataat atatatatat atatatatat acatggcctg gcaatttgaa   19980
catctatcat ctttgctttc agaattctgc acttatccta acctgggaaa tgggtcttcc   20040
ctttggaacg taatgcttag attaaactgg aaataagcct gctaatgggt cttaaacttt   20100
ctgctcttcc caatgtgcta ttgctggact ctgtattgct atagtccttt ctcatccctg   20160
cctcccgtag gtttagctac cttgttctca tgaccagaaa gggtaaaaga tcagtataaa   20220
tcccttgttg gaaatgaatt atgacagggt taactttaat cattgaggtc acttgtactg   20280
tctagcttct atcttctttg atctctttcc tttctttaag gaaaatttgc atatgtaagg   20340
tggttcttat tctataagaa atagaaacag atatattcta gcaagtgttg aaaaccttac   20400
ttgccaaact ctaggaaata gaatttcatg agaaataaat atattgtcta acacatgact   20460
tgtaatagaa atgatgtttc caacaaagca tattttatac actaattttc atgatggctt   20520
attaaaaatg tacaacttct catataaaaa ataaacagat aaaagcagtc ttgtggtaat   20580
ttgacaaatc cacgtgaaaa tgtcacacta aagcaaaaag tggagtacat atagcaatgg   20640
aaggtttaat ctctgaccct gacaagtttt acagttaaag tttaaatcca gatttcttaa   20700
acaaactaac aaaagcagaa atgacaaata ggtttctttt catttgtctg ctctagatct   20760
ctgctttgag aaggatgctg aggtcacatc taggtgcagt gggatttagt gacgtgttag   20820
aaggcaatat ctatcatggc aatacagtgg gatagcatgg atttgtacca tgtagttact   20880
atccctgctt gcttttggat cacacagaca tccttttgta tagtcaaata tgatataatt   20940
ttgtggagaa aagacactaa acatttggtg gaagagtaca gaagattaat ctgaaccaag   21000
tgcttttcaa agcacttcgc atgtactcac tcatagaatc atcataacaa cactataaat   21060
```

```
atatgctgtt attagcccca ttttccaaat ggggacattg aggcacagaa accgtcagta  21120
acttgcccaa gtgatacagc taataatgag cagagcttat tgacagatct gtcaggaagt  21180
ctgaccccac tctgtgtctt taccatttgt attaatctgc ctccaaaatt tgttgtgcaa  21240
aaaaaaaagg gtaagttttc attaacatct ttctatggca tgcattttgt aaacctagca  21300
ccacagaacg ttcatgtaac aagtgatctt gctcattatc tggaccaaac ttctgtctgt  21360
taaaggatcc tgtccttaat acccagtacc tcctcaggat ctcccagctc ttcccttgtt  21420
gagcagctct ggaaactctt tgacatattg aaccaaaatc tccctacctc tgatttgcac  21480
ctttggtgga gcaacacaaa ccaatctaca ctgtcttcca cagaatgaca atcaacatct  21540
tgtcagtgaa atatctccac catgggtgaa attcgatgag aaagagata gcagattttt  21600
aaaataaccc ataattggat aaaagtcatt ttatttgaaa acttttccc tctaaaataa  21660
cgtgatatat tttgaaagaa gaaggtgtga ggtcaggtgt ccattatgta gccagacaga  21720
tggatacgtt gttgttttac cattgccata gaaacaagtg ctatgtttat ctcattcagt  21780
gaggaagaat ttctcgggtc tttcccaaaa gttgtgatat gtgctacact gaatatggcc  21840
caccatgtct atctggacaa aataaatccc cttttaccg ggaggagtg ctacacaggg  21900
aagaggggaa ctctacttga gcatttcttc ctatgagctc tgtcaatttc ttgttatttg  21960
agattcacaa attctcttta atataacaat ctattaatgt gctatattca tgtttggaga  22020
taatgctaat tgtcaaagaa attaggcttc tagttctaac ctctagagaa catgggaaaa  22080
gaccaaagag gagtaattac agagatgtgg tttaatataa aggttttata tcaaaccgga  22140
ttcagccata ctctaggcca tgaaagtggc ttttgtaaag acggtgctga ataaaatata  22200
gcctatcaat gggttcacaa agatcagtat ttaaccttag ttttagttga aatcatattt  22260
gtaggcccat tcatttgcat accaataaag ctgaatctta gctttaaatg acttaatgta  22320
agacctgaaa cagtgtggcc ttggaaaggg catcacataa actattagga cacccgagtt  22380
ccatctccag ctctgccaac aggttttgtg actttggtaa gctcataata tttactgagc  22440
aactgtttgg ttttgagaag ttgagctggg catttaccgt tatttaattt tcatagccac  22500
tttctaagtt aggtaataca tttaccttgt acagatgaga aaatttagtc tgaagggcta  22560
atgaacaatg cccaagatca ctcagctgat aaatggcaag gctagaatgt gatgactcaa  22620
gcttttctct gcattaaact attcctatca cttcacctcc tgagttttag tgtgtatctt  22680
tgtagccacg aggtcgacat gctctgcaca ttctttgcca cattgacatt ctttgatttc  22740
agggtaaata tttcaatata atgtcctgtt ctttttatta tgattatcca tttcactgac  22800
tgctgacaga ccttttttctt aatttgtgtc atctatattg aaaatatatc tcaatcatat  22860
ttaccaaaat atgaaatctc tacttaaatg ggcttaacac actgtatcag caggatataa  22920
tttcacattt gtgttatctg taaaataaag caaaatactg cagaatttga ctcctacagt  22980
ccaaaactac agatacctt gctgacagta gaggtcactg gcaccttcca tcctctccat  23040
ccaggagatg ctcccccacaa agggtggttc ttaaatttgt ttcccaaagg gtcaggggat  23100
ggtagaccag aagctcctac aagattttac caaattcctc tttactttc ctgtcacttt  23160
tgacctggtg cctacaaata aagttactat cgtatttgtg gaaatggatc ccaaaataac  23220
tggcactaaa aaaacctgta agaagttgt tgttatggtt gtttgaacat ttaagaattg  23280
attatgagca tgtgaatcat gtaatcaaaa agtcctcggt aataaatagg gacatcgctt  23340
gtcaaatgag ttggaaaagt tttgcctgca tatatccaga gcttcatccc tgacaaaggc  23400
```

```
tcttagaacc ctccctgatg aaatacacgt tttaagttct tgagcgcatt tcttaggagt   23460
tgacaagttc tccataaggt ggcgcagtgt taacactctg ttaatggctt tttgcctttt   23520
ttaaaaagaa ttttcttcaa cttgtttgaa aaatctcagg atggacttgc ttttatacat   23580
agtgttttca catacactca gcatatttac tccatttgta gaaatatatt ttgaaattaa   23640
gtaattttca agcttttata tcttgttttg tgttggtttg ctaattttag actcactcat   23700
aatggcttct tccttcaaat atttaaatta tacatgtcta atcatttttt cttcctcaga   23760
gataagtaga agcaggtata aattaaaaac ttaccttaa atattacaga tgtgttttgt   23820
aaacttcttg gaagtgaaaa tttgcagaat caagattatt ggtgttggat tgctaggagc   23880
tggtatcaca ggtgcactct ttgcagctga accatagtag tagctaagta aacaacaaga   23940
aggtcacatg tgcaaattat gcagatgatt cagacaaaaa catcaatgca ttttagttat   24000
ttgaatatat caagtaggtg ttttgccatc gcattcagat attgttcttg tctgataccc   24060
tttagcaatt gttacaaaac tctgtctctc gtgtgtgtgt gtgtgtgtgt gtgtgtgtgt   24120
gtgtgtgtgt gtttagccca aatggaaatg cttggttata attattgtga attctaaaaa   24180
tactgaagtg gccaacattg accaaattga caagactttt ttttttttt ttttttttt     24240 ttgagacgga gttttactct tgttgcccag gctggagtgc aatggcatga tctcggctca   24300
ctgcaatctc cgcctcccgg gttcaagtga ttctgcctca gcttcctgag tagctgggat   24360
tataggcatg caccaccagg cccggctaat ttttgtatt tttagcagag acgggatttc    24420
accatgttgg ccaggctgct ctcgaactcc tgacctcagg tgatttacct gcctcagcct   24480
cccaacttgc tgggattaca ggcgtgagcc accacacctg gcctaaattg acaattcttg   24540
tcactaattt ttctttaaag ggaaaacaaa accatataca tagaatatgt agtaaatgct   24600
gtctaaccaa gtcattattt ttcaaaataa agctgattaa atattctatt ctaaataaaa   24660
aaagattcca cctcacattt tgatatattg ttgtatttag ctaaagtgca acaaatgatg   24720
aactctatca tttatgttct gaagcaaatt attgcattta attatattgc cagtctgatc   24780
tcttcagaag atgagatttt tagtgattga aactgaattg cctatttgtg ctgtttaaag   24840
cactgctcta tcagcagcat gtggtcattt tggataggtt agctcctgga tagcatctct   24900
tgaatgtact tatcatggta atatttaaac actgttcatg gtgtttacat ctcggttagg   24960
ttataaagat acatagctgc attggctttg catttccat taactttatt taataaggtc     25020
ttcgtcaagc cctaaaccct aatagaggag gtttatctgg tcagattgtc tgaatgaatt   25080
ttaaaatcaa agtctcaatt ttttgctttg atgttttcat ttttgatacc ttaaccacaa   25140
atcctaacct aaaattattc tcctagaaaa cttttctatgg aaaataatga ttaacttcat   25200
ctcttagtct ccagggtaat tgtctttatg ttatttaaca gcaacttcct aagctgagta   25260
ttttaaatgg tttacaaatt cagaatgctc aggaaactgg aaaattcagt agttgagagg   25320
acctcattct ccctttttcta tcagatatcc ctttttttctc tctaccttcc ctagttgaga   25380
aaagggaata gactttagaa ctaagatagt catttgaaaa atatgttatt gcccttactt   25440
acaaaaaaaa attggtctaa gaatactttc tcatcattca gattttaaga ttccatctga   25500
ataaagagtt cagcagctaa aataataaat ggtgattatc caacccctcc actgtaaaca   25560
tgagaacatg aagtcacaaa agctaaatg atcaactaga catccttcat tgaataattg    25620
gcagaaatgt aacaattaga aattctgtat ctttttttgtc atgtgcttta actatatttc   25680
catttccctt cccaaaaata aggaaataac ttaaatccaa cgtaatacct ctttacttga   25740
gaatttttat aatcacagca ttacaattct caggggaaaa aaatggtata aaaatgtaaa   25800
```

```
tcttaataaa agtcccaggg agtaaaactt gaaattcata cacacacaca gacacacaca    25860
cacacacaca cacacacaca cacacacaca cttcttctgg attgaattat tgcaattatt    25920
atcaactcac aattggccaa gacaacataa ctacattatg aattctaata attcctaagt    25980
agttaaagta aagcttttt ttttccaaat gcttctctta atgagatgaa tgaagtattt    26040
tgttttgggt ttttttttc tgttttctt tattttaact agttcatgta tccatgctca    26100
aagattctat tttgcaagaa gtacacaact atcaccctca cttctattca taattttgtt    26160
ttttctgacc tcattgctga aaaaacatgt ttatatttaa aagtaggtga aattggagtt    26220
ttattatagt tatttccctc ggttctataa attcctccct agttatatgt caaaaatcac    26280
atgatgattg atcattaaga attatgtgta attttttcagc ttaacaactt atttagaccc    26340
tcctacaatg ttgttgaaag caaagaactg gaaaccacca gacttgcaca aagctttgtt    26400
aactggtcat tagagtcatt cgctttgcca acaagtccta gtgtttggag ccaagaggtt    26460
ctttatatcc ccaaaagatg ctctatccaa gatgaatgag aggtgggcta ttgtttgtt    26520 tgttcttttg taaagtggga aagggtgtt tatgaacagg agttagagaa aagagagctc    26580
cgcacacctc agacaagttg taagacagat cagtcttaga aaagagaata tacagagatt    26640
aagaactcga taattgacac tcaaaactac ttatatgccc atcccttaga aagtatttcc    26700
atagacaggg ttatgtgtac acccacttga aaaccactgt cttagggaag tctcagggaa    26760
gcaatgttct gaagcatgag gaatgtggcc ttgaaataaa catctgttct cgtgcttaag    26820
caatcagcac agtcccataa gctccttttt taggggcaaa ctaccccccg tacaatgttc    26880
tgaggccttt gatgagatgg cacagctgaa agtccatgat acagaggtca agtgaattca    26940
gaaacagccc attaagttac tgggaaagta agttactggg accaattact tgctttgaat    27000
actcaggtgt gactttccaa atgtgaggaa acataattgc gtgggattat ctattgctgt    27060
gattgagctg ggagcacctg cattctaatt caaaccccac atggttgacc tgtgtggact    27120
tctagtagat cacccatatc tctgctttcc tgtccataaa acagaggagc aaattaagta    27180
tggcctgctt caaattctct gttgaatgag tattagtaca aatgtggttt tcatggacaa    27240
agccacctac aaaaattatt cacattaaat agtatgcttc taattttaa ggcattggaa    27300 attttaagta acaaaaaagt aaatttgtta gcatgataat aactgacact tgcaatgcaa    27360
tttcaagtac ttttcattat ttgtttatat atccccaaa gttttctgca ttcagaaatt    27420
agaaatcaat aaactgcagt gctatctata gcattatgta taacataaac tataaagggg    27480
actgtgatct ataaattaac ataatgtttt ttgtgaccct aactaccagc taaaatatgc    27540
actctctagc tttgatccag atctaccaag agtggagttc ccacaagtca gataacctgt    27600
cctaagaggt ccgtaccatg agatcaaggg tctttttcct tgcttttgg catttgctag    27660 agtcaggtga gatctgtctc cattctgcac tttcttctca gtgccttctg agagcttgtc    27720
ccttcatata ctcacataat tcctttaccc gactgtggga ggataaagat gagaatgaag    27780
gcatacacag cagtttatct tgaggaagag aacccaagtc tgcatccagt ttctcctcca    27840
atctaataac atcctttgaa ttagaagtcg tgcagggtgt ggtggctcaa gcctgtaatc    27900
ccagcacttt gggaggccaa ggcaggtgga tcacttgagc ccaggagttc aagaccagcc    27960
tgggcaacat ggcaaaacca catctctacc aaaaaaaaaa aaatacaaaa attatccaag    28020
tgtggtcatg cgtgcctgtt gtctcaagct actcaggagg ctgaggtggg aggatcactt    28080
gagccagaaa ggtcgaggct gcagtgagct gtgatcccac cactgcactc caccctgtct    28140
```

```
aaaaaaaaaa aaaagaaaag aaaaagaaaa caaaaagtca ctcactcatg ggcccagctt    28200
caggacaaat gttgggaagc caccatttca ggctctgcgg ccagacagtc tgggtttgac    28260
ttccagctac tgccacttaa aaactgtgtg gctttaaata cattatttaa cctttatgta    28320
aatcagtttc tcaatgagga tcataataat agcgtctttg tcacagttct ctttaagata    28380
aagggtaatc agtcacataa aaatagtata accatataag ttgtcattca aactggtatg    28440
cttttgtgag tgaacaggga tgttattaaa attatatcag acaacaggt gtgagctagt     28500 actttcttgg gaaatacagg acatagggt ttgctctata ataaacacc tggcatgata      28560 cctggacttt gcatgatacc tggaccttgt tagagttaat gggctattaa catcctatta   28620
ataaaatact aatattgcct atgggattat ggtaaaaaaa ttcttagaa tatggcattc     28680 tctttcatat tagcattttc tgaatttgtt aatttgcaac agtattttt ttgttatttt     28740 ctttcagtaa ggggagagag tactcaaata tatatgtgta ggagagcttc ttaccactat   28800
ttcacttgtt tagcccctac tttaatccct aattaggctt agttgctaga gaaaactcac    28860
tttgtccaac agaaacctaa gcatggagtg tagtgaggag attccttgct tttgctccaa   28920
tctccaccct tgtcagatga tgaaaagggg gtgatatgag gtcgatccca tggtagtagc    28980
aggactaaag tttaacttca ggaagttgac aactattttt gtttagatta aaaaaaaatt    29040
taatactgtg tcaaaaatcc agcaaaaata attggtaatt cagaagtccc atgaagtaat   29100
ctctatactt cttgccagca tagggtcttt ttaaaacatg ttctcagggt cctggctagc    29160
ctagcatcag ctgccccaaa aatggggctt ccatcatttt ttggcaaaat atcatcgaag   29220
tccagcaggc aaggttgttt gacctggatc ttttaattca acataatcct aatatgagga    29280
cataccacgt taaatttctg ttaaatacaa cttcttaacc agaattcact ttgtttgagc    29340
ctgtctatct agaggcagaa attacactgg atagttgaaa ttcttttaat atttattgcc    29400
cttctaagtc taaatttaac aaaaccagca ctctacagcc agaggacagg atttttaatc   29460
tatgtaacat gaaaagcaac agcatatgtg aaagtcatat tttattcagg agccgactaa    29520
gttcctttat tcctgataat aatatcaact ggaatagcat ttgtgtaagg cctctgtgtt    29580
tacaaagtag gccaagatac atatatcaca tgagtacctt atccttccca tcccaccaac   29640
ttaacatgca gcaggcccaa ccttatccat gaagcagcct aacgaaaaag tccaagcagt    29700
agtaccatag agcatgtttt ctgcccttct ccacagtctg gggaaagcgt gagacagctc    29760
cagaaaagat gagttcatat tcagcctggg aaagctgcac agtggccttt cctgctgctc   29820
agcatgaaat gagccatgag cagcatgaaa tcactgacca caggtgtaga gattcacagt    29880
gacataaata tctttgctgt tgagcagttg gaggaaagct gtgggaagat ttgccataag    29940
ctcctcctgg ccaaatctgc ctttataaag aaatggtcat ttaggtcaca ctgttgctga    30000
gaagcttggt aagtcccatt ccaacttcca attaaaagac ctacggagaa ttagaaaaac    30060
atgtagatga gtctatatct cagaccattt gaaggagaaa agcaaaatac cacacagtga   30120
aaaactaaaa tcttttatgt gtgaaaaaaa accttcataa acaaaattta caagaaaaa     30180 taaaggcaaa atcacaatct atataataga tgttattaaa aatacatcta agatgtttta    30240
aaattctttc aaaaatgaca aactaatatg aaaatatgca aagaaaatag aaagcaaata    30300
ccaaggggag caaaaacata tgaaaaatgt tcaaatttac taatgatgag agatgtaaat    30360
taatgtaatt agtaccatat ttgcctacaa actggaagac ttttaaaaa attgtgaaca     30420 cccagcctta gctagtatat ggagactcta tccctcttga ttttaatttt ttaacccttc    30480
ttccatttta ttaatatttg gtatcagaag aaattttgtt tttctttat tcattaattt     30540
```

```
tggcattatt ttttttagtt tcttatcaat gtaagcagga tatagttttt tttaacaaaa    30600
ttaaaagtta ctatctctta acggaagagt gtattccaac tacatttatg gtcataattg    30660
tcatgattgg tcgtaagtta tgctgcaaat ttttcaattt ctattctgct tttttatttt    30720
gtttgtatgt taagcagttt atgtcttgtt tacttttaat ttctactgaa atataaaagg    30780
cagaagtact gtagcaatta ttatcacata caaatatacc ctaagtacta attgtaataa    30840
ttactgaggc cagtaacaga agaaaaaata caattaaaca ataatttaaa atattaaata    30900
tgatagcttt aacaatttga tagactaatg tgtgttataa ttttggttta aaaaatattg    30960
gacctgaaaa aaaactcatt ggaaaaaaat cttagccaaa aaaactagtt acagtatgat    31020
cccaaatgca caataactgt acattcttag gtgtgtgtgt gtgtgtatat atatatataa    31080
tcatgggcca tacaatgaca tttaagtcaa atatggactg catatacaac agtggtccca    31140
taagattata atggagctga agaattctta tcatctagtg acgccattgc catgctcaca    31200
tcgtagcctt actttccatg cttgtggtga tgctggtgta aatgaaccta ctgcactgcc    31260
agttgtataa aagtgtaaca tatacaggcc acgcacggtg actcatgcct gtaatcccag    31320
cactttggga ggctgaggtg ggcagatcac ttaagatcag gagttcgaga ccagcctgac    31380
cagcacggtg aaacccggtc tctactaaaa gtacaaaaat tagccagttg ccatggtggg    31440
cacctgtaat ctcagctgct ctggaggctg aggcatgaga atcacttgaa cctgagaggt    31500
ggaggttgca ctgaacagag atcgtgcgac tgcacaccag cctggtatgt ataactatag    31560
tcctatatac aactataact atagccccag agcaagaccc tatctcaaaa caaaaaacaa    31620
aaaccaaaca aaaaatgtgg catatacaat tatgtgcatt acataatatg taacaataaa    31680
tgaatatgtt actggtttat gtattactat actataacctt ttattattat tttagaatgt    31740
actccttcta cttacttaaa aaaaaaaat cagtgaactg caaaaccatc tcaggcaggt    31800
ccttcaggaa gtattccaga gacaacattg ttatcattgg agatgacaac tccatgtgtt    31860
ttattgcccc tgacgacttt ccagtggaat aagatatgaa ggtagaaaac agtgtattga    31920
tgatcctgac cctgtgggct taggctaatg tgtgggtttg tgtcttagtt tttaacaaaa    31980
aagtttaaaa agaaaaaaat taatttaaaa aatcttataa aagaaataaa atattttgt    32040 acaaatgtac aatttgtgtt ttaagctgtt ttgttaaaaa agagccaaaa agttcaaaag    32100
atttaaaagc tcataaattt taaaagttac agtaagctaa atataaatta ttggagaaag    32160 aaaaatttt ttcataagtt ttgtgtaggc taagtgtaca gtgtttataa agtctacata    32220
gtgtacagta atgtcctagg ccttcacatt cactcaccac tcactcattg actcacccag    32280
agcaacttcc agtcctgtaa gctccattta taagtgccct acacaggtat accattttaa    32340
aaatctttta aactatattt ctactgtatc tttttctatgc tgtgatatgt ttagatacac    32400
aaacacttgc catcatgtta cagttgtcta cagtacccat tacagtaaca tgctgtatag    32460
gtttgtagcc taggagcaat agggtatccc atccaaccaa ggtgtgtagt aagctatatc    32520
acctaggttt gtgtaagtac actgtgtgat atttgcacaa tgacaaaatc gcccaaggat    32580
gcgtttctca gaacttatct ttgttgttaa gcaacatatc actgtatata tttgtattca    32640
tagaaaaaca gactgagagg taaatatatc aaaatggcag caaagattgt cacttattta    32700 ttagttttg gtgactttt ctctatgtat tttttctaa ttttccaaat tttatgtaat    32760
cagccatact gtgtttatat ccaaaaaaaa ccagctacta atatgaattt taacataatg    32820
cttagcaatt agtttctcag aaagtaaaaa catcacagat ttgtctaatg ccctatagca    32880
```

```
gactgtaggg attatttaga agtctggaga tccagtttac cgtggatagc cacagaccaa  32940
actctttaag aagggtgaat agttccagcc acatagctct tgaaatttgc acatggacaa  33000
atggatagga tggaacttga attgcactca gcaaaacttt ctttgtacgt tagcacataa  33060
gtcacaatct tgtggtgtcc tctagcccat agaatcatat accaagagaa cataaaacac  33120
ctcagcagct gattttttta ataataaaag tattcagtat attttctga agtcaatagg  33180 aatttaatgc aaatatagaa gtgaatgtat cttctcccag tttctagcac ttaacttcaa  33240
ttatgttgct cttttaccat aaagataaag gccgggtgcg gtggtcactc ctgtaatccc  33300
agcactttgg gaggccgagg caggcggatc accaggtcaa gagatagaga caacatagtg  33360
aaaccgcatc tctaatgaaa atacaaaaaa atagccggga gtgatggtgg gtgcctgtaa  33420
tcccagctac tcgggaggtt gaggtgggag aatcgcttga acttgggagg cagaggttgc  33480
agtgagccga aatcgtgcca ctgcactcca gcctggcgac acagtgagac tccatctcaa  33540
acaataataa taataagttt agtgtttcat ttacaaagtc ataatttgac tttgatgctt  33600 tgggattat aatccaattt gtatgtcttg ttcagcccag tggagtgcat ttgcgtggca  33660
atcatatttt acaaattata aaccaaaaca tatcagtatt ttttcagtct ttgtaaggct  33720
atagtgagtt ctcatgccaa atcactcatt tgtcattttt cttaatgaaa tttaattttt  33780
tgctattaat attgaactat tttctactga atcctgattg attatgagtg ggcaaagaga  33840
gatgctgaat taagttgatt tacagagaaa tgttaatgtt tatatgctcc cattctctgt  33900
ttctaccact taaatataat aaagatgtat aacttttat acatataaaa tataatatat  33960
aaatataata ttatataata taaatataat attatataat ataaatatat aatatatata  34020
aaatataata tataaaatat aataaagatg tataacttag agctgtcata aagtttgagc  34080 atatttaaa attaggacag ttagagataa acaaatacaa aattatttaa aaggaataag  34140
aaaagataga gtttattagc catttaaaat atactgattg ccattgggca ctaattttgt  34200
ctccaatttt gctgtaagta aatgcaaata aagaaacaca gggagttaca taaagatcaa  34260
aatagttgga aattgtataa ataaatgtaa acatttattt ggatctcaat tcaaacaaaa  34320
ttttattaca tggtaccata tatttaaaat gttgagcatc agcacaaaat agtttcagct  34380
acaattttac caaaaacaga gtgactgtat tcaaatgggc caatgtattt acctgccata  34440
catacggaaa gagtagtatc ctacccattg actgctgtct tcctacttaa tatacacatg  34500
caactgtttc acaggcactg aaaactcacc aggtccaata ttgaattacc tgcttttcaa  34560
gtcctgctga attaatcgga gttttgatt gcacataaaa attaattcgc agtcatcggg  34620
gcaacaagtg ttctgttgga agaatcctag ggcagcgaac agaatctgaa agcagctact  34680
ctctttcttc tccccacaat tcccccaagg gaatgggact aggcattaaa agcctagtgg  34740
gaaaccagga agtactttct tattctcatc tctgctgctg tatgctcctc tgcttcattt  34800
cactgcagac ctggagtatc ttcaacagtg gacgggggcc ccacaaatcc ctactttgat  34860
gtgggttctc cagttcaggt catacaaagg cgtgaactgc ttctttcttc ttactctcta  34920
gaattgcatc agagggaagc gtctttaact tcttgggcca caccatgctc tttccatcac  34980
agcctttgcc atagaatgct ctgccttttcc ccattcagca accacctttt acatatggaa  35040
aaaccaagcc tttcagaggc gttaggtaac ttgcacaaga acacacaata aatatcagag  35100
ctgggatata acccctaggtc atacatgcct gattccaggg acctatacca tctagaaacg  35160
actctttggg tgtaattgac caaagaatac attgtcagag actcataagg agagtcactg  35220
atttcagagg aacacttcct tgtagagcca tgcattcatc aaccaacaat gatttacgtt  35280
```

```
tctcagtatt actagaacac tgggctgagc aactggtaac taaacagata tataatacta    35340
gatcctaaaa gccctgatt gaaatggcag aaatgagata atcatcatac acctactcta    35400
aatggcaacc aagattttga acacataaaa catgatatat ttgccaaaca agtgatatag    35460
tcaataaatg tagatcatca tatgctacaa aattcacaag aagcctcaga ggagagatgg    35520
gcctttgatt taagtgattg ggatttcata aatccttacc ccagggattt taatggactt    35580
tatatataaa aagaaggaga gtgagaataa aacttcctgg ggagctattg taacatatca    35640
acatattata atgtcatata ccgaataaag catataagat ctatgagttt agattcttct    35700
aagagatgaa aaatacaaaa tctggaagaa gaatagagtg gaatttcttc atctgagact    35760
cttaaactct agaggattct gtttcagaat ataataccat ccccatatat cagtgtcacc    35820
tagagtttgt taaaatacag attctagatc ctcctcagtt gtattcaact catatctcag    35880
gggattggtc tcaggaatcc actgtttaaa taatcatctg agcagattat tttattttga    35940 caaccttat tccagagggt gcatgtataa gctctaggag gtatagcaca catgaaaagg    36000
ttcatgaagt cttgagcatg tacacctatc tgtctagaga aaggtcagtg actttcatca    36060
gatgcacaaa agggtctgc aatccaaaac aaaacaaaa acaaaaacaa aaaacaggtt    36120
aagtatcacc agaatatagg aaagaaggcc aaggtatttt aaagattgag aaacagaatg    36180
atttcagtat taagggaata aaaattacct agcccaggat agaagcccca acctgaggga    36240
agatctgagc atgcagtgat attaaaaaga tgataattcc aaaaactaaa aataagtatt    36300
taccatctcc actgaaggtg gaagaagaat aactatcata aaactatagc agaagaaatt    36360
gagacaggaa ataaatactt cttcacacta aaaatgctag gaatacccca gagggtagga    36420
ataaactaga taatcatcta tccaggaagt cagacacacg aaaagatatg ttatccaggc    36480
ctatctgctt tttcagcaga acacatacta tgcattcttg gctattttg ttattgtaat    36540 aaccacaaag gtcccaataa agatagagac tttatgatat ttaaggtatt ttgagtgtgt    36600
agctttatta acaatttaag ttagtctctt gttatatgtt ctatgttctt cattaatttt    36660
ccattatttt agcaagatga tcactactac agtttagtga tttcttttaa aaggcacatg    36720
ttgaacacat tatttggcta attttctact ggaaaaatat gataaatgtt ttatttaata    36780
atacccattt taaataaact aagttttgcat ttatgaatgg gataccataa aatacattgt    36840
cttgggacct gactaaaacg accccatata aactagtcaa tttcattgat ttggtcagga    36900
aaatacaaac atatcaaata tgtagtttaa cttttttatag gaaattaaaa tgttgacttt    36960
tcatccagat tgtttatata tatatgtatg tatgtatgta tgtgtgtgtg tgtgtgtata    37020
cacatgtata atcaaaacaa ggataggaag tttgtaaaat gtgtttcatg gaaagcactg    37080
taacaagcta gttaagtaat tgacataaaa attattttg ttaattttg aaatacaatt    37140 gcaaaactg attaaataag aagctaatta ctaagggcta aatttaaact aataataacc    37200 ataaaaact gtatattgaa gagttgaaaa tgtatactat agaactaaac taataaaaac    37260
atctaatgca acgtagtgaa agaaaaataa catcgggaga catcagttca gttcccattt    37320
cagccaccaa tatttgtctt aatttgttct gatatactgc agttccatgg ggtaacctag    37380
caaatgatac cttcattacc caaaatattg aactatattc ttctcatctg aagtactaaa    37440
ttcacattag aagatggtgg caatgaggga atttcactat aacctaaaac ttggaacatt    37500
gtataagaga aaaagacttt attacttcac taaacaattg aataaatgtt atatgaatgc    37560
ttatttaaaa tgaggaaaat tgtctcacaa cttttctctt acattggttt ttttttcttt    37620
```

-continued

```
ttgttttcat agaatttcaa gctcacaaaa aagtcgcaag aatagtaaca aaaaatcctg   37680
tatgttcttt atccagattt accaatccat gttctttata attttgata tttatgtttt    37740 ttctaaatca cttaatgcta agttggaaac attgtgctac tttaccctaa aatattttgt   37800
gtgtattttc taagaacaag catattcttt tacgtaacta cagctgagtt ctcaaaatca   37860
ggaaatttaa cagtgatata ataccattat ttaatgcaca attcatactt aagttccacc   37920
actaatttct tatgtcaaga atgacccaaa agaaaaaaag ccaacatgag aaaaaataaa   37980
cttcatgaga aaatacaaaa aaattcagaa gttactgaac atatgaaaga aacaaaaagg   38040
tagggatagc attaggagat atacctaatg ctaaatgatg agttaatggg tgcagcacac   38100
caacatggca catgtataca tatgtaacaa acttgcacgt tgtgcacatg taccctaaac   38160
ttaaagtata ataatgataa aattaaaaat aaaataaaaa ggtttcctct tgggggaaaa   38220
gaaaaagatg atgcagtcca ctattctcta taattcttag aggttttact ctttatataa   38280
aatcaaaata attcagagtt ttctgcaaag tctctggttt ttctttccaa aattagtcaa   38340
taggacacgt taacatttct taaacagaag tgaatgcac tatgagacag atttctctaa    38400
gcggatcatt agagcacaaa cacaattaat ggctaggcct agtgacaaag tatgccattc   38460
acttccatga aatagtgtgt gtctgtctag gggcaagagg catttagcat agaaaacagc   38520
tatcaggatt tatttcccac tttaaaaatg ctcttacact tgctgcacac acaacttaaa   38580
atcaatgact ggaagcagga aagaactgga cagcttcacc agttaagtta ctccttttcc   38640
tccaagacag tagcaaacta ttaacctgaa tgcattatct acactagtat agacatacat   38700
acagataata acattaaata aatacataaa gttattcaat gtgatacagg ttaagaaggc   38760
tgagatttga gtggatgcaa acactatttt caaatatatt tttaaattga aaattctgtt   38820
ttaaccagag aactttacat attatagcat tagctgagag agttcagttt tgtttggtaa   38880
ttccaaaggt cccacaatat ggcttagtca gcatctaact tcataatgtg gtcacagaag   38940
tcatcaccat ctcttaggcc aaggacaagt ccataaagag catacacagc ccttggtaaa   39000
taagttgagg ttatttattt ctggttttaa atatgaaatt atttcaattt tgacattctg   39060
ttgtaatttt ctttatctct caagtgaaaa ctagtggacc aaggagagat gcccatggt    39120 ctctatgaaa acattattca ctcacgcatt caaaaactgt gagtttattc atagaagtaa   39180
tagtgtcata acaatcatta tctgtgtgtc catttcagt tcataagact ttagcataca    39240
taatgttatg tcatcctcat acttactcgt gaaaggtgtg cttaagtgct aaagaataaa   39300
aagtgaagca agacaggccc atgtacttaa gaaatttaag cttacatgga gaaatacccca  39360 gctaggtgta attattttag tgggaagaat aatatttgcc cttcagcttg tttagaatat   39420
attatcccat agatttcagt tgtgtaatta cctatgtctc atataaacta tgtcttatta   39480
ttataggaaa tgctgattgt acttggagaa ctagagcata agtataaaac gaaaaatcgt   39540
aggtcagcaa gattcaataa tagtgagttt tactttcatt tttctgagta ttcaagtgaa   39600
gaattatgga aagattatta atagccatga aacaatttgt aaataatgtt gagaggaaat   39660
agagtttact gagctgggaa gattagcatc acagcttaat tactgactaa tttaattatc   39720
ttgggcaagt ttttaattct ctaaaccta gttttctcat ctgtaagatg aaggtaagag    39780
tcagtctctc tactggattc tatatagatt gaacactaca taaaacacct agtataactc   39840
aataaatgtt gtcttttgta tttgaataat tccgtatggg attatctata tatttctaaa   39900
cactagctct ctggactagg attagaataa atatttcttg taacagctgt gtgtttcttc   39960
agtaaagcct tgtgctgcaa tgatttgact ggaaaatgaa ggaggaagag aaaaatgtaa   40020
```

```
tgaaactcca gtttcagaag aatatttgtt gtcttcagtt ctataatcac tgttaggtat    40080
gagtttaata ctccctcatt atcactatta gaaataaaaa cgcttcctaa gaatggcctc    40140
ttttgatatt gtaattagta aaagtggaat tttgttggaa agggtactga catagttgag    40200
ataatgtcta cttacattta tatctttatt caaaagcatg acaattattt ttgaaggagt    40260
caggcttacc atcttgagca attctatgca ctcgtgacca gagagactat atcttaagag    40320
gcagcattgt gtacagggaa atgaatgagc tctggagcag gctctcctac tttacaaatc    40380
tcagctcatc catttacttt ctgtgtgatt ttggacttgc tccttaatca tactcagctt    40440
tactttctac tttttaaact ggagataata atacatatct tgtattatat gtataagtac    40500
aatacatact tcttagggct attgtaaata ttagactgtt atgtaatcgt tgtcaaacac    40560
ttgatacacg gatagtaaat catgtttctt agctttatat ttagctattt ggatacagaa    40620
ctttatgaca ttgacaaaac ctttatagtc atgtttctac tttagatcat tctttttata    40680
gtggtatttt caaaattata cttctgttag ataaaggcat tgatccttta ttaaccaatg    40740
gtggtctgtt ttctactata aaatgtggga taaagagatg gtctctagag caataagagt    40800
ttctatacaa ctgctaaaca ttatgaaggt aaaagcaggc tgctaacaaa cccatgagca    40860
gtgacctcca gatttacttc ccaaagaaat aacatttata gcagaagaaa actgagtact    40920 tttttaatttt actgggaaag gagaaaaaaa agcttctaaa acattgacac ttttttaggtt    40980 ttagatctac ttacctacta actttcatga gctaagaacc ccatctgtat acttcctttg    41040
aatcagagta aatccagcct ttcagagtgc ttccccacct aaaccttcca gtacctgtct    41100
aagcatctaa caatgccaca ttttttttaa aaagtctttc cttcaacctc ctctcccatt    41160
ggaaccttat ctcaatgctt cattaacaca gaaaccaata gcagtttagt gcttcatccc    41220
tcctattggt ctttgcactt caacagaggt caaaggctga taattacatt gaaagtatga    41280
agcgtaattt gtaaaaagtg tcaggcttct ggaggaaaga gttctagaac tttttgcaaa    41340
aataaaatca tactggatga ttggcgccaa gccatttttg gggcatttta gccaatacag    41400
aaaaaatgaa agtgtctatc agacatgctt ttggcttatt caaaataaaa accacattaa    41460
ttgagtccca tgaaaaaggg agtacagtta gtcctcgcct aatattgtcg acatgttctt    41520
ggtaactgtg actttaagca aaatgatgta taacgaaacc attattacat atttcaaatg    41580
taataataaa atgaagttga acaaaactat gttattagag tattttttcaa tttagattac    41640 caatttcatt gaataacaag gataaaaatg agaaaattgg catcacccttt atcctctaaa    41700 atgttagtct tcaggttatt tttagagaat taccatcttt aatccctcaa atgtgtttct    41760
aggtattttc ccactttata cttgtcacaa tcctggaagg caagtactat tatcaccctc    41820
attttgtgaa agctcatgaa agaaaagtag ttagggttga gtaagtattt tttttttttt    41880
tttttttttt ttgctttgga catgaggaat caaggctatt atatgaggta gatttgtatt    41940
gaattcctgc agaagtcctc ttgggtcttt tggcaaagga tcacccctgc catttgtatt    42000
gtaaagaatt gcttccatag gccacaatct gtccactctt ccgaaaccta accaggtggg    42060
ctgttagtaa gtctcttcta atttagggaa ccattccagt gtctgatata aagtgcttta    42120
ataattttgt ttcatgtata tcagccattg actgagcttt tggcacacca tgaagagcaa    42180
ttatgtagct ttctcattac tcttattatc catctgtaaa gaaccctgtc aataaactac    42240
attccctgct ggttggggtc tttttttaac ctaacctcct gaactttact ctactctgcc    42300
taaggcaaaa agaggagcag caaacatcag cacaaatatc aggaggactt ataaagtagt    42360
```

-continued

```
gacagaagac agtagaaaag actgaataac tagcaagagt tcccttcctg tcttcagcac   42420
tgttacactc ttggagctaa acctttcaac accagatata ctgaagatag attttatta    42480 tagaggttgc acttgccttt agacagactt catcatcttt agcagtctct ctcccaaaat   42540
tgaaaaagag ggaacttttg aaacagtgaa aactgattta ttttaccact actttgtttt   42600
attcatgtca tatatttagg acaattattt ctttatggct atcaatagat agtactttag   42660
ggtatttgat agtgttcata ctagcaaaac acatattcat cttgcattat agttgttttt   42720
taaaatatca gaaagaatta catttttaact ttgagtatat gttaatcaca ttcatgatca  42780
ttgttaattt atttatctgg tatatgtact aagtatttt cagatcaatg aattttaaaa   42840
aaacctttat gataattcat tgatgatgac ttcatcatat taaaatttta gttgctgcac   42900
attgaatttt gattaagatt tagttaaccc aatctttggg ttatttcaag tatcctaagc   42960 tagggggactt ttcttttttgt ttgtttttaa gcttccatta caagtagcgt tcacagttgg  43020
cattgttgac atggaaacta gtataaggat gaacacaatt aaagaaatca ggggttagag   43080
aatgtaaata taattgtaag atcacatata tccatattcc catggaattg tgaaattgct   43140
ttgaggagta tataaaaata aattcaagca aaagaaatat attccatgtt agctctctag   43200
attgacaatt tgctgatttc tccatcttcc aatatggcat gtgattttct gctctgtttt   43260
gtaatatgta aagttaatgt gtgatggaag gatacatttc tgaagtcaca gggcatggag   43320
gatggacata tgagaaacca aaggtagtaa tttagtatct caaatccctg ctggtatgca   43380
aagactttag taacaactca gcccaggttc cgactcaata atttccattc ccccattgcc   43440
taaagcaaat tcttctccac cgagtgaagg cacatttagc atccatatag cgttatgttg   43500
agaaattcgt aattaaatta cattaattct aatgaattca aaatacagac atttcaaaaa   43560
gaatttaacg tcctgtttat ggtcaaataa tattttataa tttaaatata ataaaactat   43620
aataataatt taacttgtac attccattgt aatctctgtg gagagccttt tccccaggca   43680
cctccaaata acttatagca aagattctca aattttttgtt tacatgggaa tcatctggaa   43740
ggcttatcaa aattctgatt gctaggcctc actaccaaag tttctggttc agtaggtctg   43800
gagtgatgcc agagaatttg catttctgac aagctctcca gtgatgtctg tgctgctggt   43860
ccagggacca cacttggaga actagtagct taaaggaccc tccatcctgc taggattgga   43920
ttttccaaca accagccatt tgaaagtttt aaaaataagc aaagaattta tataaggatg   43980
taataaggct ggagtattga caggaaatgc tttgaatggc atttaatatt actctttgtt   44040
tccagagact tgaaagttct tttcatggat aatgctgctc tcctcagtca aaggagtaa    44100 ccaccagcat ctgtgtgact aattgccatc tgtgctctct gaaaccttgc taatagaaga   44160
gcatgtcaaa gatctctaat gaattttaaa atgtaccact tgtggatgat ttgagattat   44220
ttttatgtaa aggaaattat agacctcctg tctaatatat taatcaaaaa aattgagtgt   44280
tatgattgag tgatgcggca ttaaagttag attaaaaggt ggaaatagtc acataatcaa   44340
tatagcttgt agcacgtaaa acaaaacaaa acaaacaaaa actggtccgc ctgctcagta   44400
cccatataat ctattaatgg tagttgggaa aggactaggc agtctgaata ttttgattta   44460
taaatcaaat aaattgtgat ttataaatca aaaaaatcac aacttctgac actgactttc   44520
tgtgatgatc acttaacttc tcaaacacta ttttctcatt gccacaataa gggtcaatta   44580
tgttgacctg ccccataagt aagtgagaac agtaataatt ggaaggagct cttttttagaa  44640 cttgatttt aaaaataata gtcaaaatac cttttagtat atctttgttc aatttggtta    44700
accaatttac ctgagagatc atgctatgaa actggagtac aataaagagc aatgaaaaaa   44760
```

```
agagctgtgt tttacatata gaaatgtaga aatagtgata tttgtaaggc ttttgctatt   44820
acagggagga tgtaaattag attgttactc taaacacaga cttaaatttt gccttcacat   44880
atattaacat tcgtttgatt ttccagtgac tattctaagt attttagagt ggtaatcact   44940
gacttcatcc aaaccttcat catcttttcc tttatttatt tcttcattga gtaaatacta   45000
gtatctggtg ttcttttaaa ctgtgccttg acccaatatt ttaatcaaag ttgtatgtct   45060
cagatacaag atatccaaat atgaaattag aagaaataaa gacaaatgaa aagctatctg   45120
acgtctatag gctacctgat ttaaaaataa atgaaaaata ataaaaataa atatgtagtt   45180
cttgtggttc ttcaaattgt tgatttgctt tgcaattaaa tgaaatatat atgtattagt   45240
ctattcttac attgctgtaa agaaataact gagactgagt aattcataaa gaaaagaggt   45300
ttaattaact catggttctg cagactgcac aagaagcatg gtggctcctg cttctgggga   45360
agcctcagga agtttccaag catggcagaa ggcaaggggg gtgcaggtat cttacacggt   45420
gggagcagga acaaggagag agtgggagg tgccacacac ttttaaacaa ctggatctca   45480
caagaactca tcactatcac tagaacagca ccgaaaggat agtgctaagc cagagaaatc   45540
tacacccatg gtccaatcac ctcccactag gccccacctt cagcactggg gattacagtt   45600
caacataaga tttgggtgga gacaaatata caaactatat caacatcttt attatatatt   45660
tatcatatgt ccagatgtca ttcattcatc catgcacgaa tgcatgcaat atgcattcat   45720
ataaactcat tttcgtgtaa tcatatgcct acagctatag agcacaccat tactacaaaa   45780
taaattgaag accaagattt cttacagaaa taaagccaaa ttcttttctc acaaaatttt   45840
cgataaagtt ggttaaatac tatcagtatc aggctaaatt agcaacttga atgggggtac   45900
atcagaagcc ttaatcaggc caagtatctt gtggtcaaat agaatattag tattatggaa   45960
cttcaacttt aggaaattat agtatgacct ttctttagtg tttaacttat tctttaaagg   46020
ctacatgatg aataacatat attgccaatt atctatcaaa gtcctttaag attatattac   46080 attttgaat aaaatctatt ttgataaatt agagaatgat gccttagggc ttatttatat   46140
tataccataa aatttttaga aaccatcatt ctcggcaaac tatcgcaagg acaaaaaacc   46200
aaacacggca tgttctcact cataggtggg aattgaacaa tgagaacact tggacacagg   46260
atggggaaca tcacacaccg gggcctgttg tgggctgggg gaagagggga gggatagcat   46320
taggggatat acctaatgta aatgacgagt taatgggtgc agcgcaccat cacggcacat   46380
gtatacatat gtaacaaacc tgcacgttgt gcacatgtac cctagaattt aaagtataat   46440 aaaaaattt taaatttctc agaaatattc caaatactta ttgagcatgt actttgaaca   46500
gacattgttc taggcactgg taatgcataa atgagtgtag taagcaatgg gcctgaaagt   46560
gttcaggcag catcaatctt tgttagaagt gtacgaaatt tatttaaaca tgcacttacc   46620
ttttggacta atcaaaggta tcagaacatt ttctgagcag ttttagactc tgaggaaaaa   46680
atacaaatat ttcagagctg tagataatga tatcttatat tctgaaacct cagataaacc   46740
attaggttac aatgcttctt gaatatactt accaattaaa ttttttgagg caaaaaataa   46800
caaaagtgtt cttccctgtt attaaaactg aacaggtctg tgtcttctaa agatgctatg   46860
gctttaatca ttttaactct gaagataatg tttgcttttcc cactaaatca agcctacata   46920
atggagcaca gaattctgcc ctgatgaaat gggcctccat tgagtaaagt gcttctgttg   46980
tttatattca tctttttataa tagatttgga ctactgtttt gtcttagaag cttatatgca   47040
gggctatccc tagacagcat tttgaagtgg gcaaaattta tgttgattgt gctgtttcta   47100
```

```
gaaccagtca gttatttgct aaaatggctg ctaactcgta atttgtcatt tactcagagg  47160
tcctaaagca aactgaaatt taaaaattat cactcaaaaa tcacaaaact agtacaaaaa  47220
atttaagcaa ttaaatttca agaattattt ttataagttt gtagcaatta tagtacggaa  47280
gtaattaaag cttaaaactg tactaagctt tttgggacaa cttgcattat agaaatatag  47340
acaatattta gatacaccat ttaaatatac atttatgctt ttcagtgaat aacatataat  47400
atgtattaca tattaaaagt tatatgtcat atatacattt gtataaatat attttatgtt  47460
tattttagta taatgatatg tacatatttc ataaacataa atatactaca tatatatgca  47520
attccctgaa attcttccat ttgccaagac acctattaga aaaatgagag aaaaagaag   47580 atatgttatt gagtgaatct gaagttctac taaaaacttt aaagctactt ttcatatata  47640
aacataccct ataagaaaaa atacatttca taatacaaat ccaaatttga gagaaagaga  47700
tcaggtatga agaaaaaaat agacttttcc caaaaaaact attttacttt atagttttat  47760
gttctttgga acaatttggt tcactttata ttatgttata actaacttaa tgccatgtat  47820
tcatggagtg gagtgaccca aagctagaat tttatttta attggtcaca atctcatgct  47880
gtcaaacata gactctcctt taaaagaaaa tgttgaagtc ataagtaact atgttgttga  47940
ataagcttct aaaatttttg tagttaaaag tatgaattaa catattggac tatctgtcta  48000
ttgaataaac acaggatgtc atttatttct tcttgcaaca atttgctgtt taaatgttat  48060
gacctgcctt aatggaataa aatttcatat attatcactt tacattattt catattctct  48120
agcttatctc aaaagtctta ttaacattct ttatgaccac acttaaataa gtaacccata  48180
tacaattcta tatgaatcat aatatacata taaattgcaa tctatatttt ttcctttacc  48240
atatctctga atcagtattg gttattctct gcctttttcc cccttctttg ctatactgtt  48300
tgagtcagta ttggtaattc tctgcctttt ccccccttct ttgctatact attctagaga  48360
gaatattggc catttatctc caaaggacaa gtaacagtgt gatgtattgg taagataaaa  48420
gactagatga caaaggaaat ggtatctcat ccatgctgtg ttactgttta acagtgtcat  48480
cttggagaaa atcactttat cacttagggt ccaagtttcc tcacttaaac aaacatacaa  48540
acaaaaacga tccagttcac aaagatggac tctaaagccc ctttctatat cttactgccc  48600
atgaatcact ttgaaatagt ggtttctaat ctttatgttg acttcctatc aaaacagttt  48660
attgagaagt cttgcaatat ccattgattc caatcacatc tcatctgtcc atgtctgttt  48720
actattttgc atctcatgac tttataaaaa ttaaatgtct acaagtgata gtgaaagcaa  48780
aaaggttaat agcaaaggtt aatagtgctc acgtgttcca ctagaattaa acaatgattc  48840
ccatgcctcc tccccacaaa agagattttt tttccaaaat cagtcacttt taaattaact  48900
taatacaaaa caaatctcta aactgcataa agaacattaa ctgaagaaaa atatttgaag  48960
ccattattga aatattttat attcaaggaa atcacaattt aagaattaat cctgactgac  49020
tattgtcaat ctggtttcta actgactgtt aaacttttaa attgacaaat tgactgactt  49080
aaatctctag actaactctc catccttgat ctcagtaaat atatgaactg cagtactgtt  49140
agccagaaag aatacattgt cctctgacaa agtaggtttg aattgagttc aaggcccctt  49200
tgctgtgttc aacatacaca ccatgacctg ctctgcttca tattttgctc tcttccttaa  49260
cctcaacaat tctctgccat tgatgggata agtatttcat gctgttagtt tgaacatagt  49320
actgagaaat ccaaccaggt cacttctgaa atagcctgca agcccctagt agcctagcaa  49380
cttctgttac accaaagcca gactctgtca aaaaaatctt tttaataatt ggaaaaaagt  49440
atagcaggga gctagtatta aaaggtaatg tttcctaaca tttttttgca tttgtcaagt  49500
```

-continued

```
ggaaagatag gaatgtatag aaccaaggga agataggaat gtttaagtga cttctaaaat   49560
attattatga aaaagaaact attatcattt tttgtttccc tgagtctagg aaaagaaaaa   49620
attttaagcc tcaaaatttg gaattaatgt ttttgatcat aagactttcc cagtaagaat   49680
aattataatt atgaagtatt ttgtatcaat tagatatttt ctaagcatgt tgcaggcatg   49740
gattctttta atactccaaa caacccaata aggtaaatat gtatatgagc cctttatttt   49800
taaaaatgaa gatactgatg cttagaggtt atgtgacttg ccctaaaaac tttagttttg   49860
tagtagaaac cagtagggac aaaacattca ctttatagca tgctttatga taagtatctt   49920
tgggattaat tttctggaaa aggttgtgga gtctcattag ctacttgaga caaaggatta   49980
tagatacaga tatttataaa aattacacac atatacacat atgtacatta ttttcatctg   50040
tgagaacaat tacatatgtg agccttctgt gggaagagaa cataatcaat aagtatggga   50100
caacttggag ttacattcac ttacttagta ctagaaagca ttttctcct caagcagaaa    50160
ttaagctaat aataaaatat atgagatata agaatactgt tacaatttga atatatataa   50220
cttggaaaag aaaaccagaa atgtatgttt taaaaaaacc aggctgggca cggtgtttca   50280
cgcctgtaat cccagcactt tgggaggctg aggtgggcgg atcacgaggt caggagatca   50340
agaccatcct ggctaacacg gtgaaaccgc gtctctacta aaaataccaa aaaattagcc   50400
gggcgtggtg gcaggcgcct gtagtcccag ctactcggga ggctgaggca ggagaatggc   50460
gtgaaccagg gaggcggagc ttgcagtgag ctgagatcat gccactgcac tccagcctgg   50520
gcaacagagc gaaactcgtc tcaaaaaaaa aaaaagaaa aaaaaatagt aaataaattg     50580
accaaaaatt aagggcattt gggggtggta agactctagc caacttttta tttctttata   50640
tattttcat tttacttaat gagtaacatt actactaata tgatgaaaca tatttaagga    50700
tgaaagtaga aatgtaatta tatagtgtta tagtcagagt cttagagtta taaatacatt   50760
atctgtaatt atttctagaa agtatgagca tccattagag aaattattag gcagtaatat   50820
gcacatttgt tagattttgg atcttagaaa atcagtgact tcaaaaggca acttacctca   50880
ttatcaaaat attagatatt ggaattagat atcaaatgaa taatataaaa atattagaaa   50940
cttctttata ttgacccgaa ttttatttca atagcatagt ttatacttat aaaaatagaa   51000
aaaaatcctg gacttaaaaa agcaatccaa ggtgatgttt ggcttattta ctagtgcttt   51060
tgaagtgcta ctttattcat aggataataa gaacttattt gaagcttaca gagatcaaca   51120
gaatatgagt tattttctca aagaactctc agactaggta aagacattag acatatacct   51180
aaataaaagt cagaagaaat cattgattca ttcttcaagc agtactgaat atctagtaga   51240
tgacaggaat acactagcga ataagacaca gtctctgccc tcgataacct cacagtccag   51300
gagaggaact aaataacaaa tgtagtgatt acaagaacaa tgtatatatg gattcattct   51360
tttatcacta gtctatttca agacttttat taagcacctt ctgtgtttct accaaaaaat   51420
gggaggagac cgtgagggt acagaagcat gtcaaaatta agtccttatg gaaggaata    51480
tactatccag aatgaagtag gcaactgttt gtatttgaaa ctattggaga gaaaattcaa   51540
agcaattttt ctagattcta agtggtaagg aaggaaacaa attagcaacc tgattaatcc   51600
aggaacacat tcatgatgaa agtgttcttg agcattcatt ttaacaaata aattttaatt   51660
taccatattc tattctattt caaagtgatc agtattgctt caaatgctaa tttaaaacat   51720
taactttaat aatgtagtag tagaatcatc tcaattttcc taacctattt tcaacaaact   51780
gaaaaaagc aggaagtaat aagctaatta aaaataaatt gattgtgctt cattccttga    51840
```

```
tttttgcttc caaaaggttt gccagtggca taacagaaca tgactttaaa aaataattaa   51900
cttaaatact ggtctttttt cttaattata tatatcttca tactaacatg agaggaactg   51960
tacaaaacaa gacagcatga tggaattgaa ggaagcctgg agcacagatg gcatgctggg   52020
cttttcctgc ctgtgccttg aactggcttt gtgatcttgc aaagactact aagctctttt   52080
tgactcactt agattcaaaa tgggaagatt tgaaggaaat tgtagaaata aattattgta   52140
gaaataattt taccctgcaa gtctgaaata cttcattttt ataaggtaaa tccttgacac   52200
ctaaaatttt gcatgaaaag gacatggtag gtagatggat aggtagacag gtaggtacgt   52260
gaacacacct atgtgcaagt acactcaacc tccagttctg aaagcccttg aaggacctag   52320
agggccaaaa acgaagtaga tggggacata cttcctgtcc acagagcatc taaagcaaac   52380
aatcacataa tattcaattc aatgaatgat gataaatctt gaatataaaa gagaaatagt   52440
ttcaaatgtc ttacaaattg ataaatcagt atcagcactg agatatttaa agccattttc   52500
tttatatctt tgctagattt atcatctaaa atattggata ctcaattttt aagttgataa   52560
acttaaaaat ggcttttct atgatgtgag tgatatgcct catgctgtgt ttaaaaaaat   52620
aataaatccc cgctcagaca ctcatgcaaa catacacaaa ttgtttcatt tacatactta   52680
taattatgga agttatcttt gaactattgt tcaaaaaaac aaaacaaaat attggggaaa   52740
gggaaacgga attcactgaa gttaagagca ttcagaaatt tgttggtagt tttctgattt   52800
ctccaaaatg atactgtaaa gccagagctt gaccacataa caaagttag caatcaaaat   52860 gttgtacccc ttgggatttt gataaagaga aagaattatt taattcttaa tgcagatttg   52920
aattatttaa taaagtattt aatagatatg taatggaata aaatagtatt aatagatatg   52980
taatacatat ggcaatatct atgcatcttc atatcattaa ttctgcacag ttctgaatgg   53040
gaaagagtcc ctagcaatga attatatgga tacaaaagaa tggtttggaa ttatgtggct   53100 acaaaagaa tggtttagaa aaataaaatc tagaatctag gatgaaaatt aaagggatct   53160
tatagctctg taattttac ttgtcagcag tagattctcc ccctagcttc ctgattagag   53220
gatgtacttt cttggtacct ttgttttttg tgcttaggga aaaatatct atttgggaaa   53280 tatgaatgta cacactttaa tatatggctt attcctttgt atctataaaa atgaggttgt   53340
tcctacttgc cagtagggtc tggacagtat actatttctc atgcatagaa gaggtggcca   53400
actgctgcta taccagacat atcttcctac caagtgcctt tgtatccagt gacctctgtg   53460
atctgggcca ctgaacagag gtacggtcca cccaggctgg ccccaacttt agccttactg   53520
gcaacaaatc aatcagttgg aactctgagg tactagaact tatagtccct agagctattt   53580
actaaataag atcttaatgt gacaaattgt tggatttgtt ttgaataaca ttagatgtac   53640
caggggaagg gtttggacct ttcactggct gtgaaacata gggaaggaaa tatgccacct   53700
acacagggag ccaactgaga aacaccaaat gttttatagc catggtttcc taataaaacc   53760
cctaatttgc aggaagtcat ggtgaccttt ctcgaattgc atgtatttgt tgctaatggt   53820
ctccaacacc atttaaagtg gccctataaa aagtataaat ctaaaatct caccaaaatt   53880 tggtctttgt ttctttaaat tcaatagaac tcaaagtaaa agagttcata aaaaaattgg   53940
ccccactttc aggtaggaag tgcaccatgt accatttaaa ataaataaaa atcagacaat   54000
ttctatagaa gaaacctgca tttcttgtca gaatatttgt agctatagtt agctgtctcc   54060
aaggtaaata agctaatttt tgtagagttg atgttttct cttttttata gctgtacatg   54120
gaattattac aaattaagta gggtgagagg aatgctatat ctttgctaga aataaatttt   54180
ctaaattcag caacatttac ttatacaaat aaaaatggca caataaggaa caatgaggac   54240
```

```
tgtaaaaaat agtcaataat gcttcttctg atgcaacaaa tggaaaatat tccatttact    54300
ctcttaatga ttaaatcgtg gtataagtga aatgtaggga aaacagctgg gtaaaatgcc    54360
acacatgttg tttacacatt acctgtcaag aaagtaaaaa ttatctaatt gaactaagtt    54420
ctccatacac tggtaatctc attccccacc atcaggttga atggcattta cttcctcttt    54480
gtgaactcat ttggcaattt caattcaggg tctatcttca tctcactttc cttcattaat    54540
atctaccagc tattttccat cttttttca tattccatta tttctgcttg agaaactgaa     54600
agtaatattt gcaactctga tattttcaa caactgaaaa atagttgctt cttcttcaaa     54660
aataacagca atttattcta tatttatgaa cacattttga aaaatgttta tatttgaaga    54720
tagactgtat cagtttattt tcatactgct ataaagaatt cccaagact gggtaattta     54780 tagaggaaag aggtttaatt gactcaccat tccacatggc tagggaggcc tcaggaaacc    54840
tacattcata gtcaaaggtg aaggagaagc aaggaacttc ttcacatggc agcaggagag    54900
agaagagtga gcgagcagag gggaactgct atttaaccat cagctcttat gagacttatt    54960
cactgtcatg agaatagcat ggggagtatc gcccccatga tttaatcacc tcccaccagg    55020
tctctccctt aacctgggga taataattca aaataagatt tgggtgggga cacagagcct    55080
aaccatatca cagactatat tataacagaa ttgaatttgg aaatgtcttt caaaggtatt    55140
ttaataataa tatagataat gaaaatgctc aacatattta ttgaatacta tgtgctgagg    55200
actgccaaat atttatatg tatttatcta attccccaac ttccctataa tataaagaca    55260
gactatcatt tacctaattg tacaaatgag taaactgagg ctaagagtgg ttaagtaact    55320
ttcctagggt caccctacta ataaatgaga gagccagtat gtaaatttag aaagtcaaat    55380
cctagaatca ctactctata aaattattgt aattaaaact atcatattga tgccacatat    55440
cagttttcat ttaagttatg ttaagctaac cagataatta cagcaatata aggaattcta    55500
gatatatgac aaacaagttt atagaattta aattcacaca acagaaaaaa caggagaaaa    55560
cattagtatg tacgagtgaa gactgaacat ctttaaggtc tataagttta aaaaagcctt    55620
catataagaa ctcttaaaaa atagaagatt atatacagca gtgttaataa gcataattca    55680
ctactcagtt agcatggctt aagctttta ttacataatt aacatgatca ttatgtaaga    55740
gttaaataat acaaaagatt tagataaaaa attttttctc tcaatcctac aactcatctc    55800
ctcagaggaa accactttaa actgtttctt tttttatca ttccagatat atcttggtaa     55860
atgtaaatgt atgttattta gaaacacgaa tggcataaaa ctataaatat taatgtacag    55920 tttatttta acttaacaat gctccttgaa ggtcttccca tatcatccca tagagattga    55980
tctcattctt tttaatagtt acataatatt ctatttcatt tatgaaaaat cagtattcta    56040
gattgtttct agttttttgc tgtttctaaa actgctccaa taaacatctt tgtgtactct    56100
ccacctaatt ggttgggttt aattattttg tagatattgc ccttcaaaaa gattgtatcc    56160
ctatgctccc accaataatg cagaagtgca ttttcttca tataaatacc aatgctggac     56220
aatagaagac agtttagtct ttgctaagct aacaggtggg aaaactcatg acattaattt    56280
gcacatattt aaatatgaat agaattagtt ataataaagt caagtattta tgagtagagt    56340
tttttcatat ttgaataggt catttgtgtt ttttgttcat ttttattgag ttttcatctc    56400
attgatttgt tatttgtttt cataggaatt taactacttt ctgtcacata tgttgtgaat    56460 attttttccca gttcttgatt tttttatgtt ttggagtgtg tgtgtatgtg tgtgtgtgtg    56520
gtcttgtaaa taaattttaa attcctatct tgccagaatt atcaatcttg gcttttatgc    56580
```

```
ctcctaaatt tgatgtcacc cttggaagtt cttttttctat tctgtgatta caaaaataca    56640
catattttta tctactgttc tcaatgtttc atgcttttac atttacttat tttatccacc    56700
tgaaatttat ttagatgtag ggactgaaga aggaacccat tttttcccaa aggttctgca    56760
gttgttccag tgccatttat taaataaccc atcttgtccc taccaatata aaatgtcacc    56820
tttccctata ataaattcct aaggggagtt ggacttattt ctggattttc tgtttagtta    56880
tattgaacta atctctttca aagttctcct tgtgtcaata ttttactcaa tgaggtttcc    56940
ttatcttgga ttgcaaatgt atcctcatta caaccatgag ttagaaagaa atcctaagag    57000
gtcaatgagc cacactgtct tcgcagtaac tatacacaaa gaagttcagt gtgttttgtt    57060 tcattttaa tatttcagat ccttaaagtt ttgatagctt caatgtaaga ataattaaag     57120
ttttgttttt ctttccatat agttcacctg cttttagttt tcagttatgt agtcttcaag    57180
aattctaaaa agatagcagt gctgttatgg attgtaatgc tatatttaaa aggccttttg    57240
caaaaatagg tgtagtaata atttatggaa acaaatcatt gctagtttat aatatatgat    57300
tatttaatct ttccaactat gtgaaggagc attattaata tcatctaaat ttataggtg     57360 gaaatctgtc tcagaaatgc aagtcattag cacaaggcca tatggctagc aaattaaaaa    57420
aaaaaagttc tcaaatcaaa ttctgacttt tttatagtaa tccaaagatc tttccactac    57480
ttcagatttc ctgaggttag aagcattttc aaagtttggg ctttgtgcct ggcagcgtga    57540
taggtattgg gtagtaaaaa cagcttctgt tctcactccc tatattaaga tggaattact    57600
tgtgaagtcc ataatagact aggcagaagc aaaactgaaa ttagtggtta atcatgacat    57660
cctccttgca accttatgat acctgcttct caatgcccag ctattttata ctctcatggt    57720
tctaatgtgc aaaaagccac cgcaatgtcc tacccaagtc tgtcttcctt tgacttactc    57780
ttatgctcta aaccataatt tcttttcact ttcaacactg taaatttaca gctctggatc    57840
ttaaagtggt ctcctaaaaa cccgcgataa tttaagagtg atgcaacatc atcctctatt    57900
ctgggcaatt tatattttat ggaggacttc tgacactcca ttattacttt ttaattatta    57960
aagaaatata tcgatcattt tggaaaataa gtagcattat gggaaaactt catccatcat    58020
cttataatta gagataatct ttatgtatat acatgtaaca tacttctcga ctctctttga    58080
catgcatgta tttattcttt gaagggttct actggccata atggttccta gcctcctttt    58140
tgtttgtttt ttattctagg atatgtttac aacatctttt catgatactg aattctcttc    58200
caacataatt ttaaattgct gcatagcaat ccacaatgtg tccatctccc tgttatgagg    58260
cattaggctg ttttcattgt ttggtgtaat gatactagcc ccaagtttag tatccttgca    58320
gcaaaatctt tatccacata tgattatttt cttagaataa attctgagca gtgaattcat    58380
gaatcaatgt gacacaaaat tttgaagctt tatgaaataa cttagcctaa agaaacaact    58440
tcctagtggg gcattctggt tcatccaact gtgccatcta cttatgccaa atatttgctt    58500
ataagtttgg gattatcatg gttttgaaga gccaaattaa aaccatttta tatgtgtaac    58560
agagggtgat gttaaaccct ttacatttt tgaggaaaat tttaaggtga gacttgtaaa    58620
agaaaggata ggactctggg atatggtcac actggttttg aataataatg gaaattatgc    58680
acacacatta ttttatgtat cattaaaaag aaaataaaat tcagttatac tatgactcaa    58740
tgctttctta tatttttaat ttttatttta tgattattga aagaattctt ttagatccat    58800
ttatacatag attttttacaa tatatcagtc ttgtggaaac attgaaataa aaataaagag    58860
ataaaagcaa aattgtttaa tgcaacctaa aacttcgcat tcagattttg acatttctta    58920
aatcactttt tgactcaaaa ttgtccatgt ccatattttt ctactcagct ttgaattctg    58980
```

```
atgctcattc tacaaatttg aatgtgcatt ggtaagaaag dacagacagc tttgtcatga    59040
ctgccttctg gctgacagca attataagat ccaaatctac ttttgagaca ctcaattgtg    59100
aaaaatgtgc aaatggtgta tgtgtatata tttcattaga atcaatcaaa caagagtgta    59160
gcaaaggaaa catatataag cagatatatt tgagaaacat aaacaccaaa ataataacag    59220
ctaaagtaat actattcata ataatcacaa tgatgtattt tatttgtgcc attaatcatt    59280
actaatcaga tgagattttc caagcatgca tgcattttg gtcaaaacga aaggtccctg    59340
ctttgacata cctcctttgc cacaaacaca atgagtcagg gagatagcaa ctgatgatgc    59400
ctaggagttc atctcccata gggtaataac ttcatgctgt ttgcttcaga actcctacaa    59460
attttctgct tataagtatt ttttccacac acaggaattc atatgttaga aattttttta    59520
gtcttcctta tagccatcct tgagaaaggc ttgaagaaa gtgatttaca attataagaa    59580
tcatgaattg atcagtgtaa ttcagtttgc caaaatgtat ttatctagag ggtatgaaga    59640
aaaaggattt tctactgatg tcagaaacac ttgaagatgt atttgaatcc agaagaaaaa    59700
catgttaatg tttttagaaa ggacatagat gttgctggaa tccacatggc cttggaatat    59760
aattaagtga gtggtacagt ttcaagttgc atgagcatga gattacccttt tccattagat    59820 ttctaaaagt atttctaaat aacctagatt cactacttat ttgctctgct accattttta    59880
atggctcata atgcagaggc aagctattgt ctctgaataa tagaacttt aggattatct    59940 attcgtcaat tggttgcatt cttacagaaa gagaaaataa agtttattgg gaaaatgaca    60000
tagtaccttt aaaatatgca catgaaatca agtaccccaa atcagaacat tcttaatgtt    60060
ttcaataagt aattactctg agtgcattag tacattcaca gacatgatgc tgaatataag    60120
aaattaaatt accttagatt tggtagcagc aatagagtgg cgtcaacttt agtgagctgc    60180
cataattcag attagattat tatattaata atagtgtatt attatattga aagttttact    60240
tgtttctgat aactttatat gatattcata acaacaaatt atttatcttg aagtattgaa    60300
gcactgactg gaattcctca gcatggatcc ttcatattta gagctcaata ttagcccttt    60360 acaaagtat tatagctaca aatgttttaaa gactctaaat atgtggccaa cctcagattt    60420
aaaggtgtca attattacat attatatagt atttttttctt ttctgctata gcatatagta    60480
accaaaattg aacatgcaaa aacaaattat tttctatttc tttgatggta agcttatctc    60540
ttaattgagc ataggagtta tattcagcct atgtcagcac atagactaca aattcaccat    60600
cttagttcac cttgtccttt gctttgtgca gagtatagta agtgctctga gggtgaatga    60660
aattgtgata agcaaagttc taatgattga ttcaaatata gaatgtcacc ctctatgttt    60720
ccttatcttg gattgcaaat gtatcctcat tacagtttat gctgaatgag aaaaggagca    60780
ggcccaggtc acaataaaat aaatatctat ataattttttg gaaatgaaat aaatatttat    60840
ttgtaaatga agtatctata tatttatttg taaatgaaat aaatatctat atgtttattt    60900
gtaaataaaa acaaatatct acatatttat ttataaataa aaacaaatat ctacatatta    60960
aatacttatt gcatgtcaac tgttttatgg acctaacctc cttgaagatc acattaacac    61020
tgcaagaggg gcattacaat ctccattttt caaatgagaa aatggagtct caaaaaatta    61080
acttttcgaa ggtcacacaa cttgtaaaga ccataacaga aattcagctg tagcttactc    61140
attccacgat gccatctgca aagtttaagt ggttttactg aaaaaccaac cttctagaaa    61200
acattacatt ttataataca tacagaaaca ttaagaatga aacatgggac tactactcaa    61260
ataaatggaa atataaaaag agaagaaata gcttttaaaa ccagctattc tgtgagaaag    61320
```

```
cagtggttct atactgtagt atttaataag gtgtcctagt aaataaacct atatatactt   61380
cttttaatag cagatgttat tagaaagatc ttttttcattt aaaacattta ttacataaat   61440
gatcttcctt taaaataatt ttttttcaca ttctatgtgg aacatttggg gctgccaatt   61500
gtcatttgag attactcata ggtaccctaa tttcctctga aaccagtatt acgtgaagac   61560
catgctagaa gtgcactgag aggcaaagca gtcaggaatc acaaggaagt ggcatttcca   61620
ggctttctag agtgcagaac agtgtggagg cagcagctct gtgtctgtat ttgggcaatg   61680
gacatgtatt aggagaatgt taatagttat tcctagcctt catggggtct ctggtttacc   61740
ttaaatattc tgttttgtta tataacaggc tttactgtct tactaattag atgccagctc   61800
ctaaatacga taatcatttg ttggaaggaa aacagttatc ataagttatg tcagtattgc   61860
tgtttatcaa ggaaaaaatt ttatgagtgc tatttagaac cataaaattt tccttggaat   61920
tatatgatac ccctgcatgt gtaaggggca gatgcagcca aattgcatgg agctcttcaa   61980
gaactgctga agagcatctt ccactctgca agagaaattg cctttttaatt agccttttca   62040 gattgtctgt acaagccata ataattcatt tcatcaaaaa atataattat cttaaatatt   62100
ttaggatact cagctggatt taattaagca agaggatgtc cctgtgttta tactcttcaa   62160
atggttgctg attccacgta aacttttacaa agtctcatc ttatgtgcat ttttttaaggc   62220 cctgaattac ttttattaca aattgtgatg ccataaaaga aaagaaagcc ttttctaaaa   62280
gaagaaacca tcctgaggca ctgggagaat taaaacatga gctgtacagt cagaaagact   62340
tgggtttgaa tttagattcc acctcttgct aaatgaaaga ccatgggcac gtctcttaat   62400
ctctctggga tgcacttgag ttgcttcctc aataaaatga agatgcaacg taccatacag   62460
ggctgttatg taaagtaaat agcatgatgc ctggtcactc caggtctcca aacgttttga   62520
ggtccttcct gtaatagtca caaagcatac tctgccagac atgtagtaag aagattgaac   62580
attattctgc ctacctttca gccaccactg aagaggccat agttaatggg aactgcattt   62640
tagctggggc ttagttggct cctaaggaag agcattaagc ttggctggtt ctaagtgaaa   62700
gaagtattcc aactggagga aattaaaact gggcggattt atggctggat ttaactgtgg   62760
gatctgatag taacctccac ctctctacat ttacttatat gcccatagcg catgcctacc   62820
cagaaaagaa gattctttct tttgctgggt ccaatctgct gttaagccca tccattgcat   62880
ttttatttca gatataggac ttttttcattg ctagaatttc catttgcttc tttattaaat   62940
ttttaaaatg tctcctgaaa ttccctacta cttcatccac aatggccatc attcactaca   63000
gtttcatcca ctgtattcat cattttctgt aactatttag tgtatgttta ataactgttt   63060
taaagtattg gtctgaaaag tccaacaact gtattgtcta agaatctgct atttttttt   63120 cctattcaaa aggaattaca ttttcccact tttcacatat ctagtaattt ttttattgtg   63180
gatgattctc acctctgagc ataccaat atgttcaata aattgttgat aaagtgatta   63240
ttataaaact ccatgtaagc ctagagttag atctctcaac aatgggagat tgtcttaaa   63300 ctctcccaca taacaattta ctaaattata tattacttaa ttgttttttaa ggaatttaga   63360 ttaaattttg agtagttatg aaatatatat gacataaaaa taattgtata atgaacaccc   63420
atgtactagt ttaagaagat ctttagcagt acgtgtgaat tcttctccaa tctcatccac   63480
cattcattcc ttcccactca gaagtaactt aacttgttat tctagaattt ttagttactg   63540
tgtttatgat ttattttctt aattacatat gtttgtgtcc ctatgctata tagatatagc   63600
atatatatgc atatgtgaat atatatatat atgtagagag agagagagaa agagagagag   63660 ggttttttc actaagcatg tttttacact tctctttccg ctctcaattc aaggtcacct   63720
```

```
tctctatgaa gtcttccctz atcccccagg ctccattccc taactagctt tgcttccggg    63780
cttgctcttc cccaacccat tcttcaaata gaatctcatc actctcctaa ataattttg     63840 tttgtttgtt tgtttgtttt tgtagagaca aggtctcgct ctgttgtcca ggctggatgg    63900
agtggcagtg gtgctatcat agctcactgc agctttgaac tcctgggctc aagcaatcct    63960
cccgccttgg cctctccggt agctgggact acagacacct agctaatttt aaaaaacttt    64020
tattttgtag agacagtgtc tctttatgtt gcccaggctg gtctccaact cctggcctca    64080
agcaattctc ccaatttagc ctcccaaagc actgggatta aagcttgag ccaccttacc     64140 ccaccctctt tagagaccc  tcatctcttt ttgtccaggc ttagaagtga agaatttggg    64200
ggatatacat gtgcaagctg cagtgctatc tgtagtttta aatgttctca agtaactaaa    64260
actcctttgg gaaagctttg ctactcactg atgggtgcct ccctggccca ccagatcaga    64320
taggagtctt caccgggctg tcacagagag acttggagac tttctgacct ccagtgaaag    64380
atgaactcag tgtcaatatt aacgagggac ctttccccca tggacattgg acgggtccta    64440
agtagctcct gatgttactc tgaaccagaa aaacatggag tagagaaatg ccagcctact    64500 ctgatttta ataacagctt ttaggagaag tcatagtttt atataatcaa tgtaagtaat     64560
tatcgagtac ccaccactct actctgagtt ctgctttgat caatgaaata ataaataaat    64620
gtccttgctc gtgacaaaga aatttataca aagaaaaaaa atctcaaaag tctttagtaa    64680
gagtcgttta ttcttatta agatatagat cactccaaat catctctgaa aaatcccttc     64740
taaattaaaa aagtattaaa agcattataa atgtaatgcc caactaactt gattggaggg    64800
aagttttagg tcaaacaaat gatgtaagta aatggtattt tatgtattaa tcctataaat    64860
atccactttt tgggattcaa cttaaatatt tctaattta ccataggaat ttttcagttc     64920
tgtatttaga ttttcataat atagtattgt catatatata atttatttga ttctaagttc    64980
gtagtcaggg acacagtcta caaatgcaac attattcctg gaataaataa gattagcttg    65040
agtgaatgat tttattgagt aaataaactg gaaacttcta tatttggcag aaagttaatc    65100
tccacatatg tgagtattcc aaatgttgct ttggccaaag atttagaaag aaaataaagc    65160
tagtttctgc tttgaaagca gttggcctct agagtattag attgattcta aattggaatt    65220
tttttgctga gttgtcttaa aagttttttc attttgtttt gttttttgtcc tgtgtactaa    65280 agggtccaaa aagattttgg gcttctgttt atttatatca tttgacttag gaagcctatt    65340
agttcttaaa tgttctatta ggatcttttc cttccagat aatatatttc taatacttga     65400
attttagagt tgcctgcaac tctaggagaa ggtggctcct taaattagat tttcagtagt    65460
gaaaggtaag acttcatcat ttcctgtcta aaaccccata ttgttggggg caatttaaag    65520
aaatctggag aaaagaattt tgcctggaa tcttacggga tccctctctg ccatgctttt     65580
acctgagcca atatggcacc atgctttac ctgagccaat atggcaccac agtgtcttgc     65640
tctactcaaa ttcaagagga gggaacatac accccacctc tcaatggaag agtgtccatt    65700
tcatcttata agcaaatcac atgagatgag atagaatagc taggtaattt agttttagtg    65760
cgggagtagg aaagagaaac ccaaattctc aattttaac acagcgctac agaaattact     65820
cctctgaaat cagggagaca ttactacagg ggtacattac tgcatgtacc tagggtcact    65880
aggtacatgg acagtaagat cttacagacc aagtataaat tccaaatctc ccacttcctc    65940
atctgcaaac ctgcttttct ctgagggttg ttgagagtta atttaggtaa tgaaagtaaa    66000
agccttacac cactcttggc acacagctat tataacaaac agatcactac atggatttac    66060
```

```
cagaaatcctt agccttctac ctgtaatgcc ttgactaatc ttcatttcaa acagggttag    66120
ttaaaaataa ttcaatgacc ctacccatta gaccattcaa ctacttttta aatttgtaac    66180
tctgcttatt tgctacatga gagttcaaca atggtaatag aagcagaatt agaattaagg    66240
cttaaattca ataaaactgc atataaaagt aattctattt aatagtttga ttgaattttg    66300
ttaaaaatta aaaaaaaatt tgtttaaaaa ataatgttcc accctccttt gtgagtccac    66360
atgctctctg atagccacag ttttgagagt gtagtatgcc caactggaaa atatactact    66420
ttttgctttg attcattttc cccttttctt gactaagcac attgaggggt tttcttttgt    66480
ttttgttttt gtttggtaaa atatccaata tatacattag aattatctta tgtcaacatt    66540
tgtgaaataa gtgcacactt attttttcttt ggctatatgc caaatggcaa tatatgtgtg    66600
aattgtattt actgcatatg ttttcataag attctctgag catatcttat gaaatatcat    66660
aaattggttc tagaacttgt aagttaatca gaaattctag gtttcaggaa attgggtata    66720
ttaattctta aaatgaaaat caaagaaagg ttgtcttctt catcttggtc catgtgaaca    66780
attttttctt ttttttttct tttttttga gatggagtct cactctgtca cccaggatgg    66840
agtgtagtgg tgccatctcg gctcaccgca agctctgcct cccgggttca tgccattctc    66900
ctgcctcagc ctcccaagta gctgggacta caggcgcccg ccaccatgcc tggctaaatt    66960
tttttttttt ttttttttg tatttttagt agagacgggg tttcaccatg ttagccagga    67020
tggtctcgat ctcctgacct cgtgatccac ccacctcggc ctcccaaagt gttgggatta    67080
caggcatgag acactgcgcc tgaccttctt ttttttttt aatgcagact tcatcagctt    67140
gattttagtt ctgcacaaac agtggtggag ggaaaggttt ctttggtttc ttctgctttt    67200
cttagtcact ttctttcctt ggcacctgat tcaacatcta ggctgtctcg aaaaccctac    67260
actgagggcc cctcatggca gcaccactgt tcttttctgt cctggctcct taccctcctc    67320
actgctcatt gccctgacag ctggctctcc ctttgaagta ctgctcctaa actaatgttt    67380
tctccatcag gcattaactg acatataaca cttgacttgt ccttctgacc ccacttcttt    67440
ttaaccactt tctcacccta ttagtctatt tactcgtgtg tgtgtgtgtg tgtgtgtgtt    67500
caacaaggaa gtattctggg cctccttgtt acattaaggc tgcttactct tcactgaccc    67560
taaattaatt ctaatttggc cctttgggac tttattcttt cctgatgtat tagtccattc    67620
tcacactgct aatgaagaca tacctgagac tgggtaattt ataaagaaaa agatgcttaa    67680
tggactcaca gttccacatg gctggggagg cctcacaatc atggcgaagc aggagcaaag    67740
gcatgtctta catggtggca gacaagagag catgtgcaag gtaactgccc tttataaaac    67800
aatcagatct catgagactt attcattatt atgagaatcg aatgagaaaa acccacctgc    67860
atgattcagt tacctttcac tggctccttc tcataacagg tgaggattgt gggaactaca    67920
attcaagatg agatttgggt ggggacacag tcaaaccata tcacctgatt attaagccaa    67980
cttcccagag gaaaagttca tgcataggaa aataagctag gaagctgaga atctgctggt    68040
cttatgcccc acaaccacca agtgaagcca aaaaaaaaaa aaaatcacaa tcaacaactg    68100
tttgaccaaa tagttcaaca aacaattgag ccatctggat attttggtagc gtgttataac    68160 aacagaatcc tgtttgtttt ctacagggcc atttagtaat ttttgtctgt agtgaggaga    68220
ttgttgcttt ttgcttgttt gaaggacatt aaggaaatac actaagtagc attaaacact    68280
acctctgtga ctgctcttaa agtcactgtg agttggttat gaggcctcaa gtgtgcaaat    68340
gagaaacaca cctgcaggag aatatggatg agaaaccatg aaattggtct ttaataaaaa    68400
caatgtccta aacttatgaa cctccccaaa aaacctaatc ctccttcagt gtgccctatc    68460
```

```
tcagccaatc ccatctgcat cagacatatt gtaaaagcca gaaacctagt gaagcggcat    68520
cattttctgg ggtaaataac tggggttcgt catctcatac aagaaaact aaggacacag     68580 acacacacag agagtgagtt taggagtgat agtttaatag gcaaaagaaa gagaaagaac    68640
agctttctgt cttttgagag agagggacac ctgagtggga catttggcct gaggtggagt   68700
acaccggatt ttagagacag gcttgacaaa gcaatatctg atttacatag ggcccaaaga   68760
ttggttggac caggtgtgat gtttacataa tatgtggggc ccctaatctt attatgcaaa   68820
tagagtcttt gcctagctgg caccttgtta cctgctcctt cctgtacacg gggctggcaa   68880
agagaaggga aggtggagcc gccattttga acatacctag tcccaggtgg ccttttaacc   68940
tgtataaact tctagctaga atgggatggt aaaagaagt gtgtgcgcgt gattttgcct    69000
cctattttgc acgagagagg ttctcttttt atcctatttt gtagacatgg cttatctact   69060
tctctcttga tttagtcttt ctaacgtatt atagtggaga taagaagttt agcaaagttc   69120
cctgaaggaa ggagacaggg ttgagaagac gggagagaaa gacatagtga aatgttcaca   69180
gaagaccatc cagcacatac ctgattccca ttgctgtgta tacactttgt aaatttggac   69240
aagttctttc tcctccctga gtcttggttt cttcattttc aaatgagggt ttcatattag   69300
ataatctcta atgtctgatt gtctgactca aacatctttc gtgactaaac tttcccgaat   69360
ctatcacact aattcatatc cttccacatg tcccaagtta aagtacgact attttcacaa   69420
ccaatgtatc aaactcttcc tgctttgaca aaaacagatg caactggatg tgccaactga   69480
ttctttgaaa aggaaactca aactattttt gggggggagt tctgcaaaga acattgtgac   69540
tactgagttt ttataggctt ttttttttcc acttagctat atctagtctt atctagacat   69600
cattgaaaat atgcttgaat tgcaggcctt tttcaggtgt ccttgaaatt actcagaacc   69660
ggtaccttcc ttgacacttc ttttttattaa atagtatagg tggtgggact atatcaggag   69720
tggcagacat aaatttccat aggggcccca ctgcttatac tataaaagct cttttttgcag  69780 cagcatcttc agagaggagg tgagatacca catggaaata ttgctgcacc cctaagattc   69840
ttgcataagt cttgtatggg tgcgtctgct ttagatagaa cttggagatg tcagtcacaa   69900
ttattaccaa agtgaataga taacactaac tcagtcttcc taagagaata ccagaaaaga   69960
ttaactggac agattttacc tcattcttat ggcatgaagt tattttattt caggaaactt   70020
aaattctttg ttgtactaaa ttaaaaaaat acagttttgc ttaggggaa aaaggaaaga    70080 aaaggaatag tagttgagga tattgaacat tttgaacacg tatctctctt aggtcttaaa   70140
aacttatgga tcatggtaga catatttacg agtactattt gaatgtcttc ccaagatggc   70200
agatcacagg ttttacatac ggtgggagaa agaaaaagac gctgttgagc agaggaaata   70260
atacatggtt aaagaatttc taccagaatt cattgagcac caaatattgc tgaagttaga   70320
tattgaaact atctcatggt ctattacttt gcagtcaggg gtttccttat ttccagcaca   70380
gaaataacta ttttttagcta tacttaaaca atattacaat gatagtgttt ttagggaagg   70440
caagtgtgaa atgtaagata gaatttgttg gtttttttcc ctgttggggg gaatttccaa    70500
agaagccaaa caacaataag aattaaaatg ggaaatgtgg gcaattttct ataatatcac   70560
tgaatgcttt ctgtctttgt ttgtatattg ttggaagctg tacttatggg tctattatga   70620
ctattcttca ttggccactg agattaattt cccttttataa ttttgtaatt acatttgtga   70680
aatacatttt ttaacaccta atcaccacca gggcactctt aagagatgta attagaaagc   70740
ccatcagaca ttctgtcttc agtgtattgc taattgtgtt aattcatttt tttattgcaa   70800
```

```
cttgctgttg atatcatgaa tgaagccttc attatagaga atagttctca gtgaaatggc   70860
attcccattg gtttaagagc cttcttttaa tttgagggtt gttccttatt ggggattatt   70920
gtcaaacttt ttaaaaagta tatttccagt tatctgaaga cagattgaaa gcagacccaa   70980
gcaattaagg tgagacaagt ataacctccc tctttcccct actattttct tattctgtac   71040
tccaaagcta cgccataggg aacattccta tcagcaacag tgcacaaaac acagaacaag   71100
aacaagatag ttcatttcct cttttctttt ttttcaaaag caattcccgt caatgttgca   71160
aaaattagaa aatgcaggca agcaaaatca aatcaaatca aatcaatcac tttcaatccc   71220
accatctgga gaggttctag taccatcttt gtcaccttgc tgtggaaact tgtgcaattt   71280
tcctctgtgt cgtgtgtatg tgtatgtgtg tgtgtgtgtg tgtttctaat tatttgcttt   71340
ctccttcctc agaaaaagca tatgtattca tgatatgtta actttggcct taatgttgta   71400
acttgcttag ggcaataggg tgtgagtagt tatgtcttac ctcatctgag caaagcgttg   71460
ctcccctggc aggaccatcc tctgccctga gaacagcata ttccagacga gtgttgctcc   71520
atcagccctg gtcacagaga gaaaatcatg tggagcagat ccacagaggg tgcttcagct   71580
gccccatagt tatcatgtaa cttgaggaaa agaaaaaatc atttctttta aaaaactgag   71640
atttggaggt tatttttac atagcaaatc tagtatttta cctagcctct ctaagactca   71700
gttttcatgg ctgcaaaatt acagtaacaa taatagtatc tacatgcgaa ggctattgaa   71760
aagattgaag gaggtaatac gtgtatactc atagtgcctg ctgcataata ttatattctt   71820
caagcctttt ttctattcat atataaatat atatttacaa aaatcagatt atgtcataca   71880
ttcagtttgt agtccctttt taagtaata acataccaaa aacatctatc tagataatta   71940
aatattctag tacacaattt ttaatggctg cagagtattc cattagtatc ggtgtgccaa   72000
agattaacaa attcattatt ttggacattt agattacttt caaattccac tgcattagac   72060
aaagttatga tggacatttc tacaatcaaa tctggaccaa tttataatat caagaggaaa   72120
aaaaccttag tcaagggtc tggatgtttt aagaattttg gcatatagag ttgtttacag   72180
cttacaaact tataatgtta atacagcgaa acttagccag aagatagtta tataatcttt   72240
aagagtagat caattaaaga aaaaaatcat tgacaactta ttttcaaact tcattatttt   72300
caatgggcat gtttatttaa atacgtatgt ttctagaatc agtgtgaaat gtggaaagaa   72360
aatagatttt gaagtaagaa ctgttttcaa gttctgtctc tgccgcttat tgactgtgag   72420
atcttaatca agttacttaa cttctgtgaa cctttatttc cttatatata aagtggagat   72480
ttaaatgcct atttgcattt cataggagga taatgtaatg tgtataaatt gcctggcttc   72540
tatatgcatt cagttcattt tagttccttc cttcctttcc cactagttat cccctactcc   72600 caaccctct tcaaaaaagg agtccatttt aatgttttaa tttggccaaa gactaccata   72660
tattcttgtg tatcagccaa gaaggataac agacagagtt tcttgataaa cattaggttt   72720
catctatatc tttccaaaga atatcagaat tttctctcag aacagagaac aagattggag   72780
ctctgtttcc tgtcacccac ctggcagcaa ttagttcagg acccagaacc tgcacattag   72840
caacagcaga gaagcagtga acttaagtta gagtcaactg tcagttggag aagctattgt   72900
tagtcagggt tcctttaggg aaagcgacag atcctgctca gattaattta gtcaactcag   72960
ttatttcaat tcagctcatt gactttgcat aaattctggt ttagttctgc actgcgtcct   73020
ttagctccta tcactgaatg cgtactacca ccagagagag gtgaggagat acaagatgtc   73080
ttagaaatat gagtcagcta tcagaaaaat atgaatcgga ttacctatgg atctaagtca   73140
tgtagatgcc tctagacacg ttctgaaata actgaacttc tcagttatta tcccatctgc   73200
```

```
atccccaaac aaaatcacat tagttcagat taattctttg gtattcctga ttaagtttgt    73260
ggggttgatt aaaccttgtt ttatgtgctg taatttttta tatacttaat ttttaaaaag    73320
tgaactggtg atttcatcat tgtacctcat aaatttgtaa aattataatg tgccaatttt    73380
ttaaacgtga actggcaagg tgagtcatat gcaagtttct cacaaggact aagctttctt    73440
gaataaagca ggatgttcag ttcacctgaa aaattaaatt gcacattgaa attgacttta    73500
acatcatcat tttagataaa gttcgtcaga tcagaccact gattcttagc tcttagggtc    73560
atggtgggaa acaactgcta tgatgagaac tatttgtata tcgttgctga catttagaga    73620
tccaacttgg ttggccatcc cttatatcat taatctcact taattgctct gttttttcaag   73680 ggaatctaga caattttaca gaaccttttg aactacttac acagctgtga agaaaggata    73740
atttccaagg gcactcaaat ttcaggaaaa tggattctta ataatttaa taggaagaaa     73800 aggaaagttt gtaatgatta aattacattt gatggtgctt ttctttatta gtaaatatat    73860
gcactgaaat tggaaatgca ggagcaagct tgtcttttat aaggttctag atgaaatatc    73920
tttgtatgaa atcccataag tggtgagagg attgggagat atgtgtatta aggggggtgca   73980 tgaggatagc tcccattcaa gctttctctg caatacagaa agactccgta agagcaagtc    74040
ctggatttgg attcagcaaa tatttgatga gtgaatttat aaacacagta agtgctctgc    74100
ttcattctac cccacctcca tttctgcaaa cacaaacata caaagataaa tgtatgtaca    74160
atgcatagca aggttatggg ggagaggcag aaaattaaga accccagact ggtttattgc    74220
tagtaagtat tggtacaaca gggcctgtgg ctaacagcca gcaattgttc taattggtgg    74280
atgttgcagt ggcaacaatt gttaaatacg ttgaacaaca ccccagatgt cctttttcttt   74340 aacctcattt tattcaagtc taagcacttt ctttcttaaa atagtcttga tatcagaacc    74400
aaacagaatg ttaaaggtga ctaagagaaa ttaaactggg caagaggatg aactatcatt    74460
atggttattt ctacccctac tagaccaagc tttagaactt cactgcagaa tattgaagcc    74520
aactaggaaa aatcttaat gcgagacaga ttagtaattt agaacatgaa ctaggttgga    74580
ccctatgata gagttttaat tagagctctt ccactaactt tcaaacagat ttaaaataaa    74640
tcattcagta ggttttcttt tgctcatcta tagagtgaga agttggggat atttgaattc    74700
taagatccct tccagtttca tcatttaata aaatcagttg tactttattc tgaaagagga    74760
ttttttcaac agtgtgtgta taaggacaag atgatatttt gtataaggac tatatcttaa    74820
tcccaccatt ttaaattcct gttggtattt atagaatggt ttcgtatgta tgtggcattg    74880
acttctacat aaatattta aaacttggct taaaagagtt tataacttat ggcaaccaat     74940
ttagttccac tcagtaagtc tcctgtgtaa gatataatag aagggtaatt catcagtatt    75000
tgtgaaagtg gactttcaaa accaagcacc aacatattta accaatcata tatttaccag    75060
agtttcactt agccaaacaa gcatggcaaa gtcctgcgat ttcttttcca atataataaa    75120
gaaatgctga taagtctgca acatttacct tttactgcag cttttctgc taatcaagag     75180 accaacatac ttttcattca ggaaatcaat ggaagtcaat tattacccag acgtggccat    75240
ccattccttg aatgtccatt gcacattaat attggtaaat gtaattagaa ataacagcta    75300
atttaaatga atttatttag aggatccatg gttgcagaat tttgcagaac ttttaatatc    75360
ctaacatact tgcgaatttc cagagaagag cacgtggtat ttcacatttc acaaactttg    75420
ttccagtgga ctgctcattc ctcttttgt tattaatgag tgttcacaga gatcatattt      75480
tgtaaaacca atgtggaaat tctgttttag tttatttct attacaatgt caagtagagt      75540
```

```
caatatttat ctatacattg ctatcttgtc tctgtctgcc aaatacatgt tttgtatttt    75600
agtgatggtt acattagagc ctatcttgga gtgaaaaaga cctttaatta tagtccagtt    75660
gtctaatttt ataagtaatg aaatgcatgc ccagaaagat atagtaacat gcttaagagt    75720
catgtggtga gtttgaagtt cttctgggat tacaatatgg atctcttatt cctttgccca    75780
ctattttttt ttccattatg ccatactgac ttttcttcta atatttgcca tagttgatct    75840
taacagaagt tgaaaagtta caaggaaacc ttgaacatgc taattacaat cagtttctca    75900
aaatagaaga cccttctgat aattcaattt ccatttgtcc aaaactgagt ttactttatt    75960
cttcatatat gacagtctat atgtagtgac taagaacaca gattttggaa ttagcccact    76020
taagatttct tcagtatgct tagtgattcc agtatcttca tgcttatcct ttagattgga    76080
ttatttttct cccaatctct cacatatcga agtttggctt catcttaaga aagcattgaa    76140
acacatctaa taaatgcatg atgtattttt aattaaattg atttgaatca aagagtttct    76200
atctccccct tatcatggct gctattagag ttccgatact ataaagtata cgtgaggtta    76260
caatgccttt ttcttaaatt agttttaatt agacagatca taaccaatta tccattaata    76320
atagccattt gggtaatggc acaattctga actgcacaca attctgaacc atttctctaa    76380
gatctccttg tttattaatg ttgcctgacc aactacttag atgtcatgta tttgttcatt    76440
cattgaatgc ttattgagca cttactatgt gcaaggcttt gtgttgagtc ttgtatttaa    76500
ccactctgtt acacaggatg tggtactcaa attcgaagta aagtctactt attttttgaaa   76560 acttccacca aactagtata catcattgct tcattttaaa tcttatatca ttgttttgtt    76620
tcccattagc aagtataatt aaagtcactt aaggagatgg gtcttagagt agaaattctg    76680
acaaaaacgt gaccagtaac ttttcaaaat ttgtcaagta gtttacacca tttccaccag    76740
ggttaggcta gcatcttgga gtagaaatgt gctttctagc catttcccct taatagctgg    76800
aaatatatat ccatgctgga ttattcctac cagggatttc tggactgtgg gcttttggtc    76860
tttgaacttc taggcagtga taataaaaac atcatctatg tgcttaaaaa taacagtgaa    76920
aataacatat gagttgataa atagatataa tagagatcaa gagtgatttg agactgggtt    76980
ctccatggaa actgaaaaga tatgaaggac atgctgttag atcttctcct catttatacc    77040
ctcaaaaaac atgtattgaa caagtatgat atggaaagcc ctgggctggt tgtagtcagg    77100
gatattgtta aaacagaaat agcttggtgg ttggagagac cactctgagg gcacaggact    77160
aggagtcaga acacctgatt tgtctactca gtaacttcat gactggaaac taacctaatc    77220
tcctaatctc cttgagcttt gagttgctca tccacaaact aagtgtaaaa ggagaatcta    77280
caacattttg tcttaagaac taaatcaaag aacatgtatg taagaatcta gcatggtact    77340
gaaaacacag taactattaa atgctaatta gatgatgtat acacataatg caagctacaa    77400
agtggttaag tttataagag ctcaatgtgc tcaataagag ctaagttagc atgatgatgt    77460
aaaaatacat agctgagtca ggtcattgac atgagtaaaa gaaaaagtct tatttctttc    77520
aatatgacat cattttttatt ctgtttcccc tatcatctga attatttctc ttacattgtg    77580
tgtcacactg tttacccaga acagctctcc aatgcagaaa gtgccaagtc tttctaccag    77640
ctagacttgg agcctggatt tagatagaca ttttaaactc atgaggagag taggaagaca    77700
ctctgttttg ctttatgtgg caacataaat tgggtttatg gccatattat gccttggcaa    77760
gttagttcct gtaataatga agaatgattt tcaaataggt tatataatca aggagttatc    77820
caaacagaag gctttgctgt ggcagcaaac cagcctatcc tgtggtttca caaaattcat    77880
ttgcttattc acttagactg catctacaga aacatattaa atagaattgt ctagaaagaa    77940
```

```
atgccaaatt ttgtatttga aaagattcta ggccttgggt gacaacagct catagctgtt    78000
ttgagacaag ccatgttcct tttcactact ctttgcccac attcctcatc ctactccttg    78060
ttctcatagc caagatattg gtggaaatgt tcttgacaaa tactgctcca aaggaataat    78120
cgcctgtgag atgcccatta tagtactggg cttttgtacca aggctagaga atgttgaagg    78180
cctcagaaat tccactttg cttcatgaag gggaaagaga gaaaattata agtgaaaggg    78240
cagctcgttc tcatgacttg caggcttaat caactagagt ggtttagaaa ttgccattga    78300
gctaaaagag cattttccaa aggatattct atagatgggt tattaattgt tatcacacca    78360
taaaagtgtt tcatggtcaa tcaggtttgg gaaatgaaga gttaacatca aagggggtctt   78420 tttcgtacag aaaaattaga gtctttaaag tgctaatgtc tatagtaaat ctctgagaga    78480
ataggaaaga cttaatttcc taaacttatt tggccatgga aactttattt tatgctgctt    78540
ctcatgggat tgctgctctt ctatggaaca tgcttttgga aatgccaatc tataagaata    78600
gacacattat tttcagacat tgacattttg tactcttttcc acaaaaaata aagataattt   78660
aactttgctt ttcaagtaaa tttgttcccc ttacatgaag acattctgtt caatcattat    78720
cattgattta ctgattttca ttttatttat tcacagaata aatgattccc actgatccac    78780 ccactttgc caccccagga tgcaattttc tggagagaag attagtggca agtgcccatt    78840
tgtggataca aaccagtata gattcggttg tcccaccagt aactgaacct cttacaatgg    78900
tttcttcatt tgcatgttct aaatcagcca caacaatcag attttttaggc tccacattga   78960 tctggtttag ggtctgcatt aactctggca ggatggggct cctgtccagg tttttgtttg    79020
aaaaaagtgg ttaaaagata tgccggaaat cattacccta aggagccaga ttactgagac    79080
aggtcttgta tacttctcct attcaaggag ggcatgacta agtagtcatt ctatagataa    79140
gaagctggta taaaagtgaa actctttgtt caaaaataat aataataaag ggagaagcag    79200
aaattagaat ttttttggctc cgcgagtagg gcactttaag taaagaacaa tgcttcctgt   79260
cttactaaat tatagattga cattccttag gttctgtccc taaattatcc cttaaaccaa    79320
gcaaccaaca tttactagca tttactatgt tccaggctct tctctaggtt cttgggttgc    79380
aagagtgaac aaaatccttg ctatggagat ggtaattcat caagaagcaa gtaaacaaat    79440
aatcttatgt caaagttaaa cttttgttttg attttctttg agtgatcttc ctggtgtacc   79500
agatgatttt ctggttgcag gtcttctgta tcacctattt ccattccaat ttgaaagttc    79560
tcaaggtgca tttcataccc actaactgct gtttggtgat actgtccttt ctacctgggt    79620
ccaggtttca ctctctaagg ctcaggtcag ctattctcct gaaggtcact gaactgtgaa    79680
cataacaata tcacctggaa tcttgcctgt tttaaatcct acactaatca gtctctagat    79740 tccacccca atctatccat cctttcattc tgtcttttaa tcatctcttc aactaagcca    79800
ttggcctctg tcagttcatc ccggattttc cacagttatc actctcatta actctctctc    79860
ccattctttt cttccttcta ataatctcag gaaagagaaa ttatctcatt cttcagcctg    79920
attctactct tccttgcctg cttttctctc tcaaactgat aaagcacctc ctttcttcac    79980
agctctacct gtatatgttt tcttctcccc tcctcaggag tcaccataaa gtgcttttt    80040 tcaaaaaacc atatatctac aaggcattgt ttaacccagg acaactgcag tgcaacttt    80100 ctgactagag gcaggcttgg tgagcagaga tctactatag tttgggcatg aggcatttgt    80160
tatagttcca aataatgcaa gtcttttaaaa ttaagacctc ttcaattaat aggcaaaaca    80220
aaagaaattg tttcttatct aaatcccctc tgttgtttcc gaatattcac tctcagatct    80280
```

-continued

| | | | | | |
|---|---|---|---|---|---|
| gttttcatac | tattttttgtt | ctcataagct | gtttgtgata | catgtgtaaa | tgtcatgtgt | 80340 |
| ggggctttaa | gaccatgggg | gtcccctttt | ctacagcaag | atgactgtgc | agcccattca | 80400 |
| ccttaaagtg | acaagtctcc | cattgcctcc | aatgctcctc | attttaataa | cactgttgag | 80460 |
| tcaaacagca | acttctacat | tgcaaaatat | caaatacatg | acatggatgg | taccatgtac | 80520 |
| tatcaattaa | ccatccaatc | accacatatt | caccttcata | agaagctgg | tttctcgcca | 80580 |
| tattagctct | cacatttgga | attaatgagt | aggatcatgt | caagaggaga | tttggctttt | 80640 |
| aattctggca | ccacccgtgg | tgttctacat | atccttcttc | tctcagaggc | tacattacag | 80700 |
| gacaatcatg | agcagtcacc | tttaggaatt | taatgtatgt | ctatgacttc | tttgtacttt | 80760 |
| gtaaaatgca | agatgtagac | aaagaaaact | gtgtcagttt | cacaagtatg | tatacatctc | 80820 |
| aaaaactcca | actttcacac | caggaaataa | gtctcaccca | atatatggag | gtagtgtatt | 80880 |
| cccaatcaac | aagaaagaca | caaattaaaa | gtttgcctcc | tccacctact | ttcctctcct | 80940 |
| gaatttctta | tctgtccttt | tagcaggcca | caaatctaag | agacaatttt | aatttttctc | 81000 |
| tatttctctt | catgatcaca | ctggtgcttg | ttactttaag | ggggtcctgt | attgtattcc | 81060 |
| tagccaatgg | ttcttttgcac | taacttaaag | tttgtaggga | attgctaaag | aagagtaaaa | 81120 |
| ttgcactcat | tttaatatag | aacacgagtt | ggagggatta | caacttgaag | cagggaaact | 81180 |
| ggtctagagg | ctgttgccag | ggaactgaag | agaaagatgg | tgacctgcac | taaggtagta | 81240 |
| gataggatgg | acatgtttga | aaagatccca | aaatgcagat | ggaatcagag | agtcctagag | 81300 |
| actagaagct | tggaatgaag | aagtgagtgg | aatcaggaat | gatcccaact | ttctcattca | 81360 |
| tacaattcat | ggataattgt | ggaagacact | gatatgagaa | atgcaagaaa | atggacagag | 81420 |
| aaaataatac | atttagattt | gccaatgtgg | tggtgtggtg | aggatatagt | tgtaaaaaat | 81480 |
| cagaattcca | tgttttattt | aactcattag | atcacaagcc | accatcatta | tcaataataa | 81540 |
| taaacatgtg | tatgcaattt | tgtgatgtgc | cagagatata | tagctatcta | aaaaataatt | 81600 |
| cttatctgaa | agggtttagc | attaggtaag | gttgttagga | tgtgtattta | tgtagatgaa | 81660 |
| aatacataga | aatacacaga | atgccaaatg | ggtagtttgg | gtaataaatt | tcctaagcac | 81720 |
| tcaaaaccta | ctttttttagc | ccaatttcca | cttcctaaga | ggctttatgc | tccagctaaa | 81780 |
| ttaaactatt | atattcatta | ttctttagtt | atcctaagtt | ttcctagatc | catatgttgt | 81840 |
| ttttatgtgc | tttctctgac | taagaggtct | ttgcttttca | aaaccctatt | caggttttca | 81900 |
| aattttatct | caaatataaa | ttccctccct | gatcccccaa | tcaaaaatta | tataaccatc | 81960 |
| ttataaggcc | ctatatttt | gcaatttcat | tgaacctttc | acccagtctg | catttgagtt | 82020 |
| attttgccac | atcttatatc | atttataccc | ttccccactc | agatgctcaa | cttcttatac | 82080 |
| tggaatcata | tctcatccag | ctcatattta | catttcatgt | agtgcctcag | cacttaatac | 82140 |
| gtgtgtgcgt | gtatgcttct | aatttactga | gtggacttga | aataaatcag | aaacaatgaa | 82200 |
| taatgatcaa | catataaaat | gatgtttcaa | aattataatt | tacattctca | atttcctgtt | 82260 |
| atgccaatag | gtaaactgaa | tagaatttac | ccttttgggg | acaagtataa | taggcataca | 82320 |
| ttgtagacag | taatttatat | ctggaaaaat | ctgtaaatac | tttttttta | ctatttttgt | 82380 |
| tttttaaaat | atgtgagtgc | atattttatt | ttttctttt | taaaaaataa | aattttaca | 82440 |
| cctattgacc | tgtcctctaa | gtttcctccc | ttcgcacccc | tcccaccaac | aggccttggt | 82500 |
| gtgtgttgtt | ccctctctg | tgttcatgtg | ttctcattgt | tcaactccca | cttatgagtg | 82560 |
| agaacatgtg | gtgtttggtt | ttctgttcct | gtgttagttt | gctgaggatg | atggctttca | 82620 |
| gcttcatcct | ttgcagggat | atgagctcat | tccttttat | ggctgcatag | tattccattg | 82680 |

```
tgtatatgta ccacatttc tttatacggt ctatctttga tgggcatttg ggttggttcc    82740
atgacattgt tattgtaaat agtgctgcaa taaacatacg tgtgcatgtg tctttatagt    82800
tgaatgattt gcattccttt gggtatatac ccagtaatgg gattgctggg tcaaatggta    82860
tttctggttc tagatccttg aggaattgcc atactatctt ctacaatgat tgaactaatt    82920
tacattccca ccaacagtat aaaagcattc ctcattctcc acagcctcac cagcatctat    82980
ggtttcttga cttttaata atcaccattc tgaccggtgt gacatggtat ctcactgtgg    83040
ttttgattta catttctgta atgatcagtg atgttgagct ttatttcatg tttgttggct    83100
gtgtaaatgt cttcttttga gaagtgtcca tatccttttc ccacttttg atggggttgt    83160 ttgctttctt cttgtaaatt tgtttaaatt ccttgtaaat tttggatatt agacctttgt    83220
cagttaggta gattgcaaaa attttctccc attctgtaga ttgctggttc actctgatga    83280
tagtttcttt tgctgcgcag aagttctta gtttagttag atcccatttg tcaattttgg    83340
cttttgttgc aattgctttt ggcattttg tcatgaagtc tttgcccatg tctatgtcct    83400
gaatggtatt gcctaggttt tcttctagag tttttatggt ttgtggtttt tatttaagaa    83460
tttaatccat cttgagttaa ttttgtata aggtgtaagg aagaggtcca ttttagttt    83520 tctgcatatg gctagctagt tttcccagca ccattattg aataggaaat cctttccca    83580 ttgcttgtat ttgtcaggtt tgttgaagat cagatagttg tagatgtgtg tgttatttc    83640 tgaggtctct gttctgttcc attggtctat atgtctgttt tggtaccagt gccatgctgt    83700
tttggttact gtagccttat agcatagttt gaagtcaggt agtgtgatgc ttccagcttt    83760 gttcttttg cttaggactg tcttggctat acaggttttt ttttgatccc atacgaaatt    83820
taaagtagtt ttttctaatt ctctgaaaaa tgtcaatggt agtttgatgg aatagcact    83880 gaatctataa attactttga gcagtatggc cattttcacg atatcgattc ttcctatcca    83940
tgaggatgga atgttcttcc atttgtttgt gtaatctctt atttccttga gcagtgattt    84000
gtagttctcc ttgaagaggt ccttcacatc cctctttagc tgtattcctg ggtatttat    84060 tctctttgta atgattgtga attggagttc atttgtgatt tggctctctg cttgtctatt    84120
gttggattaa aggaatgctt gtaattttg cacattgatt ttttatcctg cgactttgct    84180
gaagttactt ctcagcttaa ggagttttgg ggctgagatg atgggtatt ctaaatataa    84240 aaccatgttg tctgcaaaca cagacaattt gacttcctct attcctattt gaatacccctt    84300 catttatttc tcttgcctga ttattgccct ggccagaatt tccaatacca tgttgaatag    84360
gagcagtgag agagggtatt cttgtctatg ctggttttca aagggaatgc tttcaattat    84420
ccccattcaa tgtgatattg gctgtggatt tgtcataaat agctcttatt ttgagatatg    84480
ttccatcaat acctagtcta ttgaagtttt taacataaag ggatgttgcc ttttatcaaa    84540
ggccttttct gcatctattg agataatcat gtggttttg tcttgggttc tgtttatgtg    84600
acggattaca tttattgatt tgcgtatgtt gaaccagact tgcatctcag gatgaagccg    84660
acttgatcat ggtggatacg tttttgatg tcctcctgga ttcagtttgc cagtatttta    84720
ttgaggattt ttgcatcaat gctcatcagg gatattggcc tgaagtgttc ttcttttgtt    84780
gtgtctctgc ccggatttgg tatcaggatg atgctggctt cataaaatga attagggagg    84840
agtccctcct tttcaattct tcagaatagt ttcagaagaa atggtaccag ctcctctttg    84900
taactctggt agaattcagc tgtggatcca tttggtcctg gacatttttt ggttggtagg    84960
ccattaatta ctgcctcaat ttcagaactt gctattggtc tattcagggc tccaacttct    85020
```

```
tcctggttta gtcttgggag gttaccagga atttatcaat ttcttctaga ttttctagtt    85080
tatttgtgta gaggtgttta cagtattctc tgatggtaat ttgtatttct gtggggtcag    85140
tgatgatacc ccctttttca tattttattg tgtctatttg gtgcttctct cttttcttct    85200
ttattagtct agctagtggc ttatctattt tttaaatttt tttaaaaaac cagctcctgg    85260
ttttattgat ttttttggag ggttttttgg gtttctatgt ccttcagttc tgctctgctc    85320
ttagttattt cttgttttat gctagctttt ggattagttt gcttttgcct ctctagctct    85380
tttaattgtg atattagggt gtcgatttga gatctttgca gctttgtgat gtgtgcattt    85440
agtgctataa atttccctct taacactgct ttaactgtgt cccagagatt ctggtacatt    85500
gtctctttgt tctcattggt ttccaagaac ttcttgattt ctgcctgaat ttcattattt    85560
acccaggagt cacttgggag caggttgttc agtttccatg taattgtgtg gttttgaatg    85620
tgttttttag tcctgagttc taatttgatt gcattgtggt ctgagagact gttttgttatg   85680 attttagttc ttttgctttt gctgaggaat gttttacttc caattatgtg gtcgatttta    85740
gaataagttc catgtggtac tgagaagaat gtatattctg ttgatttggg ttggagagtt    85800
ctgtagatgt ctattaggtc cacttgatac agagctgagt tcaagccctg aatatccttg    85860 ctaatttttct gtctcattga tctctctaat attggtagta gaatgttaaa gtctcccact    85920
attattgtgt gggagtctga gtatctttgt aagtctctaa gaacttattt tatgaatctg    85980
ggtgctcctg tatagggtgc atatatattt agagtagtta gctcttgttg aactgttccc    86040
tttaccatca tgcaaggcct tctttgtctt ttttttttatc ttgttggttt aaagtctgtt    86100
ttgtcagaga ctaggattgc aacccatgct ttttttttttt ttttttttct ttccatttgc    86160
ttggtaaatt ttcctccatc cctttgtttt gaacctatgt gtgtctttgc acatgaaatg    86220
gatctcctga atatagcaca tcaatgggtc ctgacttttt attcaatttg ccagtctgtg    86280
tcttttaatt ggggcattta gcccatttac atttaaggtt agcattctta tgtgtgaatt    86340
tgatccatca tcatgatgct atctggttat tttgcacaac agttgatgca gtttctacat    86400
agtgccattg gttttatatt ttggtgtgtt tttgcagtgg ctggtactgg ttttttccttt    86460 ccatatttag tgcttctttc aggagctctt gcaaggcaga ccaaatggta acaaaatctc    86520
tcagcatttg cttgcccaga aatgatttta tttcttcttc gcttatgaag cttagtttgg    86580
ctgaatatta aattctgggt tgaaaattct tttctttaag aatgttgaat attggcctcc    86640
aatctcttct agcttgtaga gtttctgttg agaggtcttc tgttagtctg aagggctttg    86700
ctttgtaggt tactttgcct ttctctctgg ctgcccttaa tattttttca ttcatttcaa    86760
ccttggagaa tctgatgatt atgtgtcttg gggttgatct tctcatgaaa tatcttagtg    86820
gtgttctctg tatttcctga atttgcatgt tggccagtct tgctatgttg gggaagttct    86880
cctggataaa ggataggtaa attctatggg taatacagta gatatagtgc aacaggaact    86940
taccagttaa gatacagtca taaccactca cccctagttg gaatgtaggt ttcacacaac    87000
tcccactgat gaaaagaaat atatgtattt ttcaactgtt taaccctttg ttaagttttc    87060
ttgtgtaaaa ttatctgcag agccatgaaa aaccatttga tatttgtgac taagcagcct    87120
gtttggatga ttatgctctt cagtatgaat ggtgagctgt taaatgacat gctcaatcat    87180
tgctatggaa gaaatttgtt cttactagca acttgaagct taaagaaaca tttataggaa    87240
agaaaattac tcaaagcttt aaataaggct acttttagag ttggccttag actacctaga    87300
gggcatgatg attaatcttt cacaaattac agatttttatt tgttcatgtc cagtgaggtg    87360
acttcttggt ggacatcttc attgcaattt tcagcagctc tatcaatgac acatgttaac    87420
```

```
tgaagctgac atgggttgct cttgctctct tggaatgtct ttatttctgt cctaatatgc   87480
aaaggtagtg ccagaattttc ttaataggag ggcctcaggt ataacaatct agttgacagg   87540
aaaagcaatg gaatcttcac tgcatttgca tcacaagcat actgttttttt cttacgtgtg   87600 ttttttaggg tgtcttggga tgttgatcct ctttaagtca aatagaaaaa atgaaaatga   87660
aatgccatag ccaatattag agatatatta attttagtct ttgttgcttt tatatttttc   87720
taggacaaag agatcttcaa aaatcaaaaa tgaggttcac atttacaagc cggtgcttgg   87780
cactgtttct tcttctaaat gtaagtaaaa caaaagtatt caaagccatg ctaatgaaga   87840
atgctgaata aggaggaatg ttttgagtgt gatttaatta gtatttgcaa gggtaggcat   87900
tggtctccag aagccgaaac taagttcctc aaagccatta ttttgcttaa tattttgtta   87960
acaaatctct cctctgaact gtctctaatt taaattagtg tttgtggtct acccagaaat   88020
ttgagttttg tttacaaaac tttagcatta attttagaca tctccatatt atcttagaaa   88080
ttaacatagt tggtaaataa tattctcagg taaaatgttt tcatgttgaa aaaactatgt   88140
tttgaatctt agttcaaaac tatgatttga atgatagttt ctgggctgtt caatccttt   88200 aaaacatctg ggctgttcaa ttcttttaaa acttctgaac tctttcagtc tggctattga   88260
tttcaaatgt attttttcatc aaaaactgac tatggaaact tcaagtcttt ataaccact   88320 attattctat aactctttct ccaatctttt aaattatgtt cagtttgtgt aattctatat   88380
tgttttattc ctaaaagatt tagcaagtaa tcggaaatat aatcatctta gagaacacta   88440
tcaatgccta ttatttgtgt caacattgtt aacctaccat cacatcagct tcaatagcac   88500
atgaatggga gatgagtaaa ttttacgtaa atcaatgtgg agctgccttg cttcttatcc   88560
tttctgtcac atcagagtaa catttgctaa taaattacag ttggcagcaa agatcactca   88620
atatctcata ctgtcatact gacccacaca aagcttgcat agggttcgag gatttccatt   88680
gtttattaat gtgtagttat aggcctacaa gtctgtctaa actgtttgtc tttatattat   88740
tcaagaaaaa aatattgcta gtatttcata aatgttaatt taatttgtaa ggcaattttt   88800
attttgtaat attgtacatc aaataaatgg tgtatgggaa tgactattaa tgcaacccct   88860
ttgcacctat ttggataatg agtataactt attttattgt cagtttgtct tatcatttta   88920
tcctattaaa tatttctttta gataaattac agtaaaattt tctaaaagta attagtattt   88980
ggaaatgcag gtttctttat gtcactggaa atataataaa aacactaaac aagactacta   89040
tggaaactaa tagaatattt taatttgcca gtaaataccc aggccttatg tggtcttcta   89100
tggatgtaaa aatattgcta tatattattg atattgttat ttttcatagc tcaaatgaaa   89160
tcctaagtga tctggtatat gtgaatattt ttgaataatc atgcttcata aataattata   89220
ttgaacatga cagaagaaaa actaaagaaa gaactaaata ctaacaaaat tgtttgaaga   89280
ttatctaatt acctttttta ttacaaaggc tttagaaaat ttgtagtgtg ttcaaaaagc   89340
aacgtaggtc attttttattc aaaacttttta ctaatgtagt ctataattta aatattgaaa   89400
aaaatgcaca tctttgcatg agccatggac agaaacattt tatggcttgt gggcacctct   89460
tgaccagcaa gcataactga acagggcact taaatgggtt tgtgctctct ttgctgtgac   89520
agagagaaat ttgcttctct ctctgtattt ggattatata tttgatttgg aggatttgtc   89580
cataaaacaa aatttgatat gtccattttc ttcaaaacgt ttattatgtt cacactgaca   89640
cttctcagag aaaaaaaatt ttaatgacaa tgttcctaat taatccgaaa tattactttt   89700
tagacaatag attgttgtga aaatacacta actattgaac tctatcaact cgatttccat   89760
```

```
ataggtttta aagtctcagt ttgggtcacc accttcaatt agcctctttc cattaaccat   89820
aaccacccac tcaattcctc tccctcctgc gaggtataca gtaagcttag agcagcagtt   89880
ggtatacagt gagctctcag aaaaagatgc cagtgacgat gctgatgaca acaaagccaa   89940
tggtaataac aaagacataa aaattaggtt cttcagagca ggtgttattg ttacttgttt   90000
acttatctat gttcacctat ttgctttgaa tttatgatat atgcagtttc gttgtttata   90060
taatgtaagt agaattacac agtacaccag ccaggcatct gatcttacct gggaaaacca   90120
gggctaacac ttttttacaac agtgtgcttt gtcctttctt attttgaaat gtgtaagtaa   90180
ctgaaaagca aaataatta tatacattat caacattaag gatggtgaca tgaaaatctc   90240
attggttgca tcagtttgtg gattctaggt ttacatactt tttagagtag ttttgcatgt   90300
ggcaatcaat aggaagctct cccttcagca cagcagcttg ggtccataca ctcagtgggc   90360
ttgaactatt gcagagatgg accatttctc aaagttccat gaagaacagc tctgtaactg   90420
tctctgtact tctagaaact gcctgtaacc caaaagcaaa ctgactgtcc tacatcacag   90480
taggaattgc ataagcatat gaccatttca aatcagattc ctttcctgtg gattccatga   90540
ttagtgtgga taaaatcaag aatgtaagct ctatgagagc aggtggcttg ccagtttggt   90600
tcactgctga atttccagaa cctagaagag tgcctgacat gtgagaggca ctcaaagtat   90660
ttgtcgactg aaaaaaactg atgatgtttg ggctgctgac tactgctgtt ggtggcagct   90720
tggtggtcgt atgtgtgacg ccatttactt gaacctttag gagtgacatc acatatacgg   90780
cagctaaaact gctacatggg acaacaatta agagttttgt ttgtttgtat gttgaaaaat   90840
catgtaagat ggtttatatg caaagctttg aaaactgatg tttattcaga aaaacaatat   90900
gcccttaata tctcatttct atctgaatgt gaacatataa tcatattttt atttaacccc   90960
ctgaaataag tagtatagac ataacactta taataagtag gatatttgaa gtctcttaca   91020
ttgtttggta gtttcatcca atcactactg gttttatttt gtctctgtat tgctgaaaat   91080
gataccacct tcccagcaat tcttatttgt ataaaattat cagcaaaagt ttaacattta   91140
ataaacttta tgaaatttgt atatgtgtta tttttaagca gtagtaattc catgattgta   91200
attatatata tataatatac ataaaatcat acatatacat atatttatat gtttatatct   91260
atctatctgt ctgtctatct atctatctat ctatctatct atctatctat ctatctatct   91320
atacagtcag ccctctgtat ccatgggttg tacatccata gattgaacca atcttggata   91380
gaaaatattc aggaaaaaat tgtattgtaa acatacagac tattttttctt tttattattt   91440
cctaaataat acagtataac aactatttac atcatatttta cattgtacta ggtataaata   91500
atctggggat gatttaaata atacaggagg atgtacatag gttatatgca aatactacac   91560
catttttatat gaaggaccta agcatcctca gattttggta tccacatatg caaatactac   91620
accatttttat atgaagtacc taagcatcct cagattttgg tatccacagg aggtcctgca   91680
accaatcccc tgagtatacc aagggatgac tgtatgtata aacgtaatgc cccaatgggt   91740
atgttatttt aggaagaagg ccactgagac attcatctac tgttgggaaa attccatctt   91800
cagtgctcaa atatgaacca gaccaggaac tgatgcagat tattactgct catctgacaa   91860
cagaggttct aatttttcat tccttcagtg ttgaaacaat ctctactgaa ccagcttcaa   91920
acaagttcac tggagtttgt ttcaatattg caagaatgat aagatggaag ctactttcat   91980
cagcatgaat tataactact cgtatacaga ttgtcgtatt tccactgtta ctgatgttaa   92040
aactgcatta aagcaaataa aaatataatt gaaaatacaa gcatagggtt ttctacttgt   92100
tatcctcgga catactattt gcctatggtt tccatgaatt tccaactaga gcaagaaaat   92160
```

```
ctcttggttg gttgtcagcc atataaaaag agaattcaga atgttacttt tgggaagaaa    92220
gccagattta aacaaaatac ttcccagtgt ttagcatatc taatacaagt gacagataag    92280
atttatatat gacatcatgt tccatcttct aattcgattt gaagatggtg agaaaatggt    92340
ccagaaatta ataatacatc aaatgatcat tctcatatta actgaagatt ttagagccac    92400
aaaagaagaa tctaaaataa atgtataagt tgaaccaata attaatatct ctattgtgaa    92460
ggcatcatga tccattcttg ttttgatggt tgcctaatat gtaattgaat ttttaaaaca    92520
cacatattca tacaaaagtt gagtaataaa ctaaaaaaag aaacctcaac atggaatccc    92580
ttcaaattac tctttttta aaatttttgca aatcgtgttc caattccatt aggaatatct    92640 aagaattta tgactgatga ttctttattg ttcataattt caagtatcag aaatatattt    92700
tatagtgttg gtccatcttg ccagactgta agctctatga gagcacagtc tacacttatt    92760
ttattcagca ctgtatcctc agcatctggc acaatgttgg gctcatcaag tttgatcaat    92820
atttgctgac tgatctgaag accagtgggg aaagtgtcat atatcaaaag aattgtgttc    92880
agctacactg gtaaaggatt tgcacagtta taatcatttt tatgggttca ttactttctc    92940
ttctgacata aattcaagag acattaaaat tagaaatcaa caaatgtttt aaagagtagt    93000 gtcaaccta ttcacaattg gtgtccattt gaagttatca cagtaatgtt ataataatga    93060
taagtattca ccctcttctc tttgcaagat atttccacta ggatggcttg ctaccatctc    93120
caaatctaac ccaaaatagg acttacttac caaggggag aagttccccc taataaggtt    93180
ttcctttccc agcatcttcc ctttcttggg aactattttt ttccccaaat atctaggcta    93240
attatctggg ctatttgact attactgttt cccattcctt gtattcaaat atgccttcat    93300 gttttatta ttgagaaggt gctaagagtg gtactttctt gttccaacat ggactgatct    93360
agtccagcca ggccttcaac ttcctggctg cccccacccc accccgcaac tttaacctgt    93420
ggacatctga tgcctgctgc atgaatttta ctaaaaattc tcctttcaca accttcactg    93480
atcaaaaatc tacaaaacat ctttatcata tatattatgt tatataccat gttttaacaa    93540
tattagctaa aatgttttga accttttcatg tccctgacac ttggtgttta ttgtcttgtt    93600
catcctcaca acatgacaga tgataaatat tattcttacc gctcttctta ttttacgttt    93660
cctaggttga ggaaacagat ctagtgagag gttgctaacc tgctcaaagt gacaaaacaa    93720
gttttaactc tttttttgtt atctgaagat tcagataatg cagtcttgaa agcaaagtcc    93780
tgaccttctt accctcaaat atgctcccct tcaggcaaga tggttttctc acagtggctc    93840
atgcatgtca tttccaacct ccagactttt gtgggaaagg tccctccatc ccaaaaggct    93900
tctcgacccc cccttgtgcc tatgcagaaa cttcccacac tcaagataca attcaaattc    93960
taccttgtat ctgtagccat cctgaatatt tttgctccct actctctcca aactctgaat    94020
tttgattgga ttctgtgctg gacagcttag cagttagtga tgtgctgtcg tgtaggacat    94080
atacaatgac acacatggaa aacagtgagg attcaccatg aagagccagg aatatacatg    94140
tcaacttaat agggatgagt tttgtttaga aactagcaca tatagaagag tacataacac    94200
cacttctgcc atcaatacaa ttggagaaac ttcaatctta gaattgaaat ttcaacgggt    94260
atgatagaaa ttaagcagca ttcctaaatt tagaaaaagg aaagtcagtg caggctgatg    94320
tttttaggtc tcctcaaaaa aagaaaaaaa aatctctatg cagaacatgg atattaaaaa    94380
ttcgcagatt ccaacaccac taaaaacatt ggtcatagcc acaaaagaaa ttgaaatctt    94440
tataaacaca agttaggaag aacagtgtga cagagtgatc ttttcaaaca cccacattac    94500
```

```
ctttgaaaaa gagaggcttg tgatggtgat gattaactga aactgaaaaa aactattgtc  94560
aatctgtacc aaaatgcaaa tgtgctgaga taaatatcta agaaatacat tgattttttca  94620 ttagtgaaca tgaattgccc tgtacaggtc atctgctgtt gaaaccaatt taaggagatt  94680
atggtcaatt atgaggagca gaaaacatat tttgtttgtt ccatggaata gatgggataa  94740
atttctggca gtgtacacag caccaataaa atttagctga aagaatcaaa taaaaaagca  94800
tatttattga actatgtcta tttttttaata acatgattca tgattcttaa gagtaaggca  94860
aagttgattt catatttgta tttttttggaa attagattat ttgtttttgtt tacttctaaa  94920 ctttagaatc ataatacagt taaaacaatc ctagctgata aagaggtata tgagtgtgta  94980
ggtgttatcc attttcaata gtaaatggaa actaatgcaa atgtaaaatg tgccagtaga  95040
atttgtagat gaaatgtgaa acattttttt gtaatatata tgaaaaaaac tgtacataga  95100
gaccatgaat aagtattgct tagagagcaa aaataaatgt tttcaaactt tttcattgtc  95160
tcatttattt gtgctcaccc attcctcctg tctataagta actgatttttt cttttttaata  95220 cagcacccaa ccccaattct tcctgccttt tcaaatcaaa cctatccaac aatagagccc  95280
aagccatttc tttacgtcgt aggacgaaag aagatgatgg atgcacagta caaatgctat  95340
gaccgaatgc agcagttacc cgcataccaa ggagaaggta aagagaagga tatatatgaa  95400
catatgtttg aaacaccatt acagacattt tcttttgtgg ttaaatatgt gttgaataat  95460
tttaatttaa tatgccagca gttttcacag cagttttcac actatggtat gtttgtgtat  95520
ttcatgcagt gcatatgcct aatttctttg cccaagttca tctgactgca atttggctaa  95580
catctgccct catgataaaa ttaccgcaat aattcagtat tcacacctgg tgagccggaa  95640
cagtaaagga ccgagtgagg gaggggatgt acaaaatgac aggaaaggga attggaaaat  95700
agagggcaga gaatttgcct gaggtggacc ctatcaaacc ctatcttgct tggattaatt  95760
aggtagtatc ttccctttaa ctgtcaattg gttggcaacc catactattc ttccacactt  95820
tctggcccca cttccagga gaattacaaa aaggtacctc ctagccagac attgtttatc  95880
taccagcttc tctagaatgg ctgtatgtga ctgcccagat attttcaggt ctaaacatat  95940
tctattagct gtagaggacc catagaaaaa caaaagggga gatgtgatgg gcaagctcat  96000
tgcaacatcc ctttaaattc tcctacttgt cccctgaggc atttgaaaag attcaataag  96060
atcttttact atatatatat atatatatat atatttaaga cagggtctca ctctctcgcc  96120
caggacgatc ctcccacttt agcctcctga gcagttggga ctacaggtgc atgccaccat  96180
gcccagcaaa ttttttgtatt tttttgtaga gatgggtttt tgccatgttg tccatgctgg  96240
tctccaactc ctgggctcag gagaggttcc caaagtgcta ggattacagg cgtgagacac  96300
tgcatctggc ctactaccat gtacatttta agacaaccca acttggtagg gaaaaaatg  96360 gtaaaatata ctctgttact gcacattctt tgctttcaaa tagttcaagt tttagtttgt  96420
agttcttatt tttaccatttt tccttttaaac aaaaacatca agtcaactga aaggcagata  96480
catattattc ttctgtctgc agtaatttca gtgtttatca agaactgaac aggcattaga  96540
cataactctg accaaaggag aaacaatttc gttgaagcca gtgagacaat aaaaacacag  96600
aactgatatt tttggggttt tctgagagct cttttcattt tttaaataat ttttgagagc  96660
tttcttgaaa gcctggatct gattcttttg aatacatacc tttatagaag taaatcttca  96720
tggttttagg tagaattttt tttttttttt tttttttttt ttttttttttg agagagggtc  96780 ttgcagtctt tggggcattt gcttttttga tgcactcaac tttggaacct tttacaaagt  96840
agaaatagaa ccctgcttgt catccaatga gataatttgg tcacagatat gctaagccta  96900
```

```
tttgaaactt tatttccaaa ataaatgact tggcttgttt gaaatgtggt tggttatgac  96960
tggtgtagtg agctcagcta cttgtaatat cgtcttggga tcaatcttct catttagtta  97020
aatccacaag gcttcaatat caatttcctt ctaaatggcc aggtccatat tgcaatcgca  97080
cctgggatgg atggctgtgc tgggatgaca caccggctgg agtattgtcc tatcagttct  97140
gcccagatta ttttccggat tttgatccat caggtagagt gtttatttc attttatgtt   97200 cttgctatga agcttttaga gttttcatgg ttttgagaag aaaatcagat acaaaatgta  97260
cccacctaat catactccac attttagcaa cttctgaagt gtttccttaa ttgaaatact  97320
tcttagttgt acaaatatta caagctgtcc tttttttaa gtcatgttgc tggtcagtta   97380
tatgtgttgg tattaaattc tggtttataa aaatagcttt tctaaaactc tgtgaatagt  97440
tttatttaaa tgtgagtttt aaaaatttt caattgtctc actgaaaaag gggtagaaat   97500
cttaattatg aaggagaccc agatgctgaa actaaatgga ttagctatgg cacaacata   97560 taggtccctg ttaatgggtg aaatttgttc ccaagagtaa agtgagcctg agcctacagg  97620
ggttaagtgg ctctagaatc ccaattaaag aagaaaatg agtctacccc tgaaacaatg   97680
ttagaaaaat gcttttttgtg cttccttcca gagtgaaaga tctaatctgt ccctgaaaac 97740
aaaatttcac ctcagtaagg cagagataat ggaagtggaa ttgcagagga cctcttttaa  97800
aaccagtgca ggccagccac ttctgggaat tcccattgtg atggaaaagt tgggatgtga  97860
agaaagaaag ggctttgtgc tgtgccctaa atcagctaca ttcctggaat ctctaactaa  97920
atgctatttg atgataatcc ttcaggcct tattgactct tcccaatgaa tgatgcttca   97980
ttaatcttga tttgacaact acattagaag ttacttgatt ggcacgaaga gctgttgtgc  98040
aattgaggct actaggccag ttccaaagta caatgggc tcttgccaaa gtggatataa    98100
atagtgacta caaggcaagg ttttgataaa aaaatcagag atttacaggc atcgatccat  98160
cttttcagcc tggttcttat acagaaacct ctcagctgca ggataaattc attttaaaag  98220
tgtatctgaa atatatacat atattccaaa cttaaattat aaacatatac ataacataat  98280
atatatatac acatacacac acataccaaa cttaaattct tcaggatttt cttattgacc  98340
taaagcttac atcttaatga tgtacaaaac acattaatga aatgccagag gtttgtttca  98400
ctttggaaaa agtacttggt aaaagatagt gaaagagtga agaactgtat tgaaattcaa  98460
aagaggctga cattctgaag gaatatgctg gaatgtaaaa agcaaaattt aacaaggaag  98520
catttacagc cctgcacttg aagacaaaca aacaattta atggcacaga gccattaaat   98580
ggtccaaata tggtttggga cggtgattct caacccagat gccctttcac aaaatgaaaa  98640
aaaaaattgt gagcttatga aaaatgcaga tgcctgaccc ctgtccagat caatagaatt   98700
tgaatctcta gggacaggac ctcggaatct gcaagtagtt ccctgcgtg aatctggagt   98760 gagagaagca cattgtactt ttcatgggtc agtccacaca tagagtattt tagagagaaa  98820
tatcaattat caaagcacat gtggagagtc tccaggctgt tagcggaaaa tctgtgggga  98880
gtgaataatg ggggtgtttg gtttctaaag ggaagtccca gagtaaacat aatcctttct  98940
tcaagtattg aaagactcat caggtgaagt aggacaaatt cttgatagtt ataacagtta  99000
aaaccaagaa atgactcgat ccagacttta gttaaaacaa aacaaaaaat accatttgct  99060
atggccttgt tcatgagtgg aatgaccttc tttaagagta gtatctctct gcatacaata  99120
tattttccca tacctggctg cataacttca ttgaaaccaa attacattca ttttatttaa  99180
aaaaaaaact actttctgca atctaataaa tataaattgt ggccactttt aaaaattgca  99240
```

```
agtaagcttg gaagggttgt cattgacaaa taacattagc aaaataatcg acaaattttc   99300
aacatcaatt ttttgtgctg attagtgcta atccttttc acatgttgtt aatgtccaat    99360
agagatgctt taaatagggt tgtctagtg gctatctcag taaatttaca gttttaagtt   99420
ttcttattta actttgtaac agatttacat gaagcagtaa tgattctaat aggttgcttg   99480
aaaacatctt ttgcttgaaa aatgttttt tcatccattt taaataaaaa ttaaacatac    99540
aaataactct ataacctgca gtttaaatct tgcatttagt tcaataagac ctgttttggt   99600
catacaataa aaaatgatga attataccta aaaattgcca agttgaaagg attttttac    99660 tagctcttag cagattgagt aaccaaaact actaatagaa aattatttta aatattatca   99720
gatctcagtg attttcagc ccaataagtt tctcttttct ttagtatgtt atttccttag    99780
ccttttaaac aatagcagtg ttcttcaaat attaccatat gattctgatt tccacatcct   99840
gtgctaaaaa agaacatagc catctataaa agcattatct atacgtacaa caatgctttg   99900
cctttgttaa catagaaaaa tgcttcaaaa atattttccc tgagaatga tcaaagatta    99960 aaattttgtg aagattccaa atacacttgc aaaatctccc tgcatattat accaatctag  100020
gcttgctatt tgatctctca gacaataaac acatcgaatg ggtgctttga agaactggag  100080
agtatctgaa taactcagat taaatttggc aagtacattc attttagtgt ttacttgttc  100140
attatttcta tgttatttaa ttcaacctga ttttttcttt cagttgcttg gccaattcag  100200
aggttagaat ttaaatatta tcttgtagct aacaacatta tctaaaattc tttaggtcac  100260
tggaatggaa tgtagataac cttgatcatt tatgagattt caccttctag agtcccagta  100320
ccaaattaaa atattgttga ccagtattat aatacaaaag cgaggttttt tttagacaat  100380
ccagccaaat tctaattta tttcagtgcc atttagttg tttgctaaca attatactag    100440
ttttacagtg tgtttatcct gctgataata gtgtcttgat aaatattatc tcaccattct  100500
gaccactttt tactcccaat atatattgat gtgatttccc agcctcatgc actttaccca  100560
gaatctcaga tatatactca gttaataatt aagcaaaata cagaacaaag aagttttctt  100620
attatttttt aagatggagc acttgatgta gggtctggta tattttaagt tatcaaatgt  100680
tattttaaaa aattattgta gttgctatgg tggcctaata ttttagtgtg aatttcagca  100740
aagatatgag tcatccccat gagaacttat tatttctatc aagtttggaa ctttactttg  100800
tactgataca tatacactgc ctaaaaaaat taaaataaaa aaagcagcaa ggctttatca  100860
tactgtaacc agcactgaat atatcacaca aaaataattg aaaaaataat aagcctgatg  100920
ggaaccagca gacaccacaa agcaagcact tggaaaaagt tctttctcag ggctcaaaga  100980
aaatcttctt atccttttcc tccaaaatat tttagtgtaa gctgaactct taagctcagt  101040
gggcagcccc agaatcactg acctgctggt tggagggata gtaagatgtc aggctttcct  101100
cctctttgct aagcatcaat ttcaaaaaaa aaaaaaaaaa ggggggggg ccaaaccagt   101160 gttacccttt atttctatgc caaatccaac ttccaggtac catttacatc atcttatttt  101220
ctcacctaca tctgcatctt aacaataagg gcttgcctgt tttgtttcct ctgaccagtt  101280
ggcacattgc cacagaaata agaggcttaa ttagtgctta atagctctgc aatagatttg  101340
gaatcaagta gactcggatt tgattcctga cctttctacc tgctagttat ggaagggaaa  101400
tttacttata tataaaatgg gaagaacaat attcacttca aagactcatt attaacgtta  101460
aagaagataa ttctgcaaag tgctgagcac agtgcctggc accccatag cgaaggtgga   101520 gatctttaat atgccaatcc agctgagtta gggatttcat taactagcat ctatgagata  101580 cttttaaaaag tcaacattaa aggctgaagc ctggatccct atatatttc tgtgggatga   101640
```

```
agagagatga ttcaaatgaa atctcttgag aggcagaaaa atggcctctt gatatatccc   101700
ttagttttgg acttctttgt tctattggat ttaaccatat gggattggga agatttgaac   101760
atttgatcca aaaattactg tttcatacag ttaatctaat gaaaaaacat tgcaagtaaa   101820
taaagaaagg tatgttcttg ttcttctcta gtagtttcca tctataatca aaagtttaat   101880
gtctgttaaa aaattatgag gtagagtata ggtagcactt tggagtctga ccgatatcca   101940
tgtctttggg tctaaatcct ggttcaatct caagctccat gactcctctc actgtctgct   102000
ttgaatttgt aaaatgaaga tggcaatgcc tacttcacat ggctttgcta aagataaaat   102060
gagacaatac atattaatac actttgtata atacatgatt tgtgatagtc tctactgaca   102120
tactcacatt caagttctat aaagtgatta atatgttgga atggctttta agctttaatt   102180
tattattttt ccttgttggg attttgagat attaatgcaa taactgttat gtttcattaa   102240
cagaaaaggt tacaaaatac tgtgatgaaa aaggtgtttg gtttaaacat cctgaaaaca   102300
atcgaacctg gtccaactat actatgtgca atgctttcac tcctgagaaa ctgaaggtag   102360 gttcttttc acgtttcagt attgagtgag aatgtcatta tttgtacaag gaaatggacg   102420
cataactgta aaatatctgc cacaaagaag ccaacaggtt ttgtggaaag aaatcatatg   102480
ataactggta agttctagga atctctagag tagaattaga gaaaatgaca tttcacttct   102540
tggttggcac tcagagtcaa gagtcaattg aagttccgtg agcatacaga atcagtccat   102600
ttatggcagg gggataagtg tccatagagc agatgaaagg attcccaatg atgccagaaa   102660
ttaggcaaca tttcaaggga ctctctaaca tctcttttcc tggaagagtt tcaaaactac   102720
agatttttcc acaagtcaca agatagcatg cttcccctgt gttagccaca accttagttt   102780
tgtaataaag catagaaaga actcctaaag tagggcatct catcagtcca ctaaatcaga   102840
tatggctgct tagattattt tcagtggaag ttcattctca attgttagta cttgcatttt   102900
actgtatgtt aaatattttg aatattatct ctgcttagaa acatttatct aagcaaatgg   102960
cgagtgggga acagatgatc tttcttcctc aaatgtatca aaaatctgaa aaattcacca   103020
agtctacaac cagcctcctc accctacaga acaaggagtt acagttggtc aatgtttagc   103080
tgtgcagggc gtctctaagc aaccctgctg actctaacat aaacctatta tttctgtcaa   103140
agataggcct gtatactaaa taattattca gttgaaaact aaaagcacat tagtgtcttt   103200
gtttgctgtt gagatgcttt cagggtgtag aaaagttttc ttttattaaa aacaaaacaa   103260
ataacaaaaa caaacgagat gaacatatgg cttagggacc acttgaatag gagggacacc   103320
tcatcacaag cacaagctaa gggcaccaca gccagttatc tctttacaaa tggtttagtc   103380
accctgagaa tcagatgcat gtctacaccc taatggagag ctgttaataa agtctgatta   103440
ataagctatg tcacagagta gtgaattttc cgaatgagtg ttgattatga tgttacagag   103500
aaaaattata ctcatgttaa ccagattgtt gtaagtagtg caagtccaaa tcattcttag   103560
tgttgttttt ggacttctca cgtacactgg ccacatctaa gaatgaaata atttaaagaa   103620
gaaatgctac tctctaggca cttagtataa tgattaaaat gcttttcaca ttctcagtaa   103680
actatcgcaa gaacaaaaaa ccaaacaccg catattctca ctcataggtg ggaattgaac   103740
aatgagaaca catggacaca ggaagggaa catcacactc tggggactgt tgtgggtgg    103800 ggggagggt gagggatagc attgggagat atacctaatg ctagatgaca agttagtggg   103860
tgcagcgcac cagcatgtca catgtgtaca tatgtaacta acctgcacat tgtgcacatg   103920
taccctaaaa cttaaagtat aataattaac aataaaataa aataaaatat tgaaaaaata   103980
```

```
aaaataaaaa taaaaaaata aaatgctttc cacaaatctt ccatataaat atagtcacat   104040
taaaatttga aggaaccaac ctagaattca ttaaaaaaaa agtcaacctt gagaatgaca   104100
caaggatggc aactaaatta tgagttgttg atttaatctt acacatttag acaactctat   104160
ttcagaagaa caaatgtttt taaaaggagt actctggaag caactgaaaa gaatatgaat   104220
taagttatat aaattttttct tagaaataaa gtatgcaaag attttttaaa agaccgacag   104280 aagaggggt gcagatacat atccaaatta attaaggggc aagagtgttc tacatagtaa     104340
actatttaga aggaagaact tttagaaaat gctcctcctg atattgtcta caagtgaagt   104400
tagaaaaata gccagaaaat gaattcctgg gagaaaagat aggtgagtgt gtgtgtgtgt   104460
gtgtgtgtgt gtataagatt cctaaatccc tcccaagaaa gctacctgaa gattttatca   104520
gctccaatta taaccaact attctaactt tattaacatt tcctgtaaga gtaaaatgtg     104580
ctattaagag agtggtatca acaatgaaaa tgccccaaaa atatggaatg cctggtcaaa   104640
tgatgcaaca ggcacaactt aggagaagct aattagtcca ttttgaaatt ctaaggccta   104700 gaaaggaat gttcatttca ggataacaat aatgcacata accaagaaag ggctctgaat    104760
agtttggatg cattttagct gactagggct tcaatcccag actctttctg aggaaattga   104820
caagaatcaa aatgttcaag gatatataaa ttctacattt attccaggaa ttcaaagaac   104880
ttcatagaag gtattcatcc tatctacact acatttgcat tcataccaag acccaacaaa   104940
ctgttgaagg aacttaagac caaaagccaa gagattaaag tacaactaca aataataca   105000 caaattatgc ttcaccaaga aaacaagtg aaaacaaat ccctagttgc aaaagattca    105060
agtctacttc aattacagct gatgaaattg gctaaatagt acaaaatgca aaagctagtg   105120
tcaaaataga gtgaaagaga gagaaagaga gagagagaga ccagaaacac agaaacagat   105180
aaagagaaac agagagacag agaagacaga gagagggatg ggtgactgga tcaatctcta   105240 tttctctgt tgataaaatt acattataag gaaaggaaag actgtgatta ctaggaaaaa     105300
agatgctatg acattatgca ttttatgaga aggacattct tccgagtcaa cataacatta   105360
tgggagaata aataaaatta accatgatcg tgaaaaaaaa aaagaattat caaatggctg   105420
ccaaggggaa aggtttcggc ttcaaccaac taaatactaa tgatatcatt ttaaacaaag   105480
gcacagaaac ctgccaccat actctctgga ccctctgtag gtcaggacag cttggaaagt   105540
cgattactgc tttgccagtt ctgtggtata gaattatgta tccactgtct aaaagattcc   105600
agaagttaaa aaactaccag gattgcttac tgggcttagg gatgataatt tttaatgcat   105660
ttaaagctac ttctgaaata tatttttgaa tgaggtactt catctcaagg aactttattc   105720
tttgaaaatg acaatttatt ttcataaaat gacatgagta aagctaaaaa ttaatttcac   105780
tatctgaaat atttgttata attgtagtag gttttttaaaa ggaggaaaac atttgttgat   105840
ttacatatat ttagaaatag aaatgatttt ctctctgatg aatcattcat tcattgtttg   105900
tttgtttact ttttgttgtt ccagaatgca tatgttctgt actatttggc tattgtgggt   105960
cattctttgt caattttcac cctagtgatt tccctgggga ttttcgtgtt tttcaggtaa   106020
gtacactcac agcatctgct ctttattcc tcctttaagt tactgaaacg aatggtgaat    106080
tctgcaagag tggaggtggg gaagggtctt cagcaaatta caagcgacat gcaacattag   106140
gagtcatgaa gtagcaagaa aaatgaaatg aatttaaata tgcttttaat cctatctttg   106200
gggagaacag gataaattta tatcattttc aaaagtacta tatcttgaga cttcccaaaa   106260
taagacagtc ctgtgaatcc ataagtatac tgttgtaata tggtaaaggt tccatttacc   106320
atgggtaagt taccattaag ggtggtggag aggattctcc accttctttt actcccactc   106380
```

```
taattttttgg agaccatagc cacaaatcca tatataccct gcctaattat ttcttgctag  106440
catatgtaag actaaggaat aaacaagcac atcagagcat gtttctacaa aacctaattt  106500
aaataatgct tgtctttagg ttttatggtg cacaattatg cttgaaagca aaatatgaga  106560
aaacatacaa ggaaaacttg aatactttaa attatcttgt catcttacat gaatataaaa  106620
taggatcttt acaggaatgg tacatttaag ttagaaactg ttacatatgc tttcatcaca  106680
accaacttta gtgaaaataa agcactcata acattgtcct aagctggatt tctcaagtat  106740
gttcacaaat gtagattcag agtaaactgt atgtgtattt ttttttttaga cacaccacgg  106800 ttcagtaaaa atgttagaaa ctgaagtaaa ttaggtaaaa atgaaataat acatgtaagg  106860
tgcctggatt catgtctgac acataataag tgaaatatgt gtttgatatc attattatta  106920
ttattattgg tagtaataat agtcatggtg gtatcacaga aatgataaag aaaagcccctt  106980 ttgtagactc agatgaccaa caatcatcca cacttaaaaa atgtggtatg tgattaaatg  107040
tacagtgatt cacatataga atgagggggg agaagaatat atatgcattt atcactactg  107100
aactatatgt ttaaaatggt aaagatggta cattatacat ctatacttta ccgcaaaaaa  107160
taaatttaaa acatagtaga atcttaattt gattttttgtt aaaatattgt caggatagta  107220
ctaaggaaaa ttaaaccaag gggagaataa tcacctgtaa atacatcctt agtacaagta  107280 ctatttttt ccttcatcat ttttcaatct ttgtctatat cttagtcaag attcttatat  107340
tgactaagca atagaggtga acagcaattt ttaactggat agcaaatgat aacataagca  107400
aacagacaat gagctccttc cataaatggt ttaacaggag aaagactgat aaagcaaaaa  107460
gacatgaagt attaattact caaattagaa tagaagagta ttttcaatga taatgatcag  107520
aatacagtaa tcacataaca tgattaatct tggaatgtct tcattttttca attgcacttc  107580 attatggtaa ataaacacat catcatggtt ctcaaacaac ttttatttta aaatatgcca  107640
ctaaagcata ttttttaagt ttttttaaata taatcataaa aaaattgaaa gaaaaattcc  107700
ccaaatttgt aatcatgcaa ctaattgtag tcaggacttt aaaggtaata atgtcaaagg  107760
catagatctt aattctttat ttctccagtc acttaaataa gtgaggagat gtgagagcca  107820
aatcagcaaa gaaattaaga attttttttt caacgatcat ttctatatta agctactgaa  107880
gatgggtgtg ttaaagtgtg gcacaagggc aaagtagaat attttctcaac tccagttagt  107940 cccaaagcaa aatgattctg atcaaaccct tgagagagtg tggggggcaga ttgtctagaa  108000 agtacccaac tttgccctac cgtctctcag ttctaagaac caactaaaca gcaacttaaa  108060
tctggggaag aaaaacaagt cttattgatt tatcatctga gcctaataat gagaagaaat  108120
gaactgaaat agctggttct tcagagcaga cacaacaaga gacaaatgag atatgaaaag  108180
cacatatgct gagatgccaa atattcaaac caaaaaagc tgtataaaat ttttatactt  108240
gttttcaatc atatcttaaa ccttacccaa actaaaaata taaagggcat ctgtcttctt  108300
aaaatttaag tatgatccta accctttaat gttttttata tttgaatttc agaaacatta  108360
aaagtgattg tggaagtaga aaataatact gatctatcat tggaatttat ttgtgaatta  108420
gcaaattttt tccagaattt tttttcaaat actctacatc accatcacct ttaagatctt  108480
tactgcacat tacaataggt ttcataattt atgcacttaa atgggatcat ctgtgtgcaa  108540
cctgagcaaa aaatatcatc actccttac ttaattctat attcgcaggg ttgagtaatt  108600
ttgcaaactc caaacaattt tataaaactt tcaggaaacc agagtgaaaa gttacccagc  108660
tccacttctg agagctgacg ccccattcac aatcattcca ttgaaatctc actgtaaagc  108720
```

```
cctcagaact cctcaaatgt gtctcataaa aaggaggaac cctgcagctg tcctcctcaa 108780
atgagcaggc ctcctaggag gcctgcagag aaatttaaag tcactgatca tacaagaggc 108840
tttggaactg ccaatacttc actaaaaact tgggatatta ctcagaatta gtttattaaa 108900
gcatgccttt aatcttaatg taattttatt ctgagcatgc aggggaaggt aaaaggtgga 108960
attatgtaaa cttaagcaaa tagaaatcat gctccttgtg ctgttggaaa attaatgtat 109020
aaatgtacat aaagtcttca gtttaatagc agaaaattta tcttctatgc attcttccta 109080
gagaaagaca aaatgtagaa aaacaagat ttttcaggtt taattcatgg aaaagtcagc 109140
attaacaatc ttaactgttc aaaagtttga ataatagtca agatgatatg caggtcattt 109200
ctggtacacc agttaaagat agaagacagc attattagga tggtatttag tttaaaacct 109260
tcgcagaaaa aattggaatg atattatgga aagggattaa atataaacat caaattagtt 109320
cagcaagatt tcttactgct agattccaat agtaagtgtc aacaagagag ctaaaatgaa 109380
gataccctta gggaagactg gtttgggaaa gacacataaa tggacattta tttcagtttg 109440
attcttgacc attttcagca aatttccaat aaatttactt atccataaat ttcaattaca 109500 attttatcaat ttacttttct gtggaataat cctaaatatg taagcctctc attgtatcac 109560
ttcatgaaaa gcataacaga ccattcatta gcatttattt tgactcattg ttatccatgt 109620 cttttctgatt ggtatttaa atattattct tgcctgaaag ctgatagaaa tataggttgg 109680
aaaacagatg gtctcttcat tttattgtct acattacgtt acattggcca cattgacaaa 109740
aagcatatat aggtaatcat ggaggtcaac aaaagtggct tccagtggaa catactgagg 109800
gaagactgat tgctctacta cttactattc tctttgttct acgtcatctc tacatattgg 109860
gtgggtatgt gaatctgtac cttgtgtagt atccaccatt atacatctct agctgccttc 109920
ctgttgctcc aaggaaacca tgaaatcaat ggtatcaaag atggcctcct tcttccaac 109980 tcaccactgg caggacagac accaaagata actgttgatc ataccacggc atattcttca 110040
cccatagaac agtagtaata ggaaaagcaa gaattttgat tgaaagagaa tttattaatg 110100
ataaggattt tgtgctaaat caaaaggcat aaagtctctt gtcaaatagg gaagatatat 110160
aatatattgt atttgaattt tcccaggagt tttaatgcaa tccatttac ttcatttct 110220 ctcttttttt cagttctcat gtttatcatg aataacacgt gatcctaggt aaatgaaaac 110280
taaaagttac actagaagat atgacttggg cttgtaccaa ttacagaaat gattcctaat 110340 tcatatttc ccatgcacca gtaacttcaa aacaacttt acttgttttc tttttgctac 110400
tttgtttgct ttgaatgtga ctataattac actgtcttac ataggagata tacaggagaa 110460
aatactgctg tttctcaccc tgtgatagca aactgattta gtcaactggc aaaactcaag 110520
accaatatca aatgccgtct catacaacta caagctccca aaagtacac actcacacac 110580 acgtagggta ctaataactt gaaacaaatg tgaaagattt acaccagatg aactataacc 110640
atgaaaatga cttttgctt tagccttaaa atgtgacatc ttgagattca tactcaagta 110700
aatcattatc tctttctcac atttgaatga caccttgatt ggtagattat gttgtagaag 110760
taaattatgt tgtctcatcc tcctactact ggagaattta tggtacttat ggtttcccat 110820
cactcaaata ataagcaatg ttctgtccat ctaaatgtct gttttttcca taagggaat 110880 agaatatagc cagtgtcaag ttagtgctat ttctacctaa gacatctcag atctgacaaa 110940
aaaatgttgt cggcttctct catgttcatt taagcgacgt attttgtactg aggatttta 111000 atgttaattt caattaattc tctctagcat cccacacctc ttcttcagaa caattatcac 111060
agtaaaatta aattaaaaat ggcatagtat ataagggccc tgaaggcaag agcgcctgtt 111120
```

```
tgtcctctgt tatattcctg atatctacca ggtctggatc ataatgagtg cacaatcata   111180
tattttggat tattgaatga attttgaaaa atttgcaata ccttcgactc acttcaaaaa   111240
gatgactgta aatgtcatca agttagtata atacaaattt taaaactcaa tgagcaaaaa   111300
ttatattaaa actttcaaaa aacagaaact catatattag tcatacttct cctttggagg   111360
ctagcagttt atctagtttt aaactatcat tttctctgtg tttccaatga aaaatatata   111420 tattttata tagagagata cagtactctt tatatgtact gtatctatct aaatatatat   111480
atactgttta tatgcatata tgctgtatga tatattcatt tttaactagt gttgaacaac   111540
aggataatgt tccatgttag ctagttaata cgaaactgaa gaatttggca aatgttcagt   111600
atgatatgaa gtataaagta ggaaatcatc tagcatttaa tgtaattctt tggtgtactg   111660
gaaaattgct tagtggtcac agctcaaaac agaacatttt tcttaaatac attttttaaat  111720 ttaaaaaaaa atgggtatta agcccaatga tgtgtcagag agtgttctag atgtataaaa   111780
taaattcctt tagcactttc attttagtgg gaggaaagga gagaataaca ggcaataaat   111840
aaatatatac tgtgtcagca ggtgataagt gttaagaaga aaagtagagc aggcacacaa   111900
aagagtaagc tggaggtaga ggaagtatat tttattcagg gtggcttggg tttacacaag   111960
agaatgaagt taatgaagtc atttaagcta atgtacaaca gcagattatt gaacactccc   112020
caatcaaaag aaaaccaggc ttaagaatat cattgctgta tgatacattc attcatactc   112080
cttagttcta gataatgtca attatcattg gtctaagcca ggctgaatta aacaatgaat   112140
cccataatta actgctagtg agaattataa attgctgttg tgactatgaa ggatggcagg   112200
tcacagattc aactgtgctg attgcagcag tcaccagatg gaagtttatt cagtataaac   112260
gagcatgagg tttcacataa gtaatttttt tgtttaaatt taaatttgca acctaccttt   112320
agtgctatta taaaaccagt tgggtttgat ttatttaaca gacttctgta ctgctgaata   112380
gagtagtcca cagaagcgtg tgtgtaagag aaagctcttc tctaaatcct gtctttatca   112440
gagcctgcct catggatgta aattctacat cctatacctg tttaacaagt taaattttta   112500
aaaatattat ttattaatga gttactataa tcgcttcccg aaaagttgaa aactgtaact   112560
ataatagtta aaatatgctc taacagctgc ctttattact taaattgctt tttattgcag   112620
aaaattgaca actattttc ctttgaattg gaaatatagg aaggcattgt aagtaaaccc    112680
aggctatttt tgtatttcat cttctcccag aatttccttt tcaaaattct tcatttctaa   112740
ctttattcca tgaagatatt tttaggaata gttagtgtta tgagtcattg gcatgtttta   112800
cgctctcaca tggtgaatga cattatacta atatttttg ccttatcaaa tatgataaat    112860
ataagatttt catttgtcta gaataatcac cgcaattttg ttatagccat gatgtaggct   112920
ctctctattg catcaaaaaa tgaaatagga tattcaaatt aatgtttatt tatgtgaaca   112980
ttcacaccaa cacatatgta caactttatg aactggagag aaaagaataa agccccaat    113040 aaattgctta atacacaaaa ggtggggaat gactctacca agaagcagca gcacttggat   113100
agctctcatt ggatccaaat cacagtatgc ctcataatga gatttcattt gagcctatta   113160
agaattctct gcctgtgtct gagctccacc atcaggaggg ttggaaaaga ggaactacag   113220
tgatgattct agttgaaata taagatctaa gaagatggta acagaaatga tggaagagga   113280
ggatgccagg agacgtgaag tgtgtgtatg caatggctca aggacataga ttcagtacct   113340
tgtcacaggc agccttggtt ctgacttcac gctctgtgac ctcactgcc acatattttc     113400 ttcctggttg caacaatgaa cagtaggctt ttcatttgaa gcacactgca gaccctaata   113460
```

```
gttgctaatc taagagtcct tctgttaact aattttacaa catttgttat aattaaaaga 113520
gattttatca cccactcttt cagttatttt atgaagtcac cctgaggact gaaaactatg 113580
acctgctatg tttggaaaca tgttttttaa aatcaggcag aaaagtagga ataaatctga 113640
aagaggagac cagccttact ttcttctata tgttctttca tctttttttt aaagaaaata 113700
tgaaaaatat taccaaaatg ttttttttcca ggtactccaa cattttggca ctggttaatg 113760
ctttatgtta cttttttcttc caggagcctt ggctgccaaa gggtaaccct gcacaagaac 113820
atgtttctta cttacattct gaattctatg attatcatca tccacctggt tgaagtagta 113880
cccaatggag agctcgtgcg aagggacccg gtaagtactg catagttttg tttttacttt 113940
tattttaaag gatatagtac ctgtaaatag tgaacatggt gttcatgttg gacttaagca 114000 gctgttttaca tgtgtaatca tatttacttc taccgtcgag ttttgcattt tgtgaggcat 114060
atcatttcta tgtagtttct gtaagaaatt atagcagata agaatcatac aacaaaccat 114120
atatatatat atatatacat atatatatat atatatattt tttttttttt tttttttagat 114180 agagtctcac tctgttgccc aggctggagt gcagtggtgg gatctcagct cactgcaacc 114240
tccgcctccc gggttcaagc aattctcctg cctcagcctc ctgagtagct gggattacag 114300
gcatgcgaca ccatgcccgg ctaattttttt tgtattttta gtagaaacgg ggtttcacca 114360
tattggccag gctgatcttg aactcctgac ttcgtgatct gcctgcctcg gcctcccaaa 114420
atgctgggat tacaggtgtg agccaccaca cccggcccaa accatgcatt tctaagacta 114480
accagtaatt tattaacatt tatgacaaat gtattgagca cctcttgtga acatagatga 114540
tactaggtac actaaggcag tgcttccccg tgattctagt gtgccacaaa tggttacagg 114600
tgtgcctaga tattgatccc ctcttcattc tgttgccaag ttgggcttgg cccagtcatc 114660
tctcctatga gtagctattc ccttttgcta atgaaccata taaatatgat catgttttgt 114720
gtcattatgc tttggaaaag gtttataatg acacaggaaa tgcaaaagtt agggcaacag 114780
gacatacatc tctgaaactc atgcccacat gcacaattgc aacaagcaaa tatggtgact 114840
gtcctccttc tatttgagta ctatagagaa caggagagct gaaatcattt agctccatta 114900
ctgagaacca ttctggattt ttcctaccag aattgtcctg agagttgttc agaataaccc 114960
atatttgtca tcagtcttct ctctttatac tcaagatact gtttttcaca gtgatttcca 115020
atcctggctg cacttcagaa tcaacagggg agatttcata aatatgaaat agctactgtc 115080
cacatggtac tagagagtca gtaggtatga ggtggagccg aggaatatac cctggatatt 115140
tcttctgtgc tgccaagttt ggaaatcatc agccaactac tggatgaagc aaataaactg 115200 gcagggagg acagaggagg agcaccttga ggctctgctt tttcattgat atcagtccct 115260
ggtattacaa actaacaaaa accagaacta aaaaggattt tggaggttat ttatccctga 115320
ctcctcattt tacagatcag aaacttgagg ataaaaaggc aaagcaattt gcctcaaatc 115380
atataactga ttggagcggg gagcaggcac tcaaattcag gtctccttac tctcagtttt 115440
tgttctttcc tttgcattgt cacatgtgtc tctgtaaatc agtgagggct tagtaacacc 115500
aaactggttg attagttttc cacatctacc agattaattt tttaaaaatc aaatcacttt 115560
ggtgctgtga taccaagtaa ccatttactt tacagaaatt tttatttatc aatccactgt 115620
ttaaataatt tataattgca gcctctatta tttaatagtt attttgccct cagtaaatat 115680
tttcatccca aaaagtcccc aagtactcct ctgctttctc ctttgcaaac ctgctttcct 115740
taattttaac aacaaatctt ttccttattt gttaatggac tgcactttaa ttgaatgatt 115800
caaaatagtt taatgatata actgtttatt agattgagta tgaaattagg aatatttgat 115860
```

```
aatttttgtt ctgcaaaatt ggtgaatcca tatgttttat cctaatgcaa atgtggagac    115920
aatacgctgg aatctagtaa cagtagggac tattatcacc ccaggcctga atggacaagt    115980
ggagggaaag gtatatgaac ccgaagacag agaggtggtg tggtaaagga ggccctgcgg    116040
aaactgaaga cttctgtctt aggacacggc cagcctatgg caaccccaca aaaggaagtg    116100
gagaaataaa tatcccttgt tcactcactc tcatattcca gtctctactg atggtcccca    116160
tagctgagct caaccagaaa ccagagggca aggcagccct gctggagatg tacagattta    116220
tttctgtggg cccagggcag tgggagcagg atggaaagtg catctggaag cacaaataga    116280
agctatctag ctcacagtga agggccaagg gatattttca ttttttgtttc tctgcttaac    116340 tgtgttatgc aaacatctgt agatagcctc atctttcaaa actggctttt gacaattctg    116400
ccaacccaat aactaaaatg cgtgaaatct gcccagagca tgcatcctgt gtgacagtgg    116460
cgtggcgtgg gaaagcagct taatttggct tctaatggct ccagagtgtt aataattttt    116520
gtggtatgaa tatatgcaga gagacattat aatctatctt ttaaaaccat ggcatctgtt    116580
atcagagaca aagtccagtc ttacctgcag aataatggga ccaagtgtgt ttatcttgat    116640
gaattttcct ttttaatgtc aattgattta aagaaaattt atctctaatt taatctttgc    116700
aatatccgag caatggatgg aattatcccc attttttaaag ctggggaaac cgaggctcgg    116760
tgagagtaag tgtcctccgt agcatgagta cttagagatg ggattcaaat ccagacctat    116820
ctcacacagc agccaacctc tcttctttac cacttggtgc tgttgattgt ctttatttat    116880
tgtcctagaa agatgtgttc ttaaagaaat gggctcagcc attccgaagt gatcgccgcc    116940
tataaccaga catgcccact acagttaatt agggaagctg aaccccactg aggtgaaaac    117000
agaggtagaa gcaattaact aagaatctct ctgcagaaaa cagtcacatt ttggctctcc    117060
atttcccatt aagagtagaa accgtaggaa agttactctc tgtacggagc aggccaagaa    117120
atgaggcttc cgtttttgaa taatcaacta cattgatctg ggagcatgct cagtcacatt    117180
acgaagtatc ataattcttg aatagactct ttctcttctt ttttttgggag tctcacaccc    117240 atatctccct gtctcccatc tgtaaatgta aaagggactt cttatccact gtgagatctt    117300
gttcaaccta tcttcctgaa atagtcaaaa ttcaggtttt tttctgagtt tgctactaaa    117360
ttatagaaac catgtagctt tatgcatcta atgagaataa caaaaactgc tctgctcact    117420
tcccagcggt tgtcctggag cccaaagaag cataaagctt ttcaaaactc caagggcct    117480 aatattacaa gtgattgctc acaaggttgc tgtcaactct caccttatga ctaactccct    117540
aggtctctgt acttgactttt tccaacaaat ctgttactct attaattgct cttggcagtc    117600
tcattattgt cattgctaga tgtttccact ttcgtaggct ttttagggggt agacatgccc    117660 agggactctg ccagacacag cacataggct gtcccccagc caccactaag tcaaaacaca    117720
tatgccctgc agctcctgta tcacctagta acctttaata aaccccataa gcaggtgtct    117780
agggacctgg ctctgccact aggcacctga tttcctagga gaatatgagt gtgagattta    117840
gggagccaga gaaattaaca ggaaacttc ttctgtgtat agaggagtga gattgattca    117900
cccaaacaca ctaggcattc ttaaagtatg tttgaaagaa aggaaagaag cttatcttta    117960
tgacatgact agcacctggt tcttccaatg tattttttaac ctaacagact tgctggtttt    118020
agctatatga gagcaaactt cctaaggaaa aacaataaaa cattttaaag atagaatttt    118080
atcccatcaa tcaagtactt attgaccacc aaaaatgtaa cttttagccc tcaggctgaa    118140
atgaatttat actattttgg aaacatatct gtgacatccc cttcatgatc cctcacaatg    118200
```

```
agccaagtct cacatggaaa tagctttgtg agtcttgcaa ccacacatat gggggtttggt   118260
cacatttta  cctcttcaa  actgtttttt  tttttctaca gaaaacaaag aggcaaaaaa   118320
cttggatatt tttctctata tgcctaaaag ggcccatttc cctctgaagt tagacaaaat   118380
gaaaacaagc caccaataac aagccactta caatgatcaa tggggcaata tcatatgtga   118440
gaacacactg tgcctcttgc atattttcaa atgtctgttt cttccataag agaaaatttg   118500
gaaacacatg tccctcctca aatacatata aacagcatag actaaaacaa ataactaca    118560
atgacaaaac ttaattcatg tctgtagatt gtgaagcata cacttcaccc agaggaaata   118620
aactaggcta tttgttttta agcactttct ctattttaac acagtcgttt tccaatgaga   118680
gttttgttag atctcttatc taatcctcca tatacaagca acatagggtt gctctctcta   118740
ggcatgggaa aatcagttta agaaagggaa ggaaataatt ctcaagaaga catgttttat   118800
acattattca tccttgaaac tgcttatgtg ccaccaccaa caggaacaca catggtgaaa  118860
tttgtattgt atttcacctt gaaaatccat attctgtcat agaagtccaa tttcttgagt   118920
atcttttctc atccaaaaga ttattaaagt agattacagt tgaaactgta aattcagtta   118980
tcatgaaagc agttttcccc attgtaatac atttcattat gaaggggata aacaagaact   119040
aggaaagatt ttattgctat tttcaagacc catcttttct aggatagaat tcttcacttc   119100
taaggataca ggcaaaatag tatccaaagg ctgagaatca tgtcatcaac attactaagt   119160
cacatgaaga atcatatatt taaaattact tgaaataaat tattttaaat actgaatttt   119220
tcttgaaaaa ctgacactcc agaatacatt agattaaggt cctccctagc caagaaaagt   119280
agagacaagg gaaaaaaga agaagaagaa gaagaagaga caaagaaaag cagccaaaaa    119340
aaaatttggg gaaagagaag ttattgaaca ttgtcaacct acaaatattt attgaaattg   119400
caactaatat gagaacgaca accacagtta taaataaaga aaagcgtatc tatcagcatg   119460
tcatctgtca gtaattcggg catatgtttt cttcaaaaaa aacccacaat acataatttt   119520
taaagacagt ttattcttaa gcaaactaaa gacagacaga ggggtgggtt ttgtgtgttt   119580
gttgttgttg tttgtttgtt ttcattttgg accaattcag ggtcactgaa tcagcaatga   119640
ttttcctcac caatgcccat ggggatatat taaaaagtta ttttttgaag aggaagtttg   119700
ccttatccca aatgttgtca cactatttct ataaggtttt tctttggtta ttattttgtt   119760
gagggtaagg aaaacacaca cacacacaca cacacacaca cacacacaca cacaaaatgc   119820
cctgtcctca ctgtcagtgg agaatccctg tggatttgtg gtccttttcc cattaaagta   119880
gtttcttccc tgggtagttt ttggaaagtt atattatctc ctgaatggcc aagggtgaga   119940
atcttattcc ttccatgttc tttttttaaa aaaagttaaa ctcaaaataa ctcatggcat   120000
aaagaggggc tgaatacatc ctcagtttat tgagtgatgt gaaaattgcc cattgttatt   120060
tgtgtcattt gagcatttca tttccataat atctgaaatg ttattttttt tttttgttct   120120
atctgctcat tcgatgagct tcatgtgaaa agtcaggagg cagaattaaa agcattgttc   120180
ttgctgcatc taaaggaagc tagcaggata cttgtcatt  tttagaaata aatttctctc   120240
taatttttt  tatctggttc tgaaaggcac aatgcagaga gattagtttt tactggaaac   120300
ctgagcactt tgcacctcag aaactgaaac aatcgagtcc tattttctat agcctcttat   120360
ataagtaaag tcaaatgagt tccaagttct ggaaagcaac atgaatgtct tctaacctt    120420
attttttcag aacgattgag ccaccaggct gtgtaggagc ttcttcttag gtagtcacag   120480
gaagattagc ttgaatggaa tgctcagagc caagacacta gagaagacaa acccaggggt   120540
ggaaactgga ctcctgccca gcccaaggga ggctggtgca agggacagta tgtaaatgtg   120600
```

```
acagaggtaa ccgagatagc agagtttttg agatgagagg tcaatggtaa ataaaaccag    120660
attgaaatga tctatttcag tagcttatgg aaaaaactag attgggaacg aaagtgtatg    120720
atgcatttga aggacaatgc agagacagta atgccaagat gtggtaatgg aatgaagtat    120780
cctaccctgg tcatctatgc tacttcagtt tacttatatg tcaaaaccaa taaatggtct    120840
tttaaccaag gtcacatggt gcagaaaagt atagaggatt tctttattcc ttttaaagt     120900 tattatttat aattggatgc tttctcatac ggatttgaag gagaatctct tcctaaagtg    120960
gatataaaca tatacccaat ctccagtttc tttcatttgg ccgatcttgg tggtacctct    121020
acacatgaaa tcagtgactt acaaatggta tcttgtgaca tgttttacac agaaagtctt    121080
catctcaaaa tttgcagtta gcttccctg ctttgagaag gctgtcatga acttagtgca     121140
gaatttgtta tatatttgtt tttattgtca aagagcttcc aattgagatg gtagaggttt    121200
gcacactccg ttagggtatg ttggatcatt gctggaacgt tgtgaagtga cactcgattt    121260
gatatttgtt gtgcttagct ggattactcc agattacatc attgttcttg ctgaacttca    121320
ggatctaagt cctcgctctt ctacttaaca gatgaatctt taatattgag taagttactt    121380
aacctaactg tgccttgctt tcctaatgta taaaatggag atcataatag tacctttctc    121440
ataaagctgt ctgtgaaaaa taagctaata tgcctaaagt ccacaaaacg tcatctgaca    121500
cacaactctc aaaaatcagc tgtcattatt tgtattatcg ttgttagctt tatcattagg    121560
gctttatcac ctgtcaatta ctaactgtgg caccttgttc atttctgtgt gatacagcac    121620
aggaggtgtg aaactcaggg cacttgtaaa acactgctta aatctaaaag ggactaagca    121680
taaaagtaga atacacatat gtagaggctt gtaaataaca aataacctga agggctgtgg    121740
tctgaaaata tacagctaaa taagtggtgg cttgagcatc cctaatgaag agtgatataa    121800
gactctcact ataccatata gagaaaaaac cctaagagta ctaagtggtt aactttatt     121860 ccctatcac atttctttgt tgttgttgtt gttgttttgt ttttaatca gaattgtgta     121920 gagcctacac ttctgtttgc cctggtattg tcttcttaat acttccaaag tgcttccttt    121980
gccaatttca ggatcatctc ctgctgtatt tatctcagat gagacttttt tctccagtgt    122040 ttgttttta ttcttttcct aaacacacca aatcacaacc acacagttcc ataaactcaa     122100
actcattttc tctgaggctt tatcaggaat catctcaaga ttgcataaca gactcacttt    122160
taattgaaaa tgttgcatcc ttaaattcct ctggagaaag attgcagtat tttcctacaa    122220
agctgcttac tgctagactt tctgatgaag tttctacttc attcagctgg ctttaaagac    122280
tgtacaggtt gacagttttc caggtgagcc gagggtcttt ttgtccctta gtttatcaac    122340
tgaactggta ttttgacaaa aaggcctgta attcctcctt atgaggtttt aaaatatatg    122400
tgaatcaaag tcaggatgtt tctcattggg ttgtgagttt actgcaacag gagtttacaa    122460
caacaggagt tgcagtaaat tcactgcaac aagtactgag gagactctct ctgaacccta    122520
aattcttcca agatgtggtc tgcatcagca tcacctgggc ttcggttaga gatgcagaat    122580
ctcatgtagg cttttacatg ggcatcttgc gtggagttga ggtttggggt acaggtcctg    122640
tcactcaggt agtgagcata gtacccaata actggttttt caacacatac cttcctctct    122700
ccctcttgcc tctagtagtc cccagtccct gttgtttcca tgtttatgtc cttgtgtgat    122760
caatgtttaa ctctcacttg taacagagaa catgtgatac atgttttcct gttcttgcat    122820
tcataaattt aagataatgg cctccagatg catttatgtt gctgcaaagg atatgatctc    122880
attctttctt atgtctgcat ggtattccat ggtgtatatg tatcttctgt atctgtaata    122940
```

```
aaaggagaaa tttaaaaaac taaaaaataa aattaaaaga ttattatgct taaataaata   123000
aataagaaat gcagaatctc aagccccaca ccacaacttc tgaatcagag tctcaaatta   123060
tttctcatgg acaaaggctg actggtgaaa aacgaaactt gtgtgatgac cccatgaagt   123120
gggacccttt ccatcatttt tttgtttgtg tgtttgtttg ttttctctgt aattgctctt   123180
tttctgagga aatacagttt gggatggagg ggtggaaaga agggactctg agtatatttg   123240
attcagacaa aacttatttt cttttaattg aaatgataag gggagcagaa aaggacatgc   123300
ttttaaatga accccatgta aagatggcca ttgcagaaaa agtattcaat tgcatacata   123360
aataggactt cagtggcgag catccttctt agtgtcacat gtaattgaat ttggctgata   123420
aataagcctt gcatctcttc tttatgagaa aaagtgctta tggattttac atgtaatagg   123480
ttcaagggtt ttgaaaagtt ctggatgatt tgcatgcagt gtaaataatt taaaatgtg    123540 aactattgtt acgaggtgaa agcaagtata ctatcaaaat ttaactacga tgtttacagg   123600
caactatatt tttaaatatt ttatttgagg attatctcaa gaccagaaag gcattaacat   123660
aaactacaaa tcatgaaggc aggaagtgtc tcaaaaaaaa aaagtatta caactaaata    123720 gataaattgg gggaaaaaga ttactcctga aatgtagatg gactgttatt gagctacata   123780
tcctgtaata tctgaatcat ataagaccac ttttgaaga aaattgtttt atttaaattt    123840
tcccatatga ttatcctact accataattt tcatgtgatg ttacagggta tatattacag   123900
tggttcatta tctgaaattg attaaaaata aaatggtgat ggctgagtag ctcctgtctg   123960
gcaaaaacct ctcacagata acaactacaa accctgaaca aaatataaaa agaaattatc   124020
tgaagaccct ggagagagac caagacaggg agatgctaga aagaagatga gactttaaaa   124080
tggagatagt tgtgagtaga gttcccttgg ttttatccct ttccaggaca agtaaaactc   124140
tgatagaaaa ctctcaattt tactgacttg aataatataa gacagaattt agggcagcta   124200
cagctcccca aaagtgaagg aaataaatct caaaagaaa agagtcagag aagaggggcc    124260
tcagattctg tgtatatact tgtgtgtagt cttttcactga ccacataacc atgtgaatgt  124320
ggagtccatg agcacatcat acttgtttaa tatgtattat ttagtgtatg aatgaaaaga   124380
tgatctaaca gccatacccct tcatagagca ttccaacaag ctagaatacc tcatatcaaa  124440
tgtatttact ttaagaggtc tgacagagaa aacagaacat ctcaaggtag gattagggca   124500
cctttactaa tctttaaagg aggttttttcc attgtcccctt gtttgacatt tggaagttgt 124560
ttaacacttg agtaatgaac cacagtaaac tttgttccag atgaaaagtg ttcttttatg   124620
ttgtaaagtg aaaggataga tggaaaagga tagcttaaag aatgctacaa aatggtgcaa   124680
atggccatgg aatattcaca tgcccccttgg gcagcctttg cctataccca aaggcacata  124740
cgcatgccca gtctgaagac catagcgcaa agggaaacac ctgtttgacc aagactgcag   124800
gggataaatg acagggtata gcagaccctta gggactgcca tcctctaaag aactcacact  124860
ggaaacctag aaaaacttga caaaaattta agatgccccc acaggaattc atccagcatt   124920
gtaagttttc tattgatgtc agcagcctga ccgctgcaga tatgtactga tctttgtaga   124980
catttgtaag aattgtagtg ctgttaggta aaaagttccc tggaatttat ttgtcagatc   125040
atagataagc agctcttgtt tggatacttg ataaaataat attgaattag gagttaaaat   125100
gttttcaatc gaacaacgtt ataaacacta cccaaagcct tattcatttt gatttaataa   125160
gcaactactg ctcactttct atataaatat tattgggttt aagtcctgag ggtggagatg   125220
gaagaggcag cagagacata aaggtgatga atcaggtaga aacatattta acagcaatta   125280
cacattcact caatatgtag tctagatata cattaaataa aacttaataa aaaaattaac   125340
```

```
ctggccaatt taaccaacat agaccacaaa tctttatcat tcagtctctc ttaaaatgtc 125400
ttttccttca ggtaaaatat ttagaaattg acttattgat tcttcttcac ctgttcaagt 125460
aaacatcact tcacactctt ccctctgtgc taaagcaaac tgataagaaa acattttag  125520 aagcttcagg gaaatgtaaa taactatctt taatcattag agatcatgct gaacatatag 125580
aaaagtttat ttctgttttg aaacaaaact tggcagaaat aaaattggca gctttgattc 125640
agtgcaaagt attgtggagt tggtactatt tagaccattt cgaaataatt tttaaatatt 125700
ttatttatta atatgtttgt atagtgggta atgtggtttt agttgtttgc tgtaagtttc 125760
caaacatatt tatttggccc tctagtaact aagaaacag agaagatact cttcaggctc  125820
ttcattttgc ctcagttttg tccatgcgaa tttgaaaagt aaatcaacag tcagccacct 125880
cttttactgt aaagtagcct gtattgcagc ccgccaaaaa tagaaaagtt ggaataaagt 125940
agaatgtgtt tgactttggc agaatctgct aatctgttcc ttataaattt tcacacaaac 126000
tgggtagatt atttaatatt aataacataa gccccactag tctgatccat ttttctcct  126060 ctgacttaac tgagaagaga atttttaact gtcttaaaat aggctacaaa aattacttt  126120 tttagaaatc attgtacata gtggcactta tttgtttatg tatctgtctc cccaccggaa 126180
ggtaacttct ttgattgcaa gcattgaact ttatttttgc agccctagcc caggattgga 126240
cacaaaaatg caagcacagt tactgcatca aacttagcca ctgttttgaa aaaccaaaag 126300
agcttatcta aagtatgcat tttaatcaaa tcctggcaga atataggaaa catatggctg 126360
ttatttttaa ttctcctttg ccaaatttgt tttacagcaa aacaaaacta aaacatctca 126420
caaaattttc cttaatgtgt tattgtacct aaccatatga aatcaacaca gaagctgaat 126480 ctaataccc agttttacca atgagaggga gaaattgcag tagtttttg tgtgtgtgtg   126540 tgaaagctaa gagttttgt gcacacgaaa tgtatcatga gaattaagta taccctgaaa  126600
atgaaatatg cacaggcttg gccttgccaa agttttcaga gcgcttactt ttggcaacac 126660
ttccctgggt cttctctttg tgaacctgtg aagatggtga gtttcttagg agtagggact 126720
ctgtttgaca actttggatc ttctagccta ctgcctgcaa tacagtacaa gctcaataaa 126780
tatttgataa accacattcc aaatctgcat tctctgtgat cccccagccc ctcaattttc 126840
ctactctatg gtttcaaaga gtgataggac aaaatgtgtg tgtagtccct tcctgaggta 126900
ttggcatttt agtaaggaaa acagcttaa gctaaagaaa tgaaaccgta tggcatgtca  126960
ggcattctga agatgatgga aggcattctg aatggcaaga tagtattcct tagctccctg 127020
ttatacatgg taataggcct gtagtgcaaa tgatgccaag aatagttcat ggtggatttt 127080
caattgctta aaagtaggac ataggccatg atcattgctt ttcgttgttt ccacagatca 127140
gctctggtct cctttctatt tctcatactt aaggtcttcc tctatttctc atacttaagg 127200
tcttcctcta cccccaccac aacagaaaaa cacctcaaaa cattgattac ctattataag 127260
gttggtcttg tttctcaaaa acaaaaattc caaagcagtt tacatttgga ggcactcttt 127320
gctatcgatg gttcttgaac atattgccac acaagatttc ctatgttatg tagattagag 127380
gaattttctt aagtgtcctt gaaaaatata taggaaata aattcactac tgaacatcta  127440
tcttctatga agttttgagg ttgacttgat gtattagact aaggaaaacc tgtgttctat 127500
aattctgatt ccattttaa tcaaattatt ataaatgccc tttggggcat tttgtggaaa 127560
agatagatta aatagtgtac ccaattaaaa aactgaagga tcccttccgc ttgaaagtta 127620
catactgctc aacaaactgt atgttttatt aaaacatgaa ctggtagtaa gggcactgaa 127680
```

```
tagtgatatg actcattgaa gccaaagtgg ataatatggc tttcacttac atatcattca    127740
cagtggcaat tatctctttt tatattaatg aagaaaataa aatggagtat aactcacaaa    127800
ttttatctat ttttggcttc aagtatttct tgttttactt ggaagtgatg catttatatt    127860
atttgagtgc agattttgt cttgcaattt ggaagatcat actacttaaa caaaattaca     127920
ctggtgtgac ttatctttag aaagctagtg gaaagttgct tagcttattt gatctgatct    127980
gagtgacttc cttaataccc catgctgcta attaagaaac catctcagaa tgaaggtaag    128040
gactaaccct aatcaagagg ccccatcatt ttgtttaatg cctggtttac tccacccttg    128100
acagaaaggt tataattaag tcaggggcta tatgacaata tcttattcat gttgatactc    128160
ccagagctag cttagttcct ggctcatagc aggtgttcca taaatgtttg ttgaatgcaa    128220
ctgaattacc ttgaatatct tgggcacagg attcttaatc aggggcctaa attagaaatt    128280
ctgaaaaata gtttgaaaac aaaaagagag atgaggtgtg gttctgtata tttcttaaaa    128340
aattatcagg tgacactgat aaaccacctt agttatgaaa caccgatcta agtgctaaac    128400
tatttttgtg aaaaattcta atagtcagct tgatcaccta gatatttcta attatttcca    128460
tgaggtgttt cttttaaaaa tgaatagact ggtgattttt aaaatttgtg tgagcttttg    128520
aggcctttag cctccaagca atatcttgcg tcaaacccaa atatggtcaa ttctcatttt    128580
tattcatgaa ttccaccttt gcaaatttgt cttttcctat aaattgtttg taaccccccaa   128640 atcaatactc ctagcagatt tgctatcatt cacagacatt cacagaatgt ccagaaattg    128700
gagccacctg atgtacagct cccagctgag gttaaagaag gcaatgctct ctgtgccttc    128760
ttgtttcagt tctcatacta cgaacaaatg tccttttgt ggtctattta gtgccacaat     128820
ttttacattt ttatgaattt gtaaattggt tggtgatttt attgttttaa atagcccctc    128880
aagcatagta ctgaagtgct gtatgatgtt cctaagtaca agaaagctgt gatgtggctt    128940
acagagaata tgtgtgtgtt ggagttttct tcaggtagaa gtaatagtgc tattggttga    129000
gagttcagtg tgaatgaagc agcaacatat gttaaataag ttgtctttaa acaaaacaca    129060
taaaacaaag ttagctattg attgctgggt gaaaatattt gtgaccagag gcttacagga    129120
acctaaccat gtgttttccc tagaagcaat ggctcagtat ttgctatttc agttttgaa    129180 gcaactttat agaccataac tactgaaaat aacaataatt aactgtatat aaaactggaa    129240
gccaaaattg ctctgggtga caaaggcata agaccatcat ctttgttctc ttcccatctc    129300
cttctcccca agtgacagcc tccaaaacat atgcttaatt tctggatcca gaaagaatag    129360
ggcttttaaa taagaatagc cttccaaatg aatccagagt aacaactgaa tttcacattt    129420
tatttatata cttgggtgtt atgtaaatat agcaagtact tgcttagaaa atacaaaact    129480
aacattatat taaataatcc cagttaggaa ggtaatcaga tggcggggag ggaagccagt    129540
gcttttctga gccaaatata aattactttt agattacctg gtgttttaa ttatctgcac     129600 cactgtacca ctttggtcag aatcagaggt tgattctacc tctgacaatg ccatatctgc    129660
cttctcctgg gcccagaggg cttttcccta tgttcaataa accttgaaag aaaaggaaac    129720
acagtagaat atctgttggc tcagcacaac aggttttgag taaacgaatt actactctta    129780
tgcattaaat aaaatatatg gttcggaaaa ggttgctaca gtactgaaag tcacttcatg    129840
gctatcttgc ttttaagga aaggcctaa aatgcagtca aattcaaaat aaagtaagaa      129900
gcagcataat gtaaaacaga gtatttggta aaataatagt aatgcaaata accactccct    129960
aatacctaag attttgaatg ctaaattccg ttgtcattat tgttgttgtt aagacataag    130020
cacagctaag taccctcagt cacgcatcct caactgggga cattttgctc cccagggaag    130080
```

```
actgggcaac atctggagac attttgatt gtcaagagtg tgtgggagat gccactaaca  130140
tctagtggat agaaattagt tatactgcta aactcccaac aacatacaag gcagccccg   130200 caacaacaac aaaaatctac tccaaaatgc taatgtacca agatgaaaaa tcctattcca  130260
ggagtgacta gtaaataaaa gtattccatt atgcagtaca agcaatggtt atttctatac 130320
agacaacaat attaatctga ctcttccaag ggtgtggctc ctacgtctgc attgagttct  130380
cagcaaggat gtcatcctaa tctctgtgcc cagagagcgc ttgatcccaa tatacaaacc  130440
aaggctccca tatgaaaaca aaagcataaa cagcagctag gctcagcgta tctcctgggt  130500 ttatatgta aatttatcac ctgactctct cctctttact gctaaaggaa catcatcaac   130560
aaatcagtga atttcagaag cagcattaaa aatatctgcg ttatttgctt cactggccat  130620
agaaaagggg ccataaaagt catgcatcaa atccttagat ggtgcctaag attatgagtc  130680
tgacaaattg caggaaaatg aacccatctg tgtaagtccg cagaatgcaa caaggaagaa  130740
cattttgtgg actagttttc cactggctta tttggctatt tacatgtaat agcagtgatc  130800
tgtgcattca ctctgatttg tgggtatagc aggtggcaca tgtttacaga tgcttgggaa  130860
actgccttgc aagctgaatg cagatacttt ggcttgtttt cacatttgct ctgtgctccc  130920
tggcagatct ttacctgtgt cttctctga gtatcttcct ttctttctga caggtgagct   130980
gcaagatttt gcattttttc caccagtaca tgatggcctg caactatttc tggatgctct  131040
gtgaagggat ctatcttcat acactcattg tcgtggctgt gtttactgag aagcaacgct  131100
tgcggtggta ttatctcttg ggctggggta tgtattttct gcagctaagt tttgagtcac  131160
tttcacctct gtctgtatgc tttcagtctt cttctagtct tggtctcaga gaatagagtc  131220
aagtcccagg tccttcaagg aatgatgaa cacaggtact ggcaggagtt cagtctccaa   131280
aagacctgtg gaagcccttt aacaatctca actgtgctga acatgagggt ctgcacagag  131340
aaggaagata agggtgactt ccaaagggta acttcaggaa acaaacctag ctaatgatgg  131400
acacaaaatg tgtcctgatt gagagaagat ctgattaggc ctccttctgc tttattcatc  131460
acatgtttgt agagcaaagg agaatttcac attttgaatt atgtacctcc cctaccctgg  131520
cttcattttc cttcatcaag aacatttctt cctgtcaatc catcatcagg attcctccag  131580
tgaaagctca ggaagtggag tccagctgag aggcagatat aaccacacgg gcttccaagt  131640
agagcctgtg tgacatcata gcacatggca ttggctcggg aaagcttagg gctggattgt  131700
ttaagctgtg gctgcttccg tacaaactaa ggcagggtgc tgaagtcctt cagggatgct  131760
ctagaattgc tccctttccc ccagggctgc tgaaagtcca gctccccctg gtggaaggga  131820
actgaacaga aggtgaggca atgaaagaaa ataaatgctg cgataaaaac acatgctgcc  131880
ttatcaaaaa aaagtttca gccttacctt gaaacttcca taccagagga ggaactcgtg   131940
ggccatccct cactgactat agagccaagg gcttctctca ccacatccac cccacatgat  132000
gggtgactgt gactctgaga gcagaggctg tggatgcct tcaactaagc ttgcccttta   132060
atgcagcagg ctggggagcc cctacaagta ctggtaagag aggagaggtg tagtgaggag  132120
ggaggacaat ccaagggatt ttttaaaaac atcaccttt gtatttaaag ccctgcccaa   132180
caggcattgt cgccaacttt atagaaatgt gcttgggaag tcatataagc agcctagagt  132240 cttcctgca gtctgtaaac tgcagaaagg ggctggtgtt atgccatact ggtttccata   132300
acacccttac ataacagggg tacatggttt taaccaaatg cattgcccaa gcccaatggg  132360
ataatccgat aatggtgggt caatggggca gataggcggg atgcctcaaa attgaattga  132420
```

```
tgatgctaca attatttggt tgcaagcaac agagtaagat gttctaactt aagcaaatac   132480
agagaagttg tcagaatcta gcgtatctca tggaatctaa gggcagaaat atagccaggc   132540
aactaaaagg gctgtagcct gggagcagat aagccaggag ctctctccct ctgccttttg   132600
tctttgtttt tccttgcata tctgttttta cccttctctt tctttacagg ccatagacca   132660
tagggtctct gctccctcca gttttcatag taaatacatc ctgccccaaa gtttcctgag   132720
tacacatgtt tctgttccag gcactcacag aaactaaatg cccatcttta agttccaatt   132780
ctgaatagca ggacaagaaa atctgattga tccaactgaa ggcaggtagc ctaccctggt   132840
tcaataaact gtggccaaga aaattgaggg ggatgttgtc acatagtgtg aacatgtcta   132900
gtgattgtga accctccagc aaaggactga gaaaggggtc tttgtgaact gtacaggctg   132960
tctaggatat tcaccagatc acctcatctg catggctgct cccttataag gagagcagcg   133020
ctgcaccctg tttccttaac catccagtga ggttagaaat caggctatca ctatcctgct   133080
ggttccacat caggtaacag gttctcctgc tctttcctgt cctaaaacag gtcaaaattt   133140
actcaaaatg gtcttttact attttttttt ttctctttta gccccagcct tccacagaga   133200
ctaatctttc ctttccctgg ccttctcatc cgtatgtaca ccctctcaac aatttctaga   133260
tttccaaatc tggtcatgct aagaatagac tggatacaat ttaatcactg caatggcaat   133320
tctgatcatc acaatcataa taattggtgt tgatcaaatg ccttccagtc aaagacctga   133380
aaataacatt ccaccccaaa cacacacaca aacacacaca tactttctgc cagatttatt   133440
tcctttgaaa taaatctgt ggtatatttc ttttaccagt tttgattgtt caaacatct    133500 atctgccata ctcagaaaat ttttcatggg aaaaaaaggc tgtaaatgta ttcttgtcgg   133560
tgacattcag cagagacaag ggcaccctgg aaggaacaat ttatactgct cttggagtat   133620
actgatgcat tgtgaattag ttataaaact ttttggcatc atcatagaca gctcaatgaa   133680
gatatctgct taaacacat aaacaattca aaggaaaaaa ggaacaagct gctcagctgt    133740
atcaaaaaca aaggcaataa taataagtaa attgttatg tgataccttta agcttctgta   133800 atcaacaaca attcgaatga ttcaagtaga atcccaaaga acattacact tagtaacgta   133860
agcacagaac ggggagttgc taatcaatgg ttatacagat taagtaatgc aagatgagta   133920
aattttaggt atctgctgta caacattgtg cctataggta acaattttgt actatgcact   133980
taaaaatctg tttagagggc agacctgatg ctaattgttc ttgccagaat aatataaaaa   134040
tttaaattaa aaaagaact agagggattt gcacttccgt agatggactt ttggaaagat    134100
agtcaaccaa atagttctaa aatgtaatgt ttttagcatg ccaaagctaa gactatcttt   134160
ctacatgcac acacacacac acacagacac acacacacca aaattccacc aaactcatta   134220
ccactgaaaa atcacattgc caaatctgaa ctctgagaac aaaattgaca tattttaaag   134280
cagtggctcc tttcttagaa ttttaagcaa gcattatctt tggatgggag gaaaatgggt   134340
gaaattaata ccaattaatt tctcaagaaa aaaatagttt cacagaaact ttataaagtt   134400
taatggggca agagaataag tctcttctgg ataatatttt tattgtcctt tgaaaatttt   134460
tttcacatga agacagtatg ataggttcta aattttacaa tgccagaaaa gaagcaaaac   134520
ctacatactt ttaaaagatt cttgaaagtt agactgcaga aaatatgccc caaaaaagcc   134580
cagttgtatt atagcaccta atttgtttgc aggtgatgta aagcccattc atttaattca   134640
gctgtgaata atgttttccaa ttctaggatt tgaaatgaat ctcaaagaat gataagagat   134700
attgtaaaca ttagccactg ggtgaacaag tatctggtgg tgaaattctc cccaacagaa   134760
aatcaaagaa tggttctttc agtagttatt cccttccaag tctgcatggc accacttagt   134820
```

```
agtcgatttc tctccaattg aagtaacttc aaatactgaa gtttagttct caggaagatc  134880
acttattttg cagccctctc cagactgttt ctttgccttg ccttgctggt tttccccttg  134940
ttagaaatca aaggaaggaa atttccccca tggacttcta tattgaacaa atagaattta  135000
ttaaatccct cttaaaaaat gaatcctaca cagacaggat tattctgaat ctcatcatct  135060
ttggtgggaa gaatgggttg ttatggatct tgggaccttg gggagagaga aagaaaaaag  135120
aaaaaaaaac agaaaaagca aactacctaa aaggaggcat catagctaga agaaggcaaa  135180
gagccctggg cgttaaaagg tgtggggtct atactcgtct ccagatgaag tagaaagcac  135240
tttcctttct acaaaatgat gaggtgggat tcagttttcc atatacttct ctttctctct  135300
aattctaaaa tatccatctc aaaataaatc cagagacttt gtttctcttt ctgagcccaa  135360
gtgggaaaat ggtatgttag aactgctgtg aataacacaa tcatgttttg tataagcaaa  135420
ctcaaaatta tttcaggcca acattaaat ctgtggtcct attgaaaata tgcttcctgg  135480
gtttaaaagc tgaggttgtt cttaggtgaa aattcaatat tttgagaccc cttttgtat  135540
ataactcaca gaaaataaaa atgcattgat ttaattcttt cctaagacac atttcttaat  135600
ctgatgacaa taacaaaacc tctttctaca gatgtctcaa tcaaatcaaa caatattcta  135660
ctgttgtaca tctgagtaaa aagacttatt ttttcttttt taatgaaaat tacaacttta  135720
ggttatacta cagaataaaa attgatttaa aaaattataa tctggaagga cgtattgcaa  135780
taactgtgtc cattttttctg tttataaatt aaaaagtttt ttttttttta ctagcacttt  135840
gagtttagtc aaggaggtac agtaagctgc cttcataaag tttctctagc cagaacctac  135900
agaaggtagg gaatgtactg gcttctctga agtattcata ttaaaaggaa acaatcactg  135960
catgagatat aaacagacag aaaaacaaaa gagcctagaa gaaagaatgt gaacatcagc  136020
taaggcttta ggagcaatca gactattgct ttcatacacc gtcccaggtc acatccctcc  136080
ggggtgaccc agctcctctc cataagagag gccagttcac ccacaatgaa aggctttctg  136140
gtctcagtta atagtcatca ttataaacat aacaatggta ataatagtca tagtgtacct  136200
gctacattca gcaatttgta aaaggctttt aattatttgg atgctcttaa ccaaactctc  136260
aggaagcaca tgatgttcta actgggagca ttttgactgg cttgaccaaa gatgattttt  136320
gtgaaaatat caggggaaca tcttgacaga tgcactcaat ttgccagtat ttttgcaagt  136380
acactaccat tgtccatgca gctgtactta aaggttatga ccaagaaacc aagtgtgatt  136440
tgtactttc acatttgtag ggttcccgct ggtgccaacc actatccatg ctattaccag  136500
ggccgtgtac ttcaatgaca agtaagtatt atggtgatgt ttaagttaac atattcataa  136560
acaaaatgta tttgtgtatt aattgtcccc ttgccctttt tcagctgctg gctgagtgtg  136620
gaaacccatt tgctttacat aatccatgga cctgtcatgg cggcacttgt ggtgagaatt  136680
agttttttat tgcaatatta gtagtattat ctcttagttg agatttctgt gtatatagtt  136740
ctatgtatca tatgttttat aacttcaaaa tgaagctaat ttgatggtat tctgtagtaa  136800
aaaaaagcaa tttgatttta gactcttcaa aaaaacgcct tttactcaca catggagggg  136860
ttatcatgag ctcattttca ttacagactc acactataat agcaatgtag ctcatatttt  136920
aagattttta taactagatt ctcctaggta aaggtgagag gccaaggggc tgcaagaagt  136980
ttgtttgtgt tatgaacatc tagggtcttt gaaaactttg acattccaga gctctaaaag  137040
tctttggttc tgtgaactta aggtccagaa atccaaatat tcaacacaag ctcaattagt  137100
gagttagtaa taaatagtgg actcccagcc aaatgtcaga tgcttactga ggatgctaca  137160
```

```
gttcttactt acctaggatt cagtagactt ggcctcatgt cttagctcta tcatctacca   137220
gctctgaaaa tttagataaa tcaattaacc taaaaatgtc ccctgatttt tttaagggaa   137280
aagttagatt aaataatctt tcaggtactt ttggaagata atctctaact ctaggtcatt   137340
aaaacttagt actgctccat atctttatct gttaaaaata acaaaaataa taatagctac   137400
tcataaattc acgattataa aatatctcct aataaaataa taaataaagt aaaatgaagt   137460
aaaaacttta gcaattattc ctatatttaa aattctaaaa tacatatttc ttgccttaat   137520
tatctagaaa tttttaagga aatgcagatt ctaggatcca aattataaat gtgtatctga   137580
gttgagtata tgcatacttc actgtgaatg accataaatt aacagaaatt gatatatttg   137640
gaattcttat taatttcatg actaaaggaa atgcacatta gtgcatttca aaactaaaaa   137700
aaaagattca acaattaaca aggtgaatca tttatacctt aatagttgat ttttctcatt   137760
ttgaaagagc tgcccgtgca aatatgggca cttgatttat gacagcagca cttttgggca   137820
gaggaaggag atggtcaata agatatacat acagaaaaaa tatcaaacat gtatttagca   137880
actgcatatg tgtggggaaa aagtaaattc tgattccttc cacaaccaga caccaaaaaa   137940 tgtgtttta gtgaactgga ggtttaaatg taaaagacaa aacaatagag gcccccaaa   138000 aagacacatt atgttgagta tcttcatgag cttcagatac agaaagattt ctaaagcagg   138060
atacaaaagg cacttaagga agagattgat aaatcagcta cattaaaatg aagacaacat   138120
ttaaagactg aaaagacaaa acttagagtc caagaaggta tctgcaatgt tccaaataaa   138180
gactaataaa tttatgaaaa agtgttcagc tcatgtatca tcaggaaaat gcagattaaa   138240
acaagaatga ggtaatacta caccctcca ccaccccgc catagaaagg ctcatattaa   138300
aaagagtgtt cataccaagt gttggcaagg gtgatgagca actggaactg ttttatatac   138360
tgctggaggg aacataaaat taaaccactt ctctagagcc ctagaaatgc tgagccaatt   138420
gtgctacctc tcaggtagac tctcatgttc tatgtaggta acatttgttg ctcacactgg   138480
ataaacaaga attgagaaca gtgcatattc ttaagtgata cttttctgta tgatttgctc   138540
ataacaccgt atatttgcag gtcaatttct tcttttgct caacattgtc cgggtgcttg   138600
tgaccaaaat gagggaaacc catgaggcgg aatcccacat gtacctgaag gctgtgaagg   138660
ccaccatgat ccttgtgccc ctgctgggaa tccagtttgt cgtctttccc tggagacctt   138720
ccaacaagat gcttgggaag atatatgatt acgtgatgca ctctctgatt catttccagg   138780
taaggaagcc aaaggtgtat ttattcaact actgtgctta ttcagctagc tgattttaac   138840
tctaaagccc atgatctttt attattattt tacttatttg tttatttatt tatttattta   138900
tttattattt tattttattt tttttgacac agagtctcgc tctgtccacc aggctggagt   138960
gcagtggcat gatctcaact cactgcaacc tccatctccc gggctcaagc aattctccca   139020
cctcagcctc ctgagtagct gggattacag gtgtgcgcta ccacgcctgg ctaattttg   139080 tatttttagt agacgggggtt tcaccatgtt ggccaggctg gtatcaaact cctgacctca   139140
ggtattctgc ccgcctcggc ctgggattac aggtgtgagc cactgcgcac gcctgacaag   139200
cccatgatct tcaatgtcat aacatttaag cctccaattc aataagccca gccaaaattc   139260
tgaaggacac cagtttttt gaggctcttt gttgctgttt cttctgtgc ctgctttcct   139320 gtcattccca gggccctcag ctggtcccat ccaggcatgt tctccttggt catagataca   139380
gaaattgtca gatcttcctt tataaataag tgctggctct ggggtaatga ggaatttgca   139440
caaggctgtc catgcctcct gctctatcac tctccatttg tcaggtgaat gttaggaatc   139500
cattcatgac ggttcagtgc tataaaggga agttgtatcc aggcctcccc tcatgtaaga   139560
```

```
gagaatgcag tgggctctca ggggctgtcc tgggctgtcc agtgtctgcc gcactggata   139620
ggagaatggc tgccctagtt ccattcacct ttacccagat ctaaagcccc attgaaagca   139680
taatgctgta tttggatagc aagataggat gtgggagtcc ttggcaggag taattctatc   139740
acaggctctt aggccagagt tttgctgtct ctattacaaa tttcaaaata gttttatttt   139800
ctatattagg cttaatgtga ggaggaggtc aaaattaata gggccagaaa gaaagtttag   139860
ggatcgtttg aatagttcga actgttcttt tagccataat caaaacttgg gcacaagaaa   139920
tcttcaagca gtgaccagga ctcaggcagt ttcttagtcc atgtccttat ctgagcgatg   139980
aacttggcgg tgggtacagt attgcactag ttcaccatga caacatagga cacagaccca   140040
cagcctccca ctatgacact tgtcttgtaa aagatccctc tactgaattc tgcaaggtct   140100
ccatttttaa attttctaag tgtagttttt ttttttcaaa ttcaccataa tcagcatatg   140160
ctgctataaa tctccatgtt aaagggagca aaatattatt tagattagca aaatattaat   140220
ccgtccttct agccaaacga tggaatccta acaagaaaaa tatatttcta agggaatatt   140280
cttatagtgc agcactgact atgaatggta gataattctt tttcttgctt tttttttttt   140340
tcatcaggcc ttctctgggc agtctattat attgtttact aaacaacata atgcacacaa   140400
aaataacttc aactgtattt ttccttccct ttttagggct tctttgttgc gaccatctac   140460
tgcttctgca acaatgaggt aagcatgcat ttcatataat actatcactt gtttgtgtaa   140520
aggcagcatt ttttccaaag ggcctctgta caaatttcat ttcatctcac ttctacagtt   140580
gacctcatag ggttttgtga ttagcaacat gatgtttttt ccactactcc aagctgaatc   140640
ttatccatgg atgtgtagta caatggcaaa tatgattcag acaggcagtt aatttccttg   140700
ggttgcatct tgaacagatc agcaccctca ggagcaatag tgaaagctat tctggatgcc   140760
atcacaaaga gaagtcatat tcctattccc ttcggaagac ccgagccctc actagggcag   140820
agacaatctc cattcggttt gtactagttc ctcaccttct tttccagttg cttggtgcta   140880
acgccctact acttactcag cgttttgaaa atcaccctga agtgaagatt caaaaaggat   140940
tctcaaataa tctacaatgt gaatatttag atcagtaaaa tctagagagc catatggctg   141000
atccattctg ttctcagggt gtttttagcc agagttaccc ttcttccaa ccaaatcttg   141060 cctgggagcc aaatctataa aacataaaaa tggagcttct atagctccag acatccttcc   141120
aaagaacttc cagggtttta gggaacatga ttcaaaatct tcctcatttt tcagggaaga   141180
aatctgaact ccagaaagat catgtgattt acccaatgtc acaaatgcac ttatggttat   141240
aacccagact ggaacacaga tttcctgttt ttcaattaaa ctgaccaact cccaattaac   141300
ttatctatat ctataattcc ttcctggagc tatgttagta tgttttttct aggaccacac   141360
aacttttaat gccaaagcat ttttgaacat tttaaatcaa ttcctattaa gaataattcc   141420
atacaaggca aatcacattt tgccaagaca tcaatatatt actttcctat tagtaattag   141480
aaacatttct agccattgtc agttgctaat ttattctcta tctttttact aagttaaata   141540
atatttagtg agcacctaca atattttgct attctgtgac ctgttcatac ccgtttccaa   141600
ccgcaacatg acaaagtttt tgttgttcct attctccatt ttagttatta cattttattc   141660
ctttctttct tcatccattc acctaccaac tcattccttc attcaacaaa aatacattgt   141720
gcatttacta ttgctaaggg ctagactaag ggcctagaat agaaatgaaa agacatcctt   141780
ccattgcccg ctgttagagt ggcaatattt ttagaatttt aatattttt agaatgataa   141840 aaactaataa atgagtaggg cgtaagtcac cccgtgttta tatcaatttc tgtgaatgta   141900
```

```
tatccatgcc ttttgggttg tttcaggtgg catgcaaaat aaattttttg tctaaaataa 141960
tatcaaaata gagctaatat gagaaatcag gctcagtggg gcatacctgg aaaaacacaa 142020
gaggattgca tgcattcgta aaaataccac aatatttatt gtgtcttatc tatgatactg 142080
tcattggaag tgtcagacat agaaagcaaa cccaggggta ccctagcaat tgaatgtctc 142140
gagttcattt gactatatgt tatctctgat tttgaagtaa agaaaccatt tccattttca 142200
ttaagatccc gttactgggg gaaggtaaaa gtgtgacatt tctaataata tagaattgtg 142260
tactgtgcca gatgtaatat cacagaccca tggattttag gcatctgggt ctcagctggt 142320
cattctgcga atgcatcacc ttacaatatt gaacacaggc agggcactca cacatgcagg 142380
aagttatttc cagctgcatc taagataggg ctgtgatggg atggtgcctg gctgaatact 142440
gagttttagc agaaatctag ggggctaact caacataata atgagatcac atcacattgt 142500
gttatgtgca atttaatttt gattatgatt ggtatgttat cagtgaaatt attatttcat 142560
ttttgaattt tgattcatta ttggtatgtt atcagtgaaa tgatcattat gaaaatgaat 142620
tatatagaga gtcagtgggt agactagaag caggaaagga acttgaagaa ttaaagtaat 142680
agaaatcagg agaggaccat gagagcatgc ttatgtatca agcatttcct acaatgactc 142740
ttccaagtga gtggacattg attatccaaa catatcagta aattattagg tacctaagag 142800
acctgaaaaa gatgattgca gctataaaaa tgcacaattt gttttccaaga agtagcatag 142860 aaatgaaagt tctaacaaca cactagattt tctcccttt cttgtgtctt tctattctcc 142920
gtacatcgtg gataaaatag tttatagaag gaagtagcat gatcagaaac atctccattt 142980
aactgtcaca aattggagtg tgcaaaagct aaaattttgt ttatttcctg tagcttatct 143040
tgctttcaag agactattcc accagcctct agtggtttac agcagtctct ttatagaaaa 143100
tattcagtca attcaaaaag cctttgtcca aagagcaac tggctaccaa gttttaatgc 143160
cagcacctgc tgttgaagtt cacgctggtt cccttacta ctaagccctc gagaagtctt 143220
ttcacctgtg gcctccttga tgaagccaca gccctattct gattcacaag ttctttccgc 143280
caagccaccc gaggagcctg gaactccagc tcctttcttc acaccacata gagcctgtga 143340
atctatcttc agcacatgcc atagccgttg ctgctccgct gttggacatg gtgccagggg 143400
caaatgtgga gtttcttttc agggctggct attttcagga ctgtgctctc gaaacaaaaa 143460
gaaaaacttg atgtaatgga gggttcctaa gaaagcaaat gatctttttgc ttgatttctt 143520 ctgcccattt tcccaggtac tcccaccacg aagggaaatg caaggccatt tgtgtgtctt 143580
tctctcctct tcctctcagg cctcttgggg ctgtgcactc accacttccc cttcctgtct 143640
gtgagggtct ctacctatat catattctac atgttctcta ccctgtagct tttagtaaaa 143700
cactatctgc agaccagtaa gatttttcaca acatatgcaa agagaagttt cttctgttta 143760
gaaattctcc cactcaataa agcctgattt tcaatacaat gtctttctag agacataaga 143820
aagccagctt tgagtctcaa tgctaagcaa taattttcct tgttctagac cagtattctc 143880
aaacttgagt gtacatcaga atcacctgga agatttctga aaccagggat tgcttggccc 143940
cagcagcagt ttcctattca gtaggtctgg ggtggggttt gagaatttgc atttctaacc 144000
aagttcccag gtgatactga tgctgctgac ccagagactc cactttaaga accactattc 144060
tagacacaat cacacttgtt cttcaagcag tggatgacct tgacttaatg aactggggag 144120
atgtaggaaa ttttattta gaaaattaag aaatacaatg gctgaatgtt ttcaaaaagt 144180 ttaacttat cataaatgat acttaggtat tgttacccct tagagcaagg aatcttcccc 144240
aaacataaga aaagagataa tgaatgggaa tcagaaagct ctgattctat aatcaagtac 144300
```

```
tcaactcaaa ttatagagca tataaatttt gtaagataaa atcagagacc agtagagata    144360
ttgctgctat ggcctccgaa agactgaaaa gaatgttgac aacaactttg taaataatat    144420
tcacaagtat cccttagcat ctaattaata gggcttaata cgaatctagc tttcagaagt    144480
tgtataaaac cacctaggcc aggcgtggtg gctcacgcct gtaatcccag cactttggga    144540
ggccaaggcg gctggatcac aaggtcagga gattgagacc atcctggcta acacagtgaa    144600
gccccgtatc tactaaaaat acaaaaaaaa aattagccgg gcttggtggc aggcccttgt    144660
agttccagct acttgggagg ctgaggcaga agaatggggt gaacccggga ggtggagctt    144720
gcagtgagcc gagattgcgc cactgcactc cagcctggga gacagcaaga ctctgtctca    144780
aaaaaaaaca aaaaaacaaa caaacaaaaa aaaaaaccgt ctaaagtgtg caattacttt    144840
ttaacttcta gggaatttaa agtgtttttt tttttttaat catgattttt aaatgtcaag    144900
ctcaggttgc agcaggtctg ttagattgtg gtgacagtgt gaaggagtgg gcgttacaat    144960
ctttgcattc attggatcaa aactgcagag gtaaacctca ccttctattc cgcagtacat    145020
aactatagta ggtacttaga atgaactcag gaaagaaag gcaaaagaca aaacattca     145080 aatccaacca tgaagactct aaacttattt tgttttgtac aaatgtagga actgaggcct    145140
aaatatacaa aggccaaata ttacaaagct tattaataga gccaggtata atagttaagt    145200
cttcaaactg tgaggccagg gctctatttt tataagttgg caatacataa atagatataa    145260
tcaggaaaaa aagtaaagtg aatagtgtgt attgcttttt tagtgagtga tgaatttata    145320
taattcaaat cttttttgttg ttgttacatt tatcccactt acaactgaaa acatttattt    145380
tcaggagcaa caaaactctc cctgttttgt tttgttttgt ttttcagatt aaatgcccTT    145440
attcttgtca tcagagcagc atcagactca acctgtgata ttgtaggaga taattgccct    145500
tattagtcta taatttttta agtgtctttt ttatgctgct aagggcctgt tattatatga    145560
atagtttaca aatcaaagca cattgccatc tccacacaaa aggatgggtt gtaattttgg    145620
acgcaattaa agaaggccgt gaacctttct gtaataataa ctttttaaaaa ttaaaataga    145680 aatcaaaccg tttggcccca tgctgggctg tgtactttat taatataaat ggatactcta    145740
tgggagttat tttaaaagga caggtgagaa ataaaagacc tcttttttcat gctgcatact    145800 tttgcaaact aactctaaac tcataactgc ctgcttggat acttgtaaat atctgtgtaa    145860
gtttcagcta caaggataat cttggtattt aagagatgct gaatccgtgg aaattatcag    145920 cttcctttttt tttttttttt ttttgagacg gagtctcgct ctgttcccca aactggagtg    145980
cagtggcatg atctcggctc actgcaagct ccgcctccca ggttcatgcc attctcctgc    146040
ctcagcctcc tgagtagctg ggactacagg cgccggctaa ttcttagtat tttagtaga    146100 gacgggtttt caccgtgtta gccaggatgg tctcgatctc ctgatctcat gatctgcccg    146160
cctcggcctc ccaaagtgct gggattacag gcatgagcca ccacgaccgg cctatcagct    146220
tcctttgact ggagacattg cttctccaaa aatgtgctga acctgtatat ttcccagttt    146280
ctcaatgggg catttgatgg ttcctagatt ataaccctgg catttaaagc tacggtaata    146340
gtaccaccca aataaagcca ggctctgctt ggtactgtgg ctttgccaca ttctagctat    146400
atgattttgg acacattgca taacctcagt gccccatcca taaagtgaag atagtagtgc    146460
ccttcccata gggctgttgt gaggattaaa taagttaata caaatcacat acttatgata    146520
cggtacttag taaacactca ataaacagct gaaacttgtt attctatctt tgttcttgc    146580 gtggcttttt tcaatacaac tttcagctgc atggtccacc ttattcctta gcacttaaag    146640
```

```
tttttgtctt tgtccgtttt aaatcacttt agatataaag tacccttcat gcaagcactc    146700
attaacccca aaacaaaata aaacaaaact caggatgtgt tgcctccata atctgaaaag    146760
tctaatattc caaattatca gattgctaaa taattctgat tgccatttgt cacctcgaac    146820
cttacggttg ctgtgctgtg tgaagataaa ctacccccctt tagttgcttt ttgaggaatc   146880
atttgacttt gtctttctct gagtaaaatc tttaaaaata tatgaacaat actaattatt   146940
ctcagaggag attattactc tactagatac aggaaaaaaa aagtatattt gccacagaac   147000
cattcagcct tatattatac atatagtttt ataacattaa tcagttttgc tgtcattttt   147060
ctcatctctc agatttgtac aaatgtaaag tagataaaat gattccccat gatcaagtag   147120
ttacatgatt tagttcacat tatatattcc ccaggttctc tctcatgtgt ttagctgtca   147180
tatgtgagtt tggcagcaga atgaactaag gatgtatcat aaattgatgc aaatattttt   147240
atgtaagctt gttgtatgta ctgagcaata gaaactcaga aatacagaat agagattatt   147300
gcaataatct ctttttttagt tttgttcagc tatagagaaa agcaagaagt ttggagacaa   147360
caggaaggag gaacttaact actaaattga attcgtttct ataaaaagca gagctagaca   147420
agcaaattca ctgtctgtgg tactgttttc agttgtggtt attgtagttt tcatatttag   147480
agctttctga tgttagcatc tttgcctctt gttttcaata tataatttat cgtatttata   147540
aaacaagtct ggcaagtttg tttacatttt agaagtcttt caaaagaaag agaaaatctt   147600
attcttaaaa agttgtcatg gcattaacca gagatgtatc tggcataacc catctcaagt   147660
catgtcggac aaggaaaagt tcactgtacg aggccattat cataaaatcc agaactgtgc   147720
tatggtttac atatatattt ttcatgtgca cacttaaatt aaaaacttct gccttatcag   147780
ggatggtagc atataaaaag tttggtcaac ctttctccct attatgacat gtataccaca   147840
ttacctgtga aaccaaatca acttttattc attggatatg aaagctaaag aaaccttttc   147900
ttaaaactag caaacaacct tgccagggt aatttaagca agtaactcag ttcttccatt    147960
tgcaaattct tcttccaagt tgatatattc tgtggccaca gcatacacag cccagcccctt   148020
tagatcagaa ttacaatta acttctttta aatctgataa gctctaagaa cgatgttcgt    148080
acactttgca tggatcattt ctgactatca tataaaaaca aggctccttt ttctcttcca    148140
ggtccaaacc accgtgaagc gccaatgggc ccaattcaaa attcagtgga accagcgttg    148200
ggggaggcgc ccctccaacc gctctgctcg cgctgcagcc gctgctgcgg aggctggcga    148260
catcccaatt tacatctgcc atcaggagct gaggaatgaa ccagccaaca accaaggcga    148320
ggagagtgct gagatcatcc ctttgaatat catagagcaa gagtcatctg cttgaatgtg    148380
aagcaaacac agcatcgtga tcactgagcc atcatttcct gggagaaaga ccatgcattt    148440
aaagtattct ccatcctccc aggaaccgaa catatcattt gtgaagaatt attcagtgaa    148500
tttgtccatt gtaaatctga agaaagttat tcttggtact gttgctttgg gagacagtct    148560
aggaatggag tctcccactg caacttgtga actccatcat tcatccagga ctgagatgca    148620
aatgtcacag taatgcaagc aaagtatcaa agaaaaacaa tgaaattgac ctagttcaga    148680
tacagggtgc tccttgtcaa tactgagcca tttataccctt tgaaatatta aaatcactgt    148740
caatattttt attttttaact ctggatttttg aattagatta tttctgtatt tggctatgga   148800
tctgattttt aattttttta aatttcagtc aattctgatg ttactgagat gttttaccat    148860
ccttacaatg taaccacat gaactacgtg acctctgcaa gacaaagcgg ctttctaata    148920
gagagattag taaatatgtg aagaaaaaga cctgcatttg gcaggaagat gtatgctttg    148980
aatgcaaaag aaatttagag tcaatttgct gaaaacatta catgctcagc ttggttttgg    149040
```

-continued

```
acaagcctgt ccattgggca ggacctagct gttgtaaaga attggtctta atgttgaatg    149100
tattttggtt gctgatgttt ataaactgag aggtcacaaa gaatctatca ctaaaaattt    149160
ttacaaaact gccaaaaata taattcttag tggaagacaa tactcccttt aaagagagtt    149220
tgccactccc ctaaactcca ggatttataa agcaaattac tccaaggttt ataaagcaga    149280
ttacctcttg cccttgggtg ctatctagca gtaaagata aatttgttga atattggtaa      149340
ttaaaagact ccacataagt ccattaactg ctttccaccc agcttcaaag cttaaaaga    149400 gctcaggctt ttccaggaag atccaggagg gctaattaga aatcaacttg tggttgaccg    149460
cttgtttctt gttattacca aaacaggagg ggaaaaaatt aactgctcca aatttaacca    149520
taaatcaatt catgtttaac gtttctcatt aaaatccagt attatattat catatctctc    149580
tttacttccc agtataagat ttttgaaaat cctgaataaa ccagtatcgt tactggcacc    149640
tgaaattaat ttgtgaattt gcaacagtaa tcagagttac cattatttaa tttgtatgct    149700
aaatgaggag gtacattgaa accctccaaa tctccagtct catctatgtc atattttgcc    149760
actgcctttc agaagtgatt tagttgtgga aagataataa attgatttgt tatggttaca    149820
tatttagcgc acccagagaa aattaattat atttctacag agaaaatgaa tttgggatac    149880
taaagtagtt taagtctcct ttactgaatg taaggggggg atcgaaaaga aggtattttt    149940
ccaatcacag tgttatgtag tattgttcta tttttgttta caaacatgga aaacagagta    150000
tttctggcag ctgtggtaca aatgtgataa tatattgcta aaatatttta gatgttatta    150060
tgctaatata gtagggttg aagaaaacaa aatagcttat tatagaattg cacatagttc     150120
tgcccaaatt atgtgaaatg cttatgcttg tgtatatgta taaattaata cagagtacgt    150180
taaaagcaaa aa                                                       150192
```

<210> SEQ ID NO 2
<211> LENGTH: 3331
<212> TYPE: RNA
<213> ORGANISM: homo sapien

<400> SEQUENCE: 2

```
cagaauucca ggacaaagag aucuucaaaa aucaaaaaug agguucacau uuacaagccg     60
gugcuuggca cuguuucuuc uucuaaauca cccaacccca auucuuccug ccuuuucaaa    120
ucaaaccuau ccaacaauag agcccaagcc auuucuuuac gucguaggac gaaagaagau    180
gauggaugca caguacaaau gcuaugaccg aaugcagcag uuacccgcau accaaggaga    240
agguccauau ugcaaucgca ccugggaugg auggcugugc ugggaugaca caccggcugg    300
aguauugucc uaucaguucu gcccagauua uuuuccggau uuugauccau cagaaaaggu    360
uacaaaauac ugugaugaaa aaggugguug guuuaaacau ccugaaaaca aucgaaccug    420
guccaacuau acuaugugca augcuuucac uccugagaaa cugaagaaug cauauguucu    480
guacuauuug gcuauguggg ucauucuuu ucaauuuuc acccuaguga uuucccuggg    540 gauuucgug uuuucagga gccuuggcug ccaaagggua acccugcaca agaacauguu    600
ucuuacuuac auucugaauu cuaugauuau caucauccac cugguugaag uaguacccaa    660
uggagagcuc gugcgaaggg acccggugag cugcaagauu uugcauuuuu ccaccagua    720 caugauggcc ugcaacuauu ucuggaugcu cugugaaggg aucuaucuuuc auacacucau    780 ugucguggcu guguuuacug agaagcaacg cuugcggugg uauuaucucu ugggcuggg    840 guucccgcug gugccaacca cuauccaugc uauuaccagg gccguguacu ucaaugacaa    900
```

-continued

```
cugcuggcug agugggaaaa cccauuugcu uuacauaauc cauggaccug ucauggcggc    960
acuugugguc aauucuucu uuuugcucaa cauugccgg gugcuuguga ccaaaaugag    1020
ggaaacccau gaggcggaau cccacaugua ccugaaggcu gugaaggcca ccaugauccu    1080
ugugccccug cugggaaucc aguuugucgu cuuucccugg agaccuucca acaagaugcu    1140
ugggaagaua uaugauuacg ugaugcacuc ucugauucau uccagggcu cuuuguugc    1200 gaccaucuac ugcuucugca acaaugaggu ccaaaccacc gugaagcgcc aaugggccca    1260
auucaaaauu caguggaacc agcguugggg gaggcgcccc ucaaccgcu cugcucgcgc    1320 ugcagccgcu gcugcggagg cuggcgacau cccaauuuac aucugccauc aggagcugag    1380
gaaugaacca gccaacaacc aaggcgagga gagugcugag aucaucccuu ugaauaucau    1440
agagcaagag ucaucugcuu gaaugugaag gcaaacacag caucgugauc acugagccau    1500
cauuccuggg gagaaagacc augcauuuaa aguauucucc auccucccag gaaccgaaca    1560
uaucauuugu gaagaauuau ucagugaauu uguccauugu aaaucugaag aaaguuauuc    1620
uugguacugu ugcuuuggga gacagucuag gaauggaguc ucccacugca acuugugaac    1680
uccaucauuc auccaggacu gagaugcaaa ugucacagua augcaagcaa aguaucaaag    1740
aaaaacaaug aaauugaccu aguucagaua caggugcuc cuugucaaua cugagccauu    1800
uauaccuuug aaauauuaaa aucacuguca auauuuuuau uuuuaacucu ggauuuugaa    1860
uuagauuauu ucuguauuug gcauggauc ugauuuuaa uuuuuuaaaa uuucagucaa    1920
uucugauguu acugagaugu uuuaccaucc uuacaaugua aaccacauga acuacgugac    1980
cucugcaaga caaagcggcu uucuaauaga gagauuagua aauaugugaa gaaaaagacc    2040
ugcauuuggc aggaagaugu augcuuugaa ugcaaaagaa auuuagaguc aauuugcuga    2100
aaacauuaca ugcucagcuu gguuuggac aagccuguc auugggcagg accuagcugu    2160
uguaaagaau uggucuuaau guugaaugua uuuugguugc ugauguuuau aaacugagag    2220
gucacaaaga aucaucacu aaaaauuuuu acaaaacugc caaaaauaua auucuuagug    2280
gaagacaaua cuccuuuaa agagaguuug ccacuccccu aaacuccagg auuuauaaag    2340
caaauuacuc caagguuuau aaagcagauu accucuugcc cuggggugcu aucuagcagu    2400
aaaagauaaa uuguugaau auugguaauu aaaagacucc acauaagucc auuaacugcu    2460
uuccacccag cuucaaagcu uaaaaagagc ucaggcuuuu ccaggaagau ccaggagggc    2520
uaauuagaaa ucaacuugug guugaccgcu uguucuugu uauuaccaaa caggagggga    2580
aaaaauuaac ugcuccaaau uuaaccauaa ucaauucau guuuaacguu ucucauuaaa    2640
auccaguauu auauuaucau aucucucuuu acuucccagu auaagauuuu ugaaaauccu    2700
gaauaaacca guaucguuac uggcaccuga aauuauuug ugaauuugca acaguaauca    2760
gaguuaccau uauuuaauuu guaugcuaaa ugaggaggua cauugaaacc cuccaaaucu    2820
ccagucucau cuaugucaua uuuugccacu gccuuucaga agugauuuag uugugaaag    2880 auaauaaauu gauugguuau gguuacauau uuagcgcacc cagagaaaau uaauuauauu    2940
ucuacagaga aaaugaauuu gggauacuaa aguaguuuaa gucccuuua cugaauguaa    3000 gggggggauc gaaaagaagg uauuuuucca aucacagugu uaugaguauu uguucuauuu    3060
uuguuuacaa acauggaaaa cagaguauuu cuggcagcug ugguacaaau gugauaauau    3120
auugcuaaaa uauuuagau guuauuaugc uaaauagua gggguugaag aaaacaaaau    3180
agcuuauuau agaauugcac auaguucgc ccaauuaug ugaaaugcuu augcuugugu    3240
auauguauaa auuaauacag aguacguuaa aagcaaaaag auguauauuu gcauauuuuu    3300
```

-continued cuaaagaaau auauuauuca ucuuuucauu c					3331

<210> SEQ ID NO 3
<211> LENGTH: 3588
<212> TYPE: RNA
<213> ORGANISM: homo sapien

<400> SEQUENCE: 3

| | | | | | |
|---|---|---|---|---|---|
| gugcgcacgu | ccgcaccuca | cccugcggcu | gacaucuccu | gcccaggaga | ugggcgcuga | 60 |
| agcuugagcg | ccugagcccc | uggagccaca | ccugcgaaca | cccuuugcuu | cuauugagcu | 120 |
| gugcccagcc | gccagugac | agaauuccag | aauaaaugau | ucccacugau | ccacccacuu | 180 |
| uugccacccc | aggaugcaau | uucuggaga | gaagauuagu | ggacaaagag | aucuucaaaa | 240 |
| aucaaaaaug | agguucacau | uuacaagccg | gugcuuggca | cuguuucuuc | uucuaaauca | 300 |
| cccaaccccca | auucuuccug | ccuuuucaaa | ucaaaccuau | ccaacaauag | agcccaagcc | 360 |
| auuucuuuac | gucguaggac | gaaagaagau | gaugaugca | caguacaaau | gcuaugaccg | 420 |
| aaugcagcag | uuacccgcau | accaaggaga | agguccauau | ugcaaucgca | ccugggaugg | 480 |
| auggcugugc | ugggaugaca | caccggcugg | aguauugucc | uaucaguucu | gcccagauua | 540 |
| uuuuccggau | uuugauccau | cagaaaaggu | uacaaaauac | ugugaugaaa | aaggguguug | 600 |
| guuuaaacau | ccugaaaaca | aucgaaccug | guccaacuau | acaugugca | augcuuucac | 660 |
| uccugagaaa | cugaagaaug | cauauguucu | guacuauuug | gcuaugugg | gucauucuuu | 720 |
| gucaauuuuc | acccuaguga | uuucccuggg | gauuuucgug | uuuuucagaa | aauugacaac | 780 |
| uauuuuuccu | uugaauugga | aauauaggaa | ggcaugagc | cuuggcugcc | aaagggguaac | 840 |
| ccugcacaag | aacauguuuc | uuacuuacau | ucugaauucu | augauuauca | ucauccaccu | 900 |
| gguugaagua | guacccaaug | gagagcucgu | gcgaagggac | ccggugagcu | gcaagauuuu | 960 |
| gcauuuuuuc | caccaguaca | ugauggccug | caacuauuuc | uggaugcucu | gugaagggau | 1020 |
| cuaucuucau | acacucauug | ucguggcugu | guuuacugag | aagcaacgcu | ugcgguggua | 1080 |
| uuaucucuug | ggcuggggggu | ucccgcuggu | gccaaccacu | auccaugcua | uuaccagggc | 1140 |
| cguguacuuc | aaugacaacu | gcuggcugag | uggaaacc | cauuugcuuu | acauaaaucca | 1200 |
| uggaccuguc | auggcggcac | uugguggcaa | uuucuucuuu | uugcuccaaca | uguccgggu | 1260 |
| gcuugugacc | aaaaugaggg | aaacccauga | ggcggaaucc | cacauguacc | ugaaggcugu | 1320 |
| gaaggccacc | augauccuug | ugccccugcu | gggaauccag | uuugucgucu | uucccuggag | 1380 |
| accuuccaac | aagaugcuug | ggaagauaua | ugauuacgug | augcacucuc | ugauucauuu | 1440 |
| ccagggcuuc | uuuguugcga | ccaucuacug | cuucugcaac | aaugaggucc | aaaccaccgu | 1500 |
| gaagcgccaa | ugggcccaau | ucaaaauuca | guggaaccag | cguugggga | ggcgccccuc | 1560 |
| caaccgcucu | gcucgcgcug | cagccgcugc | ugcggaggcu | ggcgacaucc | caauuuacau | 1620 |
| cugccaucag | gagcugagga | augaaccagc | caacaaccaa | ggcgaggaga | gugcugagau | 1680 |
| cauccccuuug | aauaucauag | agcaagaguc | aucugcuuga | augugaagca | aacacaguau | 1740 |
| cgugaucacu | gagccaucau | uuccuggag | aaagaccaug | cauuuaaagu | auucuccauc | 1800 |
| cucccaggaa | ccgaacauau | cauuugugaa | gaauuauuca | gugaauuugu | ccauuguaaa | 1860 |
| ucugaagaaa | guuauucuug | uacuguugc | uuugggagac | agcuaggaa | uggagucucc | 1920 |
| cacugcaacu | ugugaacucc | aucauucauc | caggacugag | augcaaaugu | cacaguaaug | 1980 |
| caagcaaagu | aucaaagaaa | aacaaugaaa | uugaccuagu | ucagauacag | ggugcuccuu | 2040 |

-continued

| | |
|---|---|
| gucaauacug agccauuuau accuuugaaa uauuaaaauc acugucaaua uuuuuauuuu | 2100 |
| uaacucugga uuuugaauua gauuauuucu guauuuggcu auggaucuga uuuuuaauuu | 2160 |
| uuuuaaauuu cagucaauuc ugauguuacu gagauguuuu accauccuua caauguaaac | 2220 |
| cacaugaacu acgugaccuc ugcaagacaa agcggcuuuc uaauagagag auuaguaaau | 2280 |
| augugaagaa aaagaccugc auuuggcagg aagauguaug cuuugaaugc aaaagaaauu | 2340 |
| uagagucaau uugcugaaaa cauuacaugc ucagcuuggu uuuggacaag ccugccauu | 2400 |
| gggcaggacc uagcuguugu aaagaauugg ucuuaaugu gaauguauuu ugguugcuga | 2460 |
| uguuuauaaa cugagagguc acaaagaauc uaucacuaaa aauuuuuaca aaacugccaa | 2520 |
| aaauauaauu cuuaguggaa gacaauacuc ccuuuaaaga aagagaguuu gccacuccc | 2580 |
| uaaacuccag gauuuauaaa gcaaauuacu ccaagguuua uaaagcagau uaccucuugc | 2640 |
| ccuugggugc uaucuagcag uaaaagauaa auuuguugaa uauugguaau uaaaagacuc | 2700 |
| cacauaaguc cauuaacugc uuuccaccca gcuucaaagc uuaaaagag ucaggcuuu | 2760 |
| uccaggaaga uccaggaggg cuaauugaa aucaacuugu gguugaccgc uuguuucuug | 2820 |
| uuauuaccaa aacaggaggg gaaaaauua acugcuccaa auuuaaccau aaaucaauuc | 2880 |
| auguuuaacg uuucucauua aaauccagua uuauauauc auaucucucu uuacuuccca | 2940 |
| guauaagauu uuugaaaauc cugaauaaac caguaucguu acuggcaccu gaaauuaauu | 3000 |
| ugugaauuug caacaguaau cagaguuacc auuauuuaau uguaugcua aaugaggagg | 3060 |
| uacauugaaa cccuccaaau cuccagucuc aucuauguca uauuugcca cugccuuuca | 3120 |
| gaagugauuu aguugugaa agauaauaaa ugauuuguu augguuacau auucagcgca | 3180 |
| cccagagaaa auuauuaua uuucuacaga gaaaaugaau uggauacu aaaguaguuu | 3240 |
| aagucuccuu uacugaaugu aagggggga ucgaaaagaa gguauuuuc caaucacagu | 3300 |
| guuauguagu auuguucuau uuuuguuuac aaacauggaa aacagaguau uucuggcagc | 3360 |
| uggguacaa augugauaau auauugcuaa aauauuuuag auguuauuau gcuaauauag | 3420 |
| uagggguuga agaaaacaaa auagcuuauu auagaauugc acauaguucu gcccaaauua | 3480 |
| ugugaaaugc uuaugcuugu guauauguau aaauuaauac agaguacguu aaaagcaaaa | 3540 |
| agauguauau uugcauauuu uucuaaagaa auauauuauu caucuuuu | 3588 |

<210> SEQ ID NO 4
<211> LENGTH: 1674
<212> TYPE: RNA
<213> ORGANISM: homo sapien

<400> SEQUENCE: 4

| | |
|---|---|
| cagaauucca ggacaaagag aucuucaaaa accaaaaaug agguucacau uuacaagccg | 60 |
| gugcuuggca cuguuucuuc uucuaaauca cccaaccca auucuuccug ccuuuucaaa | 120 |
| ucaaaccuau ccaacaauag agcccaagcc auuucuuuac gucguaggac gaaagaagau | 180 |
| gauggaugca caguacaaau gcauaugccg aaugcagcag uuacccgcau accaaggaga | 240 |
| agguccauau ugcaaucgca ccugggaugg auggcugugc ugggaugaca caccggcugg | 300 |
| aguauugucc uaucaguucu gcccagauua uuuuccggau uuugauccau cagaaaaggu | 360 |
| uacaaaauac ugugaugaaa aaggguguuu guuuaaacau ccugaaaaca ucgaaccug | 420 |
| guccaacuau acuaugugca augcuuucac uccugagaaa cugaagaaug cauauguucu | 480 |
| guacauuug gcauuugugg gucauucuuu gucaauuuuc acccuaguga uucccggg | 540 |
| gauuucgug uuuucagga gccuuggcug ccaaagggua acccugcaca agaacauguu | 600 |

```
ucuuacuuac auucugaauu cuaugauuau caucauccac cugguugaag uaguacccaa      660
uggagagcuc gugcgaaggg acccggugag cugcaagauu uugcauuuuu uccaccagua      720
caugauggcc ugcaacuauu ucuggaugcu cugugaaggg aucuaucuuc auacacucau      780
ugucguggcu uguuuacug agaagcaacg cuugcggugg uauuaucucu ugggcugggg       840
guucccgcug gugccaacca cuauccaugc uauuaccagg gccguguacu caaugacaa      900 cugcuggcug agugguggaaa cccauuugcu uuacauaauc cauggaccug ucauggcggc    960 acuuggguc aauucuucu uuuugcucaa cauugccgg gugcuugugu ccaaaaugag       1020
ggaaacccau gaggcggaau cccacaugua ccugaaggcu gugaaggcca ccaugauccu    1080
ugugccccug cugggaaucc aguuugucgu cuuucccugg agaccuucca acaagaugcu    1140
ugggaagaua uaugauuacg ugaugcacuc ucugauucau uccaggcu cuuuguugc        1200 gaccaucuac ugcuucugca acaaugaggu ccaaaccacc gugaagcgcc aaugggccca    1260
auucaaaauu cagugaaacc agcguugggg gaggcgcccc uccaaccgcu cugcucgcgc    1320
ugcagccgcu gcugcggagg cuggcgacau cccaauuuac aucugccauc aggagcugag    1380
gaaugaacca gccaacaacc aaggcgagga gagucugag aucaucccuu ugaauaucau      1440
agagcaagag ucaucugcuu gaaugugaag caaacacagc aucgugauca cugagccauc    1500 auuccugg agaaagacca ugcauuuaaa guauucucca uccucccagg aaccgaacau      1560
aucauuugug aagaauuauu cagugaauuu guccauugua aaucugaaga aaguuauucu    1620
ugguacuguu gcuuugggag acagucuagg aauggagucu cccacugcaa cuug          1674

<210> SEQ ID NO 5
<211> LENGTH: 1512
<212> TYPE: RNA
<213> ORGANISM: homo sapien

<400> SEQUENCE: 5
ggacaaagag aucuucaaaa accaaaaaug agguucacau uuacaagccg gugcuuggca       60
cuguuucuuc uucuaaauca cccaaccca auucuuccug ccuuuucaaa ucaaaccuau      120
ccaacaauag agcccaagcc auucuuuac gucguaggac gaaagaagau gauggaugca      180
caguacaaau gcuaugaccg aaugcagcag uuacccgcau accaaggaga agguccauau    240
ugcaaucgca ccugggaugg auggcugugc ugggaugaca caccggcugg aguauugucc    300
uaucaguucu gcccagauua uuuuccggau uuugauccau cagaaaaggu uacaaaauac    360
ugugaugaaa aaggguguuug guuuaaacau ccugaaaaca aucgaaccug uccaacuau    420 acuaugugca augcuuucac uccugagaaa cugaagaaug cauauguucu guacuauug    480 gcuauguguc gucauucuuu gucaauuuuc acccuaguga uucccugggg auuuucgug    540 uuuucagga gccuuggcug ccaaagggua acccugcaca agaacauguu ucuuacuuac    600
auucugaauu cuaugauuau caucauccac cugguugaag uaguacccaa uggagagcuc    660
gugcgaaggg acccggugag cugcaagauu uugcauuuuu uccaccagua caugauggcc    720
ugcaacuauu ucuggaugcu cugugaaggg aucuaucuuc auacacucau ugucguggcu    780 uguuuacug agaagcaacg cuugcggugg uauuaucucu ugggcugggg guucccgcug     840
gugccaacca cuauccaugc uauuaccagg gccguguacu caaugacaa cugcuggcug     900 agugguggaaa cccauuugcu uuacauaauc cauggaccug ucauggcggc acuuggguc     960 aauucuucu uuuugcucaa cauugccgg gugcuugugu ccaaaaugag ggaaacccau     1020
```

-continued

| | |
|---|---|
| gaggcggaau cccacaugua ccugaaggcu gugaaggcca ccaugauccu ugugccccug | 1080 |
| cugggaaucc aguuugucgu cuuucccugg agaccuucca acaagaugcu ugggaagaua | 1140 |
| uaugauuacg ugaugcacuc ucugauucau uccagggcu cuuuguugc gaccaucuac | 1200 |
| ugcuucugca acaaugaggu ccaaaccacc gugaagcgcc aaugggccca auucaaaauu | 1260 |
| caguggaacc agcguugggg gaggcgcccc uccaaccgcu cugcucgcgc ugcagccgcu | 1320 |
| gcugcggagg cuggcgacau cccaauuuac aucugccauc aggagcugag gaaugaacca | 1380 |
| gccaacaacc aaggcgagga gagugcugag aucaucccuu ugaauaucau agagcaagag | 1440 |
| ucaucugcuu gaaugugaag caaacacagc aucgugauca cugagccauc auuccuggg | 1500 |
| agaaagacca ug | 1512 |

<210> SEQ ID NO 6
<211> LENGTH: 1472
<212> TYPE: RNA
<213> ORGANISM: homo sapien

<400> SEQUENCE: 6

| | |
|---|---|
| augagguuca cauuuacaag ccggugcuug gcacuguuuc uucuucuaaa ucacccaacc | 60 |
| ccaauucuuc cugccuuuuc aaaucaaacc uaccaacaa uagagcccaa gccauuucuu | 120 |
| uacgucguag gacgaaagaa gaugauggau gcacaguaca aaugcuauga ccgaaugcag | 180 |
| caguuacccg cauaccaagg agaaggucca uuugcaaccg gcaccgggag uggaugggcu | 240 |
| ugcugggaug acacaccggc uggaguauug uccuaucagu ucugcccaga uuauuuccg | 300 |
| gauuuugauc caucagaaaa gguuacaaaa uacugugaug aaaaaggugu uuggguuaaa | 360 |
| cauccugaaa acaaucgaac cugguccaac uauacuaugu gcaaugcuuu cacuccugag | 420 |
| aaacugaaga augcauagu ucuguacau uggcuauug ugggcauuc uuugucaauu | 480 |
| uucacccuag ugauuucccu ggggauuuuc guguuuuuca ggagccuugg cugccaaagg | 540 |
| guaacccugc acaagaacau guuucuuacu uacauucuga auucuaugau uaucaucauc | 600 |
| caccuggug aaguaguacc caauggagag cucgugcgaa gggacccggu gagcugcaag | 660 |
| auuuugcauu uuuccacca guacaugaug gccugcaacu auucuggau gcucugugaa | 720 |
| gggaucuauc uucauacacu cauugucgug gcuguguuua cugagaagca acgcuugcgg | 780 |
| ugguauuauc ucuuggggcug gggguucccg cuggugccaa ccacuauucca ugcuauuacc | 840 |
| agggccgugu acuucaauga caacugcugg cugagugugg aaacccauuu gcuuuacaua | 900 |
| auccauggac cugucauggc ggcacuugug ucaauuucu ucuuuuugcu caacauuguc | 960 |
| cgggugcuug ugaccaaaau gagggaaacc caugaggcgg aauccacau guaccugaag | 1020 |
| gcugugaagg ccaccaugau ccuugugccc cugcugggaa ccaguuugu cgucuuuccc | 1080 |
| uggagaccuu ccaacaagau gcuugggaag auauaugauu acgugaugca cucucugauu | 1140 |
| cauuccagg gcuucuuugu ugcgaccauc uacugcuucu gcaacaauga ggucaaaacc | 1200 |
| accgugaagc gccaaugggc ccaauucaaa auucagugga ccagcguug ggggaggcgc | 1260 |
| cccuccaacc gcucugcucg cgcugcagcc gcugcugcgg aggcuggcga caucccaauu | 1320 |
| uacaucugcc aucaggagcu gaggaaugaa ccagccaaca accaaggcga ggagagugcu | 1380 |
| gagaucaucc cuuugaauau cauagagcaa gagucaucug cuugaaugug aaggcaaaca | 1440 |
| cagcaucgug aucacugagc caucauuucc ug | 1472 |

<210> SEQ ID NO 7
<211> LENGTH: 1506

<212> TYPE: RNA
<213> ORGANISM: homo sapien

<400> SEQUENCE: 7

```
gaauuccagg acaaagagau cuucaaaaac caaaaaugag guucacauuu acaagccggu    60
gcuuggcacu guucuucuu cuaaaucacc caaccccaau ucuuccugcc uuuucaaauc    120
aaaccuaucc aacaauagag cccaagccau ucuuuacgu cguaggacga aagaagauga    180
uggaugcaca guacaaaugc uaugaccgaa ugcagcaguu acccgcauac caaggagaag   240
guccauauug caaucgcacc ugggauggau ggcugugcug ggaugacaca ccggcuggag   300
uauuguccua ucaguucgc ccagauuauu uccggauuu ugaccauca gaaaagguua    360
caaaauacug ugaugaaaaa gguguuuggu uuaaacaucc ugaaacaau cgaaccuggu   420
ccaacuauac uaugugcaau gcuuucacuc cugagaaacu gaagaaugca uauguucugu   480
acuauuuggc uauguggggu cauucuuugu caauuuucac ccuagugauu ucccuggga    540
uuuucguguu uucaggagc cuggcugcc aaagggaac ccugcacaag aacauguuuc   600
uuacuuacau ucugaauucu augauuauca ucauccaccu gguugaagua gucccaaug    660
gagagcucgu gcgaagggac ccggugagcu gcaagauuuu gcauuuuc caccaguaca   720
ugauggccug caacuauuuc uggaugcucu gugaagggau cuaucuucau acacucauug   780
ucgggcugu guuuacugag aagcaacgcu ugcggggua uuaucucuug ggcuggggu    840
ucccgcuggu gccaaccacu auccaugcua uuaccagggc cguguacuuc aaugacaacu   900
gcuggcugag uguggaaacc cauuugcuuu acauaaucca uggaccuguc augcggcac    960
uuguggucaa uuucuucuuu uugcucaaca ugguccgggu gcuugugacc aaaaugaggg   1020
aaacccauga ggcggaaucc cacauguacc ugaaggcugu gaaggccacc augauccuug   1080
ugcccugcu gggaauccag uuugucgucu ucccggag accuuccaac aagaugcuug    1140
ggaagauaua ugauuacgug augcacacuc ugauucauuu ccagggcuuc uuuguugcga   1200
ccaucuacug cuucugcaac aaugagguc aaaccaccgu gaagcgccaa ugggccaau    1260
ucaaaauuca guggaaccag cguuggggga gcgcccccuc caaccgcucu gcucgcgcug   1320
cagccgcugc ugcggaggcu ggcgacaucc caauuuacau cugccaucag gagcugagga   1380
augaaccagc caacaaccaa ggcgaggaga gugcugagau caucccuuug aauaucauag   1440
agcaagaguc aucugcuuga augugaagca aacacagcau cgugaucacu gagccaccau   1500
uuccug                                                           1506
```

<210> SEQ ID NO 8
<211> LENGTH: 1493
<212> TYPE: RNA
<213> ORGANISM: homo sapien

<400> SEQUENCE: 8

```
uuccaggaca aagagaucuu caaaaaucaa aaaugagguu cacauuuaca agccggugcu    60
uggcacuguu ucuucuucua aaucacccaa ccccaauucu uccugccuuu ucaaaucaaa   120
ccuauccaac aauagagccc aagccauuuc uuuacgucgu aggacgaaag aagaugaugg   180
augcacagua caaaugcuau gaccgaaugc agcaguaacc cgcauaccaa ggagaagguc   240
cauauugcaa ucgcaccugg gauggauggc ugugcuggga ugacaccg gcuggaguau    300
ugccuauca guucgccca gauuauuuc cggauuuga uccaucagaa aagguuacaa    360
aauacuguga ugaaaaaggu guuggguuua acauccuga aacaaucga accuggucca    420
```

| | |
|---|---|
| acuauacuau gugcaaugcu ucacuccug agaaacugaa gaaugcauau guucuguacu | 480 |
| auuuggcuau gugggucau ucuuugucaa uuuucacccu agugauuucc cuggggauuu | 540 |
| ucguguuuuu caggagccuu ggcugccaaa ggguacccu gcacaagaac auguucuua | 600 |
| cuuacauucu gaauucuaug auuaucauca uccaccuggu ugaaguagua cccaauggag | 660 |
| agcucgugcg aagggacccg gugagcugca agauuugca uuuuuccac caguacauga | 720 |
| uggccugcaa cuauuucugg augcucugug aagggaucua ucuucauaca cucauugucg | 780 |
| uggcuguguu uacugagaag caacgcuugc ggugguauua ucucuggc uggggguucc | 840 |
| cgcuggugcc aaccacuauc caugcuauua ccagggccgu guacuucaau gacaacugcu | 900 |
| ggcugagugu ggaaacccau uugcuuuaca uaauccaugg accgucaug gcggcacuug | 960 |
| uggucaauuu cuucuuuuug cucaacauug uccgggugcu ugugaccaaa augagggaaa | 1020 |
| cccaugaggc ggaaucccac auguaccuga aggcugugaa ggccaccaug auccuugugc | 1080 |
| cccgcugggg aauccaguuu gucgucuuuc ccuggagacc uuccaacaag augcuuggga | 1140 |
| agauauauga uuacgugaug cacucucuga uucauuccca gggcuucuuu guugcgacca | 1200 |
| ucuacugcuu cugcaacaau gagguccaaa ccaccgugaa gcgccaaugg gcccaauuca | 1260 |
| aaauucagug gaaccagcgu uggggggaggc gccccuccaa ccgcucugcu cgcgcugcag | 1320 |
| ccgcugcugc ggaggcuggc gacauccaa uuuacaucug ccaucaggag cugaggaaug | 1380 |
| aaccagccaa caaccaaggc gaggagagug cugagaucau cccuuugaau ucauagagc | 1440 |
| aagagucauc ugcuugaaug ugaagcaaac acagcaucgu gaucacugag cca | 1493 |

<210> SEQ ID NO 9
<211> LENGTH: 1496
<212> TYPE: RNA
<213> ORGANISM: homo sapien

<400> SEQUENCE: 9

| | |
|---|---|
| gaauuccagg acaaagagau cuucaaaaac caaaaaugag guucacauuu acaagccggu | 60 |
| gcuuggcacu guuucuucuu cuaaaaucacc caaccccaau ucuccugcc uuuucaaauc | 120 |
| aaaccuaucc aacaauagag cccaagccau uucuuuacgu cguaggacga agaagauga | 180 |
| uggaugcaca guacaaaugc uaugaccgaa ugcagcaguu acccgcauac caaggagaag | 240 |
| guccauauug caaucgcacc ugggauggau ggcugcug ggaugacaca ccggcuggag | 300 |
| uauugccua ucaguucugc ccagauuauu uuccggauuu ugauccauca gaaaagguua | 360 |
| caaaauacug ugaugaaaaa gguguuuggu uuaaacaucc ugaaaacaau cgaaccuggu | 420 |
| ccaacuauac uaugugcaau gcuuucacuc cugagaaacu gaagaaugca uaguucugu | 480 |
| acuauuggc uauuggggu cauucuugu caauuuucac ccuagugauu ccggggga | 540 |
| uuuucguguu uuucaggagc cuggcugcc aaagggaac ccugcacaag aacauguuuc | 600 |
| uuacuuacau ucugaauucu augauuauca ucaccaccu gguugaagua gucccaaug | 660 |
| gagagcucgu gcgaagggac ccggugagcu gcaagauuuu gcauuuuuc caccaguaca | 720 |
| ugauggccug caacuauuuc uggaugcucu gugaagggau cuaucuucau acacucauug | 780 |
| ucguggcugu guuacugag aagcaacgcu ugcggguggua uuaucucuug ggcuggggu | 840 |
| uccgcuggu gccaaccacu auccaugcua uuaccagggc cguguacuuc aaugacaacu | 900 |
| gcuggcugag ugggaaacc cauuugcuu acauaauca uggaccguc augcggcac | 960 |
| uuguggucaa uuucuucuuu uugcucaaca uguccggu gcuugugacc aaaaugaggg | 1020 |
| aaacccauga ggcggaaucc cacauguacc ugaaggcugu gaaggccacc augauccuug | 1080 |

```
ugccccugcu gggaauccag uuugucgucu uucccuggag accuuccaac aagaugcuug    1140
ggaagauaua ugauuacgug augcacucuc ugauucauuu ccagggcuuc uuuguugcga    1200
ccaucuacug cuucugcaac aaugaggucc aaaccaccgu gaagcgccaa ugggcccaau    1260
ucaaaauuca guggaaccag cguuggggga ggcgccccuc caaccgcucu gcucgcgcug    1320
cagccgcugc ugcggaggcu ggcgacaucc caauuuacau cugccaucag gagcugagga    1380
augaaccagc caacaaccaa ggcgaggaga gugcugagau caucccuuug aauaucauag    1440
agcaagaguc aucugcuuga augugaagca aacacagcau cgugaucacu gagcca        1496

<210> SEQ ID NO 10
<211> LENGTH: 1339
<212> TYPE: RNA
<213> ORGANISM: homo sapien

<400> SEQUENCE: 10
ccaaaaauga ggacgaaaga agaugaugga ugcacaguac aaaugcuaug accgaaugca      60
gcaguuaccc gcauaucaag gagaaggucc auauugcaau cgcaccuggg auggauggcu    120
gugcugggau gacacaccgg cuggaguauu guccaucag uucugcccag auuauuuucc    180
ggauuuugau ccaucagaaa agguuacaaa auacugugau gaaaaaggug uuggguuuaa    240
acauccugaa aacaaucgaa ccugguccaa cuauacuaug ugcaaugcuu cacuccuga    300 gaaacugaag aaugcauaug uucuguacua uuuggcuauu ggggucauu cuuugucaau    360 uuucacccua ugcgauuuccc uggggauuuu cguguuuuuc aggagccuug gcugccaaag    420
gguaacccug cacaagaaca uguuucuuac uuacauucug aauucuauga uuaucaucau    480
ccaccugguu gaaguaguac ccaauggaga gcucgugcga aaggaccgg ugagcugcaa    540 gauuuugcau uuuuccacc aguacaugau ggccugcaac uauuucugga ugcucuguga    600
agggaucuau cuucauacac ucauugcgu ggcuguguuu acugaagc aacgcuugcg    660 guggauuuau cucuuggcu gggguuccc gcuggugca ccacuaucc augcuauuac    720 cagggccgug uacuucaaug acaacugcug gcugagugug aaacccauu gcuuuacau    780 aauccaugga ccugucaugg cggcacuugu ggucaauuuc uucuuuugc ucaacauugu    840 ccggggugcuu ugaccaaaa ugagggaaac ccaugaggcg gaaucccaca uguaccugaa    900
ggcugugaag gccaccauga cccuugugcc ccugcuggga auccaguuug cgucuuucc    960 cuggagaccu ccaacaaga ugcuugggaa gauauaugau uacgugaugc acucucugau   1020
ucauuuccag ggcuucuuug uugcgaccau cuacugcuuc ugcaacaaug agguccaaac   1080
caccgugaag cgccaauggg cccaauucaa aauucagugg aaccagcguu ggggaggcg   1140 ccccuccaac cgcucugcuc gcgcugcagc cgcugcucg gaggcuggcg acaucccaau   1200
uuacaucugc caucaggagc ugaggaauga accagccaac aaccaaggcg aggagagugc   1260
ugagaucauc ccuuugaaua ucauagagca agagucaucu gcuugaaugu gaagcaaaca   1320
caguaucgug aucacugag                                                1339

<210> SEQ ID NO 11
<211> LENGTH: 1772
<212> TYPE: RNA
<213> ORGANISM: homo sapien

<400> SEQUENCE: 11
aguuauaaga gacaggaaua ccagugagaa guaugagaga gugggugga gauaauguuu      60
```

| | |
|---|---|
| agaaucucuu uugcugcccg caauuuauga aaauggcuug aaaauauuua uggucaaaga | 120 |
| ccgaaauauu ucuucaaaga agauuagcuu ugcuccauua aaaguaauga guagaaauau | 180 |
| uaaaaaaaaa aaguuuuaag uaccugagua ucuugccagc aacugaccac cacugcuaaa | 240 |
| ggugaggaga gacacagcuu ucaucauugg gacugcaguu uauuucagga caaagagauc | 300 |
| uucaaaaacc aaaaaugagg uucacauuua caagccggug cuuggcacug uuucuucuuc | 360 |
| uaaaucaccc aaccccaauu cuuccugccu uuucaaauca aaccuaucca acaauagagc | 420 |
| ccaagccauu ucuuuacguc guaggacgaa agaagaugau ggaugcacag uacaaaugcu | 480 |
| augaccgaau gcagcaguua cccgcauacc aaggagaagg uccauauugc aaucgcaccu | 540 |
| gggauggaug gcugugcugg gaugacacac cggcuggagu auugccuau caguucugcc | 600 |
| cagauuauuu uccggauuuu gauccaucag aaaagguuac aaaauacugu gaugaaaaag | 660 |
| uguuuggu uaaacauccu gaaaacaauc gaaccuggu caacuauacu augugcaaug | 720 |
| cuuucacucc ugagaaacug aagaaugcau auguucugua cuauuggcu auugugggguc | 780 |
| auucuuugc aauuuucacc cuagugauuu cccugggggau uuucguguuu ucaggagcc | 840 |
| uuggcugcca aagggguaacc cugcacaaga acauguuucu uacuuacauu cugaauucua | 900 |
| ugauuaucau cauccaccug guugaaguag uacccaaugg agagcucgug cgaagggacc | 960 |
| cggugagcug caagauuuug cauuuuuucc accaguacau gauggccugc aacuauuucu | 1020 |
| ggaugcucug ugaagggauc uaucuucaua cacucauugu cguggcugug uuuacgagaa | 1080 |
| agcaacgcuu gcgguggua uaucucuugg gcuggggguu cccgcuggug ccaaccacua | 1140 |
| uccaugcuau uaccagggcc guguacuuca augacaacug cuggcugagu guggaaaccc | 1200 |
| auuugcuuua cauaauccau ggaccuguca uggcggcacu uguggucaau uucuucuuuu | 1260 |
| ugcucaacau uguccgggug cuugugacca aaaugaggga aacccaugag gcggaauccc | 1320 |
| acauguaccu gaaggcugug aaggccacca ugauccuugu gccccugcug ggaauccagu | 1380 |
| uugucgucuu ucccuggaga ccuuccaaca agaugcuugg gaagauauau gauuacguga | 1440 |
| ugcacucucu gauucauuuc cagggcuucu uguugcgac caucuacugc uucugcaaca | 1500 |
| augaggucca aaccaccgug aagcgccaau gggcccaauu caaaauucag uggaaccagc | 1560 |
| guuggggggag gcgcccuccc aaccgcucug cucgcgcugc agccgcugcu gcggaggcug | 1620 |
| gcgacauccc aauuuacauc ugccaucagg agcugaggaa ugaaccagcc aacaaccaag | 1680 |
| gcgaggagag ugcugagauc aucccuuuga auaucauaga gcaagaguca ucugcuugaa | 1740 |
| ugugaagcaa acacaguauc gugaucacug ag | 1772 |

<210> SEQ ID NO 12
<211> LENGTH: 1530
<212> TYPE: RNA
<213> ORGANISM: homo sapien

<400> SEQUENCE: 12

| | |
|---|---|
| uugcuucuau ugagcugugc ccagccgccc agugacagaa uuccaggaca aagagaucuu | 60 |
| caaaaaccaa aaaugagguu cacauuuaca agccggugcu uggcacuguu ucuucuucua | 120 |
| aaucaccccaa ccccaauucu ccugccuuu ucaaaucaaa ccuauccaac aauagagccc | 180 |
| aagccauuuc uuuacgucgu aggacgaaag aagaugaugg augcacagua caaaugcuau | 240 |
| gaccgaaugc agcaguuacc cgcauaccaa ggagaagguc auauugcaa ucgcaccugg | 300 |
| gauggauggc ugugcuggga ugacacaccg gcuggaguau ugccuauca guucugccca | 360 |
| gauuauuuuc cggauuuuga uccaucagaa aagguuacaa aauacuguga ugaaaaaggu | 420 |

| | |
|---|---|
| guuugguuua aacauccuga aaacaaucga accuggucca acuauacuau gugcaaugcu | 480 |
| uucacuccug agaaacugaa gaaugcauau guucuguacu auuuggcuau gugggucau | 540 |
| ucuuugucaa uuuucacccu agugauuucc cuggggauuu ucguguuuuu caggagccuu | 600 |
| ggcugccaaa ggguacccu gcacaagaac auguucuu cuuacauucu gaauucuaug | 660 |
| auuaucauca uccaccuggu ugaaguagua cccaauggag agcucgugcg aagggacccg | 720 |
| gugagcugca agauuuugca uuuuuccac caguacauga uggccugcaa cuauuucugg | 780 |
| augcucugug aagggaucua ucuucauaca cucauugucg uggcugyguu acugagaag | 840 |
| caacgcuugc ggugguauua ucucuuggc ugggggguucc cgcuggugcc aaccacuauc | 900 |
| caugcuauua ccagggccgu guacuucaau gacaacugcu ggcugagugu ggaaacccau | 960 |
| uugcuuuaca uaauccaugg accgucaug gcggcacuug uggucaauuu cuucuuuuug | 1020 |
| cucaacauug uccgggugcu ugugaccaaa augagggaaa cccaugaggc ggaaucccac | 1080 |
| auguaccuga aggcugugaa ggccaccaug auccugugc cccugcuggg aauccaguuu | 1140 |
| gucgucuuuc ccuggagacc uuccaacaag augcuuggga agauauauga uuacgugaug | 1200 |
| cacucucuga uucauuucca gggcuucuuu guucgcacca ucuacugcuu cugcaacaau | 1260 |
| gagguccaaa ccaccgugaa gcgccaaugg gcccaauuca aaauucagug gaaccagcgu | 1320 |
| uggggggaggc gccccuccaa ccgcucugcu cgcgcgcag ccgcugcugc ggaggcuggc | 1380 |
| gacaucccaa uuuacaucug ccaucaggag cugaggaaug aaccagccaa caaccaaggc | 1440 |
| gaggagagug cugagaucau ccccuuugaau acauagagc aagagucauc ugcuugaaug | 1500 |
| ugaagcaaac acaguaucgu gaucacugag | 1530 |

<210> SEQ ID NO 13
<211> LENGTH: 1735
<212> TYPE: RNA
<213> ORGANISM: homo sapien

<400> SEQUENCE: 13

| | |
|---|---|
| acagcuggga gagcgcagga aggcgccggg aaggaaagcc agcccaccag cgucugggug | 60 |
| ggcugcgccg cgcggcuggc ggaccuuccc ggguuggaga ggugcgcacg uccgcaccuc | 120 |
| acccugcggc ugacaucucc ugcccaggag augggcgcug aagcuugagc gccugagucc | 180 |
| cuggagccac accugcgaac acccuuugcu ucuauugagc ugugcccagc cgcccaguga | 240 |
| cagaauucca ggacaaagag aucuucaaaa accaaaaaug agguucacau uuacaagccg | 300 |
| gugcuuggca cuguucuuc uucuaaauca cccaacccca auucuccug ccuuuucaaa | 360 |
| ucaaaccuau ccaacaauag agcccaagcc auuucuuuac gucguaggac gaaagaagau | 420 |
| gauggaugca caguacaaau gcuaugaccg aaugcagcga uuacccgcau accaaggaga | 480 |
| agguccauau ugcaaucgca ccugggaugg auggcugugc ugggaugaca caccggcugg | 540 |
| aguauugucc uaucguucu gcccagauua uuuuccggau uuugauccau cagaaaaggu | 600 |
| uacaaaauac ugugaugaaa aaggugguug guuaaacau ccugaaaaca aucgaaccug | 660 |
| guccaacuau acuaugugca augcuuucac uccugagaaa cugaagaaug cauauguucu | 720 |
| guacuauuug gcuauguggg ucauucuuu gucaauuuuc acccuaguga uuucccuggg | 780 |
| gauuucgug uuuucagga gccuggcug ccaaagggua acccugcaca agaacauguu | 840 |
| ucuuacuuac auucugaauu cuaugauau caucauccac cugguugaag uaguaccaa | 900 |
| uggagagcuc gugcgaaggg acccgguag cugcaagauu uugcauuuu uccaccagua | 960 |

-continued

| | |
|---|---|
| caugauggcc ugcaacuauu ucuggaugcu cugugaaggg aucuaucuuc auacacucau | 1020 |
| ugucgugcu uguuuacug agaagcaacg cuucggugg uauuaucucu ugggcugggg | 1080 |
| guucccgcug gugccaacca cuauccaugc uauuaccagg gccguguacu ucaaugacaa | 1140 |
| cugcuggcug agugguggaaa cccauuugcu uuacauaauc cauggaccug ucauggcggc | 1200 |
| acuuguggc aauucuucu uuuugcucaa cauugucgg gugcuuguga ccaaaaugag | 1260 |
| ggaaacccau gaggcggaau cccacacugua ccugaaggcu gugaaggcca ccaugauccu | 1320 |
| ugugccccug cugggaaucc aguuugucgu cuuucccugg agaccuucca acaagaugcu | 1380 |
| ugggaagaua uaugauuacg ugaugcacuc ucugauucau uuccagggcu ucuuguugc | 1440 |
| gaccaucuac ugcuucugca acaaugaggu ccaaaccacc gugaagcgcc aaugggccca | 1500 |
| auucaaaauu caguggaacc agcguugggg gaggcgcccc ucaaccgcu cugcucgcgc | 1560 |
| ugcagccgcu gcugcggagg cuggcgacau cccaauuuac aucugccauc aggagcugag | 1620 |
| gaaugaacca gccaacaacc aaggcgagga gagugcugag aucaucccuu ugaauaucau | 1680 |
| agagcaagag ucaucugcuu gaaugugaag caaacacagu aucgugauca cugag | 1735 |

<210> SEQ ID NO 14
<211> LENGTH: 3331
<212> TYPE: DNA
<213> ORGANISM: homo sapien

<400> SEQUENCE: 14

| | |
|---|---|
| cagaattcca ggacaaagag atcttcaaaa atcaaaaatg aggttcacat ttacaagccg | 60 |
| gtgcttggca ctgtttcttc ttctaaatca cccaaccca attcttcctg cctttcaaa | 120 |
| tcaaacctat ccaacaatag agcccaagcc atttctttac gtcgtaggac gaaagaagat | 180 |
| gatggatgca cagtacaaat gctatgaccg aatgcagcag ttacccgcat accaaggaga | 240 |
| aggtccatat tgcaatcgca cctgggatgg atggctgtgc tgggatgaca caccggctgg | 300 |
| agtattgtcc tatcagttct gcccagatta ttttccggat tttgatccat cagaaaaggt | 360 |
| tacaaaatac tgtgatgaaa aaggtgtttg gtttaaacat cctgaaaaca atcgaacctg | 420 |
| gtccaactat actatgtgca atgctttcac tcctgagaaa ctgaagaatg catatgttct | 480 |
| gtactatttg gctattgtgg gtcattcttt gtcaatttc accctagtga tttccctggg | 540 |
| gattttcgtg tttttcagga gccttggctg ccaaagggta accctgcaca gaacatgtt | 600 |
| tcttacttac attctgaatt ctatgattat catcatccac ctggttgaag tagtacccaa | 660 |
| tggagagctc gtgcgaaggg acccggtgag ctgcaagatt ttgcattttt tccaccagta | 720 |
| catgatggcc tgcaactatt tctggatgct ctgtgaaggg atctatcttc atacactcat | 780 |
| tgtcgtggct gtgtttactg agaagcaacg cttgcggtgg tattatctct gggctgggg | 840 |
| gttcccgctg gtgccaacca ctatccatgc tattaccagg gccgtgtact tcaatgacaa | 900 |
| ctgctggctg agtgtggaaa cccatttgct ttacataatc catggacctg tcatggcggc | 960 |
| acttgtggtc aatttcttct tttgctcaa cattgtccgg gtgcttgtga ccaaaatgag | 1020 |
| ggaaacccat gaggcggaat cccacatgta cctgaaggct gtgaaggcca ccatgatcct | 1080 |
| tgtgccctg ctgggaatcc agtttgtcgt ctttccctgg agaccttcca acaagatgct | 1140 |
| tgggaagata tatgattacg tgatgcactc tctgattcat ttccagggct ctttgttgc | 1200 |
| gaccatctac tgcttctgca acaatgaggt ccaaaccacc gtgaagcgcc aatgggccca | 1260 |
| attcaaaatt cagtggaacc agcgttgggg gaggcgcccc tcaaccgct ctgctcgcgc | 1320 |
| tgcagccgct gctgcggagg ctggcgacat cccaatttac atctgccatc aggagctgag | 1380 |

```
gaatgaacca gccaacaacc aaggcgagga gagtgctgag atcatccctt tgaatatcat    1440
agagcaagag tcatctgctt gaatgtgaag gcaaacacag catcgtgatc actgagccat    1500
catttcctgg gagaaagacc atgcatttaa agtattctcc atcctcccag gaaccgaaca    1560
tatcatttgt gaagaattat tcagtgaatt tgtccattgt aaatctgaag aaagttattc    1620
ttggtactgt tgctttggga gacagtctag gaatggagtc tcccactgca acttgtgaac    1680
tccatcattc atccaggact gagatgcaaa tgtcacagta atgcaagcaa agtatcaaag    1740
aaaaacaatg aaattgacct agttcagata cagggtgctc cttgtcaata ctgagccatt    1800 tataccttg aaatattaaa atcactgtca atatttttat ttttaactct ggattttgaa    1860
ttagattatt tctgtatttg gctatggatc tgattttaa tttttttaaa tttcagtcaa    1920
ttctgatgtt actgagatgt tttaccatcc ttacaatgta aaccacatga actacgtgac    1980
ctctgcaaga caaagcggct ttctaataga gagattagta aatatgtgaa gaaaaagacc    2040
tgcatttggc aggaagatgt atgctttgaa tgcaaaagaa atttagagtc aatttgctga    2100
aaacattaca tgctcagctt ggttttggac aagcctgtcc attgggcagg acctagctgt    2160
tgtaaagaat tggtcttaat gttgaatgta ttttggttgc tgatgtttat aaactgagag    2220
gtcacaaaga atctatcact aaaaatttt acaaaactgc caaaaatata attcttagtg    2280
gaagacaata ctcccttaa agagagtttg ccactcccct aaactccagg atttataaag    2340
caaattactc caaggtttat aaagcagatt acctcttgcc cttgggtgct atctagcagt    2400
aaaagataaa tttgttgaat attggtaatt aaaagactcc acataagtcc attaactgct    2460
ttccacccag cttcaaagct taaaaagagc tcaggctttt ccaggaagat ccaggagggc    2520
taattagaaa tcaacttgtg gttgaccgct tgtttcttgt tattaccaaa caggaggga    2580 aaaaattaac tgctccaaat ttaaccataa atcaattcat gtttaacgtt tctcattaaa    2640
atccagtatt atattatcat atctctcttt acttcccagt ataagatttt tgaaaatcct    2700
gaataaacca gtatcgttac tggcacctga aattaattg tgaatttgca acagtaatca    2760
gagttaccat tatttaattt gtatgctaaa tgaggaggta cattgaaacc ctccaaatct    2820
ccagtctcat ctatgtcata ttttgccact gcctttcaga agtgatttag ttgtggaaag    2880
ataataaatt gatttgttat ggttacatat ttagcgcacc cagagaaaat taattatatt    2940
tctacagaga aaatgaattt gggatactaa agtagtttaa gtctccttta ctgaatgtaa    3000 ggggggggatc gaaagaagg tattttcca atcacagtgt tatgtagtat tgttctattt    3060
ttgtttacaa acatggaaaa cagagtattt ctggcagctg tggtacaaat gtgataatat    3120
attgctaaaa tattttagat gttattatgc taatatagta ggggttgaag aaaacaaaat    3180
agcttattat agaattgcac atagttctgc ccaaattatg tgaaatgctt atgcttgtgt    3240
atatgtataa attaatacag agtacgttaa aagcaaaaag atgtatattt gcatattttt    3300
ctaaagaaat atattattca tcttttcatt c                                   3331

<210> SEQ ID NO 15
<211> LENGTH: 3588
<212> TYPE: DNA
<213> ORGANISM: homo sapien

<400> SEQUENCE: 15
gtgcgcacgt ccgcacctca ccctgcggct gacatctcct gcccaggaga tgggcgctga      60
agcttgagcg cctgagtccc tggagccaca cctgcgaaca cccttgctt ctattgagct     120
```

```
gtgcccagcc gcccagtgac agaattccag aataaatgat tcccactgat ccacccactt      180
ttgccacccc aggatgcaat tttctggaga aagattagt ggacaaagag atcttcaaaa       240
atcaaaaatg aggttcacat ttacaagccg gtgcttggca ctgtttcttc ttctaaatca      300
cccaacccca attcttcctg ccttttcaaa tcaaacctat ccaacaatag agcccaagcc      360
atttctttac gtcgtaggac gaaagaagat gatggatgca cagtacaaat gctatgaccg      420
aatgcagcag ttacccgcat accaaggaga aggtccatat tgcaatcgca cctgggatgg      480
atggctgtgc tgggatgaca caccggctgg agtattgtcc tatcagttct gcccagatta      540
ttttccggat tttgatccat cagaaaaggt tacaaaatac tgtgatgaaa aggtgtttg      600 gtttaaacat cctgaaaaca atcgaacctg gtccaactat actatgtgca atgctttcac      660
tcctgagaaa ctgaagaatg catatgttct gtactatttg gctattgtgg gtcattcttt      720
gtcaattttc accctagtga tttccctggg gattttcgtg ttttttcagaa aattgacaac      780 tattttcct ttgaattgga aatataggaa ggcattgagc cttggctgcc aaagggtaac       840
cctgcacaag aacatgtttc ttacttacat tctgaattct atgattatca tcatccacct      900
ggttgaagta gtacccaatg agagctcgt gcgaagggac ccggtgagct gcaagatttt      960
gcattttttc caccagtaca tgatggcctg caactatttc tggatgctct gtgaagggat     1020
ctatcttcat acactcattg tcgtggctgt gtttactgag aagcaacgct gcggtggta     1080 ttatctcttg ggctgggggt tcccgctggt gccaaccact atccatgcta ttaccagggc     1140
cgtgtacttc aatgacaact gctggctgag tgtggaaacc catttgcttt acataatcca     1200
tggacctgtc atggcggcac ttgtggtcaa tttcttcttt ttgctcaaca ttgtccgggt     1260
gcttgtgacc aaaatgaggg aaacccatga ggcggaatcc cacatgtacc tgaaggctgt     1320
gaaggccacc atgatccttg tgcccctgct gggaatccag tttgtcgtct ttccctggag     1380
accttccaac aagatgcttg ggaagatata tgattacgtg atgcactctc tgattcattt     1440
ccagggcttc tttgttgcga ccatctactg cttctgcaac aatgaggtcc aaaccaccgt     1500
gaagcgccaa tgggcccaat tcaaaattca gtggaaccag cgttggggga ggcgcccctc     1560
caaccgctct gctcgcgctg cagccgctgc tgcggaggct ggcgacatcc caatttacat     1620
ctgccatcag gagctgagga atgaaccagc caacaaccaa ggcgaggaga gtgctgagat     1680
catccctttg aatatcatag agcaagagtc atctgcttga atgtgaagca aacacagtat     1740
cgtgatcact gagccatcat ttcctgggag aaagaccatg catttaaagt attctccatc     1800
ctcccaggaa ccgaacatat catttgtgaa gaattattca gtgaatttgt ccattgtaaa     1860
tctgaagaaa gttattcttg gtactgttgc tttgggagac agtctaggaa tggagtctcc     1920
cactgcaact tgtgaactcc atcattcatc caggactgag atgcaaatgt cacagtaatg     1980
caagcaaagt atcaaagaaa aacaatgaaa ttgacctagt tcagatacag ggtgctcctt     2040
gtcaatactg agccatttat accttgaaa tattaaaatc actgtcaata tttttatttt      2100
taactctgga ttttgaatta gattatttct gtatttggct atggatctga tttttaattt     2160
ttttaaattt cagtcaattc tgatgttact gagatgtttt accatcctta caatgtaaac     2220
cacatgaact acgtgacctc tgcaagacaa agcggctttc taatagagag attagtaaat     2280
atgtgaagaa aaagacctgc atttggcagg aagatgtatg ctttgaatgc aaaagaaatt     2340
tagagtcaat ttgctgaaaa cattacatgc tcagcttggt tttggacaag cctgtccatt     2400
gggcaggacc tagctgttgt aaagaattgg tcttaatgtt gaatgtattt tggttgctga     2460
tgtttataaa ctgagaggtc acaaagaatc tatcactaaa aattttaca aaactgccaa      2520
```

-continued

```
aaatataatt cttagtggaa gacaatactc cctttaaaga aagagagttt gccactcccc      2580
taaactccag gatttataaa gcaaattact ccaaggttta taaagcagat tacctcttgc      2640
ccttgggtgc tatctagcag taaaagataa atttgttgaa tattggtaat taaaagactc      2700
cacataagtc cattaactgc tttccaccca gcttcaaagc ttaaaaagag ctcaggcttt      2760
tccaggaaga tccaggaggg ctaattagaa atcaacttgt ggttgaccgc ttgtttcttg      2820
ttattaccaa aacaggaggg gaaaaaatta actgctccaa atttaaccat aaatcaattc      2880
atgtttaacg tttctcatta aaatccagta ttatattatc atatctctct ttacttccca      2940
gtataagatt tttgaaaatc ctgaataaac cagtatcgtt actggcacct gaaattaatt      3000
tgtgaatttg caacagtaat cagagttacc attatttaat ttgtatgcta aatgaggagg      3060
tacattgaaa ccctccaaat ctccagtctc atctatgtca tattttgcca ctgcctttca      3120
gaagtgattt agttgtggaa agataataaa ttgatttgtt atggttacat attcagcgca      3180
cccagagaaa attaattata tttctacaga gaaaatgaat ttgggatact aaagtagttt      3240
aagtctcctt tactgaatgt aaggggggga tcgaaaagaa ggtattttc caatcacagt       3300 gttatgtagt attgttctat ttttgtttac aaacatggaa aacagagtat ttctggcagc      3360
tgtggtacaa atgtgataat atattgctaa aatatttag atgttattat gctaatatag       3420
taggggttga agaaaacaaa atagcttatt atagaattgc acatagttct gcccaaatta      3480
tgtgaaatgc ttatgcttgt gtatatgtat aaattaatac agagtacgtt aaaagcaaaa      3540
agatgtatat ttgcatattt ttctaaagaa atatattatt catctttt                   3588
```

```
<210> SEQ ID NO 16
<211> LENGTH: 1674
<212> TYPE: DNA
<213> ORGANISM: homo sapien

<400> SEQUENCE: 16
```

```
cagaattcca ggacaaagag atcttcaaaa accaaaaatg aggttcacat ttacaagccg        60
gtgcttggca ctgtttcttc ttctaaatca cccaacccca attcttcctg ccttttcaaa       120
tcaaacctat ccaacaatag agcccaagcc atttctttac gtcgtaggac gaaagaagat       180
gatggatgca cagtacaaat gctatgaccg aatgcagcag ttacccgcat accaaggaga       240
aggtccatat tgcaatcgca cctgggatgg atggctgtgc tgggatgaca caccggctgg       300
agtattgtcc tatcagttct gcccagatta ttttccggat tttgatccat cagaaaaggt      360
tacaaaatac tgtgatgaaa aaggtgtttg gtttaaacat cctgaaaaca atcgaacctg       420
gtccaactat actatgtgca atgctttcac tcctgagaaa ctgaagaatg catatgttct      480
gtactatttg gctattgtgg gtcattcttt gtcaattttc accctagtga tttccctggg      540
gattttcgtg ttttcagga gccttggctg ccaaagggta accctgcaca agaacatgtt       600
tcttacttac attctgaatt ctatgattat catcatccac ctggttgaag tagtacccaa       660
tggagagctc gtgcgaaggg acccggtgag ctgcaagatt ttgcattttt tccaccagta      720
catgatggcc tgcaactatt tctggatgct ctgtgaaggg atctatcttc atacactcat      780
tgtcgtggct gtgtttactg agaagcaacg cttgcgtggg tattatctct gggctgggg      840 gttcccgctg gtgccaacca ctatccatgc tattaccagg gccgtgtact tcaatgacaa      900
ctgctgctgc agtgtggaaa cccatttgct ttacataatc catggacctg tcatggcggc      960
acttgtggtc aatttcttct ttttgctcaa cattgtccgg gtgcttgtga ccaaaatgag     1020
```

-continued

| | | | |
|---|---|---|---|
| ggaaacccat gaggcggaat cccacatgta cctgaaggct gtgaaggcca ccatgatcct | 1080 |
| tgtgcccctg ctgggaatcc agtttgtcgt ctttccctgg agaccttcca acaagatgct | 1140 |
| tgggaagata tatgattacg tgatgcactc tctgattcat ttccagggct tctttgttgc | 1200 |
| gaccatctac tgcttctgca acaatgaggt ccaaaccacc gtgaagcgcc aatgggccca | 1260 |
| attcaaaatt cagtggaacc agcgttgggg gaggcgcccc tccaaccgct ctgctcgcgc | 1320 |
| tgcagccgct gctgcggagg ctggcgacat cccaatttac atctgccatc aggagctgag | 1380 |
| gaatgaacca gccaacaacc aaggcgagga gagtgctgag atcatccctt tgaatatcat | 1440 |
| agagcaagag tcatctgctt gaatgtgaag caaacacagc atcgtgatca ctgagccatc | 1500 |
| atttcctggg agaaagacca tgcatttaaa gtattctcca tcctcccagg aaccgaacat | 1560 |
| atcatttgtg aagaattatt cagtgaattt gtccattgta aatctgaaga aagttattct | 1620 |
| tggtactgtt gctttgggag acagtctagg aatggagtct cccactgcaa cttg | 1674 |

<210> SEQ ID NO 17
<211> LENGTH: 1512
<212> TYPE: DNA
<213> ORGANISM: homo sapien

<400> SEQUENCE: 17

| | | | |
|---|---|---|---|
| ggacaaagag atcttcaaaa accaaaaatg aggttcacat ttacaagccg gtgcttggca | 60 |
| ctgtttcttc ttctaaatca cccaaccccca attcttcctg ccttttcaaa tcaaacctat | 120 |
| ccaacaatag agcccaagcc atttctttac gtcgtaggac gaaagaagat gatggatgca | 180 |
| cagtacaaat gctatgaccg aatgcagcag ttacccgcat accaaggaga aggtccatat | 240 |
| tgcaatcgca cctgggatgg atggctgtgc tgggatgaca caccggctgg agtattgtcc | 300 |
| tatcagttct gcccagatta ttttccggat tttgatccat cagaaaaggt tacaaaatac | 360 |
| tgtgatgaaa aaggtgtttg gtttaaacat cctgaaaaca atcgaacctg gtccaactat | 420 |
| actatgtgca atgctttcac tcctgagaaa ctgaagaatg catatgttct gtactatttg | 480 |
| gctattgtgg gtcattcttt gtcaattttc accctagtga tttccctggg gattttcgtg | 540 |
| ttttcagga gccttggctg ccaaagggta accctgcaca gaacatgtt tcttacttac | 600 |
| attctgaatt ctatgattat catcatccac ctggttgaag tagtacccaa tggagagctc | 660 |
| gtgcgaaggg acccggtgag ctgcaagatt ttgcattttt tccaccagta catgatggcc | 720 |
| tgcaactatt tctggatgct ctgtgaaggg atctatcttc atacactcat tgtcgtggct | 780 |
| gtgtttactg agaagcaacg cttgcggtgg tattatctct tgggctgggg gttcccgctg | 840 |
| gtgccaacca ctatccatgc tattaccagg gccgtgtact tcaatgacaa ctgctggctg | 900 |
| agtgtggaaa cccatttgct ttacataatc catggacctg tcatggcggc acttgtggtc | 960 |
| aatttcttct ttttgctcaa cattgtccgg gtgcttgtga ccaaaatgag ggaaacccat | 1020 |
| gaggcggaat cccacatgta cctgaaggct gtgaaggcca ccatgatcct tgtgcccctg | 1080 |
| ctgggaatcc agtttgtcgt ctttccctgg agaccttcca acaagatgct tgggaagata | 1140 |
| tatgattacg tgatgcactc tctgattcat ttccagggct tctttgttgc gaccatctac | 1200 |
| tgcttctgca acaatgaggt ccaaaccacc gtgaagcgcc aatgggccca attcaaaatt | 1260 |
| cagtggaacc agcgttgggg gaggcgcccc tccaaccgct ctgctcgcgc tgcagccgct | 1320 |
| gctgcggagg ctggcgacat cccaatttac atctgccatc aggagctgag gaatgaacca | 1380 |
| gccaacaacc aaggcgagga gagtgctgag atcatccctt tgaatatcat agagcaagag | 1440 |
| tcatctgctt gaatgtgaag caaacacagc atcgtgatca ctgagccatc atttcctggg | 1500 | agaaagacca tg                                                          1512

<210> SEQ ID NO 18
<211> LENGTH: 1472
<212> TYPE: DNA
<213> ORGANISM: homo sapien

<400> SEQUENCE: 18

| | | | | | |
|---|---|---|---|---|---|
| atgaggttca | catttacaag | ccggtgcttg | gcactgtttc | ttcttctaaa | tcacccaacc | 60 |
| ccaattcttc | ctgccttttc | aaatcaaacc | tatccaacaa | tagagcccaa | gccatttctt | 120 |
| tacgtcgtag | gacgaaagaa | gatgatggat | gcacagtaca | aatgctatga | ccgaatgcag | 180 |
| cagttacccg | cataccaagg | agaaggtcca | tattgcaacc | gcacctggga | tggatggctg | 240 |
| tgctgggatg | acacaccggc | tggagtattg | tcctatcagt | tctgcccaga | ttattttccg | 300 |
| gattttgatc | catcagaaaa | ggttacaaaa | tactgtgatg | aaaaaggtgt | ttggtttaaa | 360 |
| catcctgaaa | acaatcgaac | ctggtccaac | tatactatgt | gcaatgcttt | cactcctgag | 420 |
| aaactgaaga | atgcatatgt | tctgtactat | ttggctattg | tgggtcattc | tttgtcaatt | 480 |
| ttcaccctag | tgatttccct | ggggattttc | gtgtttttca | ggagccttgg | ctgccaaagg | 540 |
| gtaaccctgc | acaagaacat | gtttcttact | tacattctga | attctatgat | tatcatcatc | 600 |
| cacctggttg | aagtagtacc | caatggagag | ctcgtgcgaa | gggacccggt | gagctgcaag | 660 |
| attttgcatt | ttttccacca | gtacatgatg | gcctgcaact | atttctggat | gctctgtgaa | 720 |
| gggatctatc | ttcatacact | cattgtcgtg | gctgtgttta | ctgagaagca | acgcttgcgg | 780 |
| tggtattatc | tcttgggctg | ggggttcccg | ctggtgccaa | ccactatcca | tgctattacc | 840 |
| agggccgtgt | acttcaatga | caactgctgg | ctgagtgtgg | aaacccattt | gctttacata | 900 |
| atccatggac | ctgtcatggc | ggcacttgtg | gtcaatttct | tcttttgct | caacattgtc | 960 |
| cgggtgcttg | tgaccaaaat | gagggaaaac | catgaggcgg | aatcccacat | gtacctgaag | 1020 |
| gctgtgaagg | ccaccatgat | ccttgtgccc | ctgctgggaa | tccagtttgt | cgtcttccc | 1080 |
| tggagacctt | ccaacaagat | gcttgggaag | atatatgatt | acgtgatgca | ctctctgatt | 1140 |
| catttccagg | gcttctttgt | tgcgaccatc | tactgcttct | gcaacaatga | ggtccaaacc | 1200 |
| accgtgaagc | gccaatgggc | ccaattcaaa | attcagtgga | ccagcgttg | ggggaggcgc | 1260 |
| ccctccaacc | gctctgctcg | cgctgcagcc | gctgctgcgg | aggctggcga | catcccaatt | 1320 |
| tacatctgcc | atcaggagct | gaggaatgaa | ccagccaaca | accaaggcga | ggagagtgct | 1380 |
| gagatcatcc | ctttgaatat | catagagcaa | gagtcatctg | cttgaatgtg | aaggcaaaca | 1440 |
| cagcatcgtg | atcactgagc | catcatttcc | tg | | | 1472 |

<210> SEQ ID NO 19
<211> LENGTH: 1506
<212> TYPE: DNA
<213> ORGANISM: homo sapien

<400> SEQUENCE: 19

| | | | | | |
|---|---|---|---|---|---|
| gaattccagg | acaaagagat | cttcaaaaac | caaaatgag | gttcacattt | acaagccggt | 60 |
| gcttggcact | gtttcttctt | ctaaatcacc | caaccccaat | tcttcctgcc | ttttcaaatc | 120 |
| aaacctatcc | aacaatagag | cccaagccat | ttctttacgt | cgtaggacga | agaagatga | 180 |
| tggatgcaca | gtacaaatgc | tatgaccgaa | tgcagcagtt | acccgcatac | caaggagaag | 240 |
| gtccatattg | caatcgcacc | tgggatggat | ggctgtgctg | ggatgacaca | ccggctggag | 300 |

```
tattgtccta tcagttctgc ccagattatt ttccggattt tgatccatca gaaaaggtta      360
caaaatactg tgatgaaaaa ggtgtttggt ttaaacatcc tgaaaacaat cgaacctggt      420
ccaactatac tatgtgcaat gctttcactc ctgagaaact gaagaatgca tatgttctgt      480
actatttggc tattgtgggt cattcttttgt caattttcac cctagtgatt tccctgggga    540
ttttcgtgtt tttcaggagc cttggctgcc aaagggtaac cctgcacaag aacatgtttc      600
ttacttacat tctgaattct atgattatca tcatccacct ggttgaagta gtacccaatg      660
gagagctcgt gcgaagggac ccggtgagct gcaagatttt gcatttttc caccagtaca       720 tgatggcctg caactatttc tggatgctct gtgaagggat ctatcttcat acactcattg      780
tcgtggctgt gtttactgag aagcaacgct gcggtggta ttatctcttg ggctgggggt       840
tcccgctggt gccaaccact atccatgcta ttaccagggc cgtgtacttc aatgacaact      900
gctggctgag tgtggaaacc catttgcttt acataatcca tggacctgtc atggcggcac      960
ttgtggtcaa tttcttcttt ttgctcaaca ttgtccgggt gcttgtgacc aaaatgaggg     1020
aaacccatga ggcggaatcc cacatgtacc tgaaggctgt gaaggccacc atgatccttg     1080
tgcccctgct gggaatccag tttgtcgtct ttccctggag accttccaac aagatgcttg     1140
ggaagatata tgattacgtg atgcactctc tgattcattt ccagggcttc tttgttgcga     1200
ccatctactg cttctgcaac aatgaggtcc aaaccaccgt gaagcgccaa tgggcccaat     1260
tcaaaattca gtgaaccag cgttggggga ggcgcccctc caaccgctct gctcgcgctg      1320
cagccgctgc tgcggaggct ggcgacatcc caatttacat ctgccatcag gagctgagga     1380
atgaaccagc caacaaccaa ggcgaggaga gtgctgagat catccctttg aatatcatag     1440
agcaagagtc atctgcttga atgtgaagca aacacagcat cgtgatcact gagccaccat     1500
ttcctg                                                                1506

<210> SEQ ID NO 20
<211> LENGTH: 1493
<212> TYPE: DNA
<213> ORGANISM: homo sapien

<400> SEQUENCE: 20
ttccaggaca aagagatctt caaaaatcaa aaatgaggtt cacatttaca agccggtgct       60
tggcactgtt tcttcttcta aatcacccaa ccccaattct tcctgccttt tcaaatcaaa      120
cctatccaac aatagagccc aagccatttc tttacgtcgt aggacgaaag aagatgatgg      180
atgcacagta caaatgctat gaccgaatgc agcagttacc cgcataccaa ggagaaggtc      240
catattgcaa tcgcacctgg gatggatggc tgtgctggga tgacacaccg gctggagtat      300
tgtcctatca gttctgccca gattattttc cggattttga tccatcagaa aaggttacaa      360
aatactgtga tgaaaaggt gtttggttta acatcctga aaacaatcga acctggtcca        420
actatactat gtgcaatgct ttcactcctg agaaactgaa gaatgcatat gttctgtact      480
atttggctat tgtgggtcat tctttgtcaa ttttcacct agtgatttcc ctggggattt       540
tcgtgttttt caggagcctt ggctgccaaa gggtaaccct gcacaagaac atgtttctta      600
cttacattct gaattctatg attatcatca tccacctggt gaagtagta cccaatggag       660 agctcgtgcg aagggacccg gtgagctgca agattttgca ttttttccac cagtacatga     720
tggcctgcaa ctatttctgg atgctctgtg aagggatcta tcttcataca ctcattgtcg     780
tggctgtgtt tactgagaag caacgcttgc ggtggtatta tctcttgggc tggggttcc       840 cgctggtgcc aaccactatc catgctatta ccagggccgt gtacttcaat gacaactgct      900
```

```
ggctgagtgt ggaaacccat ttgctttaca taatccatgg acctgtcatg cggcacttg      960 tggtcaattt cttcttttg ctcaacattg tccgggtgct tgtgaccaaa atgagggaaa     1020
cccatgaggc ggaatcccac atgtacctga aggctgtgaa ggccaccatg atccttgtgc    1080
ccctgctggg aatccagttt gtcgtctttc cctggagacc ttccaacaag atgcttggga    1140
agatatatga ttacgtgatg cactctctga ttcatttcca gggcttcttt gttgcgacca    1200
tctactgctt ctgcaacaat gaggtccaaa ccaccgtgaa cgccaatggg cccaattca    1260 aaattcagtg gaaccagcgt tgggggaggc gcccctccaa ccgctctgct cgcgctgcag    1320
ccgctgctgc ggaggctggc gacatcccaa tttacatctg ccatcaggag ctgaggaatg    1380
aaccagccaa caaccaaggc gaggagagtg ctgagatcat cccttttgaat atcatagagc   1440 aagagtcatc tgcttgaatg tgaagcaaac acagcatcgt gatcactgag cca           1493

<210> SEQ ID NO 21
<211> LENGTH: 1496
<212> TYPE: DNA
<213> ORGANISM: homo sapien

<400> SEQUENCE: 21
gaattccagg acaaagagat cttcaaaaac caaaaatgag gttcacattt acaagccggt      60
gcttggcact gtttcttctt ctaaatcacc caaccccaat tcttcctgcc ttttcaaatc     120
aaacctatcc aacaatagag cccaagccat ttctttacgt cgtaggacga agaagatga      180 tggatgcaca gtacaaatgc tatgaccgaa tgcagcagtt accgcatac caaggagaag      240 gtccatattg caatcgcacc tgggatggat ggctgtgctg ggatgacaca ccggctggag      300
tattgtccta tcagttctgc ccagattatt ttccggattt tgatccatca gaaaaggtta      360
caaaatactg tgatgaaaaa ggtgtttggt ttaaacatcc tgaaaacaat cgaacctggt      420
ccaactatac tatgtgcaat gctttcactc ctgagaaact gaagaatgca tatgttctgt      480
actatttggc tattgtgggt cattcttgt caattttcac cctagtgatt tccctgggga      540
ttttcgtgtt tttcaggagc cttggctgcc aaagggtaac cctgcacaag aacatgtttc      600
ttacttacat tctgaattct atgattatca tcatccacct ggttgaagta gtacccaatg      660
gagagctcgt gcgaagggac ccggtgagct gcaagatttt gcatttttc caccagtaca      720 tgatggcctg caactatttc tggatgctct gtgaagggat ctatcttcat acactcattg      780
tcgtggctgt gtttactgag aagcaacgct tgcggtggta ttatctcttg ggctgggggt      840
tcccgctggt gccaaccact atccatgcta ttaccagggc cgtgtacttc aatgacaact      900
gctggctgag tgtggaaacc catttgcttt acataatcca tggacctgtc atggcggcac      960
ttgtggtcaa tttcttcttt ttgctcaaca ttgtccgggt gcttgtgacc aaaatgaggg     1020
aaacccatga ggcggaatcc cacatgtacc tgaaggctgt gaaggccacc atgatccttg    1080 tgccctgct gggaatccag tttgtcgtct tccctggag accttccaac aagatgcttg      1140
ggaagatata tgattacgtg atgcactctc tgattcattt ccagggcttc tttgttgcga    1200
ccatctactg cttctgcaac aatgaggtcc aaaccaccgt gaagcgccaa tgggcccaat    1260
tcaaaattca gtggaaccag cgttggggga ggcgcccctc caaccgctct gctcgcgctg    1320
cagccgctgc tgcggaggct ggcgacatcc caatttacat ctgccatcag gagctgagga    1380
atgaaccagc caacaaccaa ggcgaggaga gtgctgagat catcccttg aatatcatag     1440 agcaagagtc atctgcttga atgtgaagca aacacagcat cgtgatcact gagcca         1496
```

<210> SEQ ID NO 22
<211> LENGTH: 1339
<212> TYPE: DNA
<213> ORGANISM: homo sapien

<400> SEQUENCE: 22

| | | | | | |
|---|---|---|---|---|---|
| ccaaaaatga | ggacgaaaga | agatgatgga | tgcacagtac | aaatgctatg | accgaatgca | 60 |
| gcagttaccc | gcatatcaag | gagaaggtcc | atattgcaat | cgcacctggg | atggatggct | 120 |
| gtgctgggat | gacacaccgg | ctggagtatt | gtcctatcag | ttctgcccag | attattttcc | 180 |
| ggattttgat | ccatcagaaa | aggttacaaa | atactgtgat | gaaaaaggtg | tttggtttaa | 240 |
| acatcctgaa | aacaatcgaa | cctggtccaa | ctatactatg | tgcaatgctt | tcactcctga | 300 |
| gaaactgaag | aatgcatatg | ttctgtacta | tttggctatt | gtgggtcatt | ctttgtcaat | 360 |
| tttcacccta | gtgatttccc | tggggattt | cgtgttttc | aggagccttg | gctgccaaag | 420 |
| ggtaaccctg | cacaagaaca | tgtttcttac | ttacattctg | aattctatga | ttatcatcat | 480 |
| ccacctggtt | gaagtagtac | ccaatggaga | gctcgtgcga | agggaccgg | tgagctgcaa | 540 |
| gattttgcat | ttttccacc | agtacatgat | ggcctgcaac | tatttctgga | tgctctgtga | 600 |
| agggatctat | cttcatacac | tcattgtcgt | ggctgtgttt | actgagaagc | aacgcttgcg | 660 |
| gtggtattat | ctcttgggct | gggggttccc | gctggtgcca | accactatcc | atgctattac | 720 |
| cagggccgtg | tacttcaatg | acaactgctg | gctgagtgtg | gaaacccatt | tgctttacat | 780 |
| aatccatgga | cctgtcatgg | cggcacttgt | ggtcaatttc | ttcttttgc | tcaacattgt | 840 |
| ccgggtgctt | gtgaccaaaa | tgagggaaac | ccatgaggcg | gaatcccaca | tgtacctgaa | 900 |
| ggctgtgaag | gccaccatga | cccttgtgcc | cctgctggga | atccagtttg | tcgtctttcc | 960 |
| ctggagacct | tccaacaaga | tgcttgggaa | gatatatgat | tacgtgatgc | actctctgat | 1020 |
| tcatttccag | ggcttctttg | ttgcgaccat | ctactgcttc | tgcaacaatg | aggtccaaac | 1080 |
| caccgtgaag | cgccaatggg | cccaattcaa | aattcagtgg | aaccagcgtt | ggggggaggcg | 1140 |
| cccctccaac | cgctctgctc | gcgctgcagc | cgctgctgcg | gaggctggcg | acatcccaat | 1200 |
| ttacatctgc | catcaggagc | tgaggaatga | accagccaac | aaccaaggcg | aggagagtgc | 1260 |
| tgagatcatc | cctttgaata | tcatagagca | agagtcatct | gcttgaatgt | gaagcaaaca | 1320 |
| cagtatcgtg | atcactgag | | | | | 1339 |

<210> SEQ ID NO 23
<211> LENGTH: 1772
<212> TYPE: DNA
<213> ORGANISM: homo sapien

<400> SEQUENCE: 23

| | | | | | |
|---|---|---|---|---|---|
| agttataaga | gacaggaata | ccagtgagaa | gtatgagaga | gtgggtggga | gataatgttt | 60 |
| agaatctctt | ttgctgcccg | caatttatga | aaatggcttg | aaaatattta | tggtcaaaga | 120 |
| ccgaaatatt | tcttcaaaga | agattagctt | tgctccatta | aaagtaatga | gtagaaatat | 180 |
| taaaaaaaaa | aagttttaag | tacctgagta | tcttgccagc | aactgaccac | cactgctaaa | 240 |
| ggtgaggaga | gacacagctt | tcatcattgg | gactgcagtt | tatttcagga | caaagagatc | 300 |
| ttcaaaaacc | aaaaatgagg | ttcacattta | caagccggtg | cttggcactg | tttcttcttc | 360 |
| taaatcaccc | aaccccaatt | cttccctgcct | tttcaaatca | aacctatcca | acaatagagc | 420 |
| ccaagccatt | tctttacgtc | gtaggacgaa | agaaagatgat | ggatgcacag | tacaaatgct | 480 |
| atgaccgaat | gcagcagtta | cccgcatacc | aaggagaagg | tccatattgc | aatcgcacct | 540 |

```
gggatggatg gctgtgctgg gatgacacac cggctggagt attgtcctat cagttctgcc    600
cagattattt tccggatttt gatccatcag aaaaggttac aaaatactgt gatgaaaaag    660
gtgtttggtt taaacatcct gaaaacaatc gaacctggtc caactatact atgtgcaatg    720
ctttcactcc tgagaaactg aagaatgcat atgttctgta ctatttggct attgtgggtc    780
attctttgtc aattttcacc ctagtgattt ccctggggat tttcgtgttt ttcaggagcc    840
ttggctgcca aagggtaacc ctgcacaaga acatgtttct tacttacatt ctgaattcta    900
tgattatcat catccacctg gttgaagtag tacccaatgg agagctcgtg cgaagggacc    960
cggtgagctg caagattttg cattttttcc accagtacat gatggcctgc aactatttct   1020
ggatgctctg tgaagggatc tatcttcata cactcattgt cgtggctgtg tttactgaga   1080
agcaacgctt gcggtggtat tatctcttgg gctgggggtt cccgctggtg ccaaccacta   1140
tccatgctat taccagggcc gtgtacttca atgacaactg ctggctgagt gtggaaaccc   1200
atttgcttta cataatccat ggacctgtca tggcggcact tgtggtcaat tcttctcttt   1260
tgctcaacat tgtccgggtg cttgtgacca aaatgaggga aacccatgag gcggaatccc   1320
acatgtacct gaaggctgtg aaggccacca tgatccttgt gccctgctgg gaatccagt   1380 ttgtcgtctt tccctggaga ccttccaaca agatgcttgg gaagatatat gattacgtga   1440
tgcactctct gattcatttc cagggcttct ttgttgcgac catctactgc ttctgcaaca   1500
atgaggtcca accaccgtga agcgccaat gggcccaatt caaaattcag tggaaccagc   1560
gttgggggag gcgcccctcc aaccgctctg ctcgcgctgc agccgctgct gcggaggctg   1620
gcgacatccc aatttacatc tgccatcagg agctgaggaa tgaaccagcc aacaaccaag   1680
gcgaggagag tgctgagatc atccctttga atatcataga gcaagagtca tctgcttgaa   1740
tgtgaagcaa acacagtatc gtgatcactg ag                                  1772
```

<210> SEQ ID NO 24
<211> LENGTH: 1530
<212> TYPE: DNA
<213> ORGANISM: homo sapien

<400> SEQUENCE: 24

```
ttgcttctat tgagctgtgc ccagccgccc agtgacagaa ttccaggaca aagagatctt     60
caaaaaccaa aaatgaggtt cacatttaca agccggtgct tggcactgtt tcttcttcta    120
aatcacccaa ccccaattct tcctgccttt tcaaatcaaa cctatccaac aatagagccc    180
aagccatttc tttacgtcgt aggacgaaag aagatgatgg atgcacagta caaatgctat    240
gaccgaatgc agcagttacc cgcataccaa ggagaaggtc catattgcaa tcgcacctgg    300
gatggatggc tgtgctggga tgacacaccg gctggagtat tgtcctatca gttctgccca    360
gattattttc cggattttga tccatcagaa aaggttacaa atactgtga tgaaaaaggt    420 gtttggttta acatcctga aaacaatcga acctggtcca actatactat gtgcaatgct    480
ttcactcctg agaaactgaa gaatgcatat gttctgtact atttggctat gtgggtcat    540 tctttgtcaa ttttcaccct agtgattccc ctggggattt cgtgttttt caggagcctt    600 ggctgccaaa gggtaaccct gcacaagaac atgtttctta cttacattct gaattctatg    660
attatcatca tccacctggt tgaagtagta cccaatggag agctcgtgcg aagggacccg    720
gtgagctgca gattttgca tttttccac cagtacatga tggcctgcaa ctatttctgg    780
atgctctgtg aagggatcta tcttcataca ctcattgtcg tggctgtgtt tactgagaag    840
```

| | |
|---|---:|
| caacgcttgc ggtggtatta tctcttgggc tgggggttcc cgctggtgcc aaccactatc | 900 |
| catgctatta ccagggccgt gtacttcaat gacaactgct ggctgagtgt ggaaacccat | 960 |
| ttgctttaca taatccatgg acctgtcatg gcggcacttg tggtcaattt cttcttttttg | 1020 |
| ctcaacattg tccgggtgct tgtgaccaaa atgagggaaa cccatgaggc ggaatcccac | 1080 |
| atgtacctga aggctgtgaa ggccaccatg atccttgtgc ccctgctggg aatccagttt | 1140 |
| gtcgtctttc cctggagacc ttccaacaag atgcttggga agatatatga ttacgtgatg | 1200 |
| cactctctga ttcatttcca gggcttcttt gttgcgacca tctactgctt ctgcaacaat | 1260 |
| gaggtccaaa ccaccgtgaa cgccaatggc cccaattca aaattcagtg gaaccagcgt | 1320 |
| tgggggaggc gcccctccaa ccgctctgct cgcgctgcag ccgctgctgc ggaggctggc | 1380 |
| gacatcccaa tttacatctg ccatcaggag ctgaggaatg aaccagccaa caaccaaggc | 1440 |
| gaggagagtg ctgagatcat cccttttgaat atcatagagc aagagtcatc tgcttgaatg | 1500 |
| tgaagcaaac acagtatcgt gatcactgag | 1530 |

<210> SEQ ID NO 25
<211> LENGTH: 1735
<212> TYPE: DNA
<213> ORGANISM: homo sapien

<400> SEQUENCE: 25

| | |
|---|---:|
| acagctggga gagcgcagga aggcgccggg aaggaaagcc agcccaccag cgtctgggtg | 60 |
| ggctgcgccg cgcggctggc ggaccttccc gggttggaga ggtgcgcacg tccgcacctc | 120 |
| accctgcggc tgcatctcc tgcccaggag atgggcgctg aagcttgagc gcctgagtcc | 180 |
| ctggagccac acctgcgaac ccctttgct tctattgagc tgtgcccagc cgcccagtga | 240 |
| cagaattcca ggcaaagag atcttcaaaa accaaaaatg aggttcacat ttacaagccg | 300 |
| gtgcttggca ctgtttcttc ttctaaatca cccaaccca attcttcctg cctttttcaaa | 360 |
| tcaaacctat ccaacaatag agcccaagcc atttctttac gtcgtaggac gaaagaagat | 420 |
| gatggatgca cagtacaaat gctatgaccg aatgcagcag ttacccgcat accaaggaga | 480 |
| aggtccatat tgcaatcgca cctgggatgg atggctgtgc tgggatgaca caccggctgg | 540 |
| agtattgtcc tatcagttct gcccagatta tttttccggat tttgatccat cagaaaaggt | 600 |
| tacaaaatac tgtgatgaaa aaggtgtttg gtttaaacat cctgaaaaca atcgaacctg | 660 |
| gtccaactat actatgtgca atgctttcac tcctgagaaa ctgaagaatg catatgttct | 720 |
| gtactatttg gctattgtgg gtcattcttt gtcaattttc accctagtga tttccctggg | 780 |
| gatttttcgtg ttttttcagga gccttggctg ccaaagggta accctgcaca gaacatgtt | 840 |
| tcttacttac attctgaatt ctatgattat catcatccac ctggttgaag tagtacccaa | 900 |
| tggagagctc gtgcgaaggg accggtgag ctgcaagatt ttgcattttt tccaccagta | 960 |
| catgatggcc tgcaactatt tctgatgct ctgtgaaggg atctatcttc atacactcat | 1020 |
| tgtcgtggct gtgtttactg agaagcaacg cttgcggtgg tattatctct tgggctgggg | 1080 |
| gttcccgctg gtgccaacca ctatccatgc tattaccagg gccgtgtact tcaatgacaa | 1140 |
| ctgctggctg agtgtggaaa cccatttgct ttacataatc catggacctg tcatggcggc | 1200 |
| acttgtggtc aatttcttct ttttgctcaa cattgtccgg gtgcttgtga ccaaaatgag | 1260 |
| ggaaacccat gaggcggaat cccacatgta cctgaaggct gtgaaggcca ccatgatcct | 1320 |
| tgtgcccctg ctgggaatcc agtttgtcgt ctttccctgg agaccttcca acaagatgct | 1380 |
| tgggaagata tatgattacg tgatgcactc tctgattcat ttccagggct ctttgttgc | 1440 |

-continued

```
gaccatctac tgcttctgca acaatgaggt ccaaaccacc gtgaagcgcc aatgggccca    1500
attcaaaatt cagtggaacc agcgttgggg gaggcgcccc tccaaccgct ctgctcgcgc    1560
tgcagccgct gctgcggagg ctggcgacat cccaatttac atctgccatc aggagctgag    1620
gaatgaacca gccaacaacc aaggcgagga gagtgctgag atcatcccctt tgaatatcat    1680 agagcaagag tcatctgctt gaatgtgaag caaacacagt atcgtgatca ctgag         1735
```

<210> SEQ ID NO 26
<211> LENGTH: 474
<212> TYPE: PRT
<213> ORGANISM: homo sapien

<400> SEQUENCE: 26

```
Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
            20                  25                  30

Thr Ile Glu Pro Lys Pro Phe Leu Tyr Val Val Gly Arg Lys Lys Met
        35                  40                  45

Met Asp Ala Gln Tyr Lys Cys Tyr Asp Arg Met Gln Gln Leu Pro Ala
    50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
            100                 105                 110

Asp Glu Lys Gly Val Trp Phe Lys His Pro Glu Asn Asn Arg Thr Trp
        115                 120                 125

Ser Asn Tyr Thr Met Cys Asn Ala Phe Thr Pro Glu Lys Leu Lys Asn
    130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Ser Leu
                165                 170                 175

Gly Cys Gln Arg Val Thr Leu His Lys Asn Met Phe Leu Thr Tyr Ile
            180                 185                 190

Leu Asn Ser Met Ile Ile Ile His Leu Val Glu Val Val Pro Asn
        195                 200                 205

Gly Glu Leu Val Arg Arg Asp Pro Val Ser Cys Lys Ile Leu His Phe
    210                 215                 220

Phe His Gln Tyr Met Met Ala Cys Asn Tyr Phe Trp Met Leu Cys Glu
225                 230                 235                 240

Gly Ile Tyr Leu His Thr Leu Ile Val Val Ala Val Phe Thr Glu Lys
                245                 250                 255

Gln Arg Leu Arg Trp Tyr Tyr Leu Leu Gly Trp Gly Phe Pro Leu Val
            260                 265                 270

Pro Thr Thr Ile His Ala Ile Thr Arg Ala Val Tyr Phe Asn Asp Asn
        275                 280                 285

Cys Trp Leu Ser Val Glu Thr His Leu Leu Tyr Ile Ile His Gly Pro
    290                 295                 300

Val Met Ala Ala Leu Val Val Asn Phe Phe Phe Leu Leu Asn Ile Val
305                 310                 315                 320
```

Arg Val Leu Val Thr Lys Met Arg Glu Thr His Glu Ala Glu Ser His
            325                 330                 335

Met Tyr Leu Lys Ala Val Lys Ala Thr Met Ile Leu Val Pro Leu Leu
            340                 345                 350

Gly Ile Gln Phe Val Val Phe Pro Trp Arg Pro Ser Asn Lys Met Leu
            355                 360                 365

Gly Lys Ile Tyr Asp Tyr Val Met His Ser Leu Ile His Phe Gln Gly
            370                 375                 380

Phe Phe Val Ala Thr Ile Tyr Cys Phe Cys Asn Asn Glu Val Gln Thr
385                 390                 395                 400

Thr Val Lys Arg Gln Trp Ala Gln Phe Lys Ile Gln Trp Asn Gln Arg
            405                 410                 415

Trp Gly Arg Arg Pro Ser Asn Arg Ser Ala Arg Ala Ala Ala Ala Ala
            420                 425                 430

Ala Glu Ala Gly Asp Ile Pro Ile Tyr Ile Cys His Gln Glu Leu Arg
            435                 440                 445

Asn Glu Pro Ala Asn Asn Gln Gly Glu Glu Ser Ala Glu Ile Ile Pro
            450                 455                 460

Leu Asn Ile Ile Glu Gln Glu Ser Ser Ala
465                 470

<210> SEQ ID NO 27
<211> LENGTH: 508
<212> TYPE: PRT
<213> ORGANISM: homo sapien

<400> SEQUENCE: 27

Met Gln Phe Ser Gly Glu Lys Ile Ser Gly Gln Arg Asp Leu Gln Lys
1               5                   10                  15

Ser Lys Met Arg Phe Thr Phe Thr Ser Arg Cys Leu Ala Leu Phe Leu
            20                  25                  30

Leu Leu Asn His Pro Thr Pro Ile Leu Pro Ala Phe Ser Asn Gln Thr
            35                  40                  45

Tyr Pro Thr Ile Glu Pro Lys Pro Phe Leu Tyr Val Val Gly Arg Lys
50                  55                  60

Lys Met Met Asp Ala Gln Tyr Lys Cys Tyr Asp Arg Met Gln Gln Leu
65                  70                  75                  80

Pro Ala Tyr Gln Gly Glu Gly Pro Tyr Cys Asn Arg Thr Trp Asp Gly
            85                  90                  95

Trp Leu Cys Trp Asp Asp Thr Pro Ala Gly Val Leu Ser Tyr Gln Phe
            100                 105                 110

Cys Pro Asp Tyr Phe Pro Asp Phe Asp Pro Ser Glu Lys Val Thr Lys
            115                 120                 125

Tyr Cys Asp Glu Lys Gly Val Trp Phe Lys His Pro Glu Asn Asn Arg
            130                 135                 140

Thr Trp Ser Asn Tyr Thr Met Cys Asn Ala Phe Thr Pro Glu Lys Leu
145                 150                 155                 160

Lys Asn Ala Tyr Val Leu Tyr Tyr Leu Ala Ile Val Gly His Ser Leu
            165                 170                 175

Ser Ile Phe Thr Leu Val Ile Ser Leu Gly Ile Phe Val Phe Phe Arg
            180                 185                 190

Lys Leu Thr Thr Ile Phe Pro Leu Asn Trp Lys Tyr Arg Lys Ala Leu
            195                 200                 205

Ser Leu Gly Cys Gln Arg Val Thr Leu His Lys Asn Met Phe Leu Thr
            210                 215                 220

Tyr Ile Leu Asn Ser Met Ile Ile Ile His Leu Val Glu Val Val
225                 230                 235                 240

Pro Asn Gly Glu Leu Val Arg Arg Asp Pro Val Ser Cys Lys Ile Leu
            245                 250                 255

His Phe His Gln Tyr Met Met Ala Cys Asn Tyr Phe Trp Met Leu
        260                 265                 270

Cys Glu Gly Ile Tyr Leu His Thr Leu Ile Val Ala Val Phe Thr
        275                 280                 285

Glu Lys Gln Arg Leu Arg Trp Tyr Tyr Leu Leu Gly Trp Gly Phe Pro
290                 295                 300

Leu Val Pro Thr Thr Ile His Ala Ile Thr Arg Ala Val Tyr Phe Asn
305                 310                 315                 320

Asp Asn Cys Trp Leu Ser Val Glu Thr His Leu Leu Tyr Ile Ile His
                325                 330                 335

Gly Pro Val Met Ala Ala Leu Val Val Asn Phe Phe Phe Leu Leu Asn
            340                 345                 350

Ile Val Arg Val Leu Val Thr Lys Met Arg Glu Thr His Glu Ala Glu
        355                 360                 365

Ser His Met Tyr Leu Lys Ala Val Lys Ala Thr Met Ile Leu Val Pro
    370                 375                 380

Leu Leu Gly Ile Gln Phe Val Val Phe Pro Trp Arg Pro Ser Asn Lys
385                 390                 395                 400

Met Leu Gly Lys Ile Tyr Asp Tyr Val Met His Ser Leu Ile His Phe
                405                 410                 415

Gln Gly Phe Phe Val Ala Thr Ile Tyr Cys Phe Cys Asn Asn Glu Val
            420                 425                 430

Gln Thr Thr Val Lys Arg Gln Trp Ala Gln Phe Lys Ile Gln Trp Asn
        435                 440                 445

Gln Arg Trp Gly Arg Arg Pro Ser Asn Arg Ser Ala Arg Ala Ala
    450                 455                 460

Ala Ala Ala Glu Ala Gly Asp Ile Pro Ile Tyr Ile Cys His Gln Glu
465                 470                 475                 480

Leu Arg Asn Glu Pro Ala Asn Asn Gln Gly Glu Glu Ser Ala Glu Ile
                485                 490                 495

Ile Pro Leu Asn Ile Ile Glu Gln Glu Ser Ser Ala
            500                 505

<210> SEQ ID NO 28
<211> LENGTH: 427
<212> TYPE: PRT
<213> ORGANISM: homo sapien

<400> SEQUENCE: 28

Met Met Asp Ala Gln Tyr Lys Cys Tyr Asp Arg Met Gln Gln Leu Pro
1               5                   10                  15

Ala Tyr Gln Gly Glu Gly Pro Tyr Cys Asn Arg Thr Trp Asp Gly Trp
            20                  25                  30

Leu Cys Trp Asp Asp Thr Pro Ala Gly Val Leu Ser Tyr Gln Phe Cys
        35                  40                  45

Pro Asp Tyr Phe Pro Asp Phe Asp Pro Ser Glu Lys Val Thr Lys Tyr
    50                  55                  60

Cys Asp Glu Lys Gly Val Trp Phe Lys His Pro Glu Asn Asn Arg Thr
65                  70                  75                  80

Trp Ser Asn Tyr Thr Met Cys Asn Ala Phe Thr Pro Glu Lys Leu Lys

```
                85                  90                  95
Asn Ala Tyr Val Leu Tyr Tyr Leu Ala Ile Val Gly His Ser Leu Ser
            100                 105                 110
Ile Phe Thr Leu Val Ile Ser Leu Gly Ile Phe Val Phe Arg Ser
        115                 120                 125
Leu Gly Cys Gln Arg Val Thr Leu His Lys Asn Met Phe Leu Thr Tyr
        130                 135                 140
Ile Leu Asn Ser Met Ile Ile Ile His Leu Val Glu Val Val Pro
145                 150                 155                 160
Asn Gly Glu Leu Val Arg Arg Asp Pro Val Ser Cys Lys Ile Leu His
            165                 170                 175
Phe Phe His Gln Tyr Met Met Ala Cys Asn Tyr Phe Trp Met Leu Cys
        180                 185                 190
Glu Gly Ile Tyr Leu His Thr Leu Ile Val Val Ala Val Phe Thr Glu
        195                 200                 205
Lys Gln Arg Leu Arg Trp Tyr Tyr Leu Leu Gly Trp Gly Phe Pro Leu
210                 215                 220
Val Pro Thr Thr Ile His Ala Ile Thr Arg Ala Val Tyr Phe Asn Asp
225                 230                 235                 240
Asn Cys Trp Leu Ser Val Glu Thr His Leu Leu Tyr Ile Ile His Gly
            245                 250                 255
Pro Val Met Ala Ala Leu Val Val Asn Phe Phe Phe Leu Leu Asn Ile
        260                 265                 270
Val Arg Val Leu Val Thr Lys Met Arg Glu Thr His Glu Ala Glu Ser
        275                 280                 285
His Met Tyr Leu Lys Ala Val Lys Ala Thr Met Ile Leu Val Pro Leu
    290                 295                 300
Leu Gly Ile Gln Phe Val Val Phe Pro Trp Arg Pro Ser Asn Lys Met
305                 310                 315                 320
Leu Gly Lys Ile Tyr Asp Tyr Val Met His Ser Leu Ile His Phe Gln
            325                 330                 335
Gly Phe Phe Val Ala Thr Ile Tyr Cys Phe Cys Asn Asn Glu Val Gln
        340                 345                 350
Thr Thr Val Lys Arg Gln Trp Ala Gln Phe Lys Ile Gln Trp Asn Gln
        355                 360                 365
Arg Trp Gly Arg Arg Pro Ser Asn Arg Ser Ala Arg Ala Ala Ala
    370                 375                 380
Ala Ala Glu Ala Gly Asp Ile Pro Ile Tyr Ile Cys His Gln Glu Leu
385                 390                 395                 400
Arg Asn Glu Pro Ala Asn Asn Gln Gly Glu Glu Ser Ala Glu Ile Ile
            405                 410                 415
Pro Leu Asn Ile Ile Glu Gln Glu Ser Ser Ala
        420                 425

<210> SEQ ID NO 29
<211> LENGTH: 443
<212> TYPE: PRT
<213> ORGANISM: homo sapien

<400> SEQUENCE: 29

Met Met Asp Ala Gln Tyr Lys Cys Tyr Asp Arg Met Gln Gln Leu Pro
1               5                   10                  15
Ala Tyr Gln Gly Glu Gly Pro Tyr Cys Asn Arg Thr Trp Asp Gly Trp
            20                  25                  30
```

```
Leu Cys Trp Asp Asp Thr Pro Ala Gly Val Leu Ser Tyr Gln Phe Cys
         35                  40                  45
Pro Asp Tyr Phe Pro Asp Phe Asp Pro Ser Glu Lys Val Thr Lys Tyr
 50                  55                  60
Cys Asp Glu Lys Gly Val Trp Phe Lys His Pro Glu Asn Asn Arg Thr
 65                  70                  75                  80
Trp Ser Asn Tyr Thr Met Cys Asn Ala Phe Thr Pro Glu Lys Leu Lys
                 85                  90                  95
Asn Ala Tyr Val Leu Tyr Leu Ala Ile Val Gly His Ser Leu Ser
             100                 105                 110
Ile Phe Thr Leu Val Ile Ser Leu Gly Ile Phe Val Phe Phe Arg Lys
         115                 120                 125
Leu Thr Thr Ile Phe Pro Leu Asn Trp Lys Tyr Arg Lys Ala Leu Ser
     130                 135                 140
Leu Gly Cys Gln Arg Val Thr Leu His Lys Asn Met Phe Leu Thr Tyr
 145                 150                 155                 160
Ile Leu Asn Ser Met Ile Ile Ile His Leu Val Glu Val Val Pro
                 165                 170                 175
Asn Gly Glu Leu Val Arg Arg Asp Pro Val Ser Cys Lys Ile Leu His
             180                 185                 190
Phe Phe His Gln Tyr Met Met Ala Cys Asn Tyr Phe Trp Met Leu Cys
         195                 200                 205
Glu Gly Ile Tyr Leu His Thr Leu Ile Val Val Ala Val Phe Thr Glu
     210                 215                 220
Lys Gln Arg Leu Arg Trp Tyr Tyr Leu Leu Gly Trp Gly Phe Pro Leu
 225                 230                 235                 240
Val Pro Thr Thr Ile His Ala Ile Thr Arg Ala Val Tyr Phe Asn Asp
                 245                 250                 255
Asn Cys Trp Leu Ser Val Glu Thr His Leu Leu Tyr Ile Ile His Gly
             260                 265                 270
Pro Val Met Ala Ala Leu Val Val Asn Phe Phe Phe Leu Leu Asn Ile
         275                 280                 285
Val Arg Val Leu Val Thr Lys Met Arg Glu Thr His Glu Ala Glu Ser
     290                 295                 300
His Met Tyr Leu Lys Ala Val Lys Ala Thr Met Ile Leu Val Pro Leu
 305                 310                 315                 320
Leu Gly Ile Gln Phe Val Val Phe Pro Trp Arg Pro Ser Asn Lys Met
                 325                 330                 335
Leu Gly Lys Ile Tyr Asp Tyr Val Met His Ser Leu Ile His Phe Gln
             340                 345                 350
Gly Phe Phe Val Ala Thr Ile Tyr Cys Phe Cys Asn Asn Glu Val Gln
         355                 360                 365
Thr Thr Val Lys Arg Gln Trp Ala Gln Phe Lys Ile Gln Trp Asn Gln
     370                 375                 380
Arg Trp Gly Arg Arg Pro Ser Asn Arg Ser Ala Arg Ala Ala Ala
 385                 390                 395                 400
Ala Ala Glu Ala Gly Asp Ile Pro Ile Tyr Ile Cys His Gln Glu Leu
                 405                 410                 415
Arg Asn Glu Pro Ala Asn Asn Gln Gly Glu Glu Ser Ala Glu Ile Ile
             420                 425                 430
Pro Leu Asn Ile Ile Glu Gln Glu Ser Ser Ala
         435                 440
```

<210> SEQ ID NO 30
<211> LENGTH: 490
<212> TYPE: PRT
<213> ORGANISM: homo sapien

<400> SEQUENCE: 30

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
            20                  25                  30

Thr Ile Glu Pro Lys Pro Phe Leu Tyr Val Val Gly Arg Lys Lys Met
        35                  40                  45

Met Asp Ala Gln Tyr Lys Cys Tyr Asp Arg Met Gln Gln Leu Pro Ala
50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
            100                 105                 110

Asp Glu Lys Gly Val Trp Phe Lys His Pro Glu Asn Asn Arg Thr Trp
        115                 120                 125

Ser Asn Tyr Thr Met Cys Asn Ala Phe Thr Pro Glu Lys Leu Lys Asn
130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Lys Leu
                165                 170                 175

Thr Thr Ile Phe Pro Leu Asn Trp Lys Tyr Arg Lys Ala Leu Ser Leu
            180                 185                 190

Gly Cys Gln Arg Val Thr Leu His Lys Asn Met Phe Leu Thr Tyr Ile
        195                 200                 205

Leu Asn Ser Met Ile Ile Ile His Leu Val Glu Val Val Pro Asn
210                 215                 220

Gly Glu Leu Val Arg Arg Asp Pro Val Ser Cys Lys Ile Leu His Phe
225                 230                 235                 240

Phe His Gln Tyr Met Met Ala Cys Asn Tyr Phe Trp Met Leu Cys Glu
                245                 250                 255

Gly Ile Tyr Leu His Thr Leu Ile Val Val Ala Val Phe Thr Glu Lys
            260                 265                 270

Gln Arg Leu Arg Trp Tyr Tyr Leu Leu Gly Trp Gly Phe Pro Leu Val
        275                 280                 285

Pro Thr Thr Ile His Ala Ile Thr Arg Ala Val Tyr Phe Asn Asp Asn
290                 295                 300

Cys Trp Leu Ser Val Glu Thr His Leu Leu Tyr Ile Ile His Gly Pro
305                 310                 315                 320

Val Met Ala Ala Leu Val Val Asn Phe Phe Leu Leu Asn Ile Val
                325                 330                 335

Arg Val Leu Val Thr Lys Met Arg Glu Thr His Glu Ala Glu Ser His
            340                 345                 350

Met Tyr Leu Lys Ala Val Lys Ala Thr Met Ile Leu Val Pro Leu Leu
        355                 360                 365

Gly Ile Gln Phe Val Val Phe Pro Trp Arg Pro Ser Asn Lys Met Leu
370                 375                 380

```
Gly Lys Ile Tyr Asp Tyr Val Met His Ser Leu Ile His Phe Gln Gly
385                 390                 395                 400

Phe Phe Val Ala Thr Ile Tyr Cys Phe Cys Asn Asn Glu Val Gln Thr
                405                 410                 415

Thr Val Lys Arg Gln Trp Ala Gln Phe Lys Ile Gln Trp Asn Gln Arg
            420                 425                 430

Trp Gly Arg Arg Pro Ser Asn Arg Ser Ala Arg Ala Ala Ala Ala Ala
        435                 440                 445

Ala Glu Ala Gly Asp Ile Pro Ile Tyr Ile Cys His Gln Glu Leu Arg
    450                 455                 460

Asn Glu Pro Ala Asn Asn Gln Gly Glu Glu Ser Ala Glu Ile Ile Pro
465                 470                 475                 480

Leu Asn Ile Ile Glu Gln Glu Ser Ser Ala
                485                 490

<210> SEQ ID NO 31
<211> LENGTH: 490
<212> TYPE: PRT
<213> ORGANISM: homo sapien

<400> SEQUENCE: 31

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
                20                  25                  30

Thr Ile Glu Pro Lys Pro Phe Leu Tyr Val Val Gly Arg Lys Lys Met
            35                  40                  45

Met Asp Ala Gln Tyr Lys Cys Tyr Asp Arg Met Gln Gln Leu Pro Ala
    50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
                100                 105                 110

Asp Glu Lys Gly Val Trp Phe Lys His Pro Glu Asn Asn Arg Thr Trp
            115                 120                 125

Ser Asn Tyr Thr Met Cys Asn Ala Phe Thr Pro Glu Lys Leu Lys Asn
        130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Lys Leu
                165                 170                 175

Thr Thr Ile Phe Pro Leu Asn Trp Lys Tyr Arg Lys Ala Leu Ser Leu
                180                 185                 190

Gly Cys Gln Arg Val Thr Leu His Lys Asn Met Phe Leu Thr Tyr Ile
        195                 200                 205

Leu Asn Ser Met Ile Ile Ile His Leu Val Glu Val Val Pro Asn
210                 215                 220

Gly Glu Leu Val Arg Arg Asp Pro Val Ser Cys Lys Ile Leu His Phe
225                 230                 235                 240

Phe His Gln Tyr Met Met Ala Cys Asn Tyr Phe Trp Met Leu Cys Glu
                245                 250                 255

Gly Ile Tyr Leu His Thr Leu Ile Val Val Ala Val Phe Thr Glu Lys
                260                 265                 270
```

```
Gln Arg Leu Arg Trp Tyr Tyr Leu Leu Gly Trp Gly Phe Pro Leu Val
        275                 280                 285

Pro Thr Thr Ile His Ala Ile Thr Arg Ala Val Tyr Phe Asn Asp Asn
    290                 295                 300

Cys Trp Leu Ser Val Glu Thr His Leu Leu Tyr Ile Ile His Gly Pro
305                 310                 315                 320

Val Met Ala Ala Leu Val Val Asn Phe Phe Phe Leu Leu Asn Ile Val
                325                 330                 335

Arg Val Leu Val Thr Lys Met Arg Glu Thr His Glu Ala Glu Ser His
            340                 345                 350

Met Tyr Leu Lys Ala Val Lys Ala Thr Met Ile Leu Val Pro Leu Leu
        355                 360                 365

Gly Ile Gln Phe Val Val Phe Pro Trp Arg Pro Ser Asn Lys Met Leu
    370                 375                 380

Gly Lys Ile Tyr Asp Tyr Val Met His Ser Leu Ile His Phe Gln Gly
385                 390                 395                 400

Phe Phe Val Ala Thr Ile Tyr Cys Phe Cys Asn Asn Glu Val Gln Thr
                405                 410                 415

Thr Val Lys Arg Gln Trp Ala Gln Phe Lys Ile Gln Trp Asn Gln Arg
            420                 425                 430

Trp Gly Arg Arg Pro Ser Asn Arg Ser Ala Arg Ala Ala Ala Ala Ala
        435                 440                 445

Ala Glu Ala Gly Asp Ile Pro Ile Tyr Ile Cys His Gln Glu Leu Arg
    450                 455                 460

Asn Glu Pro Ala Asn Asn Gln Gly Glu Glu Ser Ala Glu Ile Ile Pro
465                 470                 475                 480

Leu Asn Ile Ile Glu Gln Glu Ser Ser Ala
                485                 490

<210> SEQ ID NO 32
<211> LENGTH: 474
<212> TYPE: PRT
<213> ORGANISM: homo sapien

<400> SEQUENCE: 32

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
                20                  25                  30

Thr Ile Glu Pro Lys Pro Phe Leu Tyr Val Val Gly Arg Lys Lys Met
            35                  40                  45

Met Asp Ala Gln Tyr Lys Cys Tyr Asp Arg Met Gln Gln Leu Pro Ala
        50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
                100                 105                 110

Asp Glu Lys Gly Val Trp Phe Lys His Pro Glu Asn Asn Arg Thr Trp
            115                 120                 125

Ser Asn Tyr Thr Met Cys Asn Ala Phe Thr Pro Glu Lys Leu Lys Asn
        130                 135                 140

Ala Tyr Val Leu Tyr Tyr Leu Ala Ile Val Gly His Ser Leu Ser Ile
```

```
                145                 150                 155                 160
        Phe Thr Leu Val Ile Ser Leu Gly Ile Phe Val Phe Arg Ser Leu
                        165                 170                 175
        Gly Cys Gln Arg Val Thr Leu His Lys Asn Met Phe Leu Thr Tyr Ile
                        180                 185                 190
        Leu Asn Ser Met Ile Ile Ile His Leu Val Glu Val Pro Asn
                        195                 200                 205
        Gly Glu Leu Val Arg Arg Asp Pro Val Ser Cys Lys Ile Leu His Phe
            210                 215                 220
        Phe His Gln Tyr Met Met Ala Cys Asn Tyr Phe Trp Met Leu Cys Glu
        225                 230                 235                 240
        Gly Ile Tyr Leu His Thr Leu Ile Val Val Ala Val Phe Thr Glu Lys
                        245                 250                 255
        Gln Arg Leu Arg Trp Tyr Tyr Leu Leu Gly Trp Gly Phe Pro Leu Val
                        260                 265                 270
        Pro Thr Thr Ile His Ala Ile Thr Arg Ala Val Tyr Phe Asn Asp Asn
                        275                 280                 285
        Cys Trp Leu Ser Val Glu Thr His Leu Leu Tyr Ile Ile His Gly Pro
            290                 295                 300
        Val Met Ala Ala Leu Val Val Asn Phe Phe Phe Leu Leu Asn Ile Val
        305                 310                 315                 320
        Arg Val Leu Val Thr Lys Met Arg Glu Thr His Glu Ala Glu Ser His
                        325                 330                 335
        Met Tyr Leu Lys Ala Val Lys Ala Thr Met Ile Leu Val Pro Leu Leu
                        340                 345                 350
        Gly Ile Gln Phe Val Val Phe Pro Trp Arg Pro Ser Asn Lys Met Leu
                        355                 360                 365
        Gly Lys Ile Tyr Asp Tyr Val Met His Ser Leu Ile His Phe Gln Gly
                        370                 375                 380
        Phe Phe Val Ala Thr Ile Tyr Cys Phe Cys Asn Asn Glu Val Gln Thr
        385                 390                 395                 400
        Thr Val Lys Arg Gln Trp Ala Gln Phe Lys Ile Gln Trp Asn Gln Arg
                        405                 410                 415
        Trp Gly Arg Arg Pro Ser Asn Arg Ser Ala Arg Ala Ala Ala Ala
                        420                 425                 430
        Ala Glu Ala Gly Asp Ile Pro Ile Tyr Ile Cys His Gln Glu Leu Arg
            435                 440                 445
        Asn Glu Pro Ala Asn Asn Gln Gly Glu Glu Ser Ala Glu Ile Ile Pro
        450                 455                 460
        Leu Asn Ile Ile Glu Gln Glu Ser Ser Ala
        465                 470

<210> SEQ ID NO 33
<211> LENGTH: 474
<212> TYPE: PRT
<213> ORGANISM: homo sapien

<400> SEQUENCE: 33

Met Arg Phe Thr Phe Thr Ser Arg Cys Leu Ala Leu Phe Leu Leu Leu
        1               5                   10                  15
        Asn His Pro Thr Pro Ile Leu Pro Ala Phe Ser Asn Gln Thr Tyr Pro
                        20                  25                  30
        Thr Ile Glu Pro Lys Pro Phe Leu Tyr Val Val Gly Arg Lys Lys Met
                        35                  40                  45
```

```
Met Asp Ala Gln Tyr Lys Cys Tyr Asp Arg Met Gln Gln Leu Pro Ala
 50                  55                  60
Tyr Gln Gly Glu Gly Pro Tyr Cys Asn Arg Thr Trp Asp Gly Trp Leu
 65                  70                  75                  80
Cys Trp Asp Asp Thr Pro Ala Gly Val Leu Ser Tyr Gln Phe Cys Pro
                 85                  90                  95
Asp Tyr Phe Pro Asp Phe Asp Pro Ser Glu Lys Val Thr Lys Tyr Cys
            100                 105                 110
Asp Glu Lys Gly Val Trp Phe Lys His Pro Glu Asn Asn Arg Thr Trp
        115                 120                 125
Ser Asn Tyr Thr Met Cys Asn Ala Phe Thr Pro Glu Lys Leu Lys Asn
    130                 135                 140
Ala Tyr Val Leu Tyr Tyr Leu Ala Ile Val Gly His Ser Leu Ser Ile
145                 150                 155                 160
Phe Thr Leu Val Ile Ser Leu Gly Ile Phe Val Phe Arg Ser Leu
                165                 170                 175
Gly Cys Gln Arg Val Thr Leu His Lys Asn Met Phe Leu Thr Tyr Ile
            180                 185                 190
Leu Asn Ser Met Ile Ile Ile His Leu Val Glu Val Val Pro Asn
        195                 200                 205
Gly Glu Leu Val Arg Arg Asp Pro Val Ser Cys Lys Ile Leu His Phe
    210                 215                 220
Phe His Gln Tyr Met Met Ala Cys Asn Tyr Phe Trp Met Leu Cys Glu
225                 230                 235                 240
Gly Ile Tyr Leu His Thr Leu Ile Val Val Ala Val Phe Thr Glu Lys
                245                 250                 255
Gln Arg Leu Arg Trp Tyr Tyr Leu Leu Gly Trp Gly Phe Pro Leu Val
            260                 265                 270
Pro Thr Thr Ile His Ala Ile Thr Arg Ala Val Tyr Phe Asn Asp Asn
        275                 280                 285
Cys Trp Leu Ser Val Glu Thr His Leu Leu Tyr Ile Ile His Gly Pro
    290                 295                 300
Val Met Ala Ala Leu Val Val Asn Phe Phe Phe Leu Leu Asn Ile Val
305                 310                 315                 320
Arg Val Leu Val Thr Lys Met Arg Glu Thr His Glu Ala Glu Ser His
                325                 330                 335
Met Tyr Leu Lys Ala Val Lys Ala Thr Met Ile Leu Val Pro Leu Leu
            340                 345                 350
Gly Ile Gln Phe Val Val Phe Pro Trp Arg Pro Ser Asn Lys Met Leu
        355                 360                 365
Gly Lys Ile Tyr Asp Tyr Val Met His Ser Leu Ile His Phe Gln Gly
    370                 375                 380
Phe Phe Val Ala Thr Ile Tyr Cys Phe Cys Asn Asn Glu Val Gln Thr
385                 390                 395                 400
Thr Val Lys Arg Gln Trp Ala Gln Phe Lys Ile Gln Trp Asn Gln Arg
                405                 410                 415
Trp Gly Arg Arg Pro Ser Asn Arg Ser Ala Arg Ala Ala Ala Ala
            420                 425                 430
Ala Glu Ala Gly Asp Ile Pro Ile Tyr Ile Cys His Gln Glu Leu Arg
        435                 440                 445
Asn Glu Pro Ala Asn Asn Gln Gly Glu Glu Ser Ala Glu Ile Ile Pro
    450                 455                 460
Leu Asn Ile Ile Glu Gln Glu Ser Ser Ala
```

```
                              465                      470

<210> SEQ ID NO 34
<211> LENGTH: 490
<212> TYPE: PRT
<213> ORGANISM: homo sapien

<400> SEQUENCE: 34

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
            20                  25                  30

Thr Ile Glu Pro Lys Pro Phe Leu Tyr Val Val Gly Arg Lys Lys Met
        35                  40                  45

Met Asp Ala Gln Tyr Lys Cys Tyr Asp Arg Met Gln Gln Leu Pro Ala
    50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
            100                 105                 110

Asp Glu Lys Gly Val Trp Phe Lys His Pro Glu Asn Asn Arg Thr Trp
        115                 120                 125

Ser Asn Tyr Thr Met Cys Asn Ala Phe Thr Pro Glu Lys Leu Lys Asn
130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Lys Leu
                165                 170                 175

Thr Thr Ile Phe Pro Leu Asn Trp Lys Tyr Arg Lys Ala Leu Ser Leu
            180                 185                 190

Gly Cys Gln Arg Val Thr Leu His Lys Asn Met Phe Leu Thr Tyr Ile
        195                 200                 205

Leu Asn Ser Met Ile Ile Ile His Leu Val Glu Val Val Pro Asn
210                 215                 220

Gly Glu Leu Val Arg Arg Asp Pro Val Ser Cys Lys Ile Leu His Phe
225                 230                 235                 240

Phe His Gln Tyr Met Met Ala Cys Asn Tyr Phe Trp Met Leu Cys Glu
                245                 250                 255

Gly Ile Tyr Leu His Thr Leu Ile Val Val Ala Val Phe Thr Glu Lys
            260                 265                 270

Gln Arg Leu Arg Trp Tyr Tyr Leu Leu Gly Trp Gly Phe Pro Leu Val
        275                 280                 285

Pro Thr Thr Ile His Ala Ile Thr Arg Ala Val Tyr Phe Asn Asp Asn
    290                 295                 300

Cys Trp Leu Ser Val Glu Thr His Leu Leu Tyr Ile Ile His Gly Pro
305                 310                 315                 320

Val Met Ala Ala Leu Val Val Asn Phe Phe Phe Leu Leu Asn Ile Val
                325                 330                 335

Arg Val Leu Val Thr Lys Met Arg Glu Thr His Glu Ala Glu Ser His
            340                 345                 350

Met Tyr Leu Lys Ala Val Lys Ala Thr Met Ile Leu Val Pro Leu Leu
        355                 360                 365
```

Gly Ile Gln Phe Val Val Phe Pro Trp Arg Pro Ser Asn Lys Met Leu
370                 375                 380

Gly Lys Ile Tyr Asp Tyr Val Met His Ser Leu Ile His Phe Gln Gly
385                 390                 395                 400

Phe Phe Val Ala Thr Ile Tyr Cys Phe Cys Asn Asn Glu Val Gln Thr
                405                 410                 415

Thr Val Lys Arg Gln Trp Ala Gln Phe Lys Ile Gln Trp Asn Gln Arg
            420                 425                 430

Trp Gly Arg Arg Pro Ser Asn Arg Ser Ala Arg Ala Ala Ala Ala Ala
                435                 440                 445

Ala Glu Ala Gly Asp Ile Pro Ile Tyr Ile Cys His Gln Glu Leu Arg
450                 455                 460

Asn Glu Pro Ala Asn Asn Gln Gly Glu Glu Ser Ala Glu Ile Ile Pro
465                 470                 475                 480

Leu Asn Ile Ile Glu Gln Glu Ser Ser Ala
                485                 490

<210> SEQ ID NO 35
<211> LENGTH: 474
<212> TYPE: PRT
<213> ORGANISM: homo sapien

<400> SEQUENCE: 35

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
                20                  25                  30

Thr Ile Glu Pro Lys Pro Phe Leu Tyr Val Val Gly Arg Lys Lys Met
            35                  40                  45

Met Asp Ala Gln Tyr Lys Cys Tyr Asp Arg Met Gln Gln Leu Pro Ala
50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
                100                 105                 110

Asp Glu Lys Gly Val Trp Phe Lys His Pro Glu Asn Asn Arg Thr Trp
            115                 120                 125

Ser Asn Tyr Thr Met Cys Asn Ala Phe Thr Pro Glu Lys Leu Lys Asn
130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Ser Leu
                165                 170                 175

Gly Cys Gln Arg Val Thr Leu His Lys Asn Met Phe Leu Thr Tyr Ile
                180                 185                 190

Leu Asn Ser Met Ile Ile Ile Ile His Leu Val Glu Val Val Pro Asn
            195                 200                 205

Gly Glu Leu Val Arg Arg Asp Pro Val Ser Cys Lys Ile Leu His Phe
210                 215                 220

Phe His Gln Tyr Met Met Ala Cys Asn Tyr Phe Trp Met Leu Cys Glu
225                 230                 235                 240

Gly Ile Tyr Leu His Thr Leu Ile Val Val Ala Val Phe Thr Glu Lys
                245                 250                 255

```
Gln Arg Leu Arg Trp Tyr Tyr Leu Leu Gly Trp Gly Phe Pro Leu Val
            260                 265                 270

Pro Thr Thr Ile His Ala Ile Thr Arg Ala Val Tyr Phe Asn Asp Asn
        275                 280                 285

Cys Trp Leu Ser Val Glu Thr His Leu Leu Tyr Ile Ile His Gly Pro
    290                 295                 300

Val Met Ala Ala Leu Val Val Asn Phe Phe Leu Leu Asn Ile Val
305                 310                 315                 320

Arg Val Leu Val Thr Lys Met Arg Glu Thr His Glu Ala Glu Ser His
                325                 330                 335

Met Tyr Leu Lys Ala Val Lys Ala Thr Met Ile Leu Val Pro Leu Leu
            340                 345                 350

Gly Ile Gln Phe Val Val Phe Pro Trp Arg Pro Ser Asn Lys Met Leu
        355                 360                 365

Gly Lys Ile Tyr Asp Tyr Val Met His Ser Leu Ile His Phe Gln Gly
    370                 375                 380

Phe Phe Val Ala Thr Ile Tyr Cys Phe Cys Asn Asn Glu Val Gln Thr
385                 390                 395                 400

Thr Val Lys Arg Gln Trp Ala Gln Phe Lys Ile Gln Trp Asn Gln Arg
                405                 410                 415

Trp Gly Arg Arg Pro Ser Asn Arg Ser Ala Arg Ala Ala Ala Ala Ala
            420                 425                 430

Ala Glu Ala Gly Asp Ile Pro Ile Tyr Ile Cys His Gln Glu Leu Arg
        435                 440                 445

Asn Glu Pro Ala Asn Asn Gln Gly Glu Glu Ser Ala Glu Ile Ile Pro
    450                 455                 460

Leu Asn Ile Ile Glu Gln Glu Ser Ser Ala
465                 470

<210> SEQ ID NO 36
<211> LENGTH: 427
<212> TYPE: PRT
<213> ORGANISM: homo sapien

<400> SEQUENCE: 36

Met Met Asp Ala Gln Tyr Lys Cys Tyr Asp Arg Met Gln Gln Leu Pro
1               5                   10                  15

Ala Tyr Gln Gly Glu Gly Pro Tyr Cys Asn Arg Thr Trp Asp Gly Trp
            20                  25                  30

Leu Cys Trp Asp Asp Thr Pro Ala Gly Val Leu Ser Tyr Gln Phe Cys
        35                  40                  45

Pro Asp Tyr Phe Pro Asp Phe Asp Pro Ser Glu Lys Val Thr Lys Tyr
    50                  55                  60

Cys Asp Glu Lys Gly Val Trp Phe Lys His Pro Glu Asn Asn Arg Thr
65                  70                  75                  80

Trp Ser Asn Tyr Thr Met Cys Asn Ala Phe Thr Pro Glu Lys Leu Lys
                85                  90                  95

Asn Ala Tyr Val Leu Tyr Tyr Leu Ala Ile Val Gly His Ser Leu Ser
            100                 105                 110

Ile Phe Thr Leu Val Ile Ser Leu Gly Ile Phe Val Phe Phe Arg Ser
        115                 120                 125

Leu Gly Cys Gln Arg Val Thr Leu His Lys Asn Met Phe Leu Thr Tyr
    130                 135                 140

Ile Leu Asn Ser Met Ile Ile Ile Ile His Leu Val Glu Val Val Pro
```

```
145                 150                 155                 160
Asn Gly Glu Leu Val Arg Arg Asp Pro Val Ser Cys Lys Ile Leu His
                165                 170                 175

Phe Phe His Gln Tyr Met Met Ala Cys Asn Tyr Phe Trp Met Leu Cys
            180                 185                 190

Glu Gly Ile Tyr Leu His Thr Leu Ile Val Ala Val Phe Thr Glu
        195                 200                 205

Lys Gln Arg Leu Arg Trp Tyr Tyr Leu Leu Gly Trp Gly Phe Pro Leu
    210                 215                 220

Val Pro Thr Thr Ile His Ala Ile Thr Arg Ala Val Tyr Phe Asn Asp
225                 230                 235                 240

Asn Cys Trp Leu Ser Val Glu Thr His Leu Leu Tyr Ile Ile His Gly
            245                 250                 255

Pro Val Met Ala Ala Leu Val Val Asn Phe Phe Phe Leu Leu Asn Ile
        260                 265                 270

Val Arg Val Leu Val Thr Lys Met Arg Glu Thr His Glu Ala Glu Ser
    275                 280                 285

His Met Tyr Leu Lys Ala Val Lys Ala Thr Met Ile Leu Val Pro Leu
    290                 295                 300

Leu Gly Ile Gln Phe Val Val Phe Pro Trp Arg Pro Ser Asn Lys Met
305                 310                 315                 320

Leu Gly Lys Ile Tyr Asp Tyr Val Met His Ser Leu Ile His Phe Gln
            325                 330                 335

Gly Phe Phe Val Ala Thr Ile Tyr Cys Phe Cys Asn Asn Glu Val Gln
        340                 345                 350

Thr Thr Val Lys Arg Gln Trp Ala Gln Phe Lys Ile Gln Trp Asn Gln
    355                 360                 365

Arg Trp Gly Arg Arg Pro Ser Asn Arg Ser Ala Arg Ala Ala Ala Ala
    370                 375                 380

Ala Ala Glu Ala Gly Asp Ile Pro Ile Tyr Ile Cys His Gln Glu Leu
385                 390                 395                 400

Arg Asn Glu Pro Ala Asn Asn Gln Gly Glu Glu Ser Ala Glu Ile Ile
            405                 410                 415

Pro Leu Asn Ile Ile Glu Gln Glu Ser Ser Ala
        420                 425

<210> SEQ ID NO 37
<211> LENGTH: 443
<212> TYPE: PRT
<213> ORGANISM: homo sapien

<400> SEQUENCE: 37

Met Met Asp Ala Gln Tyr Lys Cys Tyr Asp Arg Met Gln Gln Leu Pro
1               5                   10                  15

Ala Tyr Gln Gly Glu Gly Pro Tyr Cys Asn Arg Thr Trp Asp Gly Trp
            20                  25                  30

Leu Cys Trp Asp Asp Thr Pro Ala Gly Val Leu Ser Tyr Gln Phe Cys
        35                  40                  45

Pro Asp Tyr Phe Pro Asp Phe Asp Pro Ser Glu Lys Val Thr Lys Tyr
    50                  55                  60

Cys Asp Glu Lys Gly Val Trp Phe Lys His Pro Glu Asn Asn Arg Thr
65                  70                  75                  80

Trp Ser Asn Tyr Thr Met Cys Asn Ala Phe Thr Pro Glu Lys Leu Lys
            85                  90                  95
```

```
Asn Ala Tyr Val Leu Tyr Tyr Leu Ala Ile Val Gly His Ser Leu Ser
                100                 105                 110

Ile Phe Thr Leu Val Ile Ser Leu Gly Ile Phe Val Phe Phe Arg Lys
            115                 120                 125

Leu Thr Thr Ile Phe Pro Leu Asn Trp Lys Tyr Arg Lys Ala Leu Ser
        130                 135                 140

Leu Gly Cys Gln Arg Val Thr Leu His Lys Asn Met Phe Leu Thr Tyr
145                 150                 155                 160

Ile Leu Asn Ser Met Ile Ile Ile His Leu Val Glu Val Val Pro
                165                 170                 175

Asn Gly Glu Leu Val Arg Arg Asp Pro Val Ser Cys Lys Ile Leu His
            180                 185                 190

Phe Phe His Gln Tyr Met Met Ala Cys Asn Tyr Phe Trp Met Leu Cys
        195                 200                 205

Glu Gly Ile Tyr Leu His Thr Leu Ile Val Val Ala Val Phe Thr Glu
            210                 215                 220

Lys Gln Arg Leu Arg Trp Tyr Tyr Leu Leu Gly Trp Gly Phe Pro Leu
225                 230                 235                 240

Val Pro Thr Thr Ile His Ala Ile Thr Arg Ala Val Tyr Phe Asn Asp
                245                 250                 255

Asn Cys Trp Leu Ser Val Glu Thr His Leu Leu Tyr Ile Ile His Gly
            260                 265                 270

Pro Val Met Ala Ala Leu Val Val Asn Phe Phe Leu Leu Asn Ile
        275                 280                 285

Val Arg Val Leu Val Thr Lys Met Arg Glu Thr His Glu Ala Glu Ser
290                 295                 300

His Met Tyr Leu Lys Ala Val Lys Ala Thr Met Ile Leu Val Pro Leu
305                 310                 315                 320

Leu Gly Ile Gln Phe Val Val Phe Pro Trp Arg Pro Ser Asn Lys Met
                325                 330                 335

Leu Gly Lys Ile Tyr Asp Tyr Val Met His Ser Leu Ile His Phe Gln
            340                 345                 350

Gly Phe Phe Val Ala Thr Ile Tyr Cys Phe Cys Asn Asn Glu Val Gln
        355                 360                 365

Thr Thr Val Lys Arg Gln Trp Ala Gln Phe Lys Ile Gln Trp Asn Gln
370                 375                 380

Arg Trp Gly Arg Arg Pro Ser Asn Arg Ser Arg Ala Ala Ala Ala
385                 390                 395                 400

Ala Ala Glu Ala Gly Asp Ile Pro Ile Tyr Ile Cys His Gln Glu Leu
                405                 410                 415

Arg Asn Glu Pro Ala Asn Asn Gln Gly Glu Glu Ser Ala Glu Ile Ile
            420                 425                 430

Pro Leu Asn Ile Ile Glu Gln Glu Ser Ser Ala
        435                 440

<210> SEQ ID NO 38
<211> LENGTH: 274
<212> TYPE: PRT
<213> ORGANISM: homo sapien

<400> SEQUENCE: 38

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
            20                  25                  30
```

```
Thr Ile Glu Pro Lys Pro Phe Leu Tyr Val Val Gly Arg Lys Lys Met
         35                  40                  45

Met Asp Ala Gln Tyr Lys Cys Tyr Asp Arg Met Gln Gln Leu Pro Ala
     50                  55                  60

Tyr Gln Gly Glu Gly Pro Tyr Cys Asn Arg Thr Trp Asp Gly Trp Leu
 65                  70                  75                  80

Cys Trp Asp Asp Thr Pro Ala Gly Val Leu Ser Tyr Gln Phe Cys Pro
                 85                  90                  95

Asp Tyr Phe Pro Asp Phe Asp Pro Ser Glu Lys Val Thr Lys Tyr Cys
             100                 105                 110

Asp Glu Lys Gly Val Trp Phe Lys His Pro Glu Asn Asn Arg Thr Trp
         115                 120                 125

Ser Asn Tyr Thr Met Cys Asn Ala Phe Thr Pro Glu Lys Leu Lys Asn
 130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Ser Leu
                 165                 170                 175

Gly Cys Gln Arg Val Thr Leu His Lys Asn Met Phe Leu Thr Tyr Ile
             180                 185                 190

Leu Asn Ser Met Ile Ile Ile His Leu Val Glu Val Val Pro Asn
         195                 200                 205

Gly Glu Leu Val Arg Arg Asp Pro Val Ser Cys Lys Ile Leu His Phe
 210                 215                 220

Phe His Gln Tyr Met Met Ala Cys Asn Tyr Phe Trp Met Leu Cys Glu
225                 230                 235                 240

Gly Ile Tyr Leu His Thr Leu Ile Val Val Ala Val Phe Thr Glu Lys
                 245                 250                 255

Gln Arg Leu Arg Trp Tyr Tyr Leu Leu Gly Trp Ala Pro Ala Phe His
             260                 265                 270

Arg Asp

<210> SEQ ID NO 39
<211> LENGTH: 290
<212> TYPE: PRT
<213> ORGANISM: homo sapien

<400> SEQUENCE: 39

Met Arg Phe Thr Phe Thr Ser Arg Cys Leu Ala Leu Phe Leu Leu Leu
 1               5                  10                  15

Asn His Pro Thr Pro Ile Leu Pro Ala Phe Ser Asn Gln Thr Tyr Pro
                 20                  25                  30

Thr Ile Glu Pro Lys Pro Phe Leu Tyr Val Val Gly Arg Lys Lys Met
             35                  40                  45

Met Asp Ala Gln Tyr Lys Cys Tyr Asp Arg Met Gln Gln Leu Pro Ala
         50                  55                  60

Tyr Gln Gly Glu Gly Pro Tyr Cys Asn Arg Thr Trp Asp Gly Trp Leu
 65                  70                  75                  80

Cys Trp Asp Asp Thr Pro Ala Gly Val Leu Ser Tyr Gln Phe Cys Pro
                 85                  90                  95

Asp Tyr Phe Pro Asp Phe Asp Pro Ser Glu Lys Val Thr Lys Tyr Cys
             100                 105                 110

Asp Glu Lys Gly Val Trp Phe Lys His Pro Glu Asn Asn Arg Thr Trp
         115                 120                 125
```

```
Ser Asn Tyr Thr Met Cys Asn Ala Phe Thr Pro Glu Lys Leu Lys Asn
    130             135             140

Ala Tyr Val Leu Tyr Tyr Leu Ala Ile Val Gly His Ser Leu Ser Ile
145             150              155                     160

Phe Thr Leu Val Ile Ser Leu Gly Ile Phe Val Phe Phe Arg Lys Leu
                165             170                     175

Thr Thr Ile Phe Pro Leu Asn Trp Lys Tyr Arg Lys Ala Leu Ser Leu
            180             185             190

Gly Cys Gln Arg Val Thr Leu His Lys Asn Met Phe Leu Thr Tyr Ile
        195             200             205

Leu Asn Ser Met Ile Ile Ile Ile His Leu Val Glu Val Val Pro Asn
    210             215             220

Gly Glu Leu Val Arg Arg Asp Pro Val Ser Cys Lys Ile Leu His Phe
225             230             235                     240

Phe His Gln Tyr Met Met Ala Cys Asn Tyr Phe Trp Met Leu Cys Glu
                245             250                     255

Gly Ile Tyr Leu His Thr Leu Ile Val Val Ala Val Phe Thr Glu Lys
            260             265             270

Gln Arg Leu Arg Trp Tyr Tyr Leu Leu Gly Trp Ala Pro Ala Phe His
        275             280             285

Arg Asp
    290
```